(12) United States Patent
Goix et al.

(10) Patent No.: US 8,450,069 B2
(45) Date of Patent: May 28, 2013

(54) HIGHLY SENSITIVE BIOMARKER PANELS

(75) Inventors: Philippe J. Goix, Piedmont, CA (US); Robert Puskas, Manchester, MO (US); John Todd, Lafayette, CA (US); Richard Livingston, Webster Groves, MO (US); Douglas Held, Ballwin, MO (US); Sara Le, Berkeley, CA (US)

(73) Assignee: Singulex, Inc., Alameda, CA (US)

( * ) Notice: Subject to any disclaimer, the term of this patent is extended or adjusted under 35 U.S.C. 154(b) by 0 days.

(21) Appl. No.: 12/795,414

(22) Filed: Jun. 7, 2010

(65) Prior Publication Data

US 2011/0003707 A1 Jan. 6, 2011

Related U.S. Application Data

(60) Provisional application No. 61/185,194, filed on Jun. 8, 2009.

(51) Int. Cl.
*G01N 33/53* (2006.01)
(52) U.S. Cl.
USPC .................................. 435/7.1; 436/518
(58) Field of Classification Search
None
See application file for complete search history.

(56) References Cited

U.S. PATENT DOCUMENTS

| | | |
|---|---|---|
| 4,071,298 A | 1/1978 | Falconer |
| 4,172,227 A | 10/1979 | Tryer et al. |
| 4,243,318 A | 1/1981 | Stohr |
| 4,251,733 A | 2/1981 | Hirleman |
| 4,452,773 A | 6/1984 | Molday |
| 4,521,733 A | 6/1985 | Bottomley |
| 4,768,879 A | 9/1988 | McLachlan et al. |
| 4,770,183 A | 9/1988 | Groaman et al. |
| 4,793,705 A | 12/1988 | Shera |
| 4,927,265 A | 5/1990 | Brownlee |
| 4,972,265 A | 11/1990 | Tanaka et al. |
| 4,979,824 A | 12/1990 | Mathies et al. |
| 5,002,389 A | 3/1991 | Benser |
| 5,041,733 A | 8/1991 | Noguchi et al. |
| 5,094,594 A | 3/1992 | Brennan |
| 5,108,179 A | 4/1992 | Myers |
| 5,138,170 A | 8/1992 | Noguichi et al. |
| 5,209,834 A | 5/1993 | Shera |
| 5,230,997 A | 7/1993 | Frenkel |
| 5,269,937 A | 12/1993 | Dollinger et al. |
| 5,274,240 A | 12/1993 | Mathies et al. |
| 5,290,834 A | 3/1994 | Kadota et al. |
| 5,385,707 A | 1/1995 | Miltenyi et al. |
| 5,480,614 A | 1/1996 | Kamahori |
| 5,540,494 A | 7/1996 | Purvis, Jr. et al. |
| 5,543,838 A | 8/1996 | Hosier et al. |
| 5,547,849 A | 8/1996 | Baer et al. |
| 5,571,410 A | 11/1996 | Swedberg et al. |
| 5,603,351 A | 2/1997 | Cherukuri et al. |
| 5,605,662 A | 2/1997 | Heller et al. |
| 5,633,503 A | 5/1997 | Kosaka |
| 5,645,702 A | 7/1997 | Witt et al. |
| 5,653,859 A | 8/1997 | Parton et al. |
| 5,653,939 A | 8/1997 | Hollis et al. |
| 5,658,413 A | 8/1997 | Kaltenbach et al. |
| 5,681,751 A | 10/1997 | Begg et al. |
| 5,682,038 A | 10/1997 | Hoffman |
| 5,716,825 A | 2/1998 | Hancock et al. |
| 5,730,187 A | 3/1998 | Howitz et al. |
| 5,746,901 A | 5/1998 | Balch et al. |
| 5,755,942 A | 5/1998 | Zanzucchi et al. |
| 5,770,029 A | 6/1998 | Nelson et al. |
| 5,793,485 A | 8/1998 | Gourley |
| 5,795,158 A | 8/1998 | Warinner |
| 5,795,758 A | 8/1998 | Gentry et al. |
| 5,798,222 A | 8/1998 | Goix |
| 5,807,677 A | 9/1998 | Eigen et al. |
| 5,858,195 A | 1/1999 | Ramsey |
| 5,863,801 A | 1/1999 | Southgate et al. |
| 5,925,533 A | 7/1999 | Doth et al. |
| 5,949,532 A | 9/1999 | Schrof et al. |
| 5,955,028 A | 9/1999 | Chow |
| 5,989,402 A | 11/1999 | Chow et al. |
| 5,999,250 A | 12/1999 | Hairston et al. |
| 6,033,628 A | 3/2000 | Kaltenbach et al. |
| 6,041,515 A | 3/2000 | Ally et al. |
| 6,049,380 A | 4/2000 | Goodwin et al. |
| 6,071,478 A | 6/2000 | Chow |
| 6,114,180 A | 9/2000 | Doth et al. |
| 6,131,101 A | 10/2000 | Maitino et al. |

(Continued)

FOREIGN PATENT DOCUMENTS

DE 3720844 A1 1/1989
WO WO 90/10876 A1 9/1990

(Continued)

OTHER PUBLICATIONS

Verrier et al. (Cardio. Res 1996 vol. 31, p. 181-211).*
Deliargyris et al. (Am J. Cardiology 2000 vol. 86, p. 913-918).*
Upatnieks et al.: "A kilohertz frame rate cinemagraphic PIV system for laboratory-scale turbulent and unsteady flows," Experiments in Fluids (2002), vol. 32, pp. 87-98.
Van Orden et al.: "Single-molecule identification in flowing sample streams by fluorescence burst size in intraburst fluorescence decay rate," Anal. Chem. (1998) vol. 70, pp. 1444-1451.

(Continued)

*Primary Examiner* — Jacob Cheu
(74) *Attorney, Agent, or Firm* — McDonnell Boehnen Hulbert & Berghoff LLP

(57) ABSTRACT

Cardiovascular disease, e.g., congestive heart failure, is often first diagnosed after the onset of clinical symptoms, eliminating potential for early intervention. The invention provides a multi-marker immunoassay, including cardiac pathology and vascular inflammation biomarkers, yielding a more sensitive assay for early detection of CHF in plasma. A panel consisting of cardiac pathology (cTnI, BNP) and vascular inflammation (IL-6, TNFα, IL-17a) biomarkers provided a sensitivity of 94% for association with CHF.

19 Claims, 43 Drawing Sheets

U.S. PATENT DOCUMENTS

| | | | |
|---|---|---|---|
| 6,132,580 A | 10/2000 | Mathies et al. |
| 6,140,048 A | 10/2000 | Muller et al. |
| 6,143,152 A | 11/2000 | Simpson et al. |
| 6,177,277 B1 | 1/2001 | Soini |
| 6,208,815 B1 | 3/2001 | Seidel et al. |
| 6,211,955 B1 | 4/2001 | Basiji et al. |
| 6,242,266 B1 | 6/2001 | Schleifer et al. |
| 6,249,341 B1 | 6/2001 | Basiji et al. |
| 6,280,960 B1 | 8/2001 | Carr |
| 6,309,886 B1 | 10/2001 | Ambrose et al. |
| 6,338,746 B1 | 1/2002 | Detrick et al. |
| 6,355,420 B1 | 3/2002 | Chan |
| 6,361,671 B1 | 3/2002 | Mathies et al. |
| 6,372,185 B1 | 4/2002 | Shumate et al. |
| 6,386,219 B1 | 5/2002 | Barth et al. |
| 6,388,746 B1 | 5/2002 | Eriksson et al. |
| 6,394,305 B1 | 5/2002 | Sydlosky et al. |
| 6,403,338 B1 | 6/2002 | Knapp et al. |
| 6,403,947 B1 | 6/2002 | Hoyt et al. |
| 6,473,176 B2 | 10/2002 | Basiji et al. |
| 6,482,648 B2 | 11/2002 | Doth et al. |
| 6,495,104 B1 | 12/2002 | Unno et al. |
| 6,506,609 B1 | 1/2003 | Wada et al. |
| 6,532,067 B1 | 3/2003 | Chang et al. |
| 6,533,553 B2 | 3/2003 | Caren |
| 6,537,437 B1 | 3/2003 | Galambos et al. |
| 6,554,744 B2 | 4/2003 | Schmidt |
| 6,582,903 B1 | 6/2003 | Rigler et al. |
| 6,599,436 B1 | 7/2003 | Matzke et al. |
| 6,608,680 B2 | 8/2003 | Basiji et al. |
| 6,623,613 B1 | 9/2003 | Mathies et al. |
| 6,624,785 B2 | 9/2003 | Poliak et al. |
| 6,689,323 B2 | 2/2004 | Fisher et al. |
| 6,710,871 B1 | 3/2004 | Goix |
| 6,749,734 B1 | 6/2004 | Simpson et al. |
| 6,766,817 B2 | 7/2004 | Da Silva |
| 6,783,992 B2 | 8/2004 | Robotti et al. |
| 6,802,342 B2 | 10/2004 | Fernandes et al. |
| 6,811,668 B1 | 11/2004 | Berndt et al. |
| 6,816,257 B2 | 11/2004 | Goix |
| 6,918,404 B2 | 7/2005 | Da Silva |
| 6,977,305 B2 | 12/2005 | Leung et al. |
| 6,991,907 B1 | 1/2006 | Buechler et al. |
| 7,066,586 B2 | 6/2006 | Da Silva |
| 7,074,194 B2 | 7/2006 | Crosby |
| 2002/0030812 A1 | 3/2002 | Ortyn et al. |
| 2002/0123059 A1 | 9/2002 | Ho |
| 2002/0167665 A1 | 11/2002 | Yeung et al. |
| 2003/0029995 A1 | 2/2003 | Mullins et al. |
| 2003/0078737 A1 | 4/2003 | Keys et al. |
| 2003/0109420 A1 | 6/2003 | Valkirs et al. |
| 2003/0124592 A1 | 7/2003 | Puskas |
| 2003/0222007 A1 | 12/2003 | Gu et al. |
| 2004/0166514 A1 | 8/2004 | Puskas et al. |
| 2004/0214211 A1 | 10/2004 | Gilmanshin et al. |
| 2004/0219509 A1 | 11/2004 | Valkirs et al. |
| 2004/0219604 A1 | 11/2004 | Eriksson et al. |
| 2005/0064523 A1 | 3/2005 | Wu |
| 2005/0164205 A1 | 7/2005 | Puskas |
| 2005/0221408 A1 | 10/2005 | Nalefski et al. |
| 2005/0272054 A1 | 12/2005 | Cargill et al. |
| 2006/0003333 A1 | 1/2006 | Puskas |
| 2006/0004188 A1 | 1/2006 | Leung et al. |
| 2006/0078915 A1 | 4/2006 | Fuchs et al. |
| 2006/0078998 A1 | 4/2006 | Puskas et al. |
| 2006/0099638 A1 | 5/2006 | Leung et al. |
| 2006/0160209 A1 | 7/2006 | Larson et al. |
| 2006/0228747 A1 | 10/2006 | Fuchs et al. |
| 2007/0111316 A1 | 5/2007 | Shi et al. |
| 2007/0196371 A1 | 8/2007 | Kuestner et al. |
| 2007/0259377 A1 | 11/2007 | Urdea et al. |
| 2008/0003685 A1 | 1/2008 | Goix et al. |
| 2008/0064113 A1 | 3/2008 | Goix et al. |
| 2008/0158543 A1 | 7/2008 | Puskas et al. |
| 2008/0171352 A1 | 7/2008 | Goix et al. |
| 2008/0255471 A1* | 10/2008 | Naghavi et al. ............ 600/549 |
| 2008/0261242 A1 | 10/2008 | Goix et al. |
| 2008/0300798 A1* | 12/2008 | McDevitt et al. ............ 702/19 |
| 2009/0171590 A1 | 7/2009 | Puskas et al. |
| 2009/0197344 A1 | 8/2009 | Villard-Saussine et al. |
| 2010/0173321 A1* | 7/2010 | Hamm et al. ............ 435/7.1 |
| 2010/0255518 A1 | 10/2010 | Goix et al. |
| 2010/0329929 A1 | 12/2010 | Goix et al. |
| 2011/0111524 A1 | 5/2011 | Goix et al. |

FOREIGN PATENT DOCUMENTS

| | | | |
|---|---|---|---|
| WO | WO 99/26067 A1 | 5/1999 |
| WO | WO 99/40416 A1 | 8/1999 |
| WO | WO 99/54497 A1 | 10/1999 |
| WO | WO 99/55461 A1 | 11/1999 |
| WO | WO 2004/059293 A2 | 7/2004 |
| WO | WO 2004/059293 A3 | 3/2005 |
| WO | WO 2005/089524 | 9/2005 |
| WO | WO 2005/089524 A2 | 9/2005 |
| WO | WO 2005/089524 A3 | 4/2006 |
| WO | WO 2006/036182 A2 | 4/2006 |
| WO | WO 2008/048371 | 4/2008 |

OTHER PUBLICATIONS

Van Wissen et al.: "Differential hs-CRP reduction in patients with familial hypercholesterolemia treated with aggressive or conventional statin therapy," Atherosclerosis (Dec. 2002) vol. 165, No. 2, pp. 361-366.

Von Zur Muhlen et al.: "Evaluation of Urine Proteome Pattern Analysis for Its Potential to Reflect Coronary Artery Atherosciersosis in Symptomatic Patients" J. Proteom. Res. (2009) V. 8 pp. 335-345.

Wabuyele et al.: "Single molecule detection of double-stranded DNA in poly(methylmethacrylate) and polycarbonate microfluidic devices," Electrophoresis (2001) vol. 22, pp. 3939-3948.

Wallace et al.: "Serum Troponins as Biomarkers of Drug-Induced Cardiac Toxicity," Toxicologic Pathology, (2004) vol. 32, pp. 106-121.

Willneff: "A spatio-temporal matching algorithm for 3D particle tracking velocimetry: a dissertation submitted to the Swwiss Federal Institute of Technology Zurich for the degree of Doctoral of Technical Sciences," (Sep. 2003) Diss. Eth No. 15276 (abstract). Available at http://e-collection.ethbib.ethz.ch/ecol-pool/diss/abstracts/p15276. pdf.

Wu et al.: Development and preliminary clinical validation of a high sensitivity assay for cardiac troponin using a capillary flow (single molecule) fluorescence detector. Poster presented at Oak Ridge conference. Apr. 22-22, 2006; 52:2157-2159.

Wu et al.: "Development and Preliminary Clinical Validation of a High Sensitivity Assay for Cardiac Tropoin Using a Capillary Flow (Single Molecule) Fluorescence Detector," Clinical Chemistry (2006) vol. 52, pp. 2157-2159.

Young: Singules Developing Troponin Test for earlier detection of AMI. Medical Device Daily Dec. 13, 2006.

Zetheli et al.: "Troponin I as a predictor of coronary heart disease and morality in 70-year-old mend: a community-based cohort study," Circulation (Feb. 28, 2006) vol. 113, No. 8, pp. 1071-1078.

Zhu et al.: "Fluorescence multiplexing with time-resolved and spectral discrimination using a near-IR detector," Anal. Chem (2003) vol. 75, pp. 2280-2291.

Zimmerli et al.: "Urinary Proteomic Biomakers in Coronary Artery Disease" Mol. Cell Proteomics (Feb. 2008) vol. 7, No. 2 pp. 290-298. First Published on Oct. 19, 2007.

U.S. Appl. No. 60/613,881, entitled "Continuous wave single particle detector," filed Sep. 28, 2004, Puskas.

U.S. Appl. No. 60/624,785, entitled "Sandwich assay for detection of individual molecules," filed Oct. 29, 2004, Puskas.

U.S. Appl. No. 10/718,194, entitled: "Preparation of defined highly labeled probes," filed Nov. 19, 2003, Puskas, Robert Steven.

U.S. Appl. No. 10/720,047, entitled: "Charge and mass tags for detection and analysis," filed Nov. 19, 2003, Puskas, Robert Steven.

U.S. Appl. No. 11/048,660, entitled: "System and Methods for Sample Analysis," filed Jan. 28, 2005, Puskas, Robert S. et al.

U.S. Appl. No. 11/767,196, entitled: "System and Method for Sample Analysis," filed Jun. 22, 2007, Goix, Philippe J. et al.

U.S. Appl. No. 11/784,186, entitled "Methods and Compositions for Highly Sensitive Analysis of Markers," filed Apr. 4, 2007, Goix, Philippe J.

U.S. Appl. No. 11/830,762, entitled "Methods and Compositions for Highly Sensitive Detection of Molecules," filed Jul. 30, 2007, Goix, Phillippe J.

U.S. Appl. No. 11/838,114, entitled: "System and Method for Sample Analysis," filed Aug. 13, 2007, Puskas, Robert S. et al.

U.S. Appl. No. 12/060,997, entitled: "Methods and Compositions for Highly Sensitive Analysis of Markers," filed Apr. 2, 2008, Goix, Philippe J. et al.

U.S. Appl. No. 12/276,277, entitled: "System and Method for Sample Analysis," filed Nov. 21, 2008, Puskas, Robert S. et al.

U.S. Appl. No. 12/731,500, entitled "Methods and Compositions for Highly Sensitive Detection of Molecules," filed Mar. 25, 2010, Goix, Phillippe J.

Guide to Labeling Antibodies with Alexa Fluor Dyes 24-28 (2004).

Haab et al.: "Single molecule florescence burst detection of DNA fragments separated by capillary electrophoresis," Anal Chem. (1995) vol. 67, pp. 3523-3260.

Haab et al.: "Single-molecule detection of DNA separations in microfabricated capillary electrophoresis chips employing focused molecular stream," Anal Chem. (1999) vol. 71, pp. 5137-5145.

Haugland Molecular probes handbook of fluorescent probes and research product Ninth Edition Molecular Probes Inc. (Table of Contents only) 2002.

Huse et al.: "Application of a filamento phage pVII fion protein system suitable for efficient production, screening and mutagenesis of f(ab) antibody fragments," Journal of Immunology (Dec. 15, 1992) vol. 149, No. 12, pp. 39-14-20.

Hirst et al.: "Production of plasma selectively depleted in fibrinogen by affinity chromatography," Journal of Clinical Pathology (1991) vol. 44, pp. 306-308.

Hubl et al.: "Evaluation of the Architect Stat Troponin-I assay," Clinical Laboratory Publications (2005) vol. 51, pp. 251-255.

Kaiser et al.: "Capillary electrophoresis coupled to mass spectrometer for automated and robust polypeptide determination in body fluids for clinical use" Electrophoresis (2004) V. 25 pp. 2044-2055.

Katus et al.: "Higher sensitivity troponin assyas: Quo vadis?" Eur Heart J. (Jan. 2009), vol. 30, No. 2, pp. 127-128.

Keller et al.: "Analytical applications of single-molecule detection," Analytical Chemistry (2002) vol. 74, pp. 317A-324A.

Kemp et al.: "Biochemical markers of myocardial injury," British Journal of Anaesthesia (2004) vol. 93, pp. 63-73.

Klee: "Human anti-moe antibodies," Arch Pathol Lab Med. (2000) vol. 124, pp. 921-923.

Koehnlein et al.: "Increased cardiac troponin T and C-reactive protein levels in end-stage renal disease are associated with obstructive sleep apnea," Clin Nephrol (Jan. 2007) vol. 71, No. 1, pp. 50-58.

Koerbin et al. The Comparative analytical performance of four troponin I assays at low concentration Ann Clin. Biochem. 42:19-23 (2005).

Larue et al.: "Cardiac-Specific Immunoenzymaometric Assay of Troponin I in the Early phase of Acute Myocardial Infarction," Clinical Chemistry (1993) vol. 39, pp. 972-979.

LeCaptain et al.: "Two-beam fluorescence cross-correlation spectroscopy in an electrophoretic mobility shift assay," Anal. Chem. (2002) vol. 74, pp. 1171-1176.

LeCaptain et al.: "Characterization of DNA-protein complex by capillary electrophoresis—single molecule fluorescence correlation spectroscopy," Analyst (2001) vol. 126, pp. 1279-1284.

Lexington Medical Center. Mycardial infarction redefined. NewsPath, May 2001.

Li et al.: "Ultrasensitive coincidence fluorescence detection of single DNA molecules," Anal. Chem. (2003) vol. 75, pp. 1664-1670.

Loscher et al.: "Counting of single protein molecules at interfaces and application of this technique in early-stage diagnosis," Anal. Chem (1998) vol. 70, pp. 3202-3205.

Lucey et al.: "Type 1 and type 2 cytokine dysregulation in human infectioneoplastic and inflammatory diseases," Clinical Biology Reviews (1996) vol. 9, pp. 532-562.

Ma et al.: "Single-molecule immunoassay and DNA diagnosis," Electrophoresis (2001) vol. 22, pp. 421-426.

Mair, Johannes: "Cardiac troponin I and Troponin T: Are enzymes still relevant as cardiac markers?" Clinica Chimica Acta, vol. 257 (1997) NR. 1, pp. 99-115.

Missov et al.: Circulating Cardiac Troponin I in Severe Congestive Heart Failure, Circulation, 96:2953-2958 (1997).

Nalefski et al.: "Single-molecule counting of macromolecular complexes in real time: a novel approach to quantify transcription factor—DNA and antibody-antigen interactions," FASEB Journal (2004) vol. 18, No. 8: C176.

Nguyen et al.: "Detection of single molecules of phycoerythrin in hydrodynamically focused flows by laser-induced fluorescence," Anal. Chem. (1987) vol. 59, pp. 2158-2161.

Oh et al.: "E of a dual monoclonal solid phase and a polyclonal detector to create an immunoassay for the detection of human cardiac troponin I," Clin. Biochem. (2000) vol. 33, pp. 255-262.

Ohman et al.: "Cardiac troponin T levels for risk stratification in acute mycardial ischemia," The New England Journal of Medicine (1997) vol. 335, pp. 1333-1341.

Panchuk-Voloshina et al.: "Alexa dyes a series of new fluorescent dyes that yield exceptionally bright phostotable conjugates" J. Histochem Cytochem (Sep. 1999) vol. 47 No. 9 pp. 1179-1188.

Panteghini et al.: "Evaluation of imprecision for cardiac troponin assays at low range concentrations," Clinical Chemistry (2004) vol. 50, pp. 327-332.

Panteghini: "Role and importance of biochemical markers in clinical cardiology," European Heart Journal (2004) vol. 25, pp. 1187-1196.

Panteghini: "The interfering component in cardiac troponin I immunoassays: need for further experimental evidence," Clin Chem. (2004) vol. 50, pp. 676-677.

Park. Addressing Unmet Needs in Assay Development. Medical Device Link 1-4, Mar. 2007.

Peck et al.: "Single-molecule fluorescence detection: autocorrelation criterion and experimental realization with phycoerythrim," Proc. Natl. Acad. Sci. USA (1989) vol. 86, pp. 4087-4091.

Phillips et al.: "Application of single molecule technology to rapidly map long DNA and study the conformation of stretched DNA" Nucleic Acids Research vol. 33 pp. 5829-5837 (2005).

Rigler: "Fluorescence correlations single molecule detection and large number screening" Applications in Biotechnology J. Biotechnol. (1995) vol. 41 (2-3) pp. 177-186.

Sabatine et al.: "Detection of acute changes in circulating troponin in the setting of transient stress test-induced myocardial ischaemia ing an ultrasensitive assay: results from TIMI 35," CUR Heart J. Jan. 2009 (ePub Nov. 8, 2008).

Sato et al.: "Biochemical markers of myocyte injury in heart failure," Heart (British Cardiac Society) (2004) vol. 90, pp. 1110-1113.

Sauer et al.: "Detection and identification of individual antigen molecules in human serum with pulsed semiconductor lasers," Appl. Phys. B. (1997) vol. 65, pp. 427-431.

Schiffer et al.: "High resolution proteome/peptidome analysis of body fluids by capillary electrophoresis coupled with MS" Proteomics (2006) V. 6 pp. 5615-5627.

Schulz et al.: "Cardiac troponin I: A potential marker of exercise intolerance in patients with moderate heart failure," American Heart Journal (2002) vol. 144, pp. 351-358.

Shera et al.: "Detection of single fluorescent molecules," Chemical Physics Letters (1990) vol. 174, pp. 553-557.

Shortreed et al.: "High-throughput single-molecule DNA screening based on electrophoresis," Anal. Chem. (2000) vol. 72, pp. 2879-2885.

Sidransky: "Emerging molecular markers of cancer," Nature Reviews: Cancer (2002) vol. 2, pp. 210-219.

Soper et al.: "Photon burst detection of single near-infrared fluorescent molecules," Anal. Chem. (1993) vol. 65, pp. 740-747.

Soper et al.: "Single-molecule detection in the near-IR using continuos wave diode laser excitation with an avalanche photon detector," Applied Spectroscopy (1998) vol. 52, pp. 1-6.

Stiegler et al.: "Lower cardiac troponin T and I results in heparin-plasma than in serum," Clinical Chemistry, (2000) vol. 46, pp. 1338-1344.

Tanaka et al.: "Protein and polymer analyses up to m/z 100 000 by laser ionization time-of-flight mass spectrometry," Rapid Commun. Mass. Spect. (1988) vol. 2, pp. 151-153.

Thomas, Ma et al.: "A review of troponin assay performance in Wales: can the same (method-dependent) decision limits be used in different sites?" Ann. of Clinical Biochemistry, British Medical Association, London, GB, vol. 42, No. 5, Sep. 1, 2005, pp. 351-356.

Todd, J. et al.: "Ultrasensitive flow-based immunoassays ing single-molecule counting," Clinical Chemistry, American Association for Clinical Chemistry, Washington DC, vol. 53, No. 11, Nov. 1, 2007, pp. 1990-1995.

Achar et al.: "Diagnosis of acute coronary syndrome," American Family Physician (2005) vol. 72, pp. 119-1265.

Adams et al.: "Cardiac troponin I.A. marker with high specificity for cardiac injury," Circulation (1993) vol. 88, pp. 101-106.

Adams et al.: "Comparable detection of acute myocardial infarction by creatine kinase MB isoenzyme and cardiac troponin I.," Clinical Chemistry (1994) vol. 40, pp. 1291-1295.

Al-Awadhi et al. Singapore Med. J. (2007) vol. 48, pp. 847-849.

Alexa Fluor Succinimidyl Esters. Invitrogen. Revised Jan. 4, 2006; 1-5.

Alexa Fluor Dyes Handbook. Simply the Best and Brightest: Fluorescent Dyes and Conjugates. Invitrogen. Copyright 2005. Molecular Probes. 1-33.

Ambrose et al.: "Single molecule fluorescence spectroscopy at ambient temperature," Chemical Reviews (1999) vol. 99, pp. 22929-22956.

Anazawa et al.: "Electrophoretic quantitative of nucleic acids without amplification by single molecule imaging," Anal. Chem (2002) vol. 74, pp. 5033-5038.

Antman et al.: "Cardiac-specific troponin I levels to predict the risk of mortality in patients with acute coronary syndromes," The New England Journal of Medicine (1996) vol. 335, pp. 1342-1349.

Apple et al.: "The diagnostic utility of cardiac biomarkers in detecting myocardial infarction," Clinical Cornerstone (2005) vol. 7, pp. S25-S30.

Apple et al.: "Validation of the 99th Percentile Cutoff Independent of Assay Imprecision (CV) for Cardiac Troponin monitoring for Ruling out Myocardial Infarction," Clinical Chemistry (2005) vol. 51, pp. 2198-2200.

Babuin et al.: "Troponin:the biomarker of choice for the detection of cardiac injury," Canadian Medical Association Journal (2005) vol. 173, pp. 1191-1202.

Becker et al.: "Three-dimensional photogrammetric particle-tracking velocimetry," Preparing for the Future (2005) vol. 5, No. 3; available at http://esapub.esrin.esa.it/pff/pffv5n3/beckv5nc.htm(7 pages).

Bieschke et al.: "Ultrasensitive detection of pathological prion protein aggregates by dual-color scanning for intensely fluorescent targets," Pro. Natl. Acad. Sci. (2000) vol. 97, pp. 5468-5473.

Borrebaeck, C.: Editor. Antibody Engineering. Second Edition. 1995 Oxford University Press, Oxford.

Bouchon et al.: "Cutting edge: inflammatory responses can be triggered by TREM-1 a novel receptor expressed on neutrophils and monocytes," The Journal of Immunology (2000) vol. 164, pp. 4991-4995.

Braunwald et al.: "ACC/AHA 2002 guideline update for the management of patients with unstable angina and non-ST-segment elevation mycardial infarction—A report of the American College of Cardiology/American Heart Association task force on practice guidelines (Committee on the Management of Patients with Unstable Angina)," American College of Cardiology and the American Heart Association (2002).

Brinkmeier et al.: "Two-beam cross-correlation: a method to characterize transport phenomena in micrometer-sized structures," Anal. Chem. (1999) vol. 71, pp. 609-616.

Buisson et al.: "Biochemical markers of my cardial injury," Available at http://ww.ampath.co.za/Documents/biochemicalMarkers.pdf. Accessed Sep. 20, 2007.

Castro et al.: "Fluorescence detection and size measurement of single DNA molecules," Anal. Chem. (1993) vol. 65, pp. 849-852.

Castro et al.: "Single molecule detection: applications to ultrasensitive biochemical analysis," Applied Optics (1995) vol. 34, pp. 3218-3222.

Castro et al.: "Single-molecule detection of specific nucleic acid sequences in unamplified genomic DNA," Anal. Chemistry (1997) vol. 69, pp. 3915-3920.

Castro et al.: "Single-molecule electrophoresis," Anal. Chemistry (1995) vol. 67, pp. 3181-3186.

Castro et al.: "Ultrasensitive direct detection of a specific DNA sequence of Bacillantracis in solution," The Analyst (2000) vol. 125, pp. 9-11.

Cayley: "Diagnosing the case of chest pain," American Family Physician (2005) vol. 72, pp. 2012-2021.

Chan et al.: "DNA mapping using microfluidic stretching and single-molecule detection of fluorescent site-specific tags," Genome Research (2004) vol. 14, pp. 1137-1146.

Chen et al.: "Single-molecule detection in capillary electrophoresis: molecular shot noise as a fundamental limit to chemical analysis." Anal. Chemistry (1996) vol. 68, pp. 690-696.

Cohen et al.: "The renal TGF-beta system in the db/db mouse model of diabetic nephropathy" Exp. Nephrol. (1998) vol. 6 pp. 226-233.

Colonna: "TREMS in the immune system and beyond," Nature Reviews: Immunology (2003) vol. 3, pp. 445-453.

Csiro Atralia, Image motion, tracking and registration. Available at http://www.cmis.csiro.au/IAP/Motion. Accessed Jan. 24, 2005.

D'Antoni et al. Rapid quantitative analysis using a single molecule counting Anal. Chem. 352:97-109 (2006).

Diderholm et al.: "The prognostic and therapeutic implications of increased troponin T levels and ST depression in unstable coronary artery disease: the FRISC II invasive tropoinin T electrocardiogram substudy," American Heart Journal (2002) vol. 143, pp. 760-767.

Dovichi et al.: "Laser-induced fluorescence of flowing samples as an approach to single-molecule detection in liquids," Anal. Chem. (1984) vol. 56, pp. 348-354.

Dunbar et al. Quantitative multiplexed detection of bacterial pathogens: DNA and protein applications of Luminex LabMap system J. Microbiol Methods. 2003; 53(2): 245-252.

Eder et al.: "Transforming growth factor-beta1 and beta2 in serum and urine from patients with bladder carcinoma" The J. of Urology (1996) vol. 156 pp. 953-957.

Effenhauser et al.: "Integrated capillary electrophoresis on flexible silicone microdevices: analysis of DNA restriction fragments and detection of single DNA molecules on microchips," Anal. Chem. (1997) vol. 69, pp. 3451-3457.

Eryol et al.: "Should Troponin-T Be Assessed During Exercise Stress Testing in Patients with Stable Angina Pectoris?" Anadolu Kardiyol Der. (2002) vol. 2, pp. 132-137.

Eskelinen et al.: "A new tumor marker MCA in breast cancer diagnosis" Anticancer Res. (1988) vol. 8 pp. 665-668.

Etzioni et al.: "The case for early detection," Nature Reviews: Cancer (2003) vol. 3, pp. 243-252.

Ferrieres et al.: "Human cardiac troponin I: precise identification of antigenic epitopes and prediction of secondary structure," Clinical Chemistry (1998) vol. 44, pp. 487-493.

Fister et al.: "Counting single chromphore molecules for ultrasensitive analysis and separations on microchip devices," Anal. Chem. (1998) vol. 70, pp. 431-437.

Gaze et al.: "Cardiac Troponins as Biomarkers of Drug and Toxin Induced Cardiac Toxicity and Cardioprotection," Expert Opin. Drug Metabl. Toxocol. (2005) vol. 1, pp. 715-725.

Giannitsis et al.: "Admission tropoinin T level predicts clinical outcomes, TIMI flow, and mycardial tissue perfion after primary percutaneo intervention for acute ST-segment elevation mycoardial infarction," Circulation (2001) vol. 104, pp. 630-635.

Gibot et al.: "Soluble triggering receptor expressed on muyeloid cells and the diagnosis of pneumonia," The New England Journal of Medicine (2004) vol. 350, pp. 451-458.

Glenn Research Center NASA particle Imaging Velocimetry. Available at http://www.grc.nasa.gov/www/Optlinstr/piv/background.htm and associated web pages. Accessed Jan. 26, 2005.

Goix. Fulfilling the promise of biomarkers in drug discovery and development, Drug Discovery + International, 6-7, Apr./May 2007.

Goix.Slides from presentation at clinical biomarkers summit Coronado, CA, Mar. 29-31, 2006.

Golde: "Alzheimer disease therapy: can the amyloid cascade be halted?" The Journal of Clinical Investigation (2003) vol. 11, pp. 11-18.

Guenard et al.: "Two-channel sequential single-molecule measurement," Anal. Chem. (1997) vol. 69, pp. 2426-2433.

Guide to Amine-Reactive Probes. Reviese Oct. 13, 2005.

Zen et al., "Analysis of Circulating Apoptosis Mediators and Proinflammatory Cytokines in Patients With Idiopathic Hypertrophic Cardiomyopathy Comparison Between Nonobstructive and Dilated-Phase Hypertrophic Cardiomyopathy" Int Heart J. 46(2):231-44 (2005).

* cited by examiner

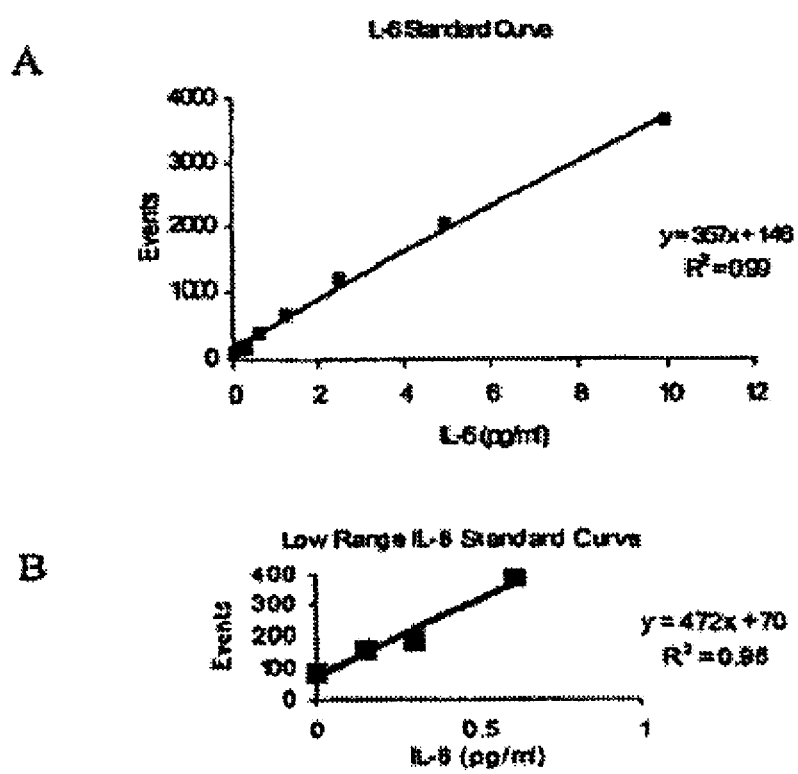
Figures 17A & B

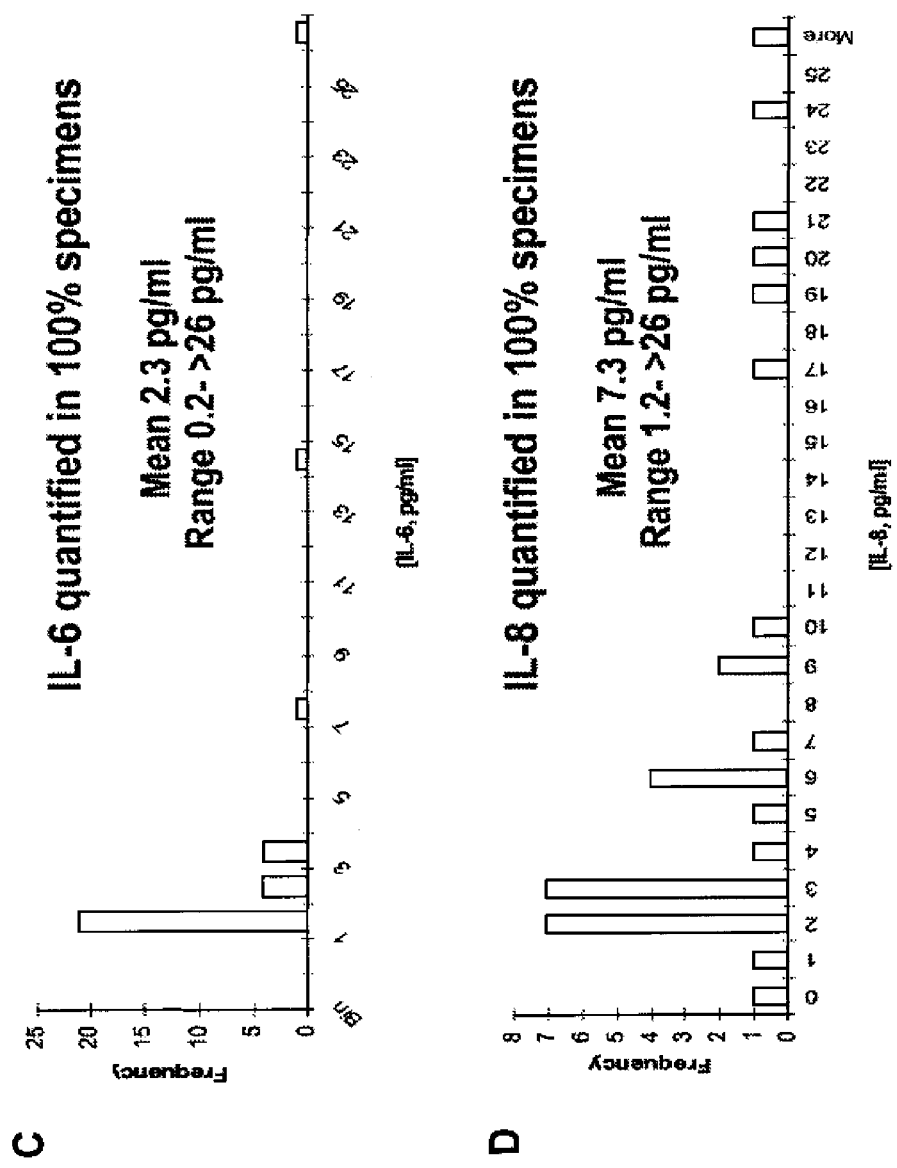
Figures 17C & D

HIGHLY SENSITIVE BIOMARKER PANELS

BACKGROUND OF THE INVENTION

Cardiovascular disease is an abnormal function of the heart and/or blood vessels. Included under this designation are such diverse medical conditions as coronary artery disease, congestive heart failure, arrhythmia, atherosclerosis, hypertension, stroke, cerebrovascular disease, peripheral vascular disease and myocardial infarction. In the United States, CVD is a major cause of death. About 40 percent of all deaths in 1997, or about one million people, were attributed to cardiovascular disease. There are an estimated 62 million people with cardiovascular disease and 50 million people with hypertension in this country.

Cardiovascular disease is a progressive process with etiologies in both cardiac muscle (cardio-pathology) and vascular inflammation. The disease process follows a continuum from early onset mild vascular inflammation to severe acute events such as acute myocardial infarction or chronic events such as heart failure. Patients with well recognized physical conditions such as hypertension, obesity, diabetes, metabolic syndrome, hyper-cholesterolemia are at varying degrees of risk for developing CVD. A challenge facing clinicians who have patients presenting with CVD risk factors is understanding their degree of risk, developing the appropriate treatment plan and then monitoring the patient for improvements in disease risk.

Ample studies have provided compelling evidence that CVD is largely preventable. The causes of cardiovascular disease range from structural defects, to infection, inflammation, environment and genetics. While some risk factors cannot be modified (genetics, age, gender), there are a number of risk factors that can be addressed through lifestyle changes or medically. These controllable risk factors include cigarette smoking, high blood pressure, obesity, diabetes, physical inactivity, and high blood cholesterol level. By the time that heart problems are detected, the underlying cause (atherosclerosis) is usually quite advanced, having progressed for decades. There is therefore increased emphasis on preventing atherosclerosis by modifying risk factors, such as healthy eating, exercise and avoidance of smoking.

CVD, e.g., congestive heart failure (CHF), is often first diagnosed after the onset of clinical symptoms, eliminating potential for early intervention. There is a need for highly sensitive detection of CVD.

SUMMARY OF THE INVENTION

In one embodiment, the present invention provides a method for detecting or monitoring a condition in a subject, comprising detecting a first marker in a first sample from the subject and detecting a second marker, wherein the first marker comprises Cardiac Troponin-I (cTnI) or Vascular Endothelial Growth Factor (VEGF), and wherein the limit of detection of the first marker is less than about 20 pg/ml. In some embodiments, the detection of at least one marker comprises contacting the sample with a label for the marker and detecting the presence or absence of the label, wherein detection of the presence of the label indicates the presence of the corresponding marker. In some embodiments, the label comprises a fluorescent moiety, and the detection comprises passing the label through a single molecule detector, wherein the single molecule detector comprises: (a) an electromagnetic radiation source for stimulating the fluorescent moiety; (b) an interrogation space for receiving electromagnetic radiation emitted from the electromagnetic source; and (c) an electromagnetic radiation detector operably connected to the interrogation space for determining an electromagnetic characteristic of the stimulated fluorescent moiety.

In some embodiments, the limit of detection of the first marker ranges from about 10 pg/ml to about 0.01 pg/ml. In some embodiments, the limit of detection of the first marker is less than about 10 pg/ml. In some embodiments, the limit of detection of the first marker is less than about 5 pg/ml. In some embodiments, the limit of detection of the first marker is less than about 1 pg/ml. In some embodiments, the limit of detection of the first marker is less than about 0.5 pg/ml. In some embodiments, the limit of detection of the first marker is less than about 0.1 pg/ml. In some embodiments, the limit of detection of the first marker is less than about 0.05 pg/ml. In some embodiments, the limit of detection of the first marker is less than about 0.01 pg/ml. In some embodiments, the limit of detection of the first marker is less than about 0.005 pg/ml. In some embodiments, the limit of detection of the first marker is less than about 0.001 pg/ml. In some embodiments, the coefficient of variation (CV) of the limit of detection ranges from about 20% to about 1%. In some embodiments, the coefficient of variation (CV) of the limit of detection ranges from about 100% to about 1%. In some embodiments, the coefficient of variation (CV) of the limit of detection ranges from about 75% to about 1%. In some embodiments, the coefficient of variation (CV) of the limit of detection ranges from about 50% to about 1%. In some embodiments, the coefficient of variation (CV) of the limit of detection ranges from about 25% to about 1%. In some embodiments, the coefficient of variation (CV) of the limit of detection ranges from about 20% to about 1%. In some embodiments, the coefficient of variation (CV) of the limit of detection ranges from about 15% to about 1%. In some embodiments, the coefficient of variation (CV) of the limit of detection ranges from about 10% to about 1%. In some embodiments, the coefficient of variation (CV) of the limit of detection ranges from about 5% to about 1%. In some embodiments, the sample size ranges from about 10 µl to about 0.1 µl. In some embodiments, the sample size ranges from about 100 µl to about 0.1 µl. In some embodiments, the sample size ranges from about 75 µl to about 0.1 µl. In some embodiments, the sample size ranges from about 50 µl to about 0.1 µl. In some embodiments, the sample size ranges from about 25 µl to about 0.1 µl. In some embodiments, the sample size ranges from about 20 µl to about 0.1 µl. In some embodiments, the sample size ranges from about 5 µl to about 0.1 µl. In some embodiments, the sample size ranges from about 1 µl to about 0.1 µl. In some embodiments, the sample size is less than about 100 µl. In some embodiments, the sample size is less than about 75 µl. In some embodiments, the sample size is less than about 50 µl. In some embodiments, the sample size is less than about 25 µl. In some embodiments, the sample size is less than about 20 µl. In some embodiments, the sample size is less than about 15 µl. In some embodiments, the sample size is less than about 10 µl. In some embodiments, the sample size is less than about 5 µl. In some embodiments, the sample size is less than about 2 µl. In some embodiments, the sample size is less than about 1 µl. In some embodiments, the sample size is less than about 0.5 µl. In some embodiments, the sample size is less than about 0.1 µl. In some embodiments, the sample size is less than about 0.05 µl. In some embodiments, the sample size is less than about 0.01 µl.

In some embodiments, the method further comprises splitting the first sample into two or more aliquots and detecting at least one marker in the two or more aliquots. In some embodiments, the sample comprises a plasma, serum, cell lysate, or tissue sample. In some embodiments, the sample comprises bronchoalveolar lavage fluid (BAL), blood, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest.

In some embodiments, the second marker comprises a biomarker, a physiological marker or a genetic marker. In some embodiments, the second marker comprises a protein. In some embodiments, at least one of the first marker and the second marker are found in a sample from a normal individual at a concentration of less than 10 pg/ml. In some embodiments, at least one of the first marker and the second marker are found in a sample from a normal individual at a concentration of less than 100 pg/ml. In some embodiments, at least one of the first marker and the second marker are found in a sample from a normal individual at a concentration of less than 75 pg/ml. In some embodiments, at least one of the first marker and the second marker are found in a sample from a normal individual at a concentration of less than 50 pg/ml. In some embodiments, at least one of the first marker and the second marker are found in a sample from a normal individual at a concentration of less than 25 pg/ml. In some embodiments, at least one of the first marker and the second marker are found in a sample from a normal individual at a concentration of less than 20 pg/ml. In some embodiments, at least one of the first marker and the second marker are found in a sample from a normal individual at a concentration of less than 15 pg/ml. In some embodiments, at least one of the first marker and the second marker are found in a sample from a normal individual at a concentration of less than 10 pg/ml. In some embodiments, at least one of the first marker and the second marker are found in a sample from a normal individual at a concentration of less than 5 pg/ml. In some embodiments, at least one of the first marker and the second marker are found in a sample from a normal individual at a concentration of less than 2 pg/ml. In some embodiments, at least one of the first marker and the second marker are found in a sample from a normal individual at a concentration of less than 1 pg/ml. In some embodiments, at least one of the first marker and the second marker are found in a sample from a normal individual at a concentration of less than 0.5 pg/ml. In some embodiments, at least one of the first marker and the second marker are found in a sample from a normal individual at a concentration of less than 0.1 pg/ml. In some embodiments, at least one of the first marker and the second marker are found in a sample from a normal individual at a concentration of less than 0.05 pg/ml. In some embodiments, at least one of the first marker and the second marker are found in a sample from a normal individual at a concentration of less than 0.01 pg/ml.

In some embodiments, the limit of detection of the second marker ranges from about 10 pg/ml to about 0.01 pg/ml. In some embodiments, the limit of detection of the second marker is less than about 10 pg/ml. In some embodiments, the limit of detection of the second marker is less than about 5 pg/ml. In some embodiments, the limit of detection of the second marker is less than about 1 pg/ml. In some embodiments, the limit of detection of the second marker is less than about 0.5 pg/ml. In some embodiments, the limit of detection of the second marker is less than about 0.1 pg/ml. In some embodiments, the limit of detection of the second marker is less than about 0.05 pg/ml. In some embodiments, the limit of detection of the second marker is less than about 0.01 pg/ml. In some embodiments, the limit of detection of the second marker is less than about 0.005 pg/ml. In some embodiments, the limit of detection of the second marker is less than about 0.001 pg/ml.

In some embodiments, the second marker comprises B-type natiuretic peptide, IL-1α, IL-113, IL-6, IL-8, IL-10, TNF-α, IFN-γ, cTnI, VEGF, insulin, GLP-1 (active), GLP-1 (total), TREM1, Leukotriene E4, Akt1, Aβ-40, Aβ-42, Fas ligand, or PSA. In some embodiments, the second marker is a cytokine. In some embodiments, the cytokine is G-CSF, MIP-1α, IL-10, IL-22, IL-8, IL-5, IL-21, INF-γ, IL-15, IL-6, TNF-α, IL-7, GM-CSF, IL-2, IL-4, IL-1α, IL-12, IL-17α, IL-1β, MCP, IL-32 or RANTES. In some embodiments, the cytokine is IL-10, IL-8, INF-γ, IL-6, TNF-α, IL-7, IL-1α, or IL-1β. In some embodiments, the second marker comprises an apolipoprotein, ischemia-modified albumin (IMA), fibronectin, C-reactive protein (CRP), B-type Natriuretic Peptide (BNP), or Myeloperoxidase (MPO).

In some embodiments, the method of the invention further comprises determining a concentration for the first marker, and determining a concentration for the second marker if the second marker comprises a protein. In some embodiments, the method of the invention comprises determining a ratio of a concentration of the first marker compared to a concentration for the second marker if the second marker comprises a protein.

In some embodiments, the second marker comprises a physiological marker. In some embodiments, the physiological marker comprises an electrocardiogram (EKG), stress testing, nuclear imaging, ultrasound, insulin tolerance, body mass index, blood pressure, age, sex, or sleep apnea.

In some embodiments, the second marker comprises a molecular marker. In some embodiments, the molecular marker comprises cholesterol, LDL/HDL/Q-LDL, triglycerides, uric acid, creatinine, blood glucose or vitamin-D. In some embodiments, the molecular marker comprises subtractions of LDL/HDL/Q-LDL or triglycerides.

In some embodiments, the second marker comprises a genetic marker. In some embodiments, the genetic marker comprises a variation in a gene encoding an apolipoprotein such as ApoE. In some embodiments, the genetic marker comprises a single nucleotide polymorphism (SNP). In some embodiments, the genetic marker comprises an insertion, deletion, fusion or other mutation. In some embodiments, the genetic marker comprises an epigenetic marker, such as DNA methylation or imprinting.

In some embodiments of the method of the invention, the condition comprises cardiac damage, an inflammatory disease, a proliferative disorder, a metabolic disorder, angiogenesis, artherosclerosis or diabetes. In some embodiments, the cardiac damage comprises myocardial infarct, necrosis, myocardial dysfunction, unstable angina, plaques, heart failure, coronary artery disease, or rheumatic heart disease. In some embodiments, the proliferative disorder comprises a cancer. In some embodiments, the cancer comprises a breast cancer, a prostate cancer, or lymphoma.

In some embodiments, the method of the invention further comprises determining a change in concentration of the markers between the first sample and a second sample from the subject, whereby the change is used to detect or monitor the condition. In some embodiments, the method of the invention further comprises determining a change in the ratio of the concentrations of the first marker and the second marker between the first sample and a second sample from the subject, whereby the change is used to detect or monitor the condition. In some embodiments, a medical procedure is performed between acquiring the first sample and the second sample from the subject. In some embodiments, the medical procedure comprises a surgical procedure, stress testing or a therapeutic intervention. In some embodiments, a series of samples from the subject are used to detect or monitor the condition. In some embodiments, the series of samples are collected over time and the change of concentration in the series of samples is assessed.

In some embodiments, monitoring according to the present invention comprises monitoring of a disease progression, disease recurrence, risk assessment, therapeutic efficacy or surgical efficacy.

In one embodiment, the present invention provides a method for detecting a single particle in a sample, comprising: (a) labeling the particle, if present in the sample, with a label; and (b) detecting the presence or absence of the label, wherein detection of the presence of the label indicates the presence of the single particle in the sample; wherein the limit of detection of the single particle is less than 20 pg/ml; and wherein the single particle comprises a single molecule, fragment, or complex of Cardiac Troponin-I (cTnI), B-type Natriuretic Peptide (BNP, proBNP or NT-proBNP), TREM-1, Interleukin 1 Alpha (IL-1α), Interleukin 1 Beta (IL-1β), Interleukin 4 (IL-4), Interleukin 6 (IL-6), Interleukin 8 (IL-8), Interleukin 10 (IL-10), Interferon gamma (IFN-γ), Tumor Necrosis Factor alpha (TNF-α), Glucagon-like peptide-1 (GLP-1), Leukotriene E4 (LTE4), Transforming Growth Factor Beta (TGFβ), Akt1, Aβ-40, Aβ-42, Fas ligand (FasL), or Vascular Endothelial Growth Factor (VEGF). In some embodiments, the limit of detection of the single particle ranges between about 10 pg/ml and about 0.01 pg/ml. In some embodiments, the limit of detection of the single particle is less than about 10 pg/ml. In some embodiments, the limit of detection of the single particle is less than about 5 pg/ml. In some embodiments, the limit of detection of the single particle is less than about 1 pg/ml. In some embodiments, the limit of detection of the single particle is less than about 0.5 pg/ml. In some embodiments, the limit of detection of the single particle is less than about 0.1 pg/ml. In some embodiments, the limit of detection of the single particle is less than about 0.05 pg/ml. In some embodiments, the limit of detection of the single particle is less than about 0.01 pg/ml. In some embodiments, the limit of detection of the single particle is less than about 0.005 pg/ml. In some embodiments, the limit of detection of the single particle is less than about 0.001 pg/ml.

In one embodiment, the present invention provides a kit comprising a composition comprising two or more antibodies to two or more biomarkers, wherein the two or more antibodies are attached to a fluorescent dye moiety, wherein the two or more biomarkers comprise particles as described above, wherein the moiety is capable of emitting at least about 200 photons when stimulated by a laser emitting light at the excitation wavelength of the moiety, wherein the laser is focused on a spot not less than about 5 microns in diameter that contains the moiety, and wherein the total energy directed at the spot by the laser is no more than about 3 microJoules, wherein the composition is packaged in suitable packaging.

In one embodiment, the present invention provides a method for detecting or monitoring a cardiovascular condition in a subject, comprising detecting two or more biomarkers, wherein the biomarkers are cardiac pathology or vascular inflammation biomarkers, and wherein the limit of detection of at least one marker is less than about 20 pg/ml. In some embodiments, the detection of at least one marker comprises contacting the sample with a label for the marker and detecting the presence or absence of the label, wherein detection of the presence of the label indicates the presence of the corresponding marker. In some embodiments, the label comprises a fluorescent moiety, and the detection comprises passing the label through a single molecule detector, wherein the single molecule detector comprises: a) an electromagnetic radiation source for stimulating the fluorescent moiety; b) an interrogation space for receiving electromagnetic radiation emitted from the electromagnetic source; and c) an electromagnetic radiation detector operably connected to the interrogation space for determining an electromagnetic characteristic of the stimulated fluorescent moiety. In some embodiments, the limit of detection of at least one marker ranges from about 10 pg/ml to about 0.01 pg/ml.

In some embodiments, the cardiac pathology biomarkers are Cardiac Troponin-I (cTnI) or B-type Natriuretic Peptide (BNP, proBNP or NT-proBNP). In some embodiments, the vascular inflammation biomarkers are Interleukin 6 (IL-6), Tumor Necrosis Factor alpha (TNF-α), or Interleukin 17a (IL-17a). In some embodiments, the condition comprises congestive heart failure and the biomarkers comprise cTnI, BNP, IL-6, TNF-α, and IL-17a.

In one embodiment, the present invention provides a method to detect a cardiovascular condition in a subject, comprising measuring a physiological biomarker and detecting one or more biomarkers in a blood sample from the subject. In some embodiments, the physiological biomarker is a stress test and the one or more biomarkers comprise cTnI. In some embodiments, the physiological biomarker is a sleep test and the one or more biomarkers comprise one or more cytokines. The one or more cytokines can comprise TNF-a, IL-6, IL-17a and/or hsCRP. In some embodiments, the physiological biomarker is Carotid intima-media thickness (CIMT) and the one or more biomarkers comprise one or more markers of vascular inflammation. The one or more markers of vascular inflammation can comprise hsCRP, IL-6, TNF-a and/or IL-1.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows an analyzer that includes one electromagnetic source and one electromagnetic detector; FIG. 1B shows an analyzer that includes two electromagnetic sources and one electromagnetic detector.

FIG. 2A shows the flow cell of an analyzer that includes one electromagnetic source; and FIG. 2B shows the flow cell of an analyzer that includes two electromagnetic sources.

FIG. 3A shows the arrangement for an analyzer that has one electromagnetic source and one electromagnetic detector; FIG. 3B shows the arrangement for an analyzer that has two electromagnetic sources and two electromagnetic detectors.

FIGS. 17A-F illustrate detection of IL-6 and IL-8. A) IL-6 standards, diluted according to a commercially available kit (R&D Systems, Minneapolis, Minn.) gave a linear response between 0.1 and 10 pg/ml. B) IL-6 standard curve below 1 pg/ml. C) and D) Distribution of IL-6 C) and IL-8 D) identified in blood bank donor EDTA specimens. E) Range of detection at low concentrations of any analyte can be extended to higher concentrations by switching the detection of the analyzer from counting molecules (digital signal) to detecting the sum of photons (analog signal) that are generated at the higher concentrations of analyte. The single particle analyzer has an expanded linear dynamic range of 6 logs. Six-log range of detection based on switching from digital to analog detection. F) Non-linearized standard curve showing range of low concentrations of IL-6 (0.1 fg/ml-10 fg/ml) determined by counting photons emitted by individual particles (digital signal), and higher range of concentrations of IL-6 (10 fg/ml-1 pg/ml).

DETAILED DESCRIPTION OF THE INVENTION

Figure 1A:
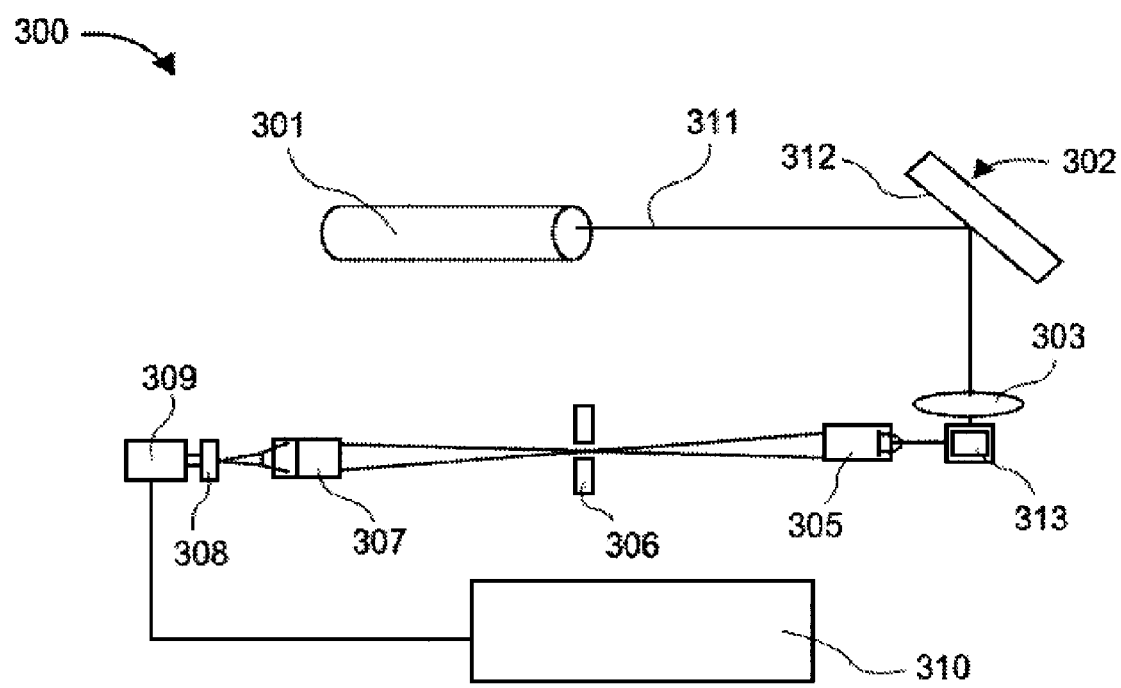
FIGS. 1A and 1B illustrate schematic diagrams of the arrangement of the components of a single particle analyzer.

Outline
I. Introduction
II. Molecules for Sensitive Detection By the Methods and Compositions of the Invention
   A. General
   B. Markers
III. Labels
   A. Binding partners
     1. Antibodies
   B. Fluorescent Moieties
     1. Dyes
     2. Quantum dots
   C. Binding Partner-Fluorescent Moiety Compositions
IV. Highly Sensitive Analysis of Molecules
   A. Sample
   B. Sample preparation
   C. Detection of molecule of interest and determination of concentration
V. Instruments and Systems Suitable for Highly Sensitive Analysis of Molecules
   A. Apparatus/System
   B. Single Particle Analyzer
     1. Electromagnetic Radiation Source
     2. Capillary Flow Cell
     3. Motive Force
     4. Detectors
   C. Sampling System
   D. Sample preparation system
   E. Sample recovery
VI. Methods Using Highly Sensitive Analysis of Molecules
   A. Methods
   B. Exemplary Markers
     1. Cardiac damage
     2. Infection
     3. Cytokines
       a. Interleukin 1
       b. Interleukin 4
       c. Interleukin 6
     4. Inflammatory Markers
       a. Leukotrine E4
       b. TGFβ
     5. Akt 1
     6. Fas ligand
     7. VEGF
     8. Amyloid beta proteins
   C. Multiple Marker Panels
     1. Multiple Biomarker Panels
     2. Mixed Marker Panels
   D. Detection and Monitoring
   E. Cardiovascular Biomarker Panels
   F. Clinical Methods
VII. Kits
VIII. Examples

I. Introduction

The invention provides instruments, kits, compositions, and methods for the highly sensitive detection of single molecules, and for the determination of the concentration of the molecules in a sample. In some embodiments, the sensitivity and precision of the instruments, compositions, methods, and kits of the invention can be achieved by a combination of factors selected from, but not limited to, electromagnetic sources of appropriate wavelength and power output, appropriate interrogation space size, high numerical aperture lenses, detectors capable of detecting single photons, and data analysis systems for counting single molecules. The instruments of the invention are referred to as "single molecule detectors" or "single particle detectors," and are also encompassed by the terms "single molecule analyzers" and "single particle analyzers." The sensitivity and precision of the kits and methods of the invention are achieved in some embodiments by the use of the instruments of the invention together with a combination of factors selected from, but not limited to, labels for molecules that exhibit characteristics that allow the molecules to be detected at the level of the single molecule, and methods assaying the label in the instruments described herein.

The instruments, kits, and methods of the invention are especially useful in the sensitive and precise detection of single molecules or small molecules, and for the determination of the concentration of the molecules in a sample.

The invention provides, in some embodiments, instruments and kits for the sensitive detection and determination of concentration of molecules by detection of single molecules, labels for such detection and determination, and methods using such instruments and labels in the analysis of samples. In particular, the sensitivity and precision of the instruments, kits, and methods of the invention make possible the detection and determination of concentration of molecules, e.g., markers for biological states, at extremely low concentrations, e.g., concentrations below about 100, 10, 1, 0.1, 0.01, or 0.001 femtomolar. In further embodiments, the instruments and kits of the invention are capable of determining a concentration of a species in a sample, e.g., the concentration of a molecule, over a large dynamic range of concentrations without the need for dilution or other treatment of samples, e.g., over a concentration range of more than $10^5$-fold, $10^6$-fold, or $10^7$-fold.

The high sensitivity of the instruments, kits, and methods of the invention allows the use of markers, e.g., biological markers, which were not previously useful because of a lack of sensitivity of detection. The high sensitivity of the instruments, kits, and methods of the invention also facilitate the establishment of new markers. There are numerous markers currently available which could be useful in determining biological states, but are not currently of practical use because of current limitations in measuring their lower concentration ranges. In some cases, abnormally high levels of the marker are detectable by current methods, but normal ranges are unknown. In some cases, abnormally high levels of the marker are detectable by current methods, but normal ranges have not been established. In some cases, upper normal ranges of the marker are detectable, but not lower normal ranges, or levels below normal. In some cases, e.g., markers of cancer or infection, any level of the marker can indicate the presence of a biological state, and enhancing sensitivity of detection is an advantage for early diagnosis. In some cases, the rate of change, or lack of change, in the concentration of a marker over multiple time points provides the most useful information, but present methods of analysis do not permit time point sampling in the early stages of a condition when it is typically most treatable. In some cases, the marker can be detected at clinically useful levels only through the use of cumbersome methods that are not practical or useful in a clinical setting, such as methods that require complex sample treatment and time-consuming analysis. In addition, there are potential markers of biological states with sufficiently low concentration that their presence remains extremely difficult or impossible to detect by current methods.

The analytical methods and compositions of the present invention provide levels of sensitivity, precision, and robustness that allow the detection of markers for biological states at concentrations at which the markers have been previously undetectable, thus allowing the "repurposing" of such markers from confirmatory markers, or markers useful only in limited research settings, to diagnostic, prognostic, treatment-directing, or other types of markers useful in clinical settings and/or in large scale clinical settings, including clinical trials. Such methods allow the determination of normal and abnormal ranges for such markers.

The markers thus repurposed can be used for, e.g., detection of normal state (normal ranges), detection of responder/non-responder (e.g., to a treatment, such as administration of a drug); detection of early disease or pathological occurrence (e.g., early detection of cancer, early detection of cardiac ischemia); disease staging (e.g., cancer); disease monitoring (e.g., diabetes monitoring, monitoring for cancer recurrence after treatment); study of disease mechanism; and study of treatment toxicity, such as toxicity of drug treatments.

The invention thus provides methods and compositions for the sensitive detection of markers, and further methods of establishing values for normal and abnormal levels of markers. In further embodiments, the invention provides methods of diagnosis, prognosis, and/or treatment selection based on values established for the markers. The invention also provides compositions for use in such methods, e.g., detection reagents for the ultrasensitive detection of markers.

II. Molecules for Sensitive Detection by the Methods and Compositions of the Invention The instruments, kits and methods of the invention can be used for the sensitive detection and determination of concentration of a number of different types of single molecules. In particular, the instruments, kits, and methods are useful in the sensitive detection and determination of concentration of markers of biological states. "Detection of a single molecule," as that term is used herein, refers to both direct and indirect detection. For example, a single molecule may be labeled with a fluorescent label, and the molecule-label complex detected in the instruments described herein. Alternatively, a single molecule may be labeled with a fluorescent label, then the fluorescent label is detached from the single molecule, and the label detected in the instruments described herein. The term detection of a single molecule encompasses both forms of detection.

A. General

Examples of molecules which can be detected using the analyzer and related methods of the present invention include: biopolymers such as proteins, nucleic acids, carbohydrates, and small molecules, both organic and inorganic. In particular, the instruments, kits, and methods described herein are useful in the detection of single molecules of proteins and small molecules in biological samples, and the determination of concentration of such molecules in the sample.

The terms "protein," "polypeptide," "peptide," and "oligopeptide," are used interchangeably herein and include any composition that includes two or more amino acids joined together by a peptide bond. It may be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which may be present in polypeptides of the present invention, include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The molecules detected by the present instruments, kits, and methods may be free or may be part of a complex, e.g., an antibody-antigen complex, or more generally a protein-protein complex, e.g., complexes of troponin or prostate specific antigen (PSA). One of skill in the art will appreciate that when referring to proteins, the present invention can detect fragments, polypeptides, mutants, variants or complexes thereof.

B. Markers of Biological States

In some embodiments, the invention provides compositions and methods for the sensitive detection of biological markers, and for the use of such markers in diagnosis, prognosis, and/or determination of methods of treatment.

Markers of the present invention may be, for example, any composition and/or molecule or a complex of compositions and/or molecules that is associated with a biological state of an organism (e.g., a condition such as a disease or a non-disease state). A marker can be, for example, a small molecule, a polypeptide, a nucleic acid, such as DNA and RNA, a lipid, such as a phospholipid or a micelle, a cellular component such as a mitochondrion or chloroplast, etc. Markers contemplated by the present invention can be previously known or unknown. For example, in some embodiments, the methods herein may identify novel polypeptides that can be used as markers for a biological state of interest or condition of interest, while in other embodiments, known polypeptides are identified as markers for a biological state of interest or condition. Using the systems of the invention it is possible that one can observe those markers, e.g., polypeptides with high potential use in determining the biological state of an organism, but that are only present at low concentrations, such as those "leaked" from diseased tissue. Other high potentially useful markers or polypeptides may be those that are related to the disease, for instance, those that are generated in the tumor-host environment. Any suitable marker that provides information regarding a biological state may be used in the methods and compositions of the invention. A "marker," as that term is used herein, includes any molecule that may be detected in a sample from an organism and whose detection or quantitation provides information about the biological state of the organism.

Biological states include but are not limited to phenotypic states; conditions affecting an organism; states of development; age; health; pathology; disease detection, process, or staging; infection; toxicity; or response to chemical, environmental, or drug factors (such as drug response phenotyping, drug toxicity phenotyping, or drug effectiveness phenotyping).

The term "organism" as used herein refers to any living being comprised of a least one cell. An organism can be as simple as a one cell organism or as complex as a mammal. An organism of the present invention is preferably a mammal. Such mammal can be, for example, a human or an animal such as a primate (e.g., a monkey, chimpanzee, etc.), a domesticated animal (e.g., a dog, cat, horse, etc.), farm animal (e.g., goat, sheep, pig, cattle, etc.), or laboratory animal (e.g., mouse, rat, etc.). Preferably, an organism is a human.

In some embodiments, the methods and compositions of the invention are directed to classes of markers, e.g., cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

Table 1 provides examples of these classes of markers that have been measured by the methods and compositions of the invention, and provides exemplary concentrations of the markers detected by the methods and compositions of the invention and number of particles that are counted by the single particle analyzer system of the invention for the particular marker.

TABLE 1

CLASSES OF MARKERS AND EXEMPLARY MARKERS IN THE CLASSES

| | Molar Conc. | Molecules |
|---|---|---|
| Cytokines | | |
| IL-12 p70 | $2.02 \times 10^{-14}$ | $6.09 \times 10^{+5}$ |
| IL-10 | $5.36 \times 10^{-14}$ | $1.61 \times 10^{+6}$ |
| IL-1 alpha | $5.56 \times 10^{-14}$ | $1.67 \times 10^{+6}$ |
| IL-3 | $5.85 \times 10^{-14}$ | $1.76 \times 10^{+6}$ |
| IL-12 p40 | $6.07 \times 10^{-14}$ | $1.83 \times 10^{+6}$ |
| IL-1ra | $6.12 \times 10^{-14}$ | $1.84 \times 10^{+6}$ |
| IL-12 | $8.08 \times 10^{-14}$ | $2.44 \times 10^{+6}$ |
| IL-6 | $9.53 \times 10^{-14}$ | $2.87 \times 10^{+6}$ |
| IL-4 | $1.15 \times 10^{-13}$ | $3.47 \times 10^{+6}$ |
| IL-18 | $1.80 \times 10^{-13}$ | $5.43 \times 10^{+6}$ |
| IP-10 | $1.88 \times 10^{-13}$ | $1.13 \times 10^{+7}$ |
| IL-5 | $1.99 \times 10^{-13}$ | $5.98 \times 10^{+6}$ |
| Eotaxin | $2.06 \times 10^{-13}$ | $1.24 \times 10^{+7}$ |
| IL-16 | $3.77 \times 10^{-13}$ | $1.14 \times 10^{+7}$ |
| MIG | $3.83 \times 10^{-13}$ | $1.15 \times 10^{+7}$ |
| IL-8 | $4.56 \times 10^{-13}$ | $1.37 \times 10^{+7}$ |
| IL-17 | $5.18 \times 10^{-13}$ | $1.56 \times 10^{+7}$ |
| IL-7 | $5.97 \times 10^{-13}$ | $1.80 \times 10^{+7}$ |
| IL-15 | $6.13 \times 10^{-13}$ | $1.84 \times 10^{+7}$ |
| IL-13 | $8.46 \times 10^{-13}$ | $2.55 \times 10^{+7}$ |
| IL-2R (soluble) | $8.89 \times 10^{-13}$ | $2.68 \times 10^{+7}$ |
| IL-2 | $8.94 \times 10^{-13}$ | $2.69 \times 10^{+7}$ |
| LIF/HILDA | $9.09 \times 10^{-13}$ | $5.47 \times 10^{+7}$ |
| IL-1 beta | $1.17 \times 10^{-12}$ | $3.51 \times 10^{+7}$ |
| Fas/CD95/Apo-1 | $1.53 \times 10^{-12}$ | $9.24 \times 10^{+7}$ |
| MCP-1 | $2.30 \times 10^{-12}$ | $6.92 \times 10^{+7}$ |
| Oncology | | |
| EGF | $4.75 \times 10^{-14}$ | $2.86 \times 10^{+6}$ |
| TNF-alpha | $6.64 \times 10^{-14}$ | $8.00 \times 10^{+6}$ |
| PSA (3rd generation) | $1.15 \times 10^{-13}$ | $6.92 \times 10^{+6}$ |
| VEGF | $2.31 \times 10^{-13}$ | $6.97 \times 10^{+6}$ |
| TGF-beta1 | $2.42 \times 10^{-13}$ | $3.65 \times 10^{+7}$ |
| FGFb | $2.81 \times 10^{-13}$ | $1.69 \times 10^{+7}$ |
| TRAIL | $5.93 \times 10^{-13}$ | $3.57 \times 10^{+7}$ |
| TNF-RI (p55) | $2.17 \times 10^{-12}$ | $2.62 \times 10^{+8}$ |

TABLE 1-continued

CLASSES OF MARKERS AND EXEMPLARY MARKERS IN THE CLASSES

| | Molar Conc. | Molecules |
|---|---|---|
| Inflammation | | |
| ICAM-1 (soluble) | $8.67 \times 10^{-15}$ | $5.22 \times 10^{+4}$ |
| RANTES | $6.16 \times 10^{-14}$ | $3.71 \times 10^{+6}$ |
| MIP-2 | $9.92 \times 10^{-14}$ | $2.99 \times 10^{+6}$ |
| MIP-1 beta | $1.98 \times 10^{-13}$ | $5.97 \times 10^{+6}$ |
| MIP-1 alpha | $2.01 \times 10^{-13}$ | $6.05 \times 10^{+6}$ |
| MMP-3 | $1.75 \times 10^{-12}$ | $5.28 \times 10^{+7}$ |
| Endocrinology | | |
| 17 beta-Estradiol (E2) | $4.69 \times 10^{-14}$ | $2.82 \times 10^{+6}$ |
| DHEA | $4.44 \times 10^{-13}$ | $2.67 \times 10^{+7}$ |
| ACTH | $1.32 \times 10^{-12}$ | $7.96 \times 10^{+7}$ |
| Gastrin | $2.19 \times 10^{-12}$ | $1.32 \times 10^{+8}$ |
| Growth Hormone (hGH) | $2.74 \times 10^{-12}$ | $1.65 \times 10^{+8}$ |
| Autoimmune | | |
| GM-CSF | $1.35 \times 10^{-13}$ | $8.15 \times 10^{+6}$ |
| C-Reactive Protein (CRP) | $3.98 \times 10^{-13}$ | $2.40 \times 10^{+7}$ |
| G-CSF | $1.76 \times 10^{-12}$ | $1.06 \times 10^{+8}$ |
| Thyroid | | |
| Cyclic AMP | $9.02 \times 10^{-15}$ | $5.43 \times 10^{+5}$ |
| Calcitonin | $3.25 \times 10^{-14}$ | $1.95 \times 10^{+6}$ |
| Parathyroid Hormone (PTH) | $1.56 \times 10^{-13}$ | $9.37 \times 10^{+6}$ |
| Cardiovascular | | |
| B-Natriuretic Peptide | $2.86 \times 10^{-13}$ | $1.72 \times 10^{+7}$ |
| NT-proBNP | $2.86 \times 10^{-12}$ | $8.60 \times 10^{+7}$ |
| C-Reactive Protein, HS | $3.98 \times 10^{-13}$ | $2.40 \times 10^{+7}$ |
| Beta-Thromboglobulin (BTG) | $5.59 \times 10^{-13}$ | $3.36 \times 10^{+7}$ |
| Diabetes | | |
| C-Peptide | $2.41 \times 10^{-15}$ | $1.45 \times 10^{+5}$ |
| Leptin | $1.89 \times 10^{-13}$ | $1.14 \times 10^{+7}$ |
| Infectious Dis. | | |
| IFN-gamma | $2.08 \times 10^{-13}$ | $1.25 \times 10^{+7}$ |
| IFN-alpha | $4.55 \times 10^{-13}$ | $2.74 \times 10^{+7}$ |
| Metabolism | | |
| Bio-Intact PTH (1-84) | $1.59 \times 10^{-12}$ | $1.44 \times 10^{+8}$ |
| PTH | $1.05 \times 10^{-13}$ | $9.51 \times 10^{+6}$ |

1. Cytokines

For both research and diagnostics, cytokines are useful as markers of a number of conditions, diseases, pathologies, and the like, and the compositions and methods of the invention include labels for detection and quantitation of cytokines and methods using such labels to determine normal and abnormal levels of cytokines, as well as methods of diagnosis, prognosis, and/or determination of treatment based on such levels.

There are currently over 100 cytokines/chemokines whose coordinate or discordant regulation is of clinical interest. In order to correlate a specific disease process with changes in cytokine levels, the ideal approach requires analyzing a sample for a given cytokine, or multiple cytokines, with high sensitivity. Exemplary cytokines that are presently used in marker panels and that may be used in methods and compositions of the invention include, but are not limited to, BDNF, CREB pS133, CREB Total, DR-5, EGF, ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene-keratinocytes (GRO-KC), HGF, ICAM-1, IFN-alpha, IFN-gamma, the interleukins IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotacin, M-CSF, monocyte chemoattractant protein-1 (MCP-1), MCP-1(MCAF), MCP-3, MCP-5, MDC, MIG, macrophage inflammatory (MIP-1 alpha), MIP-1 beta, MIP-1 gamma, MIP-2, MIP-3 beta, OSM, PDGF-BB, regulated upon activation, normal T cell expressed and secreted (RANTES), Rb (pT821), Rb (total), Rb pSpT249/252, Tau (pS214), Tau (pS396), Tau (total), Tissue Factor, tumor necrosis factor-alpha (TNF-alpha), TNF-beta, TNF-RI, TNF-RII, VCAM-1, and VEGF. In some embodiments, the cytokine is IL-12p70, IL-10, IL-1 alpha, IL-3, IL-12 p40, IL-1ra, IL-12, IL-6, IL-4, IL-18, IL-10, IL-5, eotaxin, IL-16, MIG, IL-8, IL-17, IL-7, IL-15, IL-13, IL-2R (soluble), IL-2, LIF/HILDA, IL-1 beta, Fas/CD95/Apo-1, or MCP-1.

2. Growth Factors

Growth factors include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF LigandsFGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas1, GSK-3 beta, GLI-1, Hip, GLI-2; the IGF Family IGF Ligands IGF-I, IGF-II, IGF-I Receptor (CD221) IGF-I R, and IGF Binding Protein (IGFBP) Family ALS, IGFBP-5, CTGF/CCN2, IGFBP-6, Cyr61/CCN1, IGFBP-L1, Endocan, IGFBP-rp1/IGFBP-7, IGFBP-1, IGFBP-rP10, IGFBP-2, NOV/CCN3, IGFBP-3, WISP-1/CCN4, IGFBP-4; Receptor Tyrosine Kinases Ax1, FGF R4, C1q R1/CD93, FGF R5, DDRI, Flt-3, DDR2, HGF R, Dtk, IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphB1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan Regulators, Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/IDS, GalNAc4S-65T; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, PlGF, Neuropilin-2, PlGF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt Inhibitors Dkk-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP; Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, WISP-1/CCN4.

3. Markers of Inflammation

Markers of inflammation include ICAM-1, RANTES, MIP-2, MIP-1-beta, MIP-1-alpha, and MMP-3. Further markers of inflammation include Adhesion molecules such as the integrins $\alpha1\beta1$, $\alpha2\beta1$, $\alpha3\beta1$, $\alpha4\beta1$, $\alpha5\beta1$, $\alpha6\beta1$, $\alpha7\beta1$, $\alpha8\beta1$, $\alpha9\beta1$, $\alpha V\beta1$, $\alpha4\beta7$, $\alpha6\beta4$, $\alpha D\beta2$, $\alpha L\beta2$, $\alpha M\beta2$, $\alpha V\beta3$, $\alpha V\beta5$, $\alpha V\beta6$, $\alpha V\beta8$, $\alpha X\beta2$, $\alpha IIb\beta3$, $\alpha IELb\beta7$, beta-2 integrin, beta-3 integrin, beta-2 integrin, beta-4 integrin, beta-5 integrin, beta-6 integrin, beta-7 integrin, beta-8 integrin, alpha-1 integrin, alpha-2 integrin, alpha-3 integrin, alpha-4 integrin, alpha-5 integrin, alpha-6 integrin, alpha-7 integrin, alpha-8 integrin, alpha-9 integrin, alpha-D integrin, alpha-L integrin, alpha-M integrin, alpha-V integrin, alpha-X integrin, alpha-IIb integrin, alphaIELb integrin; Integrin-associated Molecules such as Beta IG-H3, Melusin, CD47, MEPE, CD151, Osteopontin, IBSP/Sialoprotein II, RAGE, IGSF8; Selectins such as E-Selectin, P-Selectin, L-Selectin; Ligands such as CD34, GlyCAM-1, MadCAM-1, PSGL-1, vitronectic, vitronectin receptor, fibronectin, vitronectin, collagen, laminin, ICAM-1, ICAM-3, BL-CAM, LFA-2, VCAM-1, NCAM, PECAM. Further markers of inflammation include Cytokines such as IFN-$\alpha$, IFN-$\beta$, IFN-$\epsilon$, -$\kappa$, -$\tau$, and -$\zeta$, IFN-$\omega$, IFN-$\gamma$, IL29, IL28A and IL28B, IL-1, IL-1$\alpha$ and $\beta$, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, TCCR/WSX-1. Further markers of inflammation include cytokine receptors such as Common beta chain, IL-3 R alpha, IL-3 R beta, GM-CSF R, IL-5 R alpha, Common gamma Chain/IL-2 R gamma, IL-2 R alpha, IL-9 R, IL-2 R beta, IL-4 R, IL-21 R, IL-15 R alpha, IL-7 R alpha/CD127, IL-1ra/IL-1F3, IL-1 R8, IL-1 RI, IL-1 R9, IL-1 RII, IL-18 R alpha/IL-1 R5, IL-1 R3/IL-1 R AcP, IL-18 R beta/IL-1 R7, IL-1 R4/ST2 SIGIRR, IL-1 R6/IL-1 R rp2, IL-11 R alpha, IL-31 RA, CNTF R alpha, Leptin R, G-CSF R, LIF R alpha, IL-6 R, OSM R beta, IFN-alpha/beta R1, IFN-alpha/beta R2, IFN-gamma R1, IFN-gamma R2, IL-10 R alpha, IL-10 R beta, IL-20 R alpha, IL-20 R beta, IL-22 R, IL-17 R, IL-17 RD, IL-17 RC, IL-17B R, IL-13 R alpha 2, IL-23 R, IL-12 R beta 1, IL-12 R beta 2, TCCR/WSX-1, IL-13 R alpha 1. Further markers of inflammation include Chemokines such as CCL-1, CCL-2, CCL-3, CCL-4, CCL-5, CCL-6, CCL-7, CCL-8, CCL-9, CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27, CCL-28, MCK-2, MIP-2, CINC-1, CINC-2, KC, CINC-3, LIX, GRO, Thymus Chemokine-1, CXCL-1, CXCL-2, CXCL-3, CXCL-4, CXCL-5, CXCL-6, CXCL-7, CXCL-8, CXCL-9, CXCL-10, CXCL-11, CXCL-12, CXCL-13, CXCL-14, CXCL-15, CXCL -16, CXCL-17, XCL1, XCL2, Chemerin. Further markers of inflammation include chemokine receptors such as CCR-1, CCR-2, CCR-3, CCR-4, CCR-5, CCR-6, CCR-7, CCR-8, CCR-9, CCR-10, CXCR3, CXCR6, CXCR4, CXCR1, CXCR5, CXCR2, Chem R23. Further markers of inflammation include Tumor necrosis factors (TNFs), such as TNF-alpha, 4-1BB Ligand/TNFSF9, LIGHT/TNFSF14, APRIL/TNFSF13, Lymphotoxin, BAFF/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA, TNF-beta/TNFSF1B, EDA-A2, TRAIL/TNFSF10, Fas Ligand/TNFSF6, TRANCE/TNFSF11, GITR Ligand/TNFSF18, TWEAK/TNFSF12. Further markers of inflammation include TNF Superfamily Receptors such as 4-1BB/TNFRSF9, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNF R1/TNFRSF1A, DcTRAIL R1/TNFRSF23, TNF R11/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF10D, Fas/TNFRSF6, TROY/TNFRSF19, GITR/TNFRSF18, TWEAK R/TNFRSF12, HVEM/TNFRSF14, XEDAR. Further markers of inflammation include TNF Superfamily Regulators such as FADD, TRAF-2, RIP1, TRAF-3, TRADD, TRAF-4, TRAF-1, TRAF-6. Further markers of inflammation include Acute-phase reactants and acute phase proteins. Further markers of inflammation include TGF-beta superfamily ligands such as Activins, Activin A, Activin B, Activin AB, Activin C, BMPs (Bone Morphogenetic Proteins), BMP-2, BMP-7, BMP-3, BMP-8, BMP-3b/GDF-10, BMP-9, BMP-4, BMP-10, BMP-5, BMP-15/GDF-9B, BMP-6, Decapentaplegic, Growth/Differentiation Factors (GDFs), GDF-1, GDF-8, GDF-3, GDF-9 GDF-5, GDF-11, GDF-6, GDF-15, GDF-7, GDNF Family Ligands, Artemin, Neurturin, GDNF, Persephin, TGF-beta, TGF-beta, TGF-beta 3, TGF-beta 1, TGF-beta 5, LAP (TGF-beta 1), Latent TGF-beta bp1, Latent TGF-beta 1, Latent TGF-beta bp2, TGF-beta 1.2, Latent TGF-beta bp4, TGF-beta 2, Lefty, MIS/AMH, Lefty-1, Nodal, Lefty-A, Activin RIA/ALK-2, GFR alpha-1/GDNF R alpha-1, Activin RIB/ALK-4, GFR alpha-2/GDNF R alpha-2, Activin RIIA, GFR alpha-3/GDNF R alpha-3, Activin RIIB, GFR alpha-4/GDNF R alpha-4, ALK-1, MIS R11, ALK-7, Ret, BMPR-IA/ALK-3, TGF-beta RI/ALK-5, BMPR-IB/ALK-6, TGF-beta RII, BMPR-II, TGF-beta RIIb, Endoglin/CD105, TGF-beta RIII. Further markers of inflammation include TGF-beta superfamily Modulators such as Amnionless, NCAM -1/CD56, BAMBI/NMA, Noggin, BMP-1/PCP, NOMO, Caronte, PRDC, Cerberus 1, SKI, Chordin, Smad1, Chordin-Like 1, Smad2, Chordin-Like 2, Smad3, COCO, Smad4, CRIM1, Smad5, Cripto, Smad7, Crossveinless-2, Smad8, Cryptic, SOST, DAN, Latent TGF-beta bp1, Decorin, Latent TGF-beta bp2, FLRG, Latent TGF-beta bp4, Follistatin, TMEFF1/Tomoregulin-1, Follistatin-like 1, TMEFF2, GASP-1/WFIKKNRP, TSG, GASP-2/WFIKKN, TSK, Gremlin, Vasorin. Further markers of inflammation include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1. Further markers of inflammation include EGF R/ErbB Receptor Family, such as EGF R, ErbB3, ErbB2, ErbB4. Further markers of inflammation include Fibrinogen. Further markers of inflammation include SAA. Further markers of inflammation include glial markers, such as alpha.1-antitrypsin, C-reactive protein (CRP), alpha.2-macroglobulin, glial fibrillary acidic protein (GFAP), Mac-1, F4/80. Further markers of inflammation include myeloperoxidase. Further markers of inflammation include Complement markers such as C3d, C1q, C5, C4d, C4 bp, and C5a-C9. Further markers of inflammation include Major histocompatibility complex (MHC) glycoproteins, such as HLA-DR and HLA-A,D,C. Further markers of inflammation include Microglial markers, such as CR3 receptor, MHC I, MHC II, CD 31, CD11a, CD11b, CD11c, CD68, CD45RO, CD45RD, CD18, CD59, CR4, CD45, CD64, and CD44. Further markers of inflammation include alpha.2 macroglobulin receptor, Fibroblast growth factor, Fc gamma RI, Fc gamma RII, CD8, LCA (CD45), CD18, CD59, Apo J, clusterin, type 2 plasminogen activator inhibitor, CD44, Macrophage colony stimulating factor receptor, MRP14, 27E10, 4-hydroxynonenal-protein conjugates, I.kappa.B, NF.kappa.B, cPLA.sub.2, COX-2, Matrix metalloproteinases, Membrane lipid peroxidation, and ATPase activity. HSPC228, EMP1, CDC42, TLE3, SPRY2, p40BBP, HSPC060 or NAB2, or a down-regulation of HSPA1A, HSPA1B, MAPRE2 and OAS1 expression, TACE/ADAM17, alpha-1-Acid Glycoprotein, Angiopoietin-1, MIF, Angiopoietin-2, CD14, beta-Defensin 2, MMP-2, ECF-L/CHI3L3, MMP-7, EGF, MMP-9, EMAP-II, MSP, EN-RAGE, Nitric Oxide, Endothelin-1, Osteoactivin/GPNMB, FPR1, PDGF, FPRL1, Pentraxin 3/TSG-14, FPRL2, Gas6, PLUNC, GM-CSF, RAGE, S100A10, S100A8, S100A9, HIF-1 alpha, Substance P, TFPI, TGF-beta 1, TIMP-1, TIMP-2, TIMP-3, TIMP-4, TLR4, LBP, TREM-1, Leukotriene A4, Hydrolase TSG-6, Lipocalin-1, uPA, M-CSF, and VEGF.

4. Miscellaneous Markers

Oncology markers include EGF, TNF-alpha, PSA, VEGF, TGF-beta1, FGFb, TRAIL, and TNF-R1 (p55).

Markers of endocrine function include 17 beta-estradiol (E2), DHEA, ACTH, gastrin, and growth hormone (hGH).

Markers of autoimmunity include GM-CSF, C-Reactive Protein, and G-CSF.

Markers of thyroid function include cyclicAMP, calcitonin, and parathyroid hormone.

Cardiovascular markers include cardiac troponin I, cardiac troponin T, B-natriuretic peptide, NT-proBNP, C-Reactive Protein HS, and beta-thromboglobulin.

Markers of diabetes include C-peptide and leptin.

Markers of infectious disease include IFN-gamma and IFN-alpha.

Markers of metabolism include Bio-intact PTH (1-84) and PTH.

5. Markers of Biological States

Markers may indicate the presence of a particular phenotypic state of interest. Examples of phenotypic states include, phenotypes resulting from an altered environment, drug treatment, qgenetic manipulations or mutations, injury, change in diet, aging, or any other characteristic(s) of a single organism or a class or subclass of organisms.

In some embodiments, a phenotypic state of interest is a clinically diagnosed disease state. Such disease states include, for example, cancer, cardiovascular disease, inflammatory disease, autoimmune disease, neurological disease, infectious disease and pregnancy related disorders. Alternatively, states of health can be detected using markers.

Cancer phenotypes are included in some aspects of the invention. Examples of cancer include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The present invention provides methods to detect cancers. In some embodiments, the cancer comprises Acute Lymphoblastic Leukemia. In other embodiments, the cancer comprises Acute Myeloid Leukemia. In other embodiments, the cancer comprises Adrenocortical Carcinoma. In other embodiments, the cancer comprises an AIDS-Related Cancer. In other embodiments, the cancer comprises AIDS-Related Lymphoma. In other embodiments, the cancer comprises Anal Cancer. In other embodiments, the cancer comprises Appendix Cancer. In other embodiments, the cancer comprises Childhood Cerebellar Astrocytoma. In other embodiments, the cancer comprises Childhood Cerebral Astrocytoma. In other embodiments, the cancer comprises a Central Nervous System Atypical Teratoid/Rhabdoid Tumor. In other embodiments, the cancer comprises Basal Cell Carcinoma, or other Skin Cancer (Nonmelanoma). In other embodiments, the cancer comprises Extrahepatic Bile Duct Cancer. In other embodiments, the cancer comprises Bladder Cancer. In other embodiments, the cancer comprises Bone Cancer, such as Osteosarcoma or Malignant Fibrous Histiocytoma. In other embodiments, the cancer comprises Brain Stem Glioma. In other embodiments, the cancer comprises an Adult Brain Tumor. In other embodiments, the cancer comprises Brain Tumor comprising Central Nervous System Atypical Teratoid/Rhabdoid Tumor. In other embodiments, the cancer comprises a Brain Tumor comprising Cerebral Astrocytoma/Malignant Glioma. In other embodiments, the cancer comprises a Craniopharyngioma Brain Tumor. In other embodiments, the cancer comprises a Ependymoblastoma Brain Tumor. In other embodiments, the cancer comprises a Ependymoma Brain Tumor. In other embodiments, the cancer comprises a Medulloblastoma Brain Tumor. In other embodiments, the cancer comprises a Medulloepithelioma Brain Tumor. In other embodiments, the cancer comprises Brain Tumors including Pineal Parenchymal Tumors of Intermediate Differentiation. In other embodiments, the cancer comprises Brain Tumors including Supratentorial Primitive Neuroectodermal Tumors and Pineoblastoma. In other embodiments, the cancer comprises a Brain Tumor including Visual Pathway and Hypothalamic Glioma. In other embodiments, the cancer comprises Brain and Spinal Cord Tumors. In other embodiments, the cancer comprises Breast Cancer. In other embodiments, the cancer comprises Bronchial Tumors. In other embodiments, the cancer comprises Burkitt Lymphoma. In other embodiments, the cancer comprises Carcinoid Tumor. In other embodiments, the cancer comprises Gastrointestinal Carcinoid Tumor. In other embodiments, the cancer comprises Carcinoma of Unknown Primary Origin. In other embodiments, the cancer comprises Central Nervous System Atypical Teratoid/Rhabdoid Tumor. In other embodiments, the cancer comprises Central Nervous System Embryonal Tumors. In other embodiments, the cancer comprises Primary Central Nervous System Lymphoma. In other embodiments, the cancer comprises Cerebellar Astrocytoma. In other embodiments, the cancer comprises Cerebral Astrocytoma/Malignant Glioma. In other embodiments, the cancer comprises Cervical Cancer. In other embodiments, the cancer comprises Childhood Cancers. In other embodiments, the cancer comprises Chordoma. In other embodiments, the cancer comprises Chronic Lymphocytic Leukemia. In other embodiments, the cancer comprises Chronic Myelogenous Leukemia. In other embodiments, the cancer comprises Chronic Myeloproliferative Disorders. In other embodiments, the cancer comprises Colon Cancer. In other embodiments, the cancer comprises Colorectal Cancer. In other embodiments, the cancer comprises Craniopharyngioma. In other embodiments, the cancer comprises Cutaneous T-Cell Lymphoma, including Mycosis Fungoides and Sezary Syndrome. In other embodiments, the cancer comprises Central Nervous System Embryonal Tumors. In other embodiments, the cancer comprises Endometrial Cancer. In other embodiments, the cancer comprises Ependymoblastoma. In other embodiments, the cancer comprises Ependymoma. In other embodiments, the cancer comprises Esophageal Cancer. In other embodiments, the cancer comprises the Ewing Family of Tumors. In other embodiments, the cancer comprises Extracranial Germ Cell Tumor. In other embodiments, the cancer comprises Extragonadal Germ Cell Tumor. In other embodiments, the cancer comprises Extrahepatic Bile Duct Cancer. In other embodiments, the cancer comprises Intraocular Melanoma Eye Cancer. In other embodiments, the cancer comprises Retinoblastoma Eye Cancer. In other embodiments, the cancer comprises Gallbladder Cancer. In other embodiments, the cancer comprises Gastric (Stomach) Cancer. In other embodiments, the cancer comprises Gastrointestinal Carcinoid Tumor. In other embodiments, the cancer comprises Gastrointestinal Stromal Tumor (GIST). In other embodiments, the cancer comprises Gastrointestinal Stromal Cell Tumor. In other embodiments, the cancer comprises Extracranial Germ Cell Tumor. In other embodiments, the cancer comprises Extragonadal Germ Cell Tumor. In other embodiments, the cancer comprises Ovarian Germ Cell Tumor. In other embodiments, the cancer comprises Gestational Trophoblastic Tumor. In other embodiments, the cancer comprises Glioma. In other embodiments, the cancer comprises Brain Stem Glioma. In other embodiments, the cancer comprises Cerebral Astrocytoma Glioma. In other embodiments, the cancer comprises Visual Pathway or Hypothalamic Glioma. In other embodiments, the cancer comprises Hairy Cell Leukemia. In other embodiments, the cancer comprises Head and Neck Cancer. In other embodiments, the cancer comprises Hepatocellular (Liver) Cancer. In other embodiments, the cancer comprises Hodgkin Lymphoma. In other embodiments, the cancer comprises Hypopharyngeal Cancer. In other embodiments, the cancer comprises Intraocular Melanoma. In other embodiments, the cancer comprises Islet Cell Tumors (Endocrine Pancreas). In other embodiments, the cancer comprises Kaposi Sarcoma. In other embodiments, the cancer comprises Kidney (Renal Cell) Cancer. In other embodiments, the cancer comprises Laryngeal Cancer. In other embodiments, the cancer comprises Acute Lymphoblastic Leukemia. In other embodiments, the cancer comprises Acute Myeloid Leukemia. In other embodiments, the cancer comprises Chronic Lymphocytic Leukemia. In other embodiments, the cancer comprises Chronic Myelogenous Leukemia. In other embodiments, the cancer comprises Hairy Cell Leukemia. In other embodiments, the cancer comprises Lip Cancer. In other embodiments, the cancer comprises Oral Cavity Cancer. In other embodiments, the cancer comprises Primary Liver Cancer. In other embodiments, the cancer comprises Non-Small Cell Lung Cancer. In other embodiments, the cancer comprises Small Cell Lung Cancer. In other embodiments, the cancer comprises AIDS-Related Lymphoma. In other embodiments, the cancer comprises Burkitt Lymphoma. In other embodiments, the cancer comprises Cutaneous T-Cell Lymphoma. In other embodiments, the cancer comprises Mycosis Fungoides and Sézary Syndrome. In other embodiments, the cancer comprises Hodgkin Lymphoma. In other embodiments, the cancer comprises Non-Hodgkin Lymphoma. In other embodiments, the cancer comprises Primary Central Nervous System Lymphoma. In other embodiments, the cancer comprises Waldenström Macroglobulinemia. In other embodiments, the cancer comprises Malignant Fibrous Histiocytoma of Bone or Osteosarcoma. In other embodiments, the cancer comprises Medulloepithelioma. In other embodiments, the cancer comprises Melanoma. In other embodiments, the cancer comprises Intraocular (Eye) Melanoma. In other embodiments, the cancer comprises Merkel Cell Carcinoma. In other embodiments, the cancer comprises Mesothelioma. In other embodiments, the cancer comprises Metastatic Squamous Neck Cancer with Occult Primary. In other embodiments, the cancer comprises Mouth Cancer. In other embodiments, the cancer comprises Multiple Endocrine Neoplasia Syndrome. In other embodiments, the cancer comprises Multiple Myeloma/Plasma Cell Neoplasm. In other embodiments, the cancer comprises Mycosis Fungoides. In other embodiments, the cancer comprises Myelodysplastic Syndromes. In other embodiments, the cancer comprises Myelodysplastic or Myeloproliferative Diseases. In other embodiments, the cancer comprises Chronic Myelogenous Leukemia. In other embodiments, the cancer comprises Acute Myeloid Leukemia. In other embodiments, the cancer comprises Multiple Myeloma. In other embodiments, the cancer comprises Chronic Myeloproliferative Disorders. In other embodiments, the cancer comprises Nasal Cavity or Paranasal Sinus Cancer. In other embodiments, the cancer comprises Nasopharyngeal Cancer. In other embodiments, the cancer comprises Nasopharyngeal Cancer. In other embodiments, the cancer comprises Neuroblastoma. In other embodiments, the cancer comprises Non-Hodgkin Lymphoma. In other embodiments, the cancer comprises Non-Small Cell Lung Cancer. In other embodiments, the cancer comprises Oral Cancer. In other embodiments, the cancer comprises Oral Cavity Cancer. In other embodiments, the cancer comprises Oropharyngeal Cancer. In other embodiments, the cancer comprises Osteosarcoma. In other embodiments, the cancer comprises Malignant Fibrous Histiocytoma of Bone. In other embodiments, the cancer comprises Ovarian Cancer. In other embodiments, the cancer comprises Ovarian Epithelial Cancer. In other embodiments, the cancer comprises Ovarian Germ Cell Tumor. In other embodiments, the cancer comprises Ovarian Low Malignant Potential Tumor. In other embodiments, the cancer comprises Pancreatic Cancer. In other embodiments, the cancer comprises Islet Cell Tumor Pancreatic Cancer. In other embodiments, the cancer comprises Papillomatosis. In other embodiments, the cancer comprises Paranasal Sinus Cancer. In other embodiments, the cancer comprises Nasal Cavity Cancer. In other embodiments, the cancer comprises Parathyroid Cancer. In other embodiments, the cancer comprises Penile Cancer. In other embodiments, the cancer comprises Pharyngeal Cancer. In other embodiments, the cancer comprises Pheochromocytoma. In other embodiments, the cancer comprises Pineal Parenchymal Tumors of Intermediate Differentiation. In other embodiments, the cancer comprises Pineoblastoma or Supratentorial Primitive Neuroectodermal Tumors. In other embodiments, the cancer comprises Pituitary Tumor. In other embodiments, the cancer comprises Plasma Cell Neoplasm/Multiple Myeloma. In other embodiments, the cancer comprises Pleuropulmonary Blastoma. In other embodiments, the cancer comprises Primary Central Nervous System Lymphoma. In other embodiments, the cancer comprises Prostate Cancer. In other embodiments, the cancer comprises Rectal Cancer. In other embodiments, the cancer comprises Renal Cell (Kidney) Cancer. In other embodiments, the cancer comprises Renal Pelvis and Ureter, Transitional Cell Cancer. In other embodiments, the cancer comprises Respiratory Tract Carcinoma Involving the NUT Gene on Chromosome 15. In other embodiments, the cancer comprises Retinoblastoma. In other embodiments, the cancer comprises Rhabdomyosarcoma. In other embodiments, the cancer comprises Salivary Gland Cancer. In other embodiments, the cancer comprises Sarcoma of the Ewing Family of Tumors. In other embodiments, the cancer comprises Kaposi Sarcoma. In other embodiments, the cancer comprises Soft Tissue Sarcoma. In other embodiments, the cancer comprises Uterine Sarcoma. In other embodiments, the cancer comprises Sezary Syndrome. In other embodiments, the cancer comprises Nonmelanoma Skin Cancer. In other embodiments, the cancer comprises Melanoma Skin Cancer. In other embodiments, the cancer comprises Merkel Cell Skin Carcinoma. In other embodiments, the cancer comprises Small Cell Lung Cancer. In other embodiments, the cancer comprises Small Intestine Cancer. In other embodiments, the cancer comprises Squamous Cell Carcinoma, e.g., Nonmelanoma Skin Cancer. In other embodiments, the cancer comprises Metastatic Squamous Neck Cancer with Occult Primary. In other embodiments, the cancer comprises Stomach (Gastric) Cancer. In other embodiments, the cancer comprises Supratentorial Primitive Neuroectodermal Tumors. In other embodiments, the cancer comprises Cutaneous T-Cell Lymphoma, e.g., Mycosis Fungoides and Sézary Syndrome. In other embodiments, the cancer comprises Testicular Cancer. In other embodiments, the cancer comprises Throat Cancer. In other embodiments, the cancer comprises Thymoma or Thymic Carcinoma. In other embodiments, the cancer comprises Thyroid Cancer. In other embodiments, the cancer comprises Transitional Cell Cancer of the Renal Pelvis and Ureter. In other embodiments, the cancer comprises Gestational Trophoblastic Tumor. In other embodiments, the cancer comprises a Carcinoma of Unknown Primary Site. In other embodiments, the cancer comprises an Unusual Cancer of Childhood. In other embodiments, the cancer comprises Ureter and Renal Pelvis Transitional Cell Cancer. In other embodiments, the cancer comprises Urethral Cancer. In other embodiments, the cancer comprises Endometrial Uterine Cancer. In other embodiments, the cancer comprises Uterine Sarcoma. In other embodiments, the cancer comprises Vaginal Cancer. In other embodiments, the cancer comprises Visual Pathway and Hypothalamic Glioma. In other embodiments, the cancer comprises Vulvar Cancer. In other embodiments, the cancer comprises Waldenström Macroglobulinemia. In other embodiments, the cancer comprises Wilms Tumor. In other embodiments, the cancer comprises Women's Cancers.

Cardiovascular disease may be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial, pulmonary atresia, aortic valve stenosis, Raynaud's disease, cholesterol embolism, Wallenberg syndrome, Hippel-Lindau disease, and telangiectasis.

Inflammatory disease and autoimmune disease may be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemis lupus and erythematosus.

The methods and compositions of the invention can also provide laboratory information about markers of infectious disease including markers of Adenovirus, *Bordella pertussis, Chlamydia pneumoiea, Chlamydia trachomatis*, Cholera Toxin, Cholera Toxin β, *Campylobacter jejuni*, Cytomegalovirus, Diptheria Toxin, Epstein-Barr NA, Epstein-Barr EA, Epstein-Barr VCA, *Helicobacter Pylori*, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3 KD, Hepatitis E virus (HEV) orf2 6 KD, Hepatitis E virus (HEV) orf3 3 KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, *Leishmania donovani*, Lyme disease, Mumps, *M. pneumoniae, M. tuberculosis*, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15 kd, *T. pallidum* p47, *T. cruzi*, Toxoplasma, and Varicella Zoster.

III. Labels

In some embodiments, the invention provides methods and compositions that include labels for the highly sensitive detection and quantitation of molecules, e.g., markers.

One skilled in the art will recognize that many strategies can be used for labeling target molecules to enable their detection or discrimination in a mixture of particles. The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner to the molecule of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a marker, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

The antibody may be specific to any suitable marker. In some embodiments, the antibody is specific to a marker that is selected from the group consisting of cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

In some embodiments, the antibody is specific to a marker that is a cytokine. In some embodiments, the cytokine is selected from the group consisting of BDNF, CREB pS133, CREB Total, DR-5, EGF, ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene-keratinocytes (GRO-KC), HGF, ICAM-1, IFN-alpha, IFN-gamma, interleukins such as IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotacin, M-CSF, monocyte chemoattractant protein-1 (MCP-1), MCP-1(MCAF), MCP-3, MCP-5, MDC, MIG, macrophage inflammatory (MIP-1 alpha), MIP-1 beta, MIP-1 gamma, MIP-2, MIP-3 beta, OSM, PDGF-BB, regulated upon activation, normal T cell. expressed and secreted (RANTES), Rb (pT821), Rb (total), Rb pSpT249/252, Tau (pS214), Tau (pS396), Tau (total), Tissue Factor, tumor necrosis factor-alpha (TNF-alpha), TNF-beta, TNF-RI, TNF-RII, VCAM-1, and VEGF.

In some embodiments, the cytokine is selected from the group consisting of IL-12p70, IL-10, IL-1 alpha, IL-3, IL-12 p40, IL-1ra, IL-12, IL-6, IL-4, IL-18, IL-10, IL-5, Eotaxin, IL-16, MIG, IL-8, IL-17, IL-7, IL-15, IL-13, IL-2R (soluble), IL-2, LIF/HILDA, IL-1 beta, Fas/CD95/Apo-1 and MCP-1.

In some embodiments, the antibody is specific to a marker that is a growth factor. In some embodiments, the antibody is specific to a marker that is a growth factor that is TGF-beta. In some embodiments, the growth factor is GF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF Ligands, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas1, GSK-3 beta, GLI-1, Hip, GLI-2; the IGF Family IGF Ligands IGF-I, IGF-II, IGF-I Receptor (CD221)IGF-I R, and IGF Binding Protein (IGFBP) Family ALS, IGFBP-5, CTGF/CCN2, IGFBP-6, Cyr61/CCN1, IGFBP-L1, Endocan, IGFBP-rp1/IGFBP-7, IGFBP-1, IGFBP-rP10, IGFBP-2, NOV/CCN3, IGFBP-3, WISP-1/CCN4, IGFBP-4; Receptor Tyrosine Kinases Ax1, FGF R4, C1q R1/CD93, FGF R5, DDRI, Flt-3, DDR2, HGF R, Dtk, IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphB 1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan Regulators, Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/IDS, GalNAc4S-6ST; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, PlGF, Neuropilin-2, PlGF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt Inhibitors Dkk-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b ; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, or WISP-1/CCN4.

In some embodiments, the antibody is specific to a marker that is a marker for cancer (oncology marker). In some embodiments, the antibody is specific to a marker that is a marker for cancer that is EGF. In some embodiments, the antibody is specific to a marker that is a marker for cancer that is TNF-alpha. In some embodiments, the antibody is specific to a marker that is a marker for cancer that is PSA. In some embodiments, the antibody is specific to a marker that is a marker for cancer that is VEGF. In some embodiments, the antibody is specific to a marker that is a marker for cancer that is TGF-beta. In some embodiments, the antibody is specific to a marker that is a marker for cancer that is FGFb. In some embodiments, the antibody is specific to a marker that is a marker for cancer that is TRAIL. In some embodiments, the antibody is specific to a marker that is a marker for cancer that is TNF-RI (p55).

In further embodiments, the antibody is specific to a marker for cancer that is alpha-Fetoprotein. In some embodiments, the antibody is specific to a marker for cancer that is ER beta/NR3A2. In some embodiments, the antibody is specific to a marker for cancer that is ErbB2. In some embodiments, the antibody is specific to a marker for cancer that is Kallikrein 3/PSA. In some embodiments, the antibody is specific to a marker for cancer that is ER alpha/NR3A1. In some embodiments, the antibody is specific to a marker for cancer that is Progesterone R/NR3C3. In some embodiments, the antibody is specific to a marker for cancer that is A33. In some embodiments, the antibody is specific to a marker for cancer that is MIA. In some embodiments, the antibody is specific to a marker for cancer that is Aurora A. In some embodiments, the antibody is specific to a marker for cancer that is MMP-2. In some embodiments, the antibody is specific to a marker for cancer that is Bcl-2. In some embodiments, the antibody is specific to a marker for cancer that is MMP-3. In some embodiments, the antibody is specific to a marker for cancer that is Cadherin-13. In some embodiments, the antibody is specific to a marker for cancer that is MMP-9. In some embodiments, the antibody is specific to a marker for cancer that is E-Cadherin. In some embodiments, the antibody is specific to a marker for cancer that is NEK2. In some embodiments, the antibody is specific to a marker for cancer that is Carbonic Anhydrase IX. In some embodiments, the antibody is specific to a marker for cancer that is Nestin. In some embodiments, the antibody is specific to a marker for cancer that is beta-Catenin. In some embodiments, the antibody is specific to a marker for cancer that is NG2/MCSP. In some embodiments, the antibody is specific to a marker for cancer that is Cathepsin D. In some embodiments, the antibody is specific to a marker for cancer that is Osteopontin. In some embodiments, the antibody is specific to a marker for cancer that is CD44. In some embodiments, the antibody is specific to a marker for cancer that is p21/CIP1/CDKN1A. In some embodiments, the antibody is specific to a marker for cancer that is CEACAM-6. In some embodiments, the antibody is specific to a marker for cancer that is p27/Kip 1. In some embodiments, the antibody is specific to a marker for cancer that is Cornulin. In some embodiments, the antibody is specific to a marker for cancer that is p53. In some embodiments, the antibody is specific to a marker for cancer that is DPPA4. In some embodiments, the antibody is specific to a marker for cancer that is Prolactin. In some embodiments, the antibody is specific to a marker for cancer that is ECM-1. In some embodiments, the antibody is specific to a marker for cancer that is PSP94. In some embodiments, the antibody is specific to a marker for cancer that is EGF. In some embodiments, the antibody is specific to a marker for cancer that is S100B. In some embodiments, the antibody is specific to a marker for cancer that is EGF R. In some embodiments, the antibody is specific to a marker for cancer that is S100P. In some embodiments, the antibody is specific to a marker for cancer that is EMMPRIN/CD147. In some embodiments, the antibody is specific to a marker for cancer that is SCF R/c-kit. In some embodiments, the antibody is specific to a marker for cancer that is Fibroblast Activation Protein alpha/FAP. In some embodiments, the antibody is specific to a marker for cancer that is Serpin E1/PAI-1. In some embodiments, the antibody is specific to a marker for cancer that is FGF acidic. In some embodiments, the antibody is specific to a marker for cancer that is Serum Amyloid A4. In some embodiments, the antibody is specific to a marker for cancer that is FGF basic. In some embodiments, the antibody is specific to a marker for cancer that is Survivin. In some embodiments, the antibody is specific to a marker for cancer that is Galectin-3. In some embodiments, the antibody is specific to a marker for cancer that is TEM8. In some embodiments, the antibody is specific to a marker for cancer that is Glypican 3. In some embodiments, the antibody is specific to a marker for cancer that is TIMP-1. In some embodiments, the antibody is specific to a marker for cancer that is HIN-1/Secretoglobulin 3A1. In some embodiments, the antibody is specific to a marker for cancer that is TIMP-2. In some embodiments, the antibody is specific to a marker for cancer that is IGF-I. In some embodiments, the antibody is specific to a marker for cancer that is TIMP-3. In some embodiments, the antibody is specific to a marker for cancer that is IGFBP-3. In some embodiments, the antibody is specific to a marker for cancer that is TIMP-4. In some embodiments, the antibody is specific to a marker for cancer that is IL-6. In some embodiments, the antibody is specific to a marker for cancer that is TNF-alpha/TNFSF1A. In some embodiments, the antibody is specific to a marker for cancer that is Kallikrein 6/Neurosin. In some embodiments, the antibody is specific to a marker for cancer that is TRAF-4. In some embodiments, the antibody is specific to a marker for cancer that is M-CSF. In some embodiments, the antibody is specific to a marker for cancer that is uPA. In some embodiments, the antibody is specific to a marker for cancer that is Matriptase/ST14. In some embodiments, the antibody is specific to a marker for cancer that is uPAR. In some embodiments, the antibody is specific to a marker for cancer that is Mesothelin. In some embodiments, the antibody is specific to a marker for cancer that is VCAM-1. In some embodiments, the antibody is specific to a marker for cancer that is Methionine Aminopeptidase. In some embodiments, the antibody is specific to a marker for cancer that is VEGF. In some embodiments, the antibody is specific to a marker for cancer that is Methionine Aminopeptidase 2.

In some embodiments, the antibody is specific to a marker that is a marker for inflammation. In some embodiments, the antibody is specific to a marker that is a marker for inflammation that is ICAM-1. In some embodiments, the antibody is specific to a marker that is a marker for inflammation that is RANTES. In some embodiments, the antibody is specific to a marker that is a marker for inflammation that is MIP-2. In some embodiments, the antibody is specific to a marker that is a marker for inflammation that is MIP-1 beta. In some embodiments, the antibody is specific to a marker that is a marker for inflammation that is MIP-1 alpha. In some embodiments, the antibody is specific to a marker that is a marker for inflammation that is MMP-3.

In some embodiments, the antibody is specific to a marker that is a marker for endocrine function. In some embodiments, the antibody is specific to a marker that is a marker for endocrine function that is 17 beta-estradiol (E2). In some embodiments, the antibody is specific to a marker that is a marker for endocrine function that is DHEA. In some embodiments, the antibody is specific to a marker that is a marker for endocrine function that is ACTH. In some embodiments, the antibody is specific to a marker that is a marker for endocrine function that is gastrin. In some embodiments, the antibody is specific to a marker that is a marker for endocrine function that is growth hormone.

In some embodiments, the antibody is specific to a marker that is a marker for autoimmune disease. In some embodiments, the antibody is specific to a marker that is a marker for autoimmune disease that is GM-CSF. In some embodiments, the antibody is specific to a marker that is a marker for autoimmune disease that is C-reactive protein (CRP). In some embodiments, the antibody is specific to a marker that is a marker for autoimmune disease that is G-CSF.

In some embodiments, the antibody is specific to a marker for thyroid function. In some embodiments, the antibody is specific to a marker for thyroid function that is cyclic AMP. In some embodiments, the antibody is specific to a marker for thyroid function. In some embodiments, the antibody is specific to a marker for thyroid function that is calcitonin. In some embodiments, the antibody is specific to a marker for thyroid function. In some embodiments, the antibody is specific to a marker for thyroid function that is parathyroid hormone.

In some embodiments, the antibody is specific to a marker for cardiovascular function. In some embodiments, the antibody is specific to a marker for cardiovascular function that is B-natriuretic peptide. In some embodiments, the antibody is specific to a marker for cardiovascular function that is NT-proBNP. In some embodiments, the antibody is specific to a marker for cardiovascular function that is C-reactive protein, HS. In some embodiments, the antibody is specific to a marker for cardiovascular function that is beta-thromboglobulin. In some embodiments, the antibody is specific to a marker for cardiovascular function that is a cardiac troponin. In some embodiments, the antibody is specific to a marker for cardiovascular function that is cardiac troponin I. In some embodiments, the antibody is specific to a marker for cardiovascular function that is cardiac troponin T.

In some embodiments, the antibody is specific to a marker for diabetes. In some embodiments, the antibody is specific to a marker for diabetes that is C-peptide. In some embodiments, the antibody is specific to a marker for diabetes that is leptin.

In some embodiments, the antibody is specific to a marker for infectious disease. In some embodiments, the antibody is specific to a marker for infectious disease that is IFN gamma. In some embodiments, the antibody is specific to a marker for infectious disease that is IFN alpha. In some embodiments, the antibody is specific to a marker for infectious disease that is TREM-1.

In some embodiments, the antibody is specific to a marker for metabolism. In some embodiments, the antibody is specific to a marker for metabolism that is bio-intact PTH (1-84). In some embodiments, the antibody is specific to a marker for metabolism that is PTH.

In some embodiments, the antibody is specific to a marker that is IL-1 beta. In some embodiments, the antibody is specific to a marker that is TNF-alpha. In some embodiments, the antibody is specific to a marker that is IL-6. In some embodiments, the antibody is specific to a marker that is TnI (cardiac troponin I). In some embodiments, the antibody is specific to a marker that is IL-8.

In some embodiments, the antibody is specific to a marker that is Abeta 40. In some embodiments, the antibody is specific to a marker that is Abeta 42. In some embodiments, the antibody is specific to a marker that is cAMP. In some embodiments, the antibody is specific to a marker that is FAS Ligand. In some embodiments, the antibody is specific to a marker that is FGF-basic. In some embodiments, the antibody is specific to a marker that is GM-CSF. In some embodiments, the antibody is specific to a marker that is IFN-alpha. In some embodiments, the antibody is specific to a marker that is IFN-gamma. In some embodiments, the antibody is specific to a marker that is IL-1α. In some embodiments, the antibody is specific to a marker that is IL-2. In some embodiments, the antibody is specific to a marker that is IL-4. In some embodiments, the antibody is specific to a marker that is IL-5. In some embodiments, the antibody is specific to a marker that is IL-7. In some embodiments, the antibody is specific to a marker that is IL-12. In some embodiments, the antibody is specific to a marker that is In some embodiments, the antibody is specific to a marker that is IL-13. In some embodiments, the antibody is specific to a marker that is IL-17. In some embodiments, the antibody is specific to a marker that is MCP-1. In some embodiments, the antibody is specific to a marker that is MIP-1a. In some embodiments, the antibody is specific to a marker that is RANTES. In some embodiments, the antibody is specific to a marker that is VEGF.

In some embodiments, the antibody is specific to a marker that is ACE. In some embodiments, the antibody is specific to a marker that is activin A. In some embodiments, the antibody is specific to a marker that is adiponectin. In some embodiments, the antibody is specific to a marker that is adipsin. In some embodiments, the antibody is specific to a marker that is AgRP. In some embodiments, the antibody is specific to a marker that is AKT1. In some embodiments, the antibody is specific to a marker that is albumin. In some embodiments, the antibody is specific to a marker that is betacellulin. In some embodiments, the antibody is specific to a marker that is bombesin. In some embodiments, the antibody is specific to a marker that is CD14. In some embodiments, the antibody is specific to a marker that is CD-26. In some embodiments, the antibody is specific to a marker that is CD-38. In some embodiments, the antibody is specific to a marker that is CD-40L. In some embodiments, the antibody is specific to a marker that is CD-40s. In some embodiments, the antibody is specific to a marker that is CDK5. In some embodiments, the antibody is specific to a marker that is Complement C3. In some embodiments, the antibody is specific to a marker that is Complement C4. In some embodiments, the antibody is specific to a marker that is C-peptide. In some embodiments, the antibody is specific to a marker that is CRP. In some embodiments, the antibody is specific to a marker that is EGF. In some embodiments, the antibody is specific to a marker that is E-selectin. In some embodiments, the antibody is specific to a marker that is FAS. In some embodiments, the antibody is specific to a marker that is FASLG. In some embodiments, the antibody is specific to a marker that is Fetuin A. In some embodiments, the antibody is specific to a marker that is fibrinogen. In some embodiments, the antibody is specific to a marker that is ghrelin. In some embodiments, the antibody is specific to a marker that is glucagon. In some embodiments, the antibody is specific to a marker that is growth hormone. In some embodiments, the antibody is specific to a marker that is haptoglobulin. In some embodiments, the antibody is specific to a marker that is hepatocyte growth factor. In some embodiments, the antibody is specific to a marker that is HGF. In some embodiments, the antibody is specific to a marker that is ICAM1. In some embodiments, the antibody is specific to a marker that is IFNG. In some embodiments, the antibody is specific to a marker that is IGF1. In some embodiments, the antibody is specific to a marker that is IL-1RA. In some embodiments, the antibody is specific to a marker that is Il-6sr. In some embodiments, the antibody is specific to a marker that is IL-8. In some embodiments, the antibody is specific to a marker that is IL-10. In some embodiments, the antibody is specific to a marker that is IL-18. In some embodiments, the antibody is specific to a marker that is ILGFBP1. In some embodiments, the antibody is specific to a marker that is ILGFBP3. In some embodiments, the antibody is specific to a marker that is insulin-like growth factor 1. In some embodiments, the antibody is specific to a marker that is LEP. In some embodiments, the antibody is specific to a marker that is M-CSF. In some embodiments, the antibody is specific to a marker that is MMP2. In some embodiments, the antibody is specific to a marker that is MMP9. In some embodiments, the antibody is specific to a marker that is NGF. In some embodiments, the antibody is specific to a marker that is PAI-1. In some embodiments, the antibody is specific to a marker that is RAGE. In some embodiments, the antibody is specific to a marker that is RSP4. In some embodiments, the antibody is specific to a marker that is resistin. In some embodiments, the antibody is specific to a marker that is sex hormone binding globulin. In some embodiments, the antibody is specific to a marker that is SOCX3. In some embodiments, the antibody is specific to a marker that is TGF beta. In some embodiments, the antibody is specific to a marker that is thromboplastin. In some embodiments, the antibody is specific to a marker that is TNF R1. In some embodiments, the antibody is specific to a marker that is VCAM-1. In some embodiments, the antibody is specific to a marker that is VWF. In some embodiments, the antibody is specific to a marker that is TSH. In some embodiments, the antibody is specific to a marker that is EPITOME.

In some embodiments, the antibody is specific to a marker that is cardiac troponin I. In some embodiments, the antibody is specific to a marker that is TREM-1. In some embodiments, the antibody is specific to a marker that is IL-6. In some embodiments, the antibody is specific to a marker that is IL-8. In some embodiments, the antibody is specific to a marker that is Leukotriene T4. In some embodiments, the antibody is specific to a marker that is Akt1. In some embodiments, the antibody is specific to a marker that is TGF-beta. In some embodiments, the antibody is specific to a marker that is Fas ligand.

In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent molecule comprises a molecule that comprises at least one substituted indolium ring system in which the substituent on the 3-carbon of the indolium ring contains a chemically reactive group or a conjugated substance group. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules.

A. Binding Partners

Any suitable binding partner with the requisite specificity for the form of molecule, e.g., a marker, to be detected may be used. If the molecule, e.g., a marker, has several different forms, various specificities of binding partners are possible. Suitable binding partners are known in the art and include antibodies, aptamers, lectins, and receptors. A useful and versatile type of binding partner is an antibody.

1. Antibodies

In some embodiments, the binding partner is an antibody specific for a molecule to be detected. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Capture binding partners and detection binding partner pairs, e.g., capture and detection antibody pairs, may be used in embodiments of the invention. Thus, in some embodiments, a heterogeneous assay protocol is used in which, typically, two binding partners, e.g., two antibodies, are used. One binding partner is a capture partner, usually immobilized on a solid support, and the other binding partner is a detection binding partner, typically with a detectable label attached. Such antibody pairs are available from the sources described above, e.g., BiosPacific, Emeryville, Calif. Antibody pairs can also be designed and prepared by methods well-known in the art. Compositions of the invention include antibody pairs wherein one member of the antibody pair is a label as described herein, and the other member is a capture antibody.

In some embodiments it is useful to use an antibody that cross-reacts with a variety of species, either as a capture antibody, a detection antibody, or both. Such embodiments include the measurement of drug toxicity by determining, e.g., release of cardiac troponin into the blood as a marker of cardiac damage. A cross-reacting antibody allows studies of toxicity to be done in one species, e.g., a non-human species, and direct transfer of the results to studies or clinical observations of another species, e.g., humans, using the same antibody or antibody pair in the reagents of the assays, thus decreasing variability between assays. Thus, in some embodiments, one or more of the antibodies for use as a binding partner to the marker, e.g., cardiac troponin, such as cardiac troponin I, may be a cross-reacting antibody. In some embodiments, the antibody cross-reacts with the marker, e.g., cardiac troponin, from at least two species selected from the group consisting of human, monkey, dog, and mouse. In some embodiments the antibody cross-reacts with the marker e.g., cardiac troponin, from all of the group consisting of human, monkey, dog, and mouse.

B. Fluorescent Moieties

In some embodiments of labels used in the invention, the binding partner, e.g., antibody, is attached to a fluorescent moiety. The fluorescence of the moiety will be sufficient to allow detection in a single molecule detector, such as the single molecule detectors described herein.

A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein.

"Limit of detection," or LoD, as those terms are used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Fluorescent moieties, e.g., a single fluorescent dye molecule or a plurality of fluorescent dye molecules, that are useful in some embodiments of the invention may be defined in terms of their photon emission characteristics when stimulated by EM radiation. For example, in some embodiments, the invention utilizes a fluorescent moiety, e.g., a moiety comprising a single fluorescent dye molecule or a plurality of fluorescent dye molecules, that is capable of emitting an average of at least about 10, 20, 30, 40, 50, 75, 100, 125, 150, 175, 200, 225, 250, 275, 300, 350, 400, 500, 600, 700, 800, 900, or 1000, photons when simulated by a laser emitting light at the excitation wavelength of the moiety, where the laser is focused on a spot of not less than about 5 microns in diameter that contains the moiety, and where the total energy directed at the spot by the laser is no more than about 3 microJoules. It will be appreciated that the total energy may be achieved by many different combinations of power output of the laser and length of time of exposure of the dye moiety. E.g., a laser of a power output of 1 mW may be used for 3 ms, 3 mW for 1 ms, 6 mW for 0.5 ms, 12 mW for 0.25 ms, and so on.

In some embodiments, the invention utilizes a fluorescent dye moiety, e.g., a single fluorescent dye molecule or a plurality of fluorescent dye molecules, that is capable of emitting an average of at least about 50 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 100 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 150 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 300 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety e.g., a single fluorescent dye molecule or a plurality of fluorescent dye molecules, that is capable of emitting an average of at least about 500 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

In some embodiments, the fluorescent moiety comprises an average of at least about 1, 2, 3, 4, 5, 6, 7, 8, 9, or 10 fluorescent entities, e.g., fluorescent molecules. In some embodiments, the fluorescent moiety comprises an average of no more than about 2, 3, 4, 5, 6, 7, 8, 9, 10, or 11 fluorescent entities, e.g., fluorescent molecules. In some embodiments, the fluorescent moiety comprises an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 fluorescent entities. In some embodiments, the fluorescent moiety comprises an average of about 2 to 8 fluorescent moieties are attached. In some embodiments, the fluorescent moiety comprises an average of about 2 to 6 fluorescent entities. In some embodiments, the fluorescent moiety comprises an average of about 2 to 4 fluorescent entities. In some embodiments, the fluorescent moiety comprises an average of about 3 to 10 fluorescent entities. In some embodiments, the fluorescent moiety comprises an average of about 3 to 8 fluorescent entities. In some embodiments, the fluorescent moiety comprises an average of about 3 to 6 fluorescent entities. By "average" it is meant that, in a given sample that is representative of a group of labels of the invention, where the sample contains a plurality of the binding partner-fluorescent moiety units, the molar ratio of the particular fluorescent entity to the binding partner, as determined by standard analytical methods, corresponds to the number or range of numbers specified. For example, in embodiments wherein the label comprises a binding partner that is an antibody and a fluorescent moiety that comprises a plurality of fluorescent dye molecules of a specific absorbance, a spectrophotometric assay can be used in which a solution of the label is diluted to an appropriate level and the absorbance at 280 nm is taken to determine the molarity of the protein (antibody) and an absorbance at, e.g., 650 nm (for Alexa Fluor 647), is taken to determine the molarity of the fluorescent dye molecule. The ratio of the latter molarity to the former represents the average number of fluorescent entities (dye molecules) in the fluorescent moiety attached to each antibody.

1. Dyes

In some embodiments, the invention uses fluorescent moieties that comprise fluorescent dye molecules. In some embodiments, the invention utilizes a fluorescent dye molecule that is capable of emitting an average of at least about 50 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 75 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 100 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 150 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 200 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules.

In some embodiments, the invention uses a fluorescent dye moiety, e.g., a single fluorescent dye molecule or a plurality of fluorescent dye molecules, that is capable of emitting an average of at least about 50 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 100 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 150 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 300 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 500 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

A non-inclusive list of useful fluorescent entities for use in the fluorescent moieties of the invention is given in Table 2, below. In some embodiments, the fluorescent dye is selected from the group consisting of Alexa Fluor 488, Alexa Fluor 532, Alexa Fluor 647, Alexa Fluor 700, Alexa Fluor 750, Fluorescein, B-phycoerythrin, allophycocyanin, PBXL-3, and Qdot 605. In some embodiments, the fluorescent dye is selected from the group consisting of Alexa Fluor 488, Alexa Fluor 532, Alexa Fluor 700, Alexa Fluor 750, Fluorescein, B-phycoerythrin, allophycocyanin, PBXL-3, and Qdot 605.

TABLE 2

FLUORESCENT ENTITIES

| Dye | E Ex (nm) | E (M)-1 | Em (nm) | MMw |
| --- | --- | --- | --- | --- |
| Bimane | 380 | 5,700 | 458 | 282.31 |
| Dapoxyl | 373 | 22,000 | 551 | 362.83 |
| Dimethylamino coumarin-4-acetic acid | 375 | 22,000 | 470 | 344.32 |
| Marina blue | 365 | 19,000 | 460 | 367.26 |
| 8-Anilino naphthalene-1-sulfonic acid | 372 | | 480 | |
| Cascade blue | 376 | 23,000 | 420 | 607.42 |
| Alexa Fluor 405 | 402 | 35,000 | 421 | 1028.26 |
| Cascade blue | 400 | 29,000 | 420 | 607.42 |
| Cascade yellow | 402 | 24,000 | 545 | 563.54 |
| Pacific blue | 410 | 46,000 | 455 | 339.21 |
| PyMPO | 415 | 26,000 | 570 | 582.41 |
| Alexa Fluor 430 | 433 | 15,000 | 539 | 701.75 |

TABLE 2-continued

| | | | | |
|---|---|---|---|---|
| Atto-425 | 438 | | 486 | |
| NBD | 465 | 22,000 | 535 | 391.34 |
| Alexa Fluor 488 | 495 | 73,000 | 519 | 643.41 |
| Fluorescein | 494 | 79,000 | 518 | 376.32 |
| Oregon Green 488 | 496 | 76,000 | 524 | 509.38 |
| Atto 495 | 495 | | 522 | |
| Cy2 | 489 | 150,000 | 506 | 713.78 |
| DY-480-XL | 500 | 40,000 | 630 | 514.60 |
| DY-485-XL | 485 | 20,000 | 560 | 502.59 |
| DY-490-XL | 486 | 27,000 | 532 | 536.58 |
| DY-500-XL | 505 | 90,000 | 555 | 596.68 |
| DY-520-XL | 520 | 40,000 | 664 | 514.60 |
| Alexa Fluor 532 | 531 | 81,000 | 554 | 723.77 |
| BODIPY 530/550 | 534 | 77,000 | 554 | 513.31 |
| 6-HEX | 535 | 98,000 | 556 | 680.07 |
| 6-JOE | 522 | 75,000 | 550 | 602.34 |
| Rhodamine 6G | 525 | 108,000 | 555 | 555.59 |
| Atto-520 | 520 | | 542 | |
| Cy3B | 558 | 130,000 | 572 | 658.00 |
| Alexa Fluor 610 | 612 | 138,000 | 628 | |
| Alexa Fluor 633 | 632 | 159,000 | 647 | ca. 1200 |
| Alexa Fluor 647 | 650 | 250,000 | 668 | ca. 1250 |
| BODIPY 630/650 | 625 | 101,000 | 640 | 660.50 |
| Cy5 | 649 | 250,000 | 670 | 791.99 |
| Alexa Fluor 660 | 663 | 110,000 | 690 | |
| Alexa Fluor 680 | 679 | 184,000 | 702 | |
| Alexa Fluor 700 | 702 | 192,000 | 723 | |
| Alexa Fluor 750 | 749 | 240,000 | 782 | |
| B-phycoerythrin | 546, 565 | 2,410,000 | 575 | 240,000 |
| R-phycoerythrin | 480, 546, 565 | 1,960,000 | 578 | 240,000 |
| Allophycocyanin | 650 | 700,000 | 660 | 700,000 |
| PBXL-1 | 545 | | 666 | |
| PBXL-3 | 614 | | 662 | |

Atto-tec dyes

| Name | Ex (nm) | Em (nm) | QY | τ (ns) |
|---|---|---|---|---|
| Atto 425 | 436 | 486 | 0.9 | 3.5 |
| Atto 495 | 495 | 522 | 0.45 | 2.4 |
| Atto 520 | 520 | 542 | 0.9 | 3.6 |
| Atto 560 | 561 | 585 | 0.92 | 3.4 |
| Atto 590 | 598 | 634 | 0.8 | 3.7 |
| Atto 610 | 605 | 630 | 0.7 | 3.3 |
| Atto 655 | 665 | 690 | 0.3 | 1.9 |
| Atto 680 | 680 | 702 | 0.3 | 1.8 |

Dyomics Fluors

| Label | Ex (nm) | Molar absorbance* [l · mol-1 · cm-1] | Em (nm) | molecular weight# [g · mol-1] |
|---|---|---|---|---|
| DY-495/5 | 495 | 70,000 | 520 | 489.47 |
| DY-495/6 | 495 | 70,000 | 520 | 489.47 |
| DY-495X/5 | 495 | 70,000 | 520 | 525.95 |
| DY-495X/6 | 495 | 70,000 | 520 | 525.95 |
| DY-505/5 | 505 | 85,000 | 530 | 485.49 |
| DY-505/6 | 505 | 85,000 | 530 | 485.49 |
| DY-505X/5 | 505 | 85,000 | 530 | 523.97 |
| DY-505X/6 | 505 | 85,000 | 530 | 523.97 |
| DY-550 | 553 | 122,000 | 578 | 667.76 |
| DY-555 | 555 | 100.000 | 580 | 636.18 |
| DY-610 | 609 | 81.000 | 629 | 667.75 |
| DY-615 | 621 | 200.000 | 641 | 578.73 |
| DY-630 | 636 | 200.000 | 657 | 634.84 |
| DY-631 | 637 | 185.000 | 658 | 736.88 |
| DY-633 | 637 | 180.000 | 657 | 751.92 |
| DY-635 | 647 | 175.000 | 671 | 658.86 |
| DY-636 | 645 | 190.000 | 671 | 760.91 |
| DY-650 | 653 | 170.000 | 674 | 686.92 |
| DY-651 | 653 | 160.000 | 678 | 888.96 |
| DYQ-660 | 660 | 117,000 | — | 668.86 |
| DYQ-661 | 661 | 116,000 | — | 770.90 |
| DY-675 | 674 | 110.000 | 699 | 706.91 |
| DY-676 | 674 | 145.000 | 699 | 807.95 |
| DY-680 | 690 | 125.000 | 709 | 634.84 |
| DY-681 | 691 | 125.000 | 708 | 736.88 |
| DY-700 | 702 | 96.000 | 723 | 668.86 |
| DY-701 | 706 | 115.000 | 731 | 770.90 |
| DY-730 | 734 | 185.000 | 750 | 660.88 |
| DY-731 | 736 | 225.000 | 759 | 762.92 |
| DY-750 | 747 | 240.000 | 776 | 712.96 |
| DY-751 | 751 | 220.000 | 779 | 814.99 |
| DY-776 | 771 | 147.000 | 801 | 834.98 |
| DY-780-OH | 770 | 70.000 | 810 | 757.34 |
| DY-780-P | 770 | 70.000 | 810 | 957.55 |
| DY-781 | 783 | 98.000 | 800 | 762.92 |
| DY-782 | 782 | 102.000 | 800 | 660.88 |
| EVOblue-10 | 651 | 101.440 | 664 | 389.88 |
| EVOblue-30 | 652 | 102.000 | 672 | 447.51 |

Quantum Dots: Qdot 525, QD 565, QD 585, QD 605, QD 655, QD 705, QD 800

Suitable dyes for use in the invention include modified carbocyanine dyes. On such modification comprises modification of an indolium ring of the carbocyanine dye to permit a reactive group or conjugated substance at the number three position. The modification of the indolium ring provides dye conjugates that are uniformly and substantially more fluorescent on proteins, nucleic acids and other biopolymers, than conjugates labeled with structurally similar carbocyanine dyes bound through the nitrogen atom at the number one position. In addition to having more intense fluorescence emission than structurally similar dyes at virtually identical wavelengths, and decreased artifacts in their absorption spectra upon conjugation to biopolymers, the modified carbocyanine dyes have greater photostability and higher absorbance (extinction coefficients) at the wavelengths of peak absorbance than the structurally similar dyes. Thus, the modified carbocyanine dyes result in greater sensitivity in assays using the modified dyes and their conjugates. Preferred modified dyes include compounds that have at least one substituted indolium ring system in which the substituent on the 3-carbon of the indolium ring contains a chemically reactive group or a conjugated substance. Other dye compounds include compounds that incorporate an azabenzazolium ring moiety and at least one sulfonate moiety. The modified carbocyanine dyes that can be used to detect individual molecules in various embodiments of the invention are described in U.S. Pat. No. 6,977,305, which is herein incorporated by reference in its entirety. Thus, in some embodiments the labels of the invention utilize a fluorescent dye that includes a substituted indolium ring system in which the substituent on the 3-carbon of the indolium ring contains a chemically reactive group or a conjugated substance group.

In some embodiments, the label comprises a fluorescent moiety that includes one or more Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

Currently available organic fluors can be improved by rendering them less hydrophobic by adding hydrophilic groups such as polyethylene. Alternatively, currently sulfonated organic fluors such as the Alexa Fluor 647 dye can be rendered less acidic by making them zwitterionic. Particles such as antibodies that are labeled with the modified fluors are less likely to bind non-specifically to surfaces and proteins in immunoassays, and thus enable assays that have greater sensitivity and lower backgrounds. Methods for modifying and improving the properties of fluorescent dyes for the purpose of increasing the sensitivity of a system that detects single molecules are known in the art. Preferably, the modification improves the Stokes shift while maintaining a high quantum yield.

2. Quantum Dots

In some embodiments, the fluorescent label moiety that is used to detect a molecule in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical feature of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

QDs have broad excitation and narrow emission properties which, when used with color filtering, require only a single electromagnetic source to resolve individual signals during multiplex analysis of multiple targets in a single sample. Thus, in some embodiments, the analyzer system comprises one continuous wave laser and particles that are each labeled with one QD. Colloidally prepared QDs are free floating and can be attached to a variety of molecules via metal coordinating functional groups. These groups include but are not limited to thiol, amine, nitrile, phosphine, phosphine oxide, phosphonic acid, carboxylic acids or other ligands. By bonding appropriate molecules to the surface, the quantum dots can be dispersed or dissolved in nearly any solvent or incorporated into a variety of inorganic and organic films. Quantum dots (QDs) can be coupled to streptavidin directly through a maleimide ester coupling reaction or to antibodies through a meleimide-thiol coupling reaction. This yields a material with a biomolecule covalently attached on the surface, which produces conjugates with high specific activity. In some embodiments, the protein that is detected with the single molecule analyzer is labeled with one quantum dot. In some embodiments, the quantum dot is between 10 and 20 nm in diameter. In other embodiments, the quantum dot is between 2 and 10 nm in diameter. In other embodiments, the quantum dot is about 2 nm, 3 nm, 4 nm, 5 nm, 6 nm, 7 nm, 8 nm, 9 nm, 10 nm, 11 nm, 12 nm, 13 nm, 14 nm, 15v, 16 nm, 17 nm, 18 nm, 19 nm or 20 nm in diameter. Useful Quantum Dots comprise QD 605, QD 610, QD 655, and QD 705. A preferred Quantum Dot is QD 605.

C. Binding Partner-Fluorescent Moiety Compositions

The labels of the invention generally contain a binding partner, e.g., antibody, bound to a fluorescent moiety to provide the requisite fluorescence for detection and quantitation in the instruments described herein. Any suitable combination of binding partner and fluorescent moiety for detection in the single molecule detectors described herein may be used as a label in the invention. In some embodiments, the invention provides a label for a marker of a biological state, where the label includes an antibody to the marker and a fluorescent moiety. The marker may be any of the markers described above. The antibody may be any antibody as described above. A fluorescent moiety may be attached such that the label is capable of emitting an average of at least about 50, 75, 100, 125, 150, 175, 200, 225, 250, 275, 300, 350, 400, 500, 600, 700, 800, 900, or 1000, photons when simulated with a laser emitting light at the excitation wavelength of the moiety, where the laser is focused on a spot of not less than about 5 microns in diameter that contains the label, and wherein the total energy directed at the spot by the laser is no more than about 3 microJoules. In some embodiments, the fluorescent moiety may be a fluorescent moiety that is capable of emitting an average of at least about 50, 100, 150, or 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. The fluorescent moiety may be a fluorescent moiety that includes one or more dye molecules with a structure that includes a substituted indolium ring system in which the substituent on the 3-carbon of the indolium ring contains a chemically reactive group or a conjugated substance group. The label composition may include a fluorescent moiety that includes one or more dye molecules selected from the group consisting of Alexa Fluor 488, Alexa Fluor 532, Alexa Fluor 647, Alexa Fluor 700, or Alexa Fluor 750. The label composition may include a fluorescent moiety that includes one or more dye molecules selected from the group consisting of Alexa Fluor 488, Alexa Fluor 532, Alexa Fluor 700, or Alexa Fluor 750. The label composition may include a fluorescent moiety that includes one or more dye molecules that are Alexa Fluor 488. The label composition may include a fluorescent moiety that includes one or more dye molecules that are Alexa Fluor 555. The label composition may include a fluorescent moiety that includes one or more dye molecules that are Alexa Fluor 610. The label composition may include a fluorescent moiety that includes one or more dye molecules that are Alexa Fluor 647. The label composition may include a fluorescent moiety that includes one or more dye molecules that are Alexa Fluor 680. The label composition may include a fluorescent moiety that includes one or more dye molecules that are Alexa Fluor 700. The label composition may include a fluorescent moiety that includes one or more dye molecules that are Alexa Fluor 750.

In some embodiments the invention provides a composition for the detection of a marker of a biological state that includes an Alexa Fluor molecule, e.g., an Alexa Fluor molecule selected from the described groups, such as an Alexa Fluor 647 molecule attached to an antibody specific for the marker. In some embodiments the composition includes an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 Alexa Fluor 647 molecules attached to an antibody for the marker. In some embodiments the invention provides a composition for the detection a marker of a biological state that includes an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 Alexa Fluor 647 molecules attached to an antibody specific to the marker. In some embodiments the invention provides a composition for the detection of a marker of a biological state that includes an average of about 2 to 10 Alexa Fluor 647 molecules attached to an antibody specific to the marker. In some embodiments the invention provides a composition for the detection of a marker of a biological state that includes an average of about 2 to 8 Alexa Fluor 647 molecules attached to an antibody specific to the marker. In some embodiments the invention provides a composition for the detection of a marker of a biological state that includes an average of about 2 to 6 Alexa Fluor 647 molecules attached to an antibody specific to the marker. In some embodiments the invention provides a composition for the detection of a marker of a biological state that includes an average of about 2 to 4 Alexa Fluor 647 molecules attached to an antibody specific to the marker. In some embodiments the invention provides a composition for the detection of a marker of a biological state that includes an average of about 3 to 8 Alexa Fluor 647 molecules attached to an antibody specific to the marker. In some embodiments the invention provides a composition for the detection of a marker of a biological state that includes an average of about 3 to 6 Alexa Fluor 647 molecules attached to an antibody specific to the marker. In some embodiments the invention provides a composition for the detection of a marker of a biological state that includes an average of about 4 to 8 Alexa Fluor 647 molecules attached to an antibody specific to the marker.

Attachment of the fluorescent moiety, or fluorescent entities that make up the fluorescent moiety, to the binding partner, e.g., antibody, may be by any suitable means; such methods are well-known in the art and exemplary methods are given in the Examples. In some embodiments, after attachment of the fluorescent moiety to the binding partner to form a label for use in the methods of the invention, and prior to the use of the label for labeling the protein of interest, it is useful to perform a filtration step. E.g., an antibody-dye label may be filtered prior to use, e.g., through a 0.2 micron filter, or any suitable filter for removing aggregates. Other reagents for use in the assays of the invention may also be filtered, e.g., through a 0.2 micron filter, or any suitable filter. Without being bound by theory, it is thought that such filtration removes a portion of the aggregates of the, e.g., antibody-dye labels. As such aggregates can bind as a unit to the protein of interest, but upon release in elution buffer are likely to disaggregate, false positives may result; i.e., several labels will be detected from an aggregate that has bound to only a single protein molecule of interest. Regardless of theory, filtration has been found to reduce false positives in the subsequent assay and to improve accuracy and precision.

It will be appreciated that immunoassays often employ a sandwich format, in which binding partner pairs, e.g., antibodies, to the same molecule, e.g., a marker, are used. The invention also encompasses binding partner pairs, e.g., antibodies, wherein both antibodies are specific to the same molecule, e.g., the same marker, and wherein at least one member of the pair is a label as described herein. Thus, for any label that includes a binding-partner and a fluorescent moiety, the invention also encompasses a pair of binding partners wherein the first binding partner, e.g., antibody, is part of the label, and the second binding partner, e.g., antibody, is, typically, unlabeled and serves as a capture binding partner. In addition, binding partner pairs are frequently used in FRET assays. FRET assays useful in the invention are disclosed in U.S. patent application Ser. No. 11/048,660, incorporated by reference herein in its entirety, and the present invention also encompasses binding partner pairs, each of which includes a FRET label.

IV. Highly Sensitive Analysis of Molecules

In one aspect, the invention provides a method for determining the presence or absence of a single molecule, e.g., a molecule of a marker of a biological state, in a sample, by i) labeling the molecule if present, with a label; and ii) detecting the presence or absence of the label, where the detection of the presence of the label indicates the presence of the single molecule in the sample. In some embodiments, the method is capable of detecting the molecule at a limit of detection of less than about 100, 80, 60, 50, 40, 30, 20, 15, 12, 10, 9, 8, 7, 6, 5, 4, 3, 2, 1, 0.9, 0.8, 0.7, 0.6, 0.5, 0.4, 0.3, 0.2, 0.1, 0.05, 0.01, 0.005, or 0.001 femtomolar. In some embodiments, the method is capable of detecting the molecule at a limit of detection of less than about 100 femtomolar. In some embodiments, the method is capable of detecting the molecule at a limit of detection of less than about 10 femtomolar. In some embodiments, the method is capable of detecting the molecule at a limit of detection of less than about 1 femtomolar. In some embodiments, the method is capable of detecting the molecule at a limit of detection of less than about 0.1 femtomolar. In some embodiments, the method is capable of detecting the molecule at a limit of detection of less than about 0.01 femtomolar. In some embodiments, the method is capable of detecting the molecule at a limit of detection of less than about 0.001 femtomolar. Detection limits may be determined by use of an appropriate standard, e.g., National Institute of Standards and Technology reference standard material.

The methods also provide methods of determining a concentration of a molecule, e.g., a marker indicative of a biological state, in a sample by detecting single molecules of the molecule in the sample. The "detecting" of a single molecule includes detecting the molecule directly or indirectly. In the case of indirect detection, labels that correspond to single molecules, e.g., labels attached to the single molecules, can be detected.

In some embodiments, the invention provides a method for determining the presence or absence of a single molecule of a protein in a biological sample, comprising labeling said molecule with a label and detecting the presence or absence of said label in a single molecule detector, wherein said label comprises a fluorescent moiety that is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. The single molecule detector may, in some embodiments, comprise not more than one interrogation space. The limit of detection of the single molecule in the sample may be less than about 10, 1, 0.1, 0.01, or 0.001 femtomolar. In some embodiments, the limit of detection is less than about 1 femtomolar. The detecting may comprise detecting electromagnetic radiation emitted by said fluorescent moiety. The method may further comprise exposing said fluorescent moiety to electromagnetic radiation, e.g., electromagnetic radiation provided by a laser, such as a laser with a power output of about 2, 3, 4, 5, 6, 7, 8, 9, 10, 11, 12, 13, 14, 15, 16, 17, 18, 19, 20 mW. In some embodiments, the laser stimulus provides light to the interrogation space for between about 10-1000 microseconds, or about 1000, 250, 100, 50, 25 or 10 microseconds. In some embodiments, the label further comprises a binding partner specific for binding said molecule, such as an antibody. In some embodiments, the fluorescent moiety comprises a fluorescent dye molecule, such as a dye molecule that comprises at least one substituted indolium ring system in which the substituent on the 3-carbon of the indolium ring contains a chemically reactive group or a conjugated substance. In some embodiments, the dye molecule is an AlexFluor molecule selected from the group consisting of Alexa Fluor 488, Alexa Fluor 532, Alexa Fluor 647, Alexa Fluor 680 or Alexa Fluor 700. In some embodiments, the dye molecule is an Alexa Fluor 647 dye molecule. In some embodiments, the fluorescent moiety comprises a plurality of Alexa Fluor 647 molecules. In some embodiments, the plurality of Alexa Fluor 647 molecules comprises about 2-4 Alexa Fluor 647 molecules, or about 3-6 Alexa Fluor 647 molecules. In some embodiments, the fluorescent moiety is a quantum dot. The method may further comprise measuring the concentration of said protein in the sample.

In some embodiments, detecting the presence or absence of said label comprises: (i) passing a portion of said sample through an interrogation space; (ii) subjecting said interrogation space to exposure to electromagnetic radiation, said electromagnetic radiation being sufficient to stimulate said fluorescent moiety to emit photons, if said label is present; and (iii) detecting photons emitted during said exposure of step (ii). The method may further comprise determining a background photon level in said interrogation space, wherein said background level represents the average photon emission of the interrogation space when it is subjected to electromagnetic radiation in the same manner as in step (ii), but without label in the interrogation space. The method may further comprise comparing the amount of photons detected in step (iii) to a threshold photon level, wherein said threshold photon level is a function of said background photon level, wherein an amount of photons detected in step (iii) greater that the threshold level indicates the presence of said label, and an amount of photons detected in step (iii) equal to or less than the threshold level indicates the absence of said label.

A. Sample

The sample may be any suitable sample. Typically, the sample is a biological sample, e.g., a biological fluid. Such fluids include, without limitation, bronchoalveolar lavage fluid (BAL), blood, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest.

In some embodiments, the sample is a blood sample. In some embodiments the sample is a plasma sample. In some embodiments the sample is a serum sample. In some embodiments, the sample is a urine sample. In some embodiments, the sample is a nasal swab. In some embodiments, the sample is a cell lysate. In some embodiments, the sample is a tissue sample.

B. Sample Preparation

In general, any method of sample preparation may be used that produces a label corresponding to a molecule of interest, e.g., a marker of a biological state to be measured, where the label is detectable in the instruments described herein. As is known in the art, sample preparation in which a label is added to one or more molecules may be performed in a homogeneous or heterogeneous format. In some embodiments, the sample preparation is formed in a homogenous format. In analyzer systems employing a homogenous format, unbound label is not removed from the sample. See, e.g., U.S. patent application Ser. No. 11/048,660. In some embodiments, the particle or particles of interest are labeled by addition of labeled antibody or antibodies that bind to the particle or particles of interest.

In some embodiments, a heterogeneous assay format is used, where, typically, a step is employed for removing unbound label. Such assay formats are well-known in the art. One particularly useful assay format is a sandwich assay, e.g., a sandwich immunoassay. In this format, the molecule of interest, e.g., marker of a biological state, is captured, e.g., on a solid support, using a capture binding partner. Unwanted molecules and other substances may then optionally be washed away, followed by binding of a label comprising a detection binding partner and a detectable label, e.g., fluorescent moiety. Further washes remove unbound label, then the detectable label is released, usually though not necessarily still attached to the detection binding partner. In alternative embodiments, sample and label are added to the capture binding partner without a wash in between, e.g., at the same time. Other variations will be apparent to one of skill in the art.

In some embodiments, the method for detecting the molecule of interest, e.g., marker of a biological state, uses a sandwich assay with antibodies, e.g., monoclonal antibodies as capture binding partners. The method comprises binding molecules in a sample to a capture antibody that is immobilized on a binding surface, and binding the label comprising a detection antibody to the molecule to form a "sandwich" complex. The label comprises the detection antibody and a fluorescent moiety, as described herein, which is detected, e.g., using the single molecule analyzers of the invention. Both the capture and detection antibodies specifically bind the molecule. Many examples of sandwich immunoassays are known, and some are described in U.S. Pat. No. 4,168,146 to Grubb et al. and U.S. Pat. No. 4,366,241 to Tom et al., both of which are incorporated herein by reference. Further examples specific to specific markers are described in the Examples.

The capture binding partner may be attached to a solid support, e.g., a microtiter plate or paramagnetic beads. In some embodiments, the invention provides a binding partner for a molecule of interest, e.g., marker of a biological state, attached to a paramagnetic bead. Any suitable binding partner that is specific for the molecule that it is wished to capture may be used. The binding partner may be an antibody, e.g., a monoclonal antibody. Production and sources of antibodies are described elsewhere herein. It will be appreciated that antibodies identified herein as useful as a capture antibody may also be useful as detection antibodies, and vice versa.

The attachment of the binding partner, e.g., antibody, to the solid support may be covalent or noncovalent. In some embodiments, the attachment is noncovalent. An example of a noncovalent attachment well-known in the art is biotin-avidin/streptavidin interactions. Thus, in some embodiments, a solid support, e.g., a microtiter plate or a paramagnetic bead, is attached to the capture binding partner, e.g., antibody, through noncovalent attachment, e.g., biotin-avidin/streptavidin interactions. In some embodiments, the attachment is covalent. Thus, in some embodiments, a solid support, e.g., a microtiter plate or a paramagnetic bead, is attached to the capture binding partner, e.g., antibody, through covalent attachment.

The capture antibody can be covalently attached in an orientation that optimizes the capture of the molecule of interest. For example, in some embodiments, a binding partner, e.g., an antibody, is attached in a orientated manner to a solid support, e.g., a microtiter plate or a paramagnetic microparticle.

An exemplary protocol for oriented attachment of an antibody to a solid support is as follows: IgG is dissolved in 0.1M sodium acetate buffer, pH 5.5 to a final concentration of 1 mg/ml. An equal volume of ice-cold 20 mM sodium periodate in 0.1 M sodium acetate, pH 5.5 is added. The IgG is allowed to oxidize for ½ hour on ice. Excess periodate reagent is quenched by the addition of 0.15 volume of 1 M glycerol. Low molecular weight byproducts of the oxidation reaction are removed by ultrafiltration. The oxidized IgG fraction is diluted to a suitable concentration (typically 0.5 micrograms IgG per ml) and reacted with hydrazide-activated multiwell plates for at least two hours at room temperature. Unbound IgG is removed by washing the multiwell plate with borate buffered saline or another suitable buffer. The plate may be dried for storage, if desired. A similar protocol may be followed for microbeads if the material of the microbead is suitable for such attachment.

In some embodiments, the solid support is a microtiter plate. In some embodiments, the solid support is a paramagnetic bead. An exemplary paramagnetic bead is Streptavidin C1 (Dynal, 650.01-03). Other suitable beads will be apparent to those of skill in the art. Methods for attachment of antibodies to paramagnetic beads are well-known in the art. One example is given in Example 2.

The molecule of interest is contacted with the capture binding partner, e.g., capture antibody immobilized on a solid support. Some sample preparation may be used; e.g., preparation of serum from blood samples or concentration procedures before the sample is contacted with the capture antibody. Protocols for binding of proteins in immunoassays are well-known in the art and are included in the Examples.

The time allowed for binding will vary depending on the conditions; it will be apparent that shorter binding times are desirable in some settings, especially in a clinical setting. The use of, e.g., paramagnetic beads can reduce the time required for binding. In some embodiments, the time allowed for binding of the molecule of interest to the capture binding partner, e.g., an antibody, is less that about 12, 10, 8, 6, 4, 3, 2, or 1 hours, or less than about 60, 50, 40, 30, 25, 20, 15, 10, or 5 minutes. In some embodiments, the time allowed for binding of the molecule of interest to the capture binding partner, e.g., an antibody, is less than about 60 minutes. In some embodiments, the time allowed for binding of the molecule of interest to the capture binding partner, e.g., an antibody, is less than about 40 minutes. In some embodiments, the time allowed for binding of the molecule of interest to the capture binding partner, e.g., an antibody, is less than about 30 minutes. In some embodiments, the time allowed for binding of the molecule of interest to the capture binding partner, e.g., an antibody, is less than about 20 minutes. In some embodiments, the time allowed for binding of the molecule of interest to the capture binding partner, e.g., an antibody, is less than about 15 minutes. In some embodiments, the time allowed for binding of the molecule of interest to the capture binding partner, e.g., an antibody, is less than about 10 minutes. In some embodiments, the time allowed for binding of the molecule of interest to the capture binding partner, e.g., an antibody, is less than about 5 minutes.

In some embodiments, following the binding of particles of the molecule of interest to the capture binding partner, e.g., a capture antibody, particles that bound nonspecifically, as well as other unwanted substances in the sample, are washed away leaving substantially only specifically bound particles of the molecule of interest. In other embodiments, no wash is used between additions of sample and label, which can reduce sample preparation time. Thus, in some embodiments, the time allowed for both binding of the molecule of interest to the capture binding partner, e.g., an antibody, and binding of the label to the molecule of interest, is less that about 12, 10, 8, 6, 4, 3, 2, or 1 hours, or less than about 60, 50, 40, 30, 25, 20, 15, 10, or minutes. In some embodiments, the time allowed for both binding of the molecule of interest to the capture binding partner, e.g., an antibody, and binding of the label to the molecule of interest, is less that about 60 minutes. In some embodiments, the time allowed for both binding of the molecule of interest to the capture binding partner, e.g., an antibody, and binding of the label to the molecule of interest, is less that about 50 minutes. In some embodiments, the time allowed for both binding of the molecule of interest to the capture binding partner, e.g., an antibody, and binding of the label to the molecule of interest, is less than about 40 minutes. In some embodiments, the time allowed for both binding of the molecule of interest to the capture binding partner, e.g., an antibody, and binding of the label to the molecule of interest, is less than about 30 minutes. In some embodiments, the time allowed for both binding of the molecule of interest to the capture binding partner, e.g., an antibody, and binding of the label to the molecule of interest, is less than about 20 minutes. In some embodiments, the time allowed for both binding of the molecule of interest to the capture binding partner, e.g., an antibody, and binding of the label to the molecule of interest, is less than about 15 minutes. In some embodiments, the time allowed for both binding of the molecule of interest to the capture binding partner, e.g., an antibody, and binding of the label to the molecule of interest, is less than about 10 minutes. In some embodiments, the time allowed for both binding of the molecule of interest to the capture binding partner, e.g., an antibody, and binding of the label to the molecule of interest, is less than about 5 minutes.

Some immunoassay diagnostic reagents, including the capture and signal antibodies used to measure the molecule of interest, can be derived from animal sera. Endogenous human heterophilic antibodies, or human anti-animal antibodies, which have the ability to bind to immunoglobulins of other species, are present in the serum or plasma of more than 10% of patients. These circulating heterophilic antibodies can interfere with immunoassay measurements. In sandwich immunoassays, these heterophilic antibodies can either bridge the capture and detection (diagnostic) antibodies, thereby producing a false-positive signal, or they can block the binding of the diagnostic antibodies, thereby producing a false-negative signal. In competitive immunoassays, the heterophilic antibodies can bind to the analytic antibody and inhibit its binding to the molecule of interest. They can also either block or augment the separation of the antibody-molecule of interest complex from free molecule of interest, especially when antispecies antibodies are used in the separation systems. Therefore, the impact of these heterophilic antibody interferences is difficult to predict and it can be advantageous to block the binding of heterophilic antibodies.

In some embodiments of the invention, the immunoassay includes the step of depleting the sample of heterophilic antibodies using one or more heterophilic antibody blockers. Methods for removing heterophilic antibodies from samples to be tested in immunoassays are known and include: heating the specimen in a sodium acetate buffer, pH 5.0, for 15 minutes at 90° C. and centrifuging at 1200 g for 10 minutes; precipitating the heterophilic immunoglobulins using polyethylene glycol (PEG); immunoextracting the interfering heterophilic immunoglobulins from the specimen using protein A or protein G; or adding nonimmune mouse IgG. Embodiments of the methods of the invention contemplate preparing the sample prior to analysis with the single molecule detector. The appropriateness of the method of pretreatment can be determined Biochemicals to minimize immunoassay interference caused by heterophilic antibodies are commercially available. For example, a product called MAK33, which is an IgG1 monoclonal antibody to h-CK-MM, can be obtained from Boehringer Mannheim. The MAK33 plus product contains a combination of IgG1 and IgG1-Fab. polyMAK33 contains IgG1-Fab polymerized with IgG1, and the polyMAC 2b/2a contains IgG2a-Fab polymerized with IgG2b. Bioreclamation Inc., East Meadow, N.Y., markets a second commercial source of biochemicals to neutralize heterophilic antibodies known as Immunoglobulin Inhibiting Reagent. This product is a preparation of immunoglobulins (IgG and IgM) from multiple species, mainly murine IgG2a, IgG2b, and IgG3 from Balb/c mice. In some embodiments the heterophilic antibody can be immunoextracted from the sample using methods known in the art, e.g., depleting the sample of the heterophilic antibody by binding the interfering antibody to protein A or protein G. In some embodiments, the heterophilic antibody can be neutralized using one or more heterophilic antibody blockers. Heterophilic blockers can be selected from the group consisting of anti-isotype heterophilic antibody blockers, anti-idiotype heterophilic antibody blockers, and anti-anti-idiotype heterophilic antibody blockers. In some embodiments, a combination of heterophilic antibody blockers can be used.

Label is added either with or following the addition of sample and washing. Protocols for binding antibodies and other immunolabels to proteins and other molecules are well-known in the art. If the label binding step is separate from that of capture binding, the time allowed for label binding can be important, e.g., in clinical applications or other time sensitive settings. In some embodiments, the time allowed for binding of the molecule of interest to the label, e.g., an antibody-dye, is less than about 12, 10, 8, 6, 4, 3, 2, or 1 hours, or less than about 60, 50, 40, 30, 25, 20, 15, 10, or 5 minutes. In some embodiments, the time allowed for binding of the molecule of interest to the label, e.g., an antibody-dye, is less than about 60 minutes. In some embodiments, the time allowed for binding of the molecule of interest to the label, e.g., an antibody-dye, is less than about 50 minutes. In some embodiments, the time allowed for binding of the molecule of interest to the label, e.g., an antibody-dye, is less than about 40 minutes. In some embodiments, the time allowed for binding of the molecule of interest to the label, e.g., an antibody-dye, is less than about 30 minutes. In some embodiments, the time allowed for binding of the molecule of interest to the label, e.g., an antibody-dye, is less than about 20 minutes. In some embodiments, the time allowed for binding of the molecule of interest to the label, e.g., an antibody-dye, is less than about 15 minutes. In some embodiments, the time allowed for binding of the molecule of interest to the label, e.g., an antibody-dye, is less than about 10 minutes. In some embodiments, the time allowed for binding of the molecule of interest to the label, e.g., an antibody-dye, is less than about 5 minutes. Excess label is removed by washing.

In some embodiments, the label is not eluted from the protein of interest. In other embodiments, the label is eluted from the protein of interest. Preferred elution buffers are effective in releasing the label without generating significant background. It is useful if the elution buffer is bacteriostatic. Elution buffers used in the invention can comprise a chaotrope, a buffer, an albumin to coat the surface of the microtiter plate, and a surfactant selected so as to produce a relatively low background. The chaotrope can comprise urea, a guanidinium compound, or other useful chaotropes. The buffer can comprise borate buffered saline, or other useful buffers. The protein carrier can comprise, e.g., an albumin, such as human, bovine, or fish albumin, an IgG, or other useful carriers. The surfactant can comprise an ionic or nonionic detergent including Tween 20, Triton X-100, sodium dodecyl sulfate (SDS), and others.

In another embodiment, the solid phase binding assay can be a competitive binding assay. One such method is as follows. First, a capture antibody immobilized on a binding surface is competitively bound by i) a molecule of interest, e.g., marker of a biological state, in a sample, and ii) a labeled analog of the molecule comprising a detectable label (the detection reagent). Second, the amount of the label using a single molecule analyzer is measured. Another such method is as follows. First, an antibody having a detectable label (the detection reagent) is competitively bound to i) a molecule of interest, e.g., marker of a biological state in a sample, and ii) an analog of the molecule that is immobilized on a binding surface (the capture reagent). Second, the amount of the label using a single molecule analyzer is measured. An "analog of a molecule" refers, herein, to a species that competes with a molecule for binding to a capture antibody. Examples of competitive immunoassays are disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

C. Detection of Molecule of Interest and Determination of Concentration

Following elution, the label is run through a single molecule detector in, e.g., the elution buffer. A processing sample may contain no label, a single label, or a plurality of labels. The number of labels corresponds or is proportional to (if dilutions or fractions of samples are used) the number of molecules of the molecule of interest, e.g., marker of a biological state captured during the capture step.

Any suitable single molecule detector capable of detecting the label used with the molecule of interest may be used. Suitable single molecule detectors are described herein. Typically the detector will be part of a system that includes an automatic sampler for sampling prepared samples, and, optionally, a recovery system to recover samples.

In some embodiments, the processing sample is analyzed in a single molecule analyzer that utilizes a capillary flow system, and that includes a capillary flow cell, a laser to illuminate an interrogation space in the capillary through which processing sample is passed, a detector to detect radiation emitted from the interrogation space, and a source of motive force to move a processing sample through the interrogation space. In some embodiments, the single molecule analyzer further comprises a microscope objective lens that collects light emitted from processing sample as it passes through the interrogation space, e.g., a high numerical aperture microscope objective. In some embodiments, the laser and detector are in a confocal arrangement. In some embodiments, the laser is a continuous wave laser. In some embodiments, the detector is an avalanche photodiode detector. In some embodiments, the source of motive force is a pump to provide pressure. In some embodiments, the invention provides an analyzer system that includes a sampling system capable of automatically sampling a plurality of samples providing a fluid communication between a sample container and the interrogation space. In some embodiments, the interrogation space has a volume of between about 0.001 and 500 pL, or between about 0.01 pL and 100 pL, or between about 0.01 pL and 10 pL, or between about 0.01 pL and 5 pL, or between about 0.01 pL and 0.5 pL, or between about 0.02 pL and about 300 pL, or between about 0.02 pL and about 50 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.004 pL and 100 pL. In some embodiments, the interrogation space has a volume between about 0.02 pL and 50 pL. In some embodiments, the interrogation space has a volume between about 0.001 pL and 10 pL. In some embodiments, the interrogation space has a volume between about 0.001 pL and 10 pL. In some embodiments, the interrogation space has a volume between about 0.01 pL and 5 pL. In some embodiments, the interrogation space has a volume between about 0.02 pL and 5 pL. In some embodiments, the interrogation space has a volume between about 0.05 pL and 5 pL. In some embodiments, the interrogation space has a volume between about 0.05 pL and 10 pL. In some embodiments, the interrogation space has a volume between about 0.5 pL and about 5 pL. In some embodiments, the interrogation space has a volume between about 0.02 pL and about 0.5 pL.

In some embodiments, the interrogation space has a volume of more than about 1 $\mu m^3$, more than about 2 $\mu m^3$, more than about 3 $\mu m^3$, more than about 4 $\mu m^3$, more than about 5 $\mu m^3$, more than about 10 $\mu m^3$, more than about 15 $\mu m^3$, more than about 30 $\mu m^3$, more than about 50 $\mu m^3$, more than about 75 $\mu m^3$, more than about 100 $\mu m^3$, more than about 150 $\mu m^3$, more than about 200 $\mu m^3$, more than about 250 $\mu m^3$, more than about 300 $\mu m^3$, more than about 400 $\mu m^3$, more than about 500 $\mu m^3$, more than about 550 $\mu m^3$, more than about 600 $\mu m^3$, more than about 750 $\mu m^3$, more than about 1000 $\mu m^3$, more than about 2000 $\mu m^3$, more than about 4000 $\mu m^3$, more than about 6000 $\mu m^3$, more than about 8000 $\mu m^3$, more than about 10000 $\mu m^3$, more than about 12000 $\mu m^3$, more than about 13000 $\mu m^3$, more than about 14000 $\mu m^3$, more than about 15000 $\mu m^3$, more than about 20000 $\mu m^3$, more than about 30000 $\mu m^3$, more than about 40000 $\mu m^3$, or more than about 50000 $\mu m^3$. In some embodiments, the interrogation space is of a volume less than about 50000 $\mu m^3$, less than about 40000 $\mu m^3$, less than about 30000 $\mu m^3$, less than about 20000 $\mu m^3$, less than about 15000 $\mu m^3$, less than about 14000 $\mu m^3$, less than about 13000 $\mu m^3$, less than about 12000 $\mu m^3$, less than about 11000 $\mu m^3$, less than about 9500 $\mu m^3$, less than about 8000 $\mu m^3$, less than about 6500 $\mu m^3$, less than about 6000 $\mu m^3$, less than about 5000 $\mu m^3$, less than about 4000 $\mu m^3$, less than about 3000 $\mu m^3$, less than about 2500 $\mu m^3$, less than about 2000 $\mu m^3$, less than about 1500 $\mu m^3$, less than about 1000 $\mu m^3$, less than about 800 $\mu m^3$, less than about 600 $\mu m^3$, less than about 400 $\mu m^3$, less than about 200 $\mu m^3$, less than about 100 $\mu m^3$, less than about 75 $\mu m^3$, less than about 50 $\mu m^3$, less than about 25 $\mu m^3$, less than about 20 $\mu m^3$, less than about 15 $\mu m^3$, less than about 14 $\mu m^3$, less than about 13 $\mu m^3$, less than about 12 $\mu m^3$, less than about 11 $\mu m^3$, less than about 10 $\mu m^3$, less than about 5 $\mu m^3$, less than about 4 $\mu m^3$, less than about 3 $\mu m^3$, less than about 2 $\mu m^3$, or less than about 1 $\mu m^3$. In some embodiments, the volume of the interrogation space is between about 1 $\mu m^3$ and about 10000 $\mu m^3$. In some embodiments, the interrogation space is between about 1 $\mu m^3$ and about 1000 $\mu m^3$. In some embodiments, the interrogation space is between about 1 $\mu m^3$ and about 100 $\mu m^3$. In some embodiments, the interrogation space is between about 1 $\mu m^3$ and about 50 $\mu m^3$. In some embodiments, the interrogation space is between about 1 $\mu m^3$ and about 10 $\mu m^3$. In some embodiments, the interrogation space is between about 2 $\mu m^3$ and about 10 $\mu m^3$. In some embodiments, the interrogation space is between about 3 $\mu m^3$ and about 7 $\mu m^3$.

In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space, an avalanche photodiode detector to detect radiation emitted from the interrogation space, and a pump to provide pressure to move a processing sample through the interrogation space, where the interrogation space is between about 0.02 pL and about 50 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.004 pL and about 100 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 10 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 5 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.5 pL and about 5 pL. In any of these embodiments the analyzer may contain not more than one interrogation space.

In some embodiments, the single molecule detector comprises a scanning analyzer system, as disclosed in U.S. patent application Ser. No. 12/338,955, filed Dec. 18, 2008 and entitled "Scanning Analyzer for Single Molecule Detection and Methods of Use." In some embodiments, the single molecule detector used in the methods of the invention uses a sample plate, a continuous wave laser directed toward a sample plate in which the sample is contained, a high numerical aperture microscope objective lens that collects light emitted from the sample as interrogation space is translated through the sample, wherein the lens has a numerical aperture of at least about 0.8, an avalanche photodiode detector to detect radiation emitted from the interrogation space, and a scan motor with a moveable mirror to translate the interrogation space through the sample wherein the interrogation space is between about 1 $\mu m^3$ and about 10000 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 $\mu m^3$ and about 1000 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 $\mu m^3$ and about 100 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 1 $\mu m^3$ and about 10 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 2 $\mu m^3$ and about 10 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 2 $\mu m^3$ and about 8 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, wherein the lens has a numerical aperture of at least about 0.8, an avalanche photodiode detector to detect radiation emitted from the interrogation space, and a scan motor for translating the interrogation space through the sample, wherein the interrogation space is between about 3 $\mu m^3$ and about 7 $\mu m^3$. In any of these embodiments, the analyzer can contain only one interrogation space.

In other embodiments, the single molecule detector used in the methods of the invention uses a sample plate, a continuous wave laser directed toward a sample plate in which the sample is contained, a high numerical aperture microscope objective lens that collects light emitted from the sample as interrogation space is translated through the sample, an avalanche photodiode detector to detect radiation emitted from the interrogation space, and a scan motor with a moveable mirror to translate the interrogation space through the sample wherein the interrogation space is between about 1 $\mu m^3$ and about 10000 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 $\mu m^3$ and about 1000 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 $\mu m^3$ and about 100 $\mu m^3$. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 1 $\mu m^3$ and about 10 µm³. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 2 µm³ and about 10 µm³. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 2 µm³ and about 8 µm³. In some embodiments, the single molecule detector used in the methods of the invention uses a sample plate, a continuous wave laser directed toward an interrogation space located within the sample, a high numerical aperture microscope objective lens that collects light emitted from the sample as the interrogation space is translated through the sample, an avalanche photodiode detector to detect radiation emitted from the interrogation space, and a scan motor for translating the interrogation space through the sample, wherein the interrogation space is between about 3 µm³ and about 7 µm³. In any of these embodiments, the analyzer can contain only one interrogation space.

In some embodiments, the single molecule detector is capable of determining a concentration for a molecule of interest in a sample where sample may range in concentration over a range of at least about 100-fold, or 1000-fold, or 10,000-fold, or 100,000-fold, or 300,00-fold, or 1,000,000-fold, or 10,000,000-fold, or 30,000,000-fold.

In some embodiments, the methods of the invention utilize a single molecule detector capable detecting a difference of less than about 50%, 40%, 30%, 20%, 15%, or 10% in concentration of an analyte between a first sample and a second sample that are introduced into the detector, where the volume of the first sample and said second sample introduced into the analyzer is less than about 100, 90, 80, 70, 60, 50, 40, 30, 20, 15, 10, 5, 4, 3, 2, or 1 µl, and wherein the analyte is present at a concentration of less than about 100, 90, 80, 70, 60, 50, 40, 30, 20, 15, 10, 5, 4, 3, 2, or 1 femtomolar. In some embodiments, the methods of the invention utilize a single molecule detector capable detecting a difference of less than about 50% in concentration of an analyte between a first sample and a second sample that are introduced into the detector, where the volume of the first sample and said second sample introduced into the analyzer is less than about 100 µl, and wherein the analyte is present at a concentration of less than about 100 femtomolar. In some embodiments, the methods of the invention utilize a single molecule detector capable detecting a difference of less than about 40% in concentration of an analyte between a first sample and a second sample that are introduced into the detector, where the volume of the first sample and said second sample introduced into the analyzer is less than about 50 µl, and wherein the analyte is present at a concentration of less than about 50 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 20 µl, and wherein the analyte is present at a concentration of less than about 20 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 10 µl, and wherein the analyte is present at a concentration of less than about 10 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 5 µl, and wherein the analyte is present at a concentration of less than about 5 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 5 µl, and wherein the analyte is present at a concentration of less than about 50 femtomolar.

The single molecule detector and systems are described in more detail below. Further embodiments of single molecule analyzers useful in the methods of the invention, such as detectors with more than one interrogation window, detectors utilize electrokinetic or electrophoretic flow, and the like, may be found in U.S. patent application Ser. No. 11/048,660, incorporated by reference herein in its entirety.

Between runs the instrument may be washed. A wash buffer that maintains the salt and surfactant concentrations of the sample may be used in some embodiments to maintain the conditioning of the capillary; i.e., to keep the capillary surface relatively constant between samples to reduce variability.

A feature that contributes to the extremely high sensitivity of the instruments and methods of the invention is the method of detecting and counting labels, which, in some embodiments, are attached to single molecules to be detected or, more typically, correspond to a single molecule to be detected. Briefly, the processing sample flowing through the capillary or contained on a sample plate is effectively divided into a series of detection events, by subjecting a given interrogation space of the capillary to EM radiation from a laser that emits light at an appropriate excitation wavelength for the fluorescent moiety used in the label for a predetermined period of time, and detecting photons emitted during that time. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. In some embodiments, processing sample concentration is dilute enough that, for a large percentage of detection events, the detection event represents only one label passing through the window, which corresponds to a single molecule of interest in the original sample, that is, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant.

Although other bin times can be used without departing from the scope of the present invention, in some embodiments the bin times are selected in the range of about 1 microsecond to about 5 ms. In some embodiments, the bin time is more than about 1, 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is less than about 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is about 1 to 1000 microseconds. In some embodiments, the bin time is about 1 to 750 microseconds. In some embodiments, the bin time is about 1 to 500 microseconds. In some embodiments, the bin time is about 1 to 250 microseconds. In some embodiments, the bin time is about 1 to 100 microseconds. In some embodiments, the bin time is about 1 to 50 microseconds. In some embodiments, the bin time is about 1 to 40 microseconds. In some embodiments, the bin time is about 1 to 30 microseconds. In some embodiments, the bin time is about 1 to 25 microseconds. In some embodiments, the bin time is about 1 to 20 microseconds. In some embodiments, the bin time is about 1 to 10 microseconds. In some embodiments, the bin time is about 1 to 7.5 microseconds. In some embodiments, the bin time is about 1 to 5 microseconds. In some embodiments, the bin time is about 5 to 500 microseconds. In some embodiments, the bin time is about 5 to 250 microseconds. In some embodiments, the bin time is about 5 to 100 microseconds. In some embodiments, the bin time is about 5 to 50 microseconds. In some embodiments, the bin time is about 5 to 20 microseconds. In some embodiments, the bin time is about 5 to 10 microseconds. In some embodiments, the bin time is about 10 to 500 microseconds. In some embodiments, the bin time is about 10 to 250 microseconds. In some embodiments, the bin time is about 10 to 100 microseconds. In some embodiments, the bin time is about 10 to 50 microseconds. In some embodiments, the bin time is about 10 to 30 microseconds. In some embodiments, the bin time is about 10 to 20 microseconds. In some embodiments, the bin time is about 1 microsecond. In some embodiments, the bin time is about 2 microseconds. In some embodiments, the bin time is about 3 microseconds. In some embodiments, the bin time is about 4 microseconds. In some embodiments, the bin time is about 5 microseconds. In some embodiments, the bin time is about 6 microseconds. In some embodiments, the bin time is about 7 microseconds. In some embodiments, the bin time is about 8 microseconds. In some embodiments, the bin time is about 9 microseconds. In some embodiments, the bin time is about 10 microseconds. In some embodiments, the bin time is about 11 microseconds. In some embodiments, the bin time is about 12 microseconds. In some embodiments, the bin time is about 13 microseconds. In some embodiments, the bin time is about 14 microseconds. In some embodiments, the bin time is about 5 microseconds. In some embodiments, the bin time is about 15 microseconds. In some embodiments, the bin time is about 16 microseconds. In some embodiments, the bin time is about 17 microseconds. In some embodiments, the bin time is about 18 microseconds. In some embodiments, the bin time is about 19 microseconds. In some embodiments, the bin time is about 20 microseconds. In some embodiments, the bin time is about 25 microseconds. In some embodiments, the bin time is about 30 microseconds. In some embodiments, the bin time is about 40 microseconds. In some embodiments, the bin time is about 50 microseconds. In some embodiments, the bin time is about 100 microseconds. In some embodiments, the bin time is about 250 microseconds. In some embodiments, the bin time is about 500 microseconds. In some embodiments, the bin time is about 750 microseconds. In some embodiments, the bin time is about 1000 microseconds.

In some embodiments, determining the concentration of a particle-label complex in a sample comprises determining the background noise level. In some embodiments, the background noise level is determined from the mean noise level, or the root-mean-square noise. In other cases, a typical noise value or a statistical value is chosen. In most cases, the noise is expected to follow a Poisson distribution.

Thus, as a label is encountered in the interrogation space, it is irradiated by the laser beam to generate a burst of photons. The photons emitted by the label are discriminated from background light or background noise emission by considering only the bursts of photons that have energy above a predetermined threshold energy level which accounts for the amount of background noise that is present in the sample. Background noise typically comprises low frequency emission produced, for example, by the intrinsic fluorescence of non-labeled particles that are present in the sample, the buffer or diluent used in preparing the sample for analysis, Raman scattering and electronic noise. In some embodiments, the value assigned to the background noise is calculated as the average background signal noise detected in a plurality of bins, which are measurements of photon signals that are detected in an interrogation space during a predetermined length of time. Thus in some embodiments, background noise is calculated for each sample as a number specific to that sample.

Given the value for the background noise, the threshold energy level can be assigned. As discussed above, the threshold value is determined to discriminate true signals (due to fluorescence of a label) from the background noise. Care must be taken in choosing a threshold value such that the number of false positive signals from random noise is minimized while the number of true signals which are rejected is also minimized Methods for choosing a threshold value include determining a fixed value above the noise level and calculating a threshold value based on the distribution of the noise signal. In one embodiment, the threshold is set at a fixed number of standard deviations above the background level. Assuming a Poisson distribution of the noise, using this method one can estimate the number of false positive signals over the time course of the experiment. In some embodiments, the threshold level is calculated as a value of 4 sigma above the background noise. For example, given an average background noise level of 200 photons, the analyzer system establishes a threshold level of $4\sqrt{200}$ above the average background/noise level of 200 photons to be 256 photons. Thus, in some embodiments, determining the concentration of a label in a sample includes establishing the threshold level above which photon signals represent the presence of a label. Conversely, photon signals that have an energy level that is not greater than that of the threshold level indicate the absence of a label.

Many bin measurements are taken to determine the concentration of a sample, and the absence or presence of a label is ascertained for each bin measurement. Typically, 60,000 measurements or more can made in one minute (e.g., in embodiments in which the bin size is 1 ms—for smaller bin sizes the number of measurements is correspondingly larger, e.g., 6,000,000 measurements per minute for a bin size of 10 microseconds). Thus, no single measurement is crucial and the method provides for a high margin of error. The bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements. Thus, in some embodiments, determining the concentration of a label in a sample comprises detecting the bin measurements that reflect the presence of a label.

The signal to noise ratio or the sensitivity of the analyzer system can be increased by minimizing the time that background noise is detected during a bin measurement in which a particle-label complex is detected. For example, in a bin measurement lasting 1 millisecond during which one particle-label complex is detected when passing across an interrogation space within 250 microseconds, 750 microseconds of the 1 millisecond are spent detecting background noise emission. The signal to noise ratio can be improved by decreasing the bin time. In some embodiments, the bin time is 1 millisecond. In other embodiments, the bin time is 750, 500, 250 microseconds, 100 microseconds, 50 microseconds, 25 microseconds or 10 microseconds. Other bin times are as described herein.

Other factors that affect measurements are the brightness or dimness of the fluorescent moiety, the flow rate, and the power of the laser. Various combinations of the relevant factors that allow for detection of label will be apparent to those of skill in the art. In some embodiments, the bin time is adjusted without changing the flow rate. It will be appreciated by those of skill in the art that as bin time decreases, laser power output directed at the interrogation space must increase to maintain a constant total energy applied to the interrogation space during the bin time. For example, if bin time is decreased from 1000 microseconds to 250 microseconds, as a first approximation, laser power output must be increased approximately four-fold. These settings allow for the detection of the same number of photons in a 250 μs as the number of photons counted during the 1000 μs given the previous settings, and allow for faster analysis of sample with lower backgrounds and thus greater sensitivity. In addition, flow rates may be adjusted in order to speed processing of sample. These numbers are merely exemplary, and the skilled practitioner can adjust the parameters as necessary to achieve the desired result.

In some embodiments, the interrogation space encompasses the entire cross-section of the sample stream. When the interrogation space encompasses the entire cross-section of the sample stream, only the number of labels counted and the volume passing through a cross-section of the sample stream in a set length of time are needed to calculate the concentration of the label in the processing sample. In some embodiments, the interrogation space can be defined to be smaller than the cross-sectional area of sample stream by, for example, the interrogation space is defined by the size of the spot illuminated by the laser beam. In some embodiments, the interrogation space can be defined by adjusting the apertures 306 (FIG. 1A) or 358 and 359 (FIG. 1B) of the analyzer and reducing the illuminated volume that is imaged by the objective lens to the detector. In the embodiments when the interrogation space is defined to be smaller than the cross-sectional area of sample stream, the concentration of the label can be determined by interpolation of the signal emitted by the complex from a standard curve that is generated using one or more samples of known standard concentrations. In yet other embodiments, the concentration of the label can be determined by comparing the measured particles to an internal label standard. In embodiments when a diluted sample is analyzed, the dilution factor is accounted in calculating the concentration of the molecule of interest in the starting sample.

As discussed above, when the interrogation space encompasses the entire cross-section of the sample stream, only the number of labels counted passing through a cross-section of the sample stream in a set length of time (bin) and the volume of sample that was interrogated in the bin are needed to calculate the concentration the sample. The total number of labels contained in the "yes" bins is determined and related to the sample volume represented by the total number of bins used in the analysis to determine the concentration of labels in the processing sample. Thus, in one embodiment, determining the concentration of a label in a processing sample comprises determining the total number of labels detected "yes" bins and relating the total number of detected labels to the total sample volume that was analyzed. The total sample volume that is analyzed is the sample volume that is passed through the capillary flow cell and across the interrogation space in a specified time interval. Alternatively, the concentration of the label complex in a sample is determined by interpolation of the signal emitted by the label in a number of bins from a standard curve that is generated by determining the signal emitted by labels in the same number of bins by standard samples containing known concentrations of the label.

In some embodiments, the number of individual labels that are detected in a bin is related to the relative concentration of the particle in the processing sample. At relatively low concentrations, for example at concentrations below about $10^{-16}$ M the number of labels is proportional to the photon signal that is detected in a bin. Thus, at low concentrations of label the photon signal is provided as a digital signal. At relatively higher concentrations, for example at concentrations greater than about $10^{-16}$ M, the proportionality of photon signal to a label is lost as the likelihood of two or more labels crossing the interrogation space at about the same time and being counted as one becomes significant. Thus, in some embodiments, individual particles in a sample of a concentration greater than about $10^{-16}$ M are resolved by decreasing the length of time of the bin measurement.

Alternatively, in other embodiments, the total photon signal that is emitted by a plurality of particles that are present in any one bin is detected. These embodiments allow for single molecule detectors of the invention wherein the dynamic range is at least 3, 3.5, 4, 4.5, 5.5, 6, 6.5, 7, 7.5, 8, or more than 8 logs.

"Dynamic range," as that term is used herein, refers to the range of sample concentrations that may be quantitated by the instrument without need for dilution or other treatment to alter the concentration of successive samples of differing concentrations, where concentrations are determined with an accuracy appropriate for the intended use. For example, if a microtiter plate contains a sample of 1 femtomolar concentration for an analyte of interest in one well, a sample of 10,000 femtomolar concentration for an analyte of interest in another well, and a sample of 100 femtomolar concentration for the analyte in a third well, an instrument with a dynamic range of at least 4 logs and a lower limit of quantitation of 1 femtomolar is able to accurately quantitate the concentration of all the samples without the need for further treatment to adjust concentration, e.g., dilution. Accuracy may be determined by standard methods, e.g., using a series of standards of concentrations that span the dynamic range and constructing a standard curve. Standard measures of fit of the resulting standard curve may be used as a measure of accuracy, e.g., an $r^2$ greater than about 0.7, 0.75, 0.8, 0.85, 0.9, 0.91, 0.92, 0.93, 0.94, 0.95, 0.96, 0.97, 0.98, or 0.99.

Increased dynamic range is achieved by altering the manner in which data from the detector is analyzed, and/or by the use of an attenuator between the detector and the interrogation space. At the low end of the range, where processing sample is sufficiently dilute that each detection event, i.e., each burst of photons above a threshold level in a bin (the "event photons"), likely represents only one label, the data is analyzed to count detection events as single molecules. Thereby each bin is analyzed as a simple "yes" or "no" for the presence of label, as described above. For a more concentrated processing sample, where the likelihood of two or more labels occupying a single bin becomes significant, the number of event photons in a significant number of bins is found to be substantially greater than the number expected for a single label, e.g., the number of event photons in a significant number of bins corresponds to two-fold, three-fold, or more, than the number of event photons expected for a single label. For these samples, the instrument changes its method of data analysis to one of integrating the total number of event photons for the bins of the processing sample. This total will be proportional to the total number of labels that were in all the bins. For an even more concentrated processing sample, where many labels are present in most bins, background noise becomes an insignificant portion of the total signal from each bin, and the instrument changes its method of data analysis to one of counting total photons per bin (including background). An even further increase in dynamic range can be achieved by the use of an attenuator between the flow cell and the detector, when concentrations are such that the intensity of light reaching the detector would otherwise exceed the capacity of the detector for accurately counting photons, i.e., saturate the detector.

The instrument may include a data analysis system that receives input from the detector and determines the appropriate analysis method for the sample being run, and outputs values based on such analysis. The data analysis system may further output instructions to use or not use an attenuator, if an attenuator is included in the instrument.

By utilizing such methods, the dynamic range of the instrument can be dramatically increased. Thus, in some embodiments, the instrument is capable of measuring concentrations of samples over a dynamic range of more than about 1000 (3 log), 10,000 (4 log), 100,000 (5 log), 350,000 (5.5 log), 1,000,000 (6 log), 3,500,000 (6.5 log), 10,000,000 (7 log), 35,000,000 (7.5 log), or 100,000,000 (8 log). In some embodiments, the instrument is capable of measuring concentrations of samples over a dynamic range of more than about 100,000 (5 log). In some embodiments, the instrument is capable of measuring concentrations of samples over a dynamic range of more than about 1,000,000 (6 log). In some embodiments, the instrument is capable of measuring concentrations of samples over a dynamic range of more than about 10,000,000 (7 log). In some embodiments, the instrument is capable of measuring the concentrations of samples over a dynamic range of from about 1-10 femtomolar to at least about 1000; 10,000; 100,000; 350,000; 1,000,000; 3,500,000; 10,000,000; or 35,000,000 femtomolar. In some embodiments, the instrument is capable of measuring the concentrations of samples over a dynamic range of from about 1-10 femtomolar to at least about 10,000 femtomolar. In some embodiments, the instrument is capable of measuring the concentrations of samples over a dynamic range of from about 1-10 femtomolar to at least about 100,000 femtomolar. In some embodiments, the instrument is capable of measuring the concentrations of samples over a dynamic range of from about 1-10 femtomolar to at least about 1,000,000 femtomolar. In some embodiments, the instrument is capable of measuring the concentrations of samples over a dynamic range of from about 1-10 femtomolar to at least about 10,000,000.

In some embodiments, an analyzer or analyzer system of the invention is capable of detecting an analyte, e.g., a biomarker, at a limit of detection of less than 1 nanomolar, or 1 picomolar, or 1 femtomolar, or 1 attomolar, or 1 zeptomolar. In some embodiments, the analyzer or analyzer system is capable of detecting a change in concentration of the analyte, or of multiple analytes, e.g., a biomarker or biomarkers, from one sample to another sample of less than about 0.1%, 1%, 2%, 5%, 10%, 20%, 30%, 40%, 50%, 60%, 70% or 80% when the biomarker is present at a concentration of less than 1 nanomolar, or 1 picomolar, or 1 femtomolar, or 1 attomolar, or 1 zeptomolar, in the samples, and when the size of each of the sample is less than about 100, 50, 40, 30, 20, 10, 5, 2, 1, 0.1, 0.01, 0.001, or 0.0001 µl. In some embodiments, the analyzer or analyzer system is capable of detecting a change in concentration of the analyte from a first sample to a second sample of less than about 20%, when the analyte is present at a concentration of less than about 1 picomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 100 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 50 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 5 µl. In some embodiments, the analyzer or analyzer system is capable of detecting a change in concentration of the analyte from a first sample to a second sample of less than about 20%, when the analyte is present at a concentration of less than about 1 femtomolar, and when the size of each of the samples is less than about 5 µA The single molecule detectors of the present invention are capable of detecting molecules of interest in a highly sensitive manner with a very low coefficient of variation (CV). In some embodiments, the CV is less than about 50%, 40%, 30%, 25%, 20%, 15%, 10%, 5%, or less than about 1%. In some embodiments, the CV is less than about 50%. In some embodiments, the CV is less than about 40%. In some embodiments, the CV is less than about 30%. In some embodiments, the CV is less than about 25%. In some embodiments, the CV is less than about 20%. In some embodiments, the CV is less than about 15%. In some embodiments, the CV is less than about 10%. In some embodiments, the CV is less than about 5%. In some embodiments, the CV is less than about 1%. In some embodiments, the limit of detection (LOD) is less than about 100 pg/ml and the CV is less than about 10%. In some embodiments, the limit of detection (LOD) is less than about 50 pg/ml and the CV is less than about 10%. In some embodiments, the limit of detection (LOD) is less than about 40 pg/ml and the CV is less than about 10%. In some embodiments, the limit of detection (LOD) is less than about 30 pg/ml and the CV is less than about 10%. In some embodiments, the limit of detection (LOD) is less than about 20 pg/ml and the CV is less than about 10%. In some embodiments, the limit of detection (LOD) is less than about 15 pg/ml and the CV is less than about 10%. In some embodiments, the limit of detection (LOD) is less than about 10 pg/ml and the CV is less than about 10%. In some embodiments, the limit of detection (LOD) is less than about 5 pg/ml and the CV is less than about 10%. In some embodiments, the limit of detection (LOD) is less than about 1 pg/ml and the CV is less than about 10%. In some embodiments, the limit of detection (LOD) is less than about 0.05 pg/ml and the CV is less than about 10%. In some embodiments, the limit of detection (LOD) is less than about 0.01 pg/ml and the CV is less than about 10%. In some embodiments, the limit of detection (LOD) is less than about 10 pg/ml and the CV is less than about 50%. In some embodiments, the limit of detection (LOD) is less than about 10 pg/ml and the CV is less than about 25%. In some embodiments, the limit of detection (LOD) is less than about 10 pg/ml and the CV is less than about 10%. In some embodiments, the limit of detection (LOD) is less than about 10 pg/ml and the CV is less than about 5%. In some embodiments, the limit of detection (LOD) is less than about 10 pg/ml and the CV is less than about 1%. In some embodiments, the limit of detection (LOD) is less than about 5 pg/ml and the CV is less than about 100%. In some embodiments, the limit of detection (LOD) is less than about 5 pg/ml and the CV is less than about 50%. In some embodiments, the limit of detection (LOD) is less than about 5 pg/ml and the CV is less than about 25%. In some embodiments, the limit of detection (LOD) is less than about 5 pg/ml and the CV is less than about 10%. In some embodiments, the limit of detection (LOD) is less than about 5 pg/ml and the CV is less than about 5%. In some embodiments, the limit of detection (LOD) is less than about 5 pg/ml and the CV is less than about 1%. In some embodiments, the limit of detection (LOD) is less than about 1 pg/ml and the CV is less than about 100%. In some embodiments, the limit of detection (LOD) is less than about 1 pg/ml and the CV is less than about 50%. In some embodiments, the limit of detection (LOD) is less than about 1 pg/ml and the CV is less than about 25%. In some embodiments, the limit of detection (LOD) is less than about 1 pg/ml and the CV is less than about 10%. In some embodiments, the limit of detection (LOD) is less than about 1 pg/ml and the CV is less than about 5%. In some embodiments, the limit of detection (LOD) is less than about 1 pg/ml and the CV is less than about 1%.

V. Instruments and Systems Suitable for Highly Sensitive Analysis of Molecules

The methods of the invention utilize analytical instruments of high sensitivity, e.g., single molecule detectors. Such single molecule detectors include embodiments as hereinafter described.

In some embodiments, the invention provides an analyzer system kit for detecting a single protein molecule in a sample, said system includes an analyzer system for detecting a single protein molecule in a sample and least one label that includes a fluorescent moiety and a binding partner for the protein molecule, where the analyzer includes an electromagnetic radiation source for stimulating the fluorescent moiety; a capillary flow cell for passing the label; a source of motive force for moving the label in the capillary flow cell; an interrogation space defined within the capillary flow cell for receiving electromagnetic radiation emitted from the electromagnetic source; and an electromagnetic radiation detector operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules.

Figure 15:
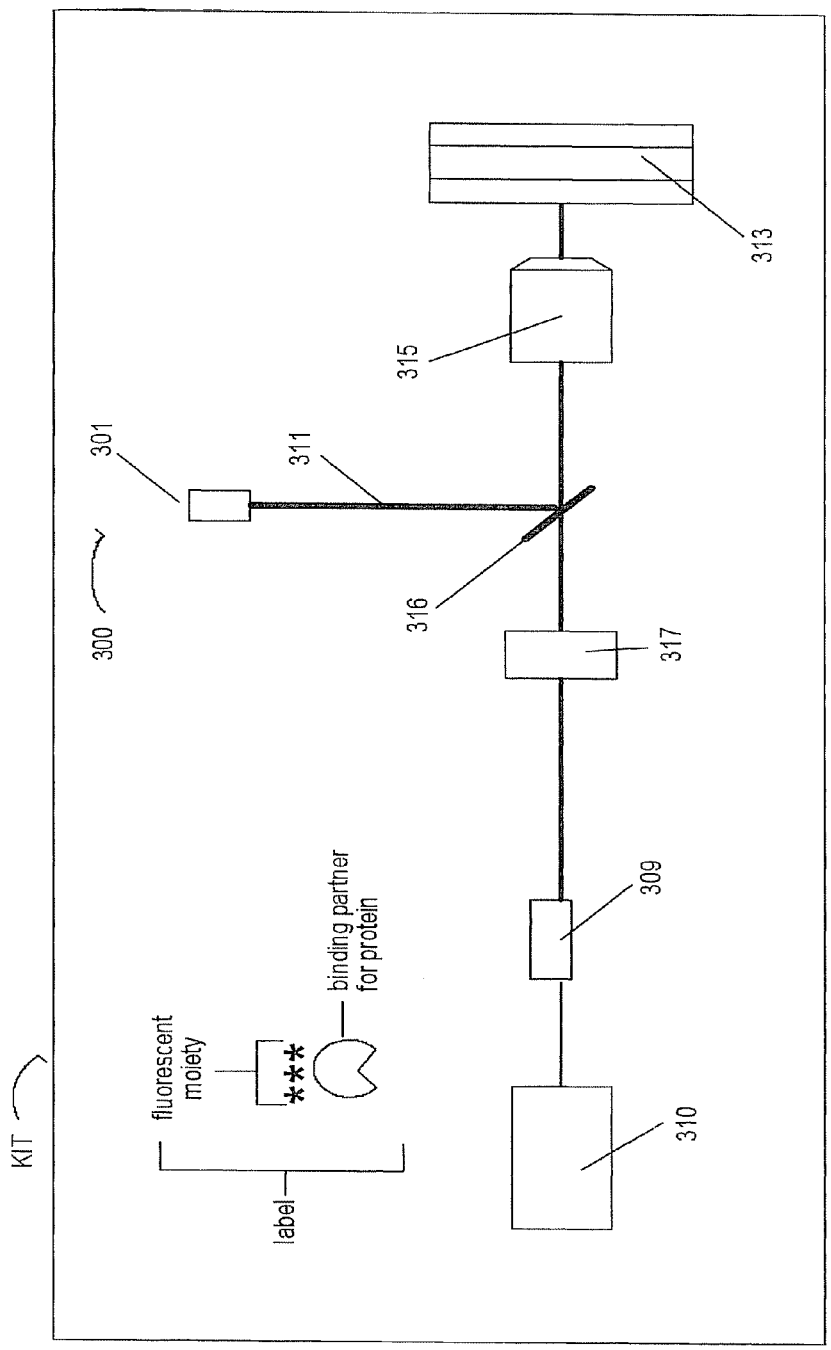
FIG. 15 illustrates a schematic representation of a kit that includes an analyzer system for detecting a single protein molecule in a sample and least one label that includes a fluorescent moiety and a binding partner for the protein molecule, where the analyzer includes an electromagnetic radiation source for stimulating the fluorescent moiety; a capillary flow cell for passing the label; a source of motive force for moving the label in the capillary flow cell; an interrogation space defined within the capillary flow cell for receiving electromagnetic radiation emitted from the electromagnetic source; and an electromagnetic radiation detector operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules.

One embodiment of an analyzer kit of the invention is depicted in FIG. 15. The kit includes a label for a protein molecule that includes a binding partner for a protein molecule and a fluorescent moiety. The kit further includes an analyzer system for detecting a single protein molecule (300) that includes an electromagnetic radiation source 301 for stimulating the fluorescent moiety, a capillary flow cell 313 for passing the label; a source of motive force for moving the label in the capillary flow cell (not shown); an interrogation space defined within the capillary flow cell for receiving electromagnetic radiation emitted from the electromagnetic source 314 (FIG. 2A); and an electromagnetic radiation detector 309 operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments, the beam 311 from an electromagnetic radiation source 301 is focused by the microscope objective 315 to form one interrogation space 314 (FIG. 2A) within the capillary flow cell 313. The microscope objective may have a numerical aperture of equal to or greater than 0.7, 0.8, 0.9, or 1.0 in some embodiments.

In some embodiments of the analyzer system kit, the analyzer comprises not more than one interrogation space. In some embodiments, the electromagnetic radiation source is a laser that has a power output of at least about 3, 5, 10, or 20 mW. In some embodiments, the fluorescent moiety comprises a fluorescent molecule. In some embodiments, the fluorescent molecule is a dye molecule, such as a dye molecule that comprises at least one substituted indolium ring system in which the substituent on the 3-carbon of the indolium ring contains a chemically reactive group or a conjugated substance. In some embodiments, the fluorescent moiety is a quantum dot. In some embodiments, the electromagnetic radiation source is a continuous wave electromagnetic radiation source, such as a light-emitting diode or a continuous wave laser. In some embodiments, the motive force is pressure. In some embodiments, the detector is an avalanche photodiode detector. In some embodiments, the analyzer utilizes a confocal optical arrangement for deflecting a laser beam onto said interrogation space and for imaging said stimulated dye molecule (shown in FIGS. 1, 3), wherein said confocal optical arrangement comprises an objective lens having a numerical aperture of at least about 0.8. In some embodiments, the analyzer further comprises a sampling system capable of automatically sampling a plurality of samples and providing a fluid communication between a sample container and said interrogation space. In some embodiments, the analyzer system further comprises a sample recovery system in fluid communication with said interrogation space, wherein said recovery system is capable of recovering substantially all of said sample. In some embodiments, the kit further includes instructions for use of the system.

A. Apparatus/System

In one aspect, the methods described herein utilize an analyzer system capable of detecting a single molecule in a sample. In one embodiment, the analyzer system is capable of single molecule detection of a fluorescently labeled particle wherein the analyzer system detects energy emitted by an excited fluorescent label in response to exposure by an electromagnetic radiation source when the single particle is present in an interrogation space defined within a capillary flow cell fluidly connected to the sampling system of the analyzer system. In a further embodiment of the analyzer system, the single particle moves through the interrogation space of the capillary flow cell by means of a motive force. In another embodiment of the analyzer system, an automatic sampling system may be included in the analyzer system for introducing the sample into the analyzer system. In another embodiment of the analyzer system, a sample preparation system may be included in the analyzer system for preparing a sample. In a further embodiment, the analyzer system may contain a sample recovery system for recovering at least a portion of the sample after analysis is complete.

In one aspect, the analyzer system consists of an electromagnetic radiation source for exciting a single particle labeled with a fluorescent label. In one embodiment, the electromagnetic radiation source of the analyzer system is a laser. In a further embodiment, the electromagnetic radiation source is a continuous wave laser.

In a typical embodiment, the electromagnetic radiation source excites a fluorescent moiety attached to a label as the label passes through the interrogation space of the capillary flow cell. In some embodiments, the fluorescent label moiety includes one or more fluorescent dye molecules. In some embodiments, the fluorescent label moiety is a quantum dot. Any fluorescent moiety as described herein may be used in the label.

A label is exposed to electromagnetic radiation when the label passes through an interrogation space located within the capillary flow cell. The interrogation space is typically fluidly connected to a sampling system. In some embodiments the label passes through the interrogation space of the capillary flow cell due to a motive force to advance the label through the analyzer system. The interrogation space is positioned such that it receives electromagnetic radiation emitted from the radiation source. In some embodiments, the sampling system is an automated sampling system capable of sampling a plurality of samples without intervention from a human operator.

The label passes through the interrogation space and emits a detectable amount of energy when excited by the electromagnetic radiation source. In one embodiment, an electromagnetic radiation detector is operably connected to the interrogation space. The electromagnetic radiation detector is capable of detecting the energy emitted by the label, e.g., by the fluorescent moiety of the label.

In a further embodiment of the analyzer system, the system further includes a sample preparation mechanism where a sample may be partially or completely prepared for analysis by the analyzer system. In some embodiments of the analyzer system, the sample is discarded after it is analyzed by the system. In other embodiments, the analyzer system further includes a sample recovery mechanism whereby at least a portion, or alternatively all or substantially all, of the sample may be recovered after analysis. In such an embodiment, the sample can be returned to the origin of the sample. In some embodiments, the sample can be returned to microtiter wells on a sample microtiter plate. The analyzer system typically further consists of a data acquisition system for collecting and reporting the detected signal.

B. Single Particle Analyzer

As shown in FIG. 1A, described herein is one embodiment of an analyzer system 300. The analyzer system 300 includes an electromagnetic radiation source 301, a mirror 302, a lens 303, a capillary flow cell 313, a microscopic objective lens 305, an aperture 306, a detector lens 307, a detector filter 308, a single photon detector 309, and a processor 310 operatively connected to the detector.

Figure 2A:
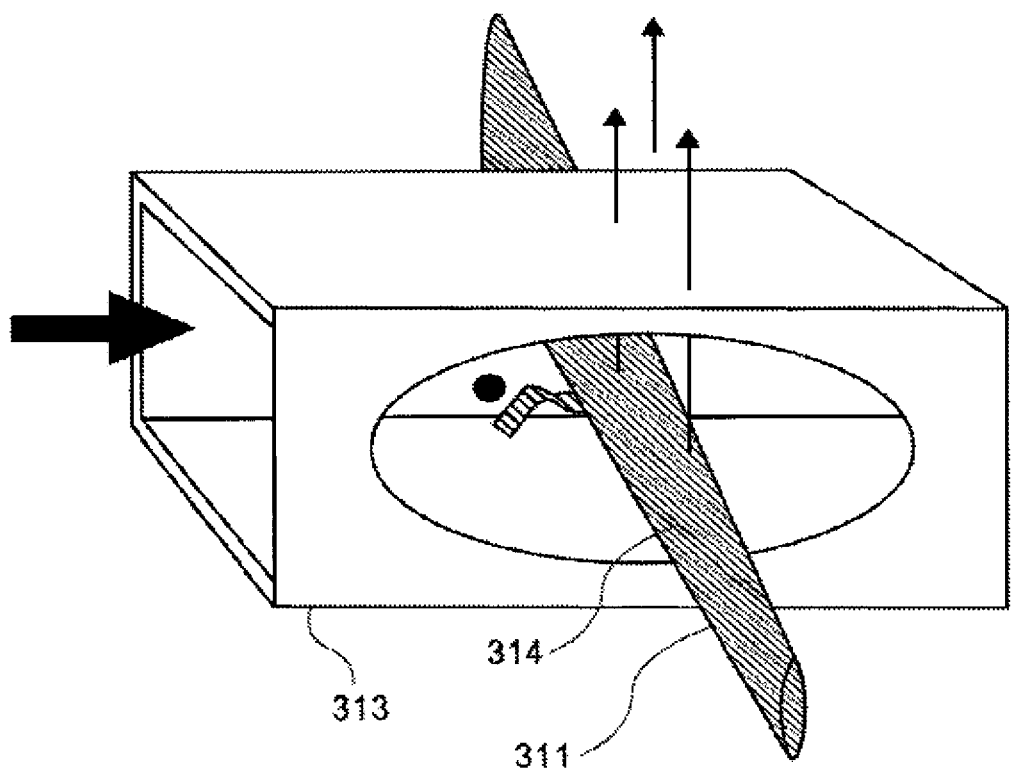
FIGS. 2A and 2B illustrate schematic diagrams of a capillary flow cell for a single particle analyzer.

In operation the electromagnetic radiation source 301 is aligned so that its output 311 is reflected off of a front surface 312 of mirror 302. The lens 303 focuses the beam 311 onto a single interrogation space (an illustrative example of an interrogation space 314 is shown in FIG. 2A) in the capillary flow cell 313. The microscope objective lens 305 collects light from sample particles and forms images of the beam onto the aperture 306. The aperture 306 affects the fraction of light emitted by the specimen in the interrogation space of the capillary flow cell 313 that can be collected. The detector lens 307 collects the light passing through the aperture 306 and focuses the light onto an active area of the detector 309 after it passes through the detector filters 308. The detector filters 308 minimize aberrant noise signals due to light scatter or ambient light while maximizing the signal emitted by the excited fluorescent moiety bound to the particle. The processor 310 processes the light signal from the particle according to the methods described herein.

In one embodiment, the microscope objective lens 305 is a high numerical aperture microscope objective. As used herein, "high numerical aperture lens" include a lens with a numerical aperture of equal to or greater than 0.6. The numerical aperture is a measure of the number of highly diffracted image-forming light rays captured by the objective. A higher numerical aperture allows increasingly oblique rays to enter the objective lens and thereby produce a more highly resolved image. Additionally, the brightness of an image increases with a higher numerical aperture. High numerical aperture lenses are commercially available from a variety of vendors, and any one lens having a numerical aperture of equal to or greater than approximately 0.6 may be used in the analyzer system. In some embodiments, the lens has a numerical aperture of about 0.6 to about 1.3. In some embodiments, the lens has a numerical aperture of about 0.6 to about 1.0. In some embodiments, the lens has a numerical aperture of about 0.7 to about 1.2. In some embodiments, the lens has a numerical aperture of about 0.7 to about 1.0. In some embodiments, the lens has a numerical aperture of about 0.7 to about 0.9. In some embodiments, the lens has a numerical aperture of about 0.8 to about 1.3. In some embodiments, the lens has a numerical aperture of about 0.8 to about 1.2. In some embodiments, the lens has a numerical aperture of about 0.8 to about 1.0. In some embodiments, the lens has a numerical aperture of at least about 0.6. In some embodiments, the lens has a numerical aperture of at least about 0.7. In some embodiments, the lens has a numerical aperture of at least about 0.8. In some embodiments, the lens has a numerical aperture of at least about 0.9. In some embodiments, the lens has a numerical aperture of at least about 1.0. In some embodiments, the aperture of the microscope objective lens 305 is approximately 1.25. In an embodiment where a microscope objective lens 305 of 0.8 is used, a Nikon 60×/0.8 NA Achromat lens (Nikon, Inc., USA) can be used.

In some embodiments, the electromagnetic radiation source 301 is a laser that emits light in the visible spectrum. In all embodiments, the electromagnetic radiation source is set such that wavelength of the laser is set such that it is of a sufficient wavelength to excite the fluorescent label attached to the particle. In some embodiments, the laser is a continuous wave laser with a wavelength of 639 nm. In other embodiments, the laser is a continuous wave laser with a wavelength of 532 nm. In other embodiments, the laser is a continuous wave laser with a wavelength of 422 nm. In other embodiments, the laser is a continuous wave laser with a wavelength of 405 nm. Any continuous wave laser with a wavelength suitable for exciting a fluorescent moiety as used in the methods and compositions of the invention may be used without departing from the scope of the invention.

In a single particle analyzer system 300, as each particle passes through the beam 311 of the electromagnetic radiation source, the particle enters into an excited state. When the particle relaxes from its excited state, a detectable burst of light is emitted. The excitation-emission cycle is repeated many times by each particle in the length of time it takes for it to pass through the beam allowing the analyzer system 300 to detect tens to thousands of photons for each particle as it passes through an interrogation space 314. Photons emitted by fluorescent particles are registered by the detector 309 (FIG. 1A) with a time delay indicative of the time for the particle label complex to pass through the interrogation space. The photon intensity is recorded by the detector 309 and sampling time is divided into bins, which are uniform, arbitrary, time segments with freely selectable time channel widths. The number of signals contained in each bin evaluated. One or a combination of several statistical analytical methods are employed in order to determine when a particle is present. Such methods include determining the baseline noise of the analyzer system and setting a signal strength for the fluorescent label at a statistical level above baseline noise to eliminate false positive signals from the detector.

The electromagnetic radiation source 301 is focused onto a capillary flow cell 313 of the analyzer system 300 where the capillary flow cell 313 is fluidly connected to the sample system. An interrogation space 314 is shown in FIG. 2A. The beam 311 from the continuous wave electromagnetic radiation source 301 of FIG. 1A is optically focused to a specified depth within the capillary flow cell 313. The beam 311 is directed toward the sample-filled capillary flow cell 313 at an angle perpendicular to the capillary flow cell 313. The beam 311 is operated at a predetermined wavelength that is selected to excite a particular fluorescent label used to label the particle of interest. The size or volume of the interrogation space 314 is determined by the diameter of the beam 311 together with the depth at which the beam 311 is focused. Alternatively, the interrogation space can be determined by running a calibration sample of known concentration through the analyzer system.

When single molecules are detected in the sample concentration, the beam size and the depth of focus required for single molecule detection are set and thereby define the size of the interrogation space 314. The interrogation space 314 is set such that, with an appropriate sample concentration, only one particle is present in the interrogation space 314 during each time interval over which time observations are made.

It will be appreciated that the detection interrogation volume as defined by the beam is not perfectly spherically shaped, and typically is a "bow-tie" shape. However, for the purposes of definition, "volumes" of interrogation spaces are defined herein as the volume encompassed by a sphere of a diameter equal to the focused spot diameter of the beam. The focused spot of the beam 311 may have various diameters without departing from the scope of the present invention. In some embodiments, the diameter of the focused spot of the beam is about 1 to about 5, 10, 15, or 20 microns, or about 5 to about 10, 15, or 20 microns, or about 10 to about 20 microns, or about 10 to about 15 microns. In some embodiments, the diameter of the focused spot of the beam is about 1, 2, 3, 4, 5, 6, 7, 8, 9, 10, 11, 12, 13, 14, 15, 16, 17, 18, 19, or 20 microns. In some embodiments, the diameter of the focused spot of the beam is about 5 microns. In some embodiments, the diameter of the focused spot of the beam is about 10 microns. In some embodiments, the diameter of the focused spot of the beam is about 12 microns. In some embodiments, the diameter of the focused spot of the beam is about 13 microns. In some embodiments, the diameter of the focused spot of the beam is about 14 microns. In some embodiments, the diameter of the focused spot of the beam is about 15 microns. In some embodiments, the diameter of the focused spot of the beam is about 16 microns. In some embodiments, the diameter of the focused spot of the beam is about 17 microns. In some embodiments, the diameter of the focused spot of the beam is about 18 microns. In some embodiments, the diameter of the focused spot of the beam is about 19 microns. In some embodiments, the diameter of the focused spot of the beam is about 20 microns.

Figure 1B:
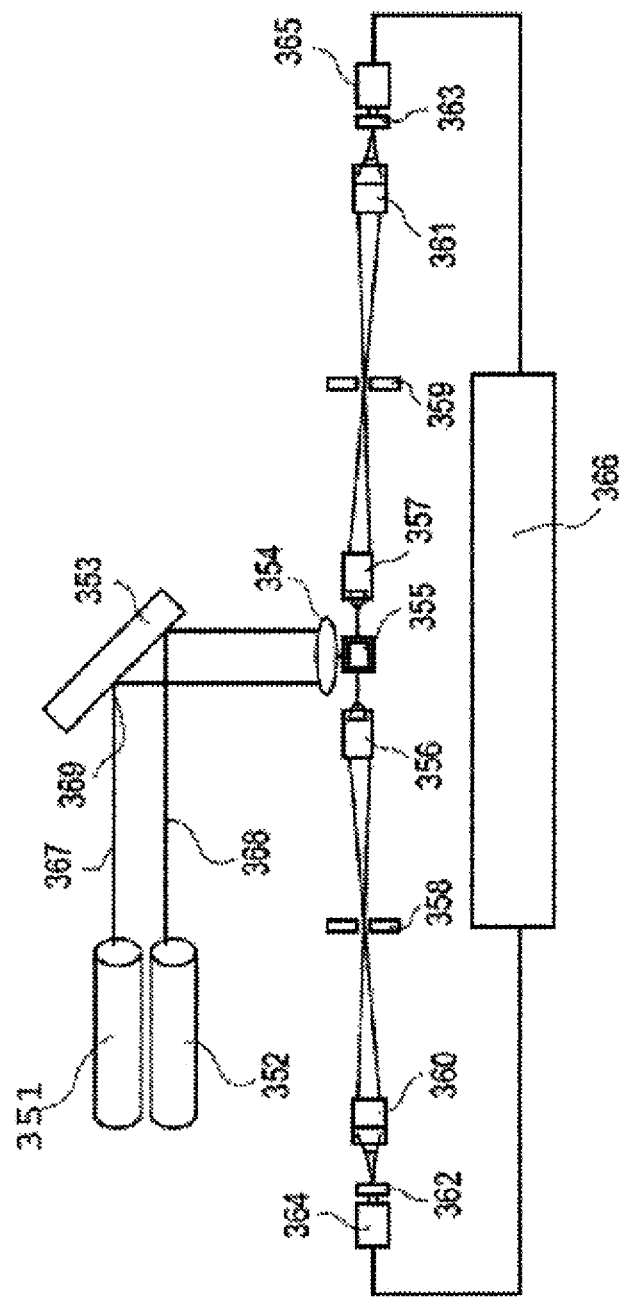

In an alternate embodiment of the single particle analyzer system, more than one electromagnetic radiation source can be used to excite particles labeled with fluorescent labels of different wavelengths. In another alternate embodiment, more than one interrogation space in the capillary flow cell can be used. In another alternate embodiment, multiple detectors can be employed to detect different emission wavelengths from the fluorescent labels. An illustration incorporating each of these alternative embodiments of an analyzer system is shown in FIG. 1B. These embodiments are incorporated by reference from previous U.S. patent application Ser. No. 11/048,660.

In some embodiments of the analyzer system 300, a motive force is required to move a particle through the capillary flow cell 313 of the analyzer system 300. In one embodiment, the motive force can be a form of pressure. The pressure used to move a particle through the capillary flow cell can be generated by a pump. In some embodiments, a Scivex, Inc. HPLC pump can be used. In some embodiments where a pump is used as a motive force, the sample can pass through the capillary flow cell at a rate of 1 µL/min to about 20 µL/min, or about 5 µL/min to about 20 µL/min. In some embodiments, the sample can pass through the capillary flow cell at a rate of about 5 µL/min. In some embodiments, the sample can pass through the capillary flow cell at a rate of about 10 µL/min. In some embodiments, the sample can pass through the capillary flow cell at a rate of about 15 µL/min. In some embodiments, the sample can pass through the capillary flow cell at a rate of about 20 µL/min. In some embodiments, an electrokinetic force can be used to move the particle through the analyzer system. Such a method has been previously disclosed and is incorporated by reference from previous U.S. patent application Ser. No. 11/048,660.

In one aspect of the analyzer system 300, the detector 309 of the analyzer system detects the photons emitted by the fluorescent label. In one embodiment, the photon detector is a photodiode. In a further embodiment, the detector is an avalanche photodiode detector. In some embodiments, the photodiodes can be silicon photodiodes with a wavelength detection of 190 nm and 1100 nm. When germanium photodiodes are used, the wavelength of light detected is between 400 nm to 1700 nm. In other embodiments, when an indium gallium arsenide photodiode is used, the wavelength of light detected by the photodiode is between 800 nm and 2600 nm. When lead sulfide photodiodes are used as detectors, the wavelength of light detected is between 1000 nm and 3500 nm.

In some embodiments, the optics of the electromagnetic radiation source 301 and the optics of the detector 309 are arranged in a conventional optical arrangement. In such an arrangement, the electromagnetic radiation source and the detector are aligned on different focal planes. The arrangement of the laser and the detector optics of the analyzer system as shown in FIGS. 1A and 1B is that of a conventional optical arrangement.

Figure 3A:
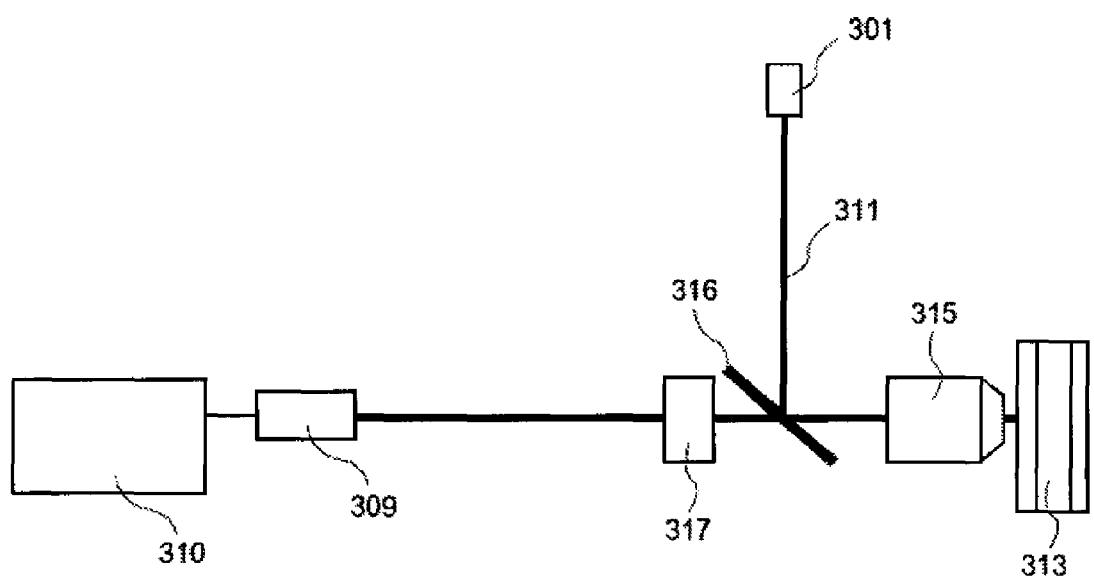
FIGS. 3A and 3B illustrate schematic diagrams showing the conventional (A) and confocal (B) positioning of laser and detector optics of a single particle analyzer.
Figure 3B:
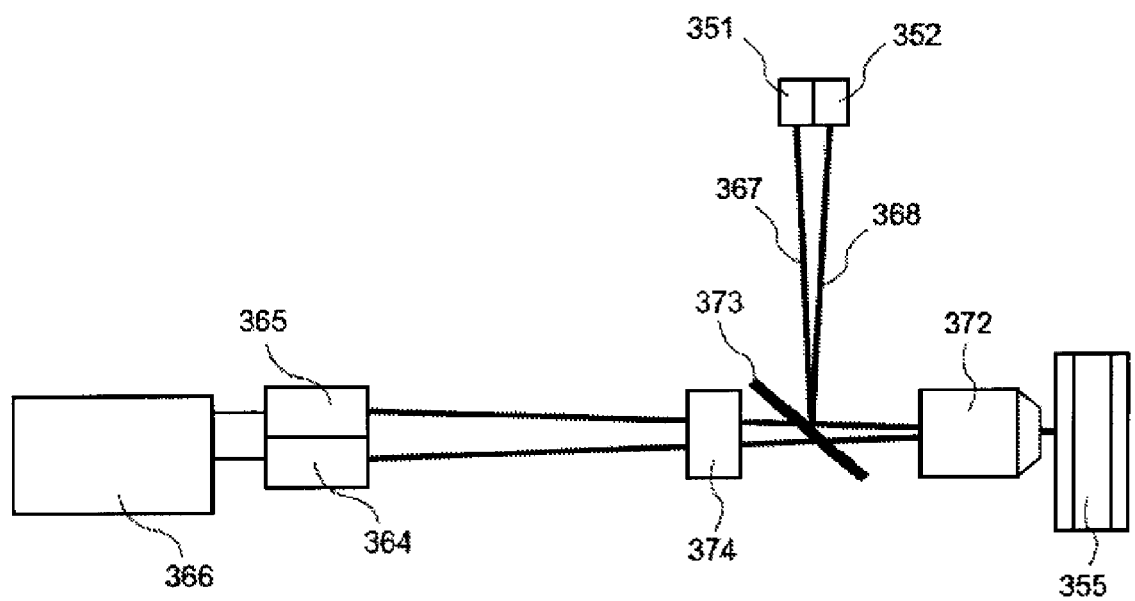

In some embodiments, the optics of the electromagnetic radiation source and the optics of the detector are arranged in a confocal optical arrangement. In such an arrangement, the electromagnetic radiation source 301 and the detector 309 are aligned on the same focal plane. The confocal arrangement renders the analyzer more robust because the electromagnetic radiation source 301 and the detector optics 309 do not need to be realigned if the analyzer system is moved. This arrangement also makes the use of the analyzer more simplified because it eliminates the need to realign the components of the analyzer system. The confocal arrangement for the analyzer 300 (FIG. 1A) and the analyzer 355 (FIG. 1B) are shown in FIGS. 3A and 3B respectively. FIG. 3A shows that the beam 311 from an electromagnetic radiation source 301 is focused by the microscope objective 315 to form one interrogation space 314 (FIG. 2A) within the capillary flow cell 313. A dichroic mirror 316, which reflects laser light but passes fluorescent light, is used to separate the fluorescent light from the laser light. Filter 317 that is positioned in front of the detector eliminates any non-fluorescent light at the detector. In some embodiments, an analyzer system configured in a confocal arrangement can comprise two or more interrogations spaces. Such a method has been previously disclosed and is incorporated by reference from previous U.S. patent application Ser. No. 11/048,660.

The laser can be a tunable dye laser, such as a helium-neon laser. The laser can be set to emit a wavelength of 632.8 nm. Alternatively, the wavelength of the laser can be set to emit a wavelength of 543.5 nm or 1523 nm. Alternatively, the electromagnetic laser can be an argon ion laser. In such an embodiment, the argon ion laser can be operated as a continuous gas laser at about 25 different wavelengths in the visible spectrum, the wavelength set between 408.9 and 686.1 nm but at its optimum performance set between 488 and 514.5 nm.

1. Electromagnetic Radiation Source

In some embodiments of the analyzer system a chemiluminescent label may be used. In such an embodiment, it may not be necessary to utilize an EM source for detection of the particle. In another embodiment, the extrinsic label or intrinsic characteristic of the particle is a light-interacting label or characteristic, such as a fluorescent label or a light-scattering label. In such an embodiment, a source of EM radiation is used to illuminate the label and/or the particle. EM radiation sources for excitation of fluorescent labels are preferred.

In some embodiments, the analyzer system consists of an electromagnetic radiation source 301. Any number of radiation sources may be used in any one analyzer system 300 without departing from the scope of the invention. Multiple sources of electromagnetic radiation have been previously disclosed and are incorporated by reference from previous U.S. patent application Ser. No. 11/048,660. In some embodiments, all the continuous wave electromagnetic (EM) radiation sources emit electromagnetic radiation at the same wavelengths. In other embodiments, different sources emit different wavelengths of EM radiation.

In one embodiment, the EM source(s) 301, 351, 352 are continuous wave lasers producing wavelengths of between 200 nm and 1000 nm. Such EM sources have the advantage of being small, durable and relatively inexpensive. In addition, they generally have the capacity to generate larger fluorescent signals than other light sources. Specific examples of suitable continuous wave EM sources include, but are not limited to: lasers of the argon, krypton, helium-neon, helium-cadmium types, as well as, tunable diode lasers (red to infrared regions), each with the possibility of frequency doubling. The lasers provide continuous illumination with no accessory electronic or mechanical devices, such as shutters, to interrupt their illumination. In an embodiment where a continuous wave laser is used, an electromagnetic radiation source of 3 mW may be of sufficient energy to excite a fluorescent label. A beam from a continuous wave laser of such energy output may be between 2 to 5 μm in diameter. The time of exposure of the particle to laser beam in order to be exposed to 3 mW may be a time period of about 1 msec. In alternate embodiments, the time of exposure to the laser beam may be equal to or less than about 500 μsec. In an alternate embodiment, the time of exposure may be equal to or less than about 100 μsec. In an alternate embodiment, the time of exposure may be equal to or less than about 50 μsec. In an alternate embodiment, the time of exposure may be equal to or less than about 10 μsec.

LEDs are another low-cost, high reliability illumination source. Recent advances in ultra-bright LEDs and dyes with high absorption cross-section and quantum yield support the applicability of LEDs to single particle detection. Such lasers could be used alone or in combination with other light sources such as mercury arc lamps, elemental arc lamps, halogen lamps, arc discharges, plasma discharges, light-emitting diodes, or combination of these.

In other embodiments, the EM source could be in the form of a pulse wave laser. In such an embodiment, the pulse size of the laser is an important factor. In such an embodiment, the size, focus spot, and the total energy emitted by the laser is important and must be of sufficient energy as to be able to excite the fluorescent label. When a pulse laser is used, a pulse of longer duration may be required. In some embodiments a laser pulse of 2 nanoseconds may be used. In some embodiments a laser pulse of 5 nanoseconds may be used. In some embodiments a pulse of between 2 to 5 nanoseconds may be used.

The optimal laser intensity depends on the photo bleaching characteristics of the single dyes and the length of time required to traverse the interrogation space (including the speed of the particle, the distance between interrogation spaces if more than one is used and the size of the interrogation space(s)). To obtain a maximal signal, it is desirable to illuminate the sample at the highest intensity which will not result in photo bleaching a high percentage of the dyes. The preferred intensity is one such that no more that 5% of the dyes are bleached by the time the particle has traversed the interrogation space.

The power of the laser is set depending on the type of dye molecules that need to be stimulated and the length of time the dye molecules are stimulated, and/or the speed with which the dye molecules pass through the capillary flow cell. Laser power is defined as the rate at which energy is delivered by the beam and is measured in units of Joules/second, or Watts. It will be appreciated that the greater the power output of the laser, the shorter the time that the laser illuminates the particle may be, while providing a constant amount of energy to the interrogation space while the particle is passing through the space. Thus, in some embodiments, the combination of laser power and time of illumination is such that the total energy received by the interrogation space during the time of illumination is more than about 0.1, 0.5, 1, 2, 3, 4, 5, 6, 7, 8, 9, 10, 12, 15, 20, 25, 30, 35, 40, 45, 50, 60, 70, 80, 90, or 100 microJoule. In some embodiments, the combination of laser power and time of illumination is such that the total energy received by the interrogation space during the time of illumination is less than about 0.5, 1, 2, 3, 4, 5, 6, 7, 8, 9, 10, 12, 15, 20, 25, 30, 35, 40, 45, 50, 60, 70, 80, 90, 100, or 110 microJoule. In some embodiments, the combination of laser power and time of illumination is such that the total energy received by the interrogation space during the time of illumination is between about 0.1 and 100 microJoule. In some embodiments, the combination of laser power and time of illumination is such that the total energy received by the interrogation space during the time of illumination is between about 1 and 100 microJoule. In some embodiments, the combination of laser power and time of illumination is such that the total energy received by the interrogation space during the time of illumination is between about 1 and 50 microJoule. In some embodiments, the combination of laser power and time of illumination is such that the total energy received by the interrogation space during the time of illumination is between about 2 and 50 microJoule. In some embodiments, the combination of laser power and time of illumination is such that the total energy received by the interrogation space during the time of illumination is between about 3 and 60 microJoule. In some embodiments, the combination of laser power and time of illumination is such that the total energy received by the interrogation space during the time of illumination is between about 3 and 50 microJoule. In some embodiments, the combination of laser power and time of illumination is such that the total energy received by the interrogation space during the time of illumination is between about 3 and 40 microJoule. In some embodiments, the combination of laser power and time of illumination is such that the total energy received by the interrogation space during the time of illumination is between about 3 and 30 microJoule. In some embodiments, the combination of laser power and time of illumination is such that the total energy received by the interrogation space during the time of illumination is about 1 microJoule. In some embodiments, the combination of laser power and time of illumination is such that the total energy received by the interrogation space during the time of illumination is about 3 microJoule. In some embodiments, the combination of laser power and time of illumination is such that the total energy received by the interrogation space during the time of illumination is about 5 microJoule. In some embodiments, the combination of laser power and time of illumination is such that the total energy received by the interrogation space during the time of illumination is about 10 microJoule. In some embodiments, the combination of laser power and time of illumination is such that the total energy received by the interrogation space during the time of illumination is about 15 microJoule. In some embodiments, the combination of laser power and time of illumination is such that the total energy received by the interrogation space during the time of illumination is about 20 microJoule. In some embodiments, the combination of laser power and time of illumination is such that the total energy received by the interrogation space during the time of illumination is about 30 microJoule. In some embodiments, the combination of laser power and time of illumination is such that the total energy received by the interrogation space during the time of illumination is about 40 microJoule. In some embodiments, the combination of laser power and time of illumination is such that the total energy received by the interrogation space during the time of illumination is about 50 microJoule. In some embodiments, the combination of laser power and time of illumination is such that the total energy received by the interrogation space during the time of illumination is about 60 microJoule. In some embodiments, the combination of laser power and time of illumination is such that the total energy received by the interrogation space during the time of illumination is about 70 microJoule. In some embodiments, the combination of laser power and time of illumination is such that the total energy received by the interrogation space during the time of illumination is about 80 microJoule. In some embodiments, the combination of laser power and time of illumination is such that the total energy received by the interrogation space during the time of illumination is about 90 microJoule. In some embodiments, the combination of laser power and time of illumination is such that the total energy received by the interrogation space during the time of illumination is about 100 microJoule.

In some embodiments, the laser power output is set to at least about 1 mW, 2 mW, 3 mW, 4 mW, 5 mW, 6, mw, 7 mW, 8 mW, 9 mW, 10 mW, 13 mW, 15 mW, 20 mW, 25 mW, 30 mW, 40 mW, 50 mW, 60 mW, 70 mW, 80 mW, 90 mW, 100 mW, or more than 100 mW. In some embodiments, the laser power output is set to at least about 1 mW. In some embodiments, the laser power output is set to at least about 3 mW. In some embodiments, the laser power output is set to at least about 5 mW. In some embodiments, the laser power output is set to at least about 10 mW. In some embodiments, the laser power output is set to at least about 15 mW. In some embodiments, the laser power output is set to at least about 20 mW. In some embodiments, the laser power output is set to at least about 30 mW. In some embodiments, the laser power output is set to at least about 40 mW. In some embodiments, the laser power output is set to at least about 50 mW. In some embodiments, the laser power output is set to at least about 60 mW. In some embodiments, the laser power output is set to at least about 90 mW.

The time that the laser illuminates the interrogation space can be set to no less than about 1, 2, 3, 4, 5, 10, 15, 20, 30, 40, 50, 60, 70, 80, 90, 100, 150, 200, 150, 300, 350, 400, 450, 500, 600, 700, 800, 900, or 1000 microseconds. The time that the laser illuminates the interrogation space can be set to no more than about 2, 3, 4, 5, 10, 15, 20, 30, 40, 50, 60, 70, 80, 90, 100, 150, 200, 150, 300, 350, 400, 450, 500, 600, 700, 800, 900, 1000, 1500, or 2000 microseconds. The time that the laser illuminates the interrogation space can be set between about 1 and 1000 microseconds. The time that the laser illuminates the interrogation space can be set between about 5 and 500 microseconds. The time that the laser illuminates the interrogation space can be set between about 5 and 100 microseconds. The time that the laser illuminates the interrogation space can be set between about 10 and 100 microseconds. The time that the laser illuminates the interrogation space can be set between about 10 and 50 microseconds. The time that the laser illuminates the interrogation space can be set between about 10 and 20 microseconds. The time that the laser illuminates the interrogation space can be set between about 5 and 50 microseconds. The time that the laser illuminates the interrogation space can be set between about 1 and 100 microseconds. In some embodiments, the time that the laser illuminates the interrogation space is about 1 microsecond. In some embodiments, the time that the laser illuminates the interrogation space is about 5 microseconds. In some embodiments, the time that the laser illuminates the interrogation space is about 10 microseconds. In some embodiments, the time that the laser illuminates the interrogation space is about 25 microseconds. In some embodiments, the time that the laser illuminates the interrogation space is about 50 microseconds. In some embodiments, the time that the laser illuminates the interrogation space is about 100 microseconds. In some embodiments, the time that the laser illuminates the interrogation space is about 250 microseconds. In some embodiments, the time that the laser illuminates the interrogation space is about 500 microseconds. In some embodiments, the time that the laser illuminates the interrogation space is about 1000 microseconds.

For example, the time that the laser illuminates the interrogation space can be set to 1 millisecond, 250 microseconds, 100 microseconds, 50 microseconds, 25 microseconds or 10 microseconds with a laser that provides a power output of 3 mW, 4 mw, 5 mW, or more than 5 mW. In some embodiments, a label is illuminated with a laser that provides a power output of 3 mW and illuminates the label for about 1000 microseconds. In other embodiments, a label is illuminated for less than 1000 milliseconds with a laser providing a power output of not more than about 20 mW. In other embodiments, the label is illuminated with a laser power output of 20 mW for less than or equal to about 250 microseconds. In some embodiments, the label is illuminated with a laser power output of about 5 mW for less than or equal to about 1000 microseconds.

2. Capillary Flow Cell

The capillary flow cell is fluidly connected to the sample system. In one embodiment, the interrogation space 314 of an analyzer system is determined by the cross sectional area of the corresponding beam 311 and by a segment of the beam within the field of view of the detector 309. In one embodiment of the analyzer system, the interrogation space 314 has a volume, as defined herein, of between about between about 0.01 and 500 pL, or between about 0.01 pL and 100 pL, or between about 0.01 pL and 10 pL, or between about 0.01 pL and 1 pL, or between about 0.01 pL and 0.5 pL, or between about 0.02 pL and about 300 pL, or between about 0.02 pL and about 50 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.01 pL and 10 pL. In some embodiments, the interrogation space 314 has a volume between about 0.01 pL and 1 pL. In some embodiments, the interrogation space 314 has a volume between about 0.02 pL and about 5 pL. In some embodiments, the interrogation space 314 has a volume between about 0.02 pL and about 0.5 pL. In some embodiments, the interrogation space 314 has a volume between about 0.05 pL and about 0.2 pL. In some embodiments, the interrogation space 314 has a volume of about 0.1 pL. Other useful interrogation space volumes are as described herein. It should be understood by one skilled in the art that the interrogation space 314 can be selected for maximum performance of the analyzer. Although very small interrogation spaces have been shown to minimize the background noise, large interrogation spaces have the advantage that low concentration samples can be analyzed in a reasonable amount of time. In embodiments in which two interrogation spaces 370 and 371 are used, volumes such as those described herein for a single interrogation space 314 may be used.

In one embodiment of the present invention, the interrogation spaces are large enough to allow for detection of particles at concentrations ranging from about 1000 femtomolar (fM) to about 1 zeptomolar (zM). In one embodiment of the present invention, the interrogation spaces are large enough to allow for detection of particles at concentrations ranging from about 1000 fM to about 1 attomolar (aM). In one embodiment of the present invention, the interrogation spaces are large enough to allow for detection of particles at concentrations ranging from about 10 fM to about 1 attomolar (aM). In many cases, the large interrogation spaces allow for the detection of particles at concentrations of less than about 1 fM without additional pre-concentration devices or techniques. One skilled in the art will recognize that the most appropriate interrogation space size depends on the brightness of the particles to be detected, the level of background signal, and the concentration of the sample to be analyzed.

The size of the interrogation space 314 can be limited by adjusting the optics of the analyzer. In one embodiment, the diameter of the beam 311 can be adjusted to vary the volume of the interrogation space 314.

In another embodiment, the field of view of the detector 309 can be varied. Thus, the source 301 and the detector 309 can be adjusted so that single particles will be illuminated and detected within the interrogation space 314. In another embodiment, the width of aperture 306 (FIG. 1A) that determine the field of view of the detector 309 is variable. This configuration allows for altering the interrogation space, in near real time, to compensate for more or less concentrated samples, ensuring a low probability of two or more particles simultaneously being within an interrogation space. Similar alterations for two or more interrogation spaces, 370 and 371, may performed.

In another embodiment, the interrogation space can be defined through the use of a calibration sample of known concentration that is passed through the capillary flow cell prior to the actual sample being tested. When only one single particle is detected at a time in the calibration sample as the sample is passing through the capillary flow cell, the depth of focus together with the diameter of the beam of the electromagnetic radiation source determines the size of the interrogation space in the capillary flow cell.

Figure 2B:
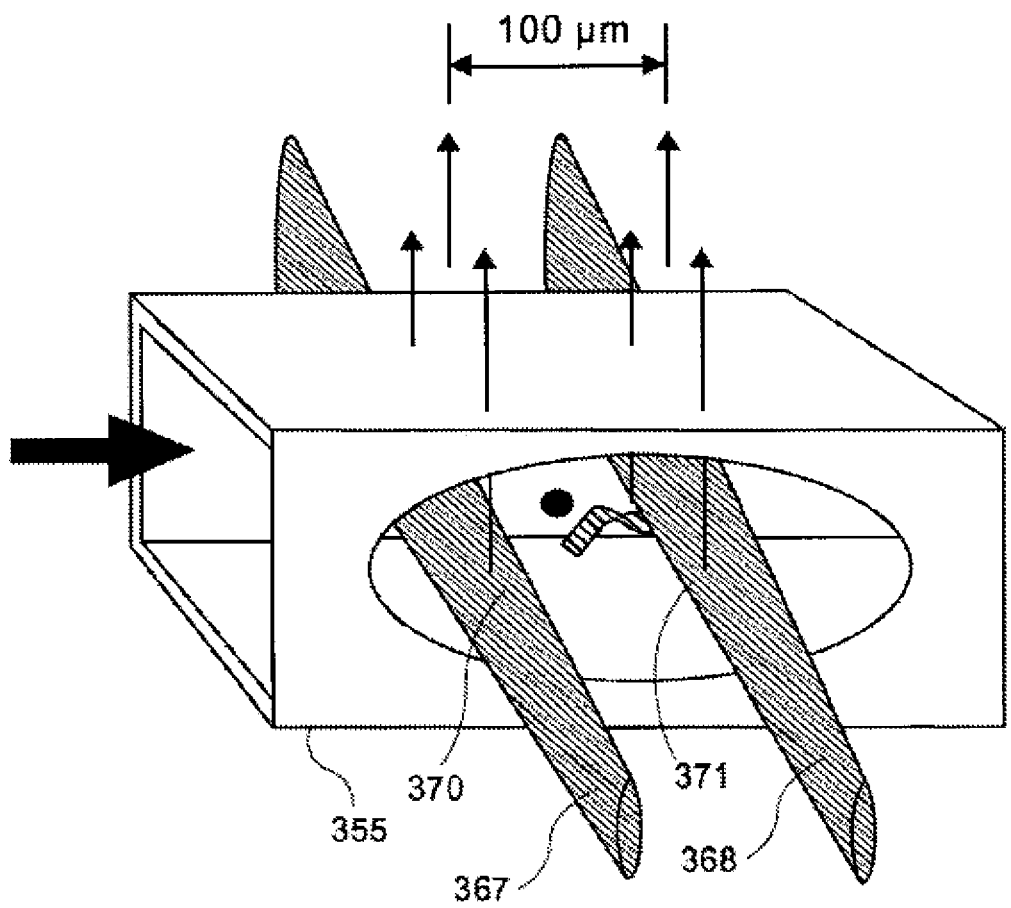

Physical constraints to the interrogation spaces can also be provided by a solid wall. In one embodiment, the wall is one or more of the walls of a flow cell 313 (FIG. 2A), when the sample fluid is contained within a capillary. In one embodiment, the cell is made of glass, but other substances transparent to light in the range of about 200 to about 1,000 nm or higher, such as quartz, fused silica, and organic materials such as Teflon, nylon, plastics, such as polyvinylchloride, polystyrene, and polyethylene, or any combination thereof, may be used without departing from the scope of the present invention. Although other cross-sectional shapes (e.g., rectangular, cylindrical) may be used without departing from the scope of the present invention, in one embodiment the capillary flow cell 313 has a square cross section. In another embodiment, the interrogation space may be defined at least in part by a channel (not shown) etched into a chip (not shown). Similar considerations apply to embodiments in which two interrogation spaces are used (370 and 371 in FIG. 2B).

The interrogation space is bathed in a fluid. In one embodiment, the fluid is aqueous. In other embodiments, the fluid is non-aqueous or a combination of aqueous and non-aqueous fluids. In addition the fluid may contain agents to adjust pH, ionic composition, or sieving agents, such as soluble macroparticles or polymers or gels. It is contemplated that valves or other devices may be present between the interrogation spaces to temporarily disrupt the fluid connection. Interrogation spaces temporarily disrupted are considered to be connected by fluid.

In another embodiment of the invention, an interrogation space is the single interrogation space present within the flow cell 313 which is constrained by the size of a laminar flow of the sample material within a diluent volume, also called sheath flow. In these and other embodiments, the interrogation space can be defined by sheath flow alone or in combination with the dimensions of the illumination source or the field of view of the detector. Sheath flow can be configured in numerous ways, including: The sample material is the interior material in a concentric laminar flow, with the diluent volume in the exterior; the diluent volume is on one side of the sample volume; the diluent volume is on two sides of the sample material; the diluent volume is on multiple sides of the sample material, but not enclosing the sample material completely; the diluent volume completely surrounds the sample material; the diluent volume completely surrounds the sample material concentrically; the sample material is the interior material in a discontinuous series of drops and the diluent volume completely surrounds each drop of sample material.

In some embodiments, single molecule detectors of the invention comprise no more than one interrogation space. In some embodiments, multiple interrogation spaces are used. Multiple interrogation spaces have been previously disclosed and are incorporated by reference from U.S. patent application Ser. No. 11/048,660. One skilled in the art will recognize that in some cases the analyzer will contain a plurality of distinct interrogation spaces. In some embodiments, the analyzer contains 2, 3, 4, 5, 6 or more distinct interrogation spaces.

3. Motive Force

In one embodiment of the analyzer system, the particles are moved through the interrogation space by a motive force. In some embodiments, the motive force for moving particles is pressure. In some embodiments, the pressure is supplied by a pump, and air pressure source, a vacuum source, a centrifuge, or a combination thereof. In some embodiments, the motive force for moving particles is an electrokinetic force. The use of an electrokinetic force as a motive force has been previously disclosed in a prior application and is incorporated by reference from U.S. patent application Ser. No. 11/048,660.

In one embodiment, pressure can be used as a motive force to move particles through the interrogation space of the capillary flow cell. In a further embodiment, pressure is supplied to move the sample by means of a pump. Suitable pumps are known in the art. In one embodiment, pumps manufactured for HPLC applications, such as those made by Scivax, Inc. can be used as a motive force. In other embodiments, pumps manufactured for microfluidics applications can be used when smaller volumes of sample are being pumped. Such pumps are described in U.S. Pat. Nos. 5,094,594, 5,730,187, 6,033,628, and 6,533,553, which discloses devices which can pump fluid volumes in the nanoliter or picoliter range. Preferably all materials within the pump that come into contact with sample are made of highly inert materials, e.g., polyetheretherketone (PEEK), fused silica, or sapphire.

A motive force is necessary to move the sample through the capillary flow cell to push the sample through the interrogation space for analysis. A motive force is also required to push a flushing sample through the capillary flow cell after the sample has been passed through. A motive force is also required to push the sample back out into a sample recovery vessel, when sample recovery is employed. Standard pumps come in a variety of sizes, and the proper size may be chosen to suit the anticipated sample size and flow requirements. In some embodiments, separate pumps are used for sample analysis and for flushing of the system. The analysis pump may have a capacity of approximately 0.000001 mL to approximately 10 mL, or approximately 0.001 mL to approximately 1 mL, or approximately 0.01 mL to approximately 0.2 mL, or approximately 0.005, 0.01, 0.05, 0.1, or 0.5 mL. Flush pumps may be of larger capacity than analysis pumps. Flush pumps may have a volume of about 0.01 mL to about 20 mL, or about 0.1 mL to about 10 mL, or about 0.1 mL to about 2 mL, or about or about 0.05, 0.1, 0.5, 1, 5, or 10 mL. These pump sizes are illustrative only, and those of skill in the art will appreciate that the pump size may be chosen according to the application, sample size, viscosity of fluid to be pumped, tubing dimensions, rate of flow, temperature, and other factors well known in the art. In some embodiments, pumps of the system are driven by stepper motors, which are easy to control very accurately with a microprocessor.

In preferred embodiments, the flush and analysis pumps are used in series, with special check valves to control the direction of flow. The plumbing is designed so that when the analysis pump draws up the maximum sample, the sample does not reach the pump itself. This is accomplished by choosing the ID and length of the tubing between the analysis pump and the analysis capillary such that the tubing volume is greater than the stroke volume of the analysis pump.

4. Detectors

In one embodiment, light (e.g., light in the ultra-violet, visible or infrared range) emitted by a fluorescent label after exposure to electromagnetic radiation is detected. The detector 309 (FIG. 1A), or detectors (364, 365, FIG. 1B), is capable of capturing the amplitude and duration of photon bursts from a fluorescent moiety, and further converting the amplitude and duration of the photon burst to electrical signals. Detection devices such as CCD cameras, video input module cameras, and Streak cameras can be used to produce images with contiguous signals. In another embodiment, devices such as a bolometer, a photodiode, a photodiode array, avalanche photodiodes, and photomultipliers which produce sequential signals may be used. Any combination of the aforementioned detectors may also be used. In one embodiment, avalanche photodiodes are used for detecting photons.

Using specific optics between an interrogation space 314 (FIG. 2A) and its corresponding detector 309 (FIG. 1A), several distinct characteristics of the emitted electromagnetic radiation can be detected including: emission wavelength, emission intensity, burst size, burst duration, and fluorescence polarization. In some embodiments, the detector 309 is a photodiode that is used in reverse bias. A photodiode set in reverse bias usually has an extremely high resistance. This resistance is reduced when light of an appropriate frequency shines on the P/N junction. Hence, a reverse biased diode can be used as a detector by monitoring the current running through it. Circuits based on this effect are more sensitive to light than ones based on zero bias.

In one embodiment of the analyzer system, the photodiode can be an avalanche photodiode, which can be operated with much higher reverse bias than conventional photodiodes, thus allowing each photo-generated carrier to be multiplied by avalanche breakdown, resulting in internal gain within the photodiode, which increases the effective responsiveness (sensitivity) of the device. The choice of photodiode is determined by the energy or emission wavelength emitted by the fluorescently labeled particle. In some embodiments, the photodiode is a silicon photodiode that detects energy in the range of 190-1100 nm; in another embodiment the photodiode is a germanium photodiode that detects energy in the range of 800-1700 nm; in another embodiment the photodiode is an indium gallium arsenide photodiode that detects energy in the range of 800-2600 nm; and in yet other embodiments, the photodiode is a lead sulfide photodiode that detects energy in the range of between less than 1000 nm to 3500 nm. In some embodiments, the avalanche photodiode is a single-photon detector designed to detect energy in the 400 nm to 1100 nm wavelength range. Single photon detectors are commercially available (e.g., Perkin Elmer, Wellesley, Mass.).

In some embodiments, the detector is an avalanche photodiode detector that detects energy between 300 nm and 1700 nm. In one embodiment, silicon avalanche photodiodes can be used to detect wavelengths between 300 nm and 1100 nm. Indium gallium arsenic photodiodes can be used to detect wavelengths between 900 nm and 1700 nm. In some embodiments, an analyzer system can comprise at least one detector; in other embodiments, the analyzer system can comprise at least two detectors, and each detector can be chosen and configured to detect light energy at a specific wavelength range. For example, two separate detectors can be used to detect particles that have been tagged with different labels, which upon excitation with an EM source, will emit photons with energy in different spectra. In one embodiment, an analyzer system can comprise a first detector that can detect fluorescent energy in the range of 450-700 nm such as that emitted by a green dye (e.g., Alexa Fluor 546); and a second detector that can detect fluorescent energy in the range of 620-780 nm such as that emitted by a far-red dye (e.g., Alexa Fluor 647). Detectors for detecting fluorescent energy in the range of 400-600 nm such as that emitted by blue dyes (e.g., Hoechst 33342), and for detecting energy in the range of 560-700 nm such as that emitted by red dyes (Alexa Fluor 546 and Cy3) can also be used.

A system comprising two or more detectors can be used to detect individual particles that are each tagged with two or more labels that emit light in different spectra. For example, two different detectors can detect an antibody that has been tagged with two different dye labels. Alternatively, an analyzer system comprising two detectors can be used to detect particles of different types, each type being tagged with different dye molecules, or with a mixture of two or more dye molecules. For example, two different detectors can be used to detect two different types of antibodies that recognize two different proteins, each type being tagged with a different dye label or with a mixture of two or more dye label molecules. By varying the proportion of the two or more dye label molecules, two or more different particle types can be individually detected using two detectors. It is understood that three or more detectors can be used without departing from the scope of the invention.

It should be understood by one skilled in the art that one or more detectors can be configured at each interrogation space, whether one or more interrogation spaces are defined within a flow cell, and that each detector may be configured to detect any of the characteristics of the emitted electromagnetic radiation listed above. The use of multiple detectors, e.g., for multiple interrogation spaces, has been previously disclosed in a prior application and is incorporated by reference here from U.S. patent application Ser. No. 11/048,660. Once a particle is labeled to render it detectable (or if the particle possesses an intrinsic characteristic rendering it detectable), any suitable detection mechanism known in the art may be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation may be detected including: emission wavelength, emission intensity, burst size, burst duration, fluorescence polarization, and any combination thereof.

C. Sampling System

In a further embodiment, the analyzer system may include a sampling system to prepare the sample for introduction into the analyzer system. The sampling system included is capable of automatically sampling a plurality of samples and providing a fluid communication between a sample container and a first interrogation space.

In some embodiments, the analyzer system of the invention includes a sampling system for introducing an aliquot of a sample into the single particle analyzer for analysis. Any mechanism that can introduce a sample may be used. Samples can be drawn up using either a vacuum suction created by a pump or by pressure applied to the sample that would push liquid into the tube, or by any other mechanism that serves to introduce the sample into the sampling tube. Generally, but not necessarily, the sampling system introduces a sample of known sample volume into the single particle analyzer; in some embodiments where the presence or absence of a particle or particles is detected, precise knowledge of the sample size is not critical. In preferred embodiments the sampling system provides automated sampling for a single sample or a plurality of samples. In embodiments where a sample of known volume is introduced into the system, the sampling system provides a sample for analysis of more than about 0.0001, 0.001, 0.01, 0.1, 1, 2, 5, 10, 20, 30, 40, 50, 60, 70, 80, 90, 100, 150, 200, 500, 1000, 1500, or 2000 µl. In some embodiments the sampling system provides a sample for analysis of less than about 2000, 1000, 500, 200, 100, 90, 80, 70, 60, 50, 40, 30, 20, 10, 5, 2, 1, 0.1, 0.01, or 0.001 µl. In some embodiments the sampling system provides a sample for analysis of between about 0.01 and 1500 µl, or about 0.1 and 1000 µl, or about 1 and 500 µl, or about 1 and 100 µl, or about 1 and 50 µl, or about 1 and 20 µl. In some embodiments, the sampling system provides a sample for analysis between about 5 µl and 200 µl, or about 5 µl and about 100 µl, or about 5 µl and 50 µl. In some embodiments, the sampling system provides a sample for analysis between about 10 µl and 200 µl, or between about 10 µl and 100 µl, or between about 10 µl and 50 µl. In some embodiments, the sampling system provides a sample for analysis between about 0.5 µl and about 50 µl.

Because of the sensitivity of the methods of the present invention, very small sample volumes can be used. For example, the methods here can be used to measure VEGF in small sample volumes, e.g., 10 µl or less, compared to the standard sample volume of 100 µl. The present invention enables a greater number of samples to provide quantifiable results in small volume samples compared to other methods. For example, a lysate prepared from a typical 1 mm needle biopsy may have a volume less than or equal to 10 µl. Using the present invention, such sample can be assayed. In some embodiments, the present invention allows the use of sample volume under 100 µl. In some embodiments, the present invention allows the use of sample volume under 90 µl. In some embodiments, the present invention allows the use of sample volume under 80 µl. In some embodiments, the present invention allows the use of sample volume under 70 µl. In some embodiments, the present invention allows the use of sample volume under 60 µl. In some embodiments, the present invention allows the use of sample volume under 50 µl. In some embodiments, the present invention allows the use of sample volume under 40 µl. In some embodiments, the present invention allows the use of sample volume under 30 µl. In some embodiments, the present invention allows the use of sample volume under 25 µl. In some embodiments, the present invention allows the use of sample volume under 20 µl. In some embodiments, the present invention allows the use of sample volume under 15 µl. In some embodiments, the present invention allows the use of sample volume under 10 µl. In some embodiments, the present invention allows the use of sample volume under 5 µl. In some embodiments, the present invention allows the use of sample volume under 1 µl. In some embodiments, the present invention allows the use of sample volume under 0.05 µl. In some embodiments, the present invention allows the use of sample volume under 0.01 µl. In some embodiments, the present invention allows the use of sample volume under 0.005 µl. In some embodiments, the present invention allows the use of sample volume under 0.001 µl. In some embodiments, the present invention allows the use of sample volume under 0.0005 µl. In some embodiments, the present invention allows the use of sample volume under 0.0001 µl.

In some embodiments, the sampling system provides a sample size that can be varied from sample to sample. In these embodiments, the sample size may be any one of the sample sizes described herein, and may be changed with every sample, or with sets of samples, as desired.

Sample volume accuracy, and sample to sample volume precision of the sampling system, is required for the analysis at hand. In some embodiments, the precision of the sampling volume is determined by the pumps used, typically represented by a CV of less than about 50, 40, 30, 20, 10, 5, 4, 3, 2, 1, 0.5, 0.1, 0.05, or 0.01% of sample volume. In some embodiments, the sample to sample precision of the sampling system is represented by a CV of less than about 50, 40, 30, 20, 10, 5, 4, 3, 2, 1, 0.5, 0.1, 0.05, or 0.01%. In some embodiments, the intra-assay precision of the sampling system is represented by a CV of less than about 10, 5, 1, 0.5, or 0.1%. In some embodiments, the intra-assay precision of the sampling system shows a CV of less than about 10%. In some embodiments, the interassay precision of the sampling system is represented by a CV of less than about 5%. In some embodiments, the interassay precision of the sampling system shows a CV of less than about 1%. In some embodiments, the interassay precision of the sampling system is represented by a CV of less than about 0.5%. In some embodiments, the interassay precision of the sampling system shows a CV of less than about 0.1%.

In some embodiments, the sampling system provides low sample carryover, advantageous in that an additional wash step is not required between samples. Thus, in some embodiments, sample carryover is less than about 1, 0.5, 0.1, 0.05, 0.04, 0.03, 0.02, 0.01, 0.005, or 0.001%. In some embodiments, sample carryover is less than about 0.02%. In some embodiments, sample carryover is less than about 0.01%.

In some embodiments the sampler provides a sample loop. In these embodiments, multiple samples are drawn into tubing sequentially and each is separated from the others by a "plug" of buffer. The samples typically are read one after the other with no flushing in between. Flushing is done once at the end of the loop. In embodiments where a buffer "plug" is used, the plug may be recovered ejecting the buffer plug into a separate well of a microtiter plate.

The sampling system may be adapted for use with standard assay equipment, for example, a 96-well microtiter plate, or, preferably, a 384-well plate. In some embodiments the system includes a 96 well plate positioner and a mechanism to dip the sample tube into and out of the wells, e.g., a mechanism providing movement along the X, Y, and Z axes. In some embodiments, the sampling system provides multiple sampling tubes from which samples may be stored and extracted from, when testing is commenced. In some embodiments, all samples from the multiple tubes are analyzed on one detector. In other embodiments, multiple single molecule detectors may be connected to the sample tubes. Samples may be prepared by steps that include operations performed on sample in the wells of the plate prior to sampling by the sampling system, or sample may be prepared within the analyzer system, or some combination of both.

D. Sample Preparation System

Sample preparation includes the steps necessary to prepare a raw sample for analysis. These steps can involve, by way of example, one or more steps of: separation steps such as centrifugation, filtration, distillation, chromatography; concentration, cell lysis, alteration of pH, addition of buffer, addition of diluents, addition of reagents, heating or cooling, addition of label, binding of label, cross-linking with illumination, separation of unbound label, inactivation and/or removal of interfering compounds and any other steps necessary for the sample to be prepared for analysis by the single particle analyzer. In some embodiments, blood is treated to separate out plasma or serum. Additional labeling, removal of unbound label, and/or dilution steps may also be performed on the serum or plasma sample.

In some embodiments, the analyzer system includes a sample preparation system that performs some or all of the processes needed to provide a sample ready for analysis by the single particle analyzer. This system may perform any or all of the steps listed above for sample preparation. In some embodiments samples are partially processed by the sample preparation system of the analyzer system. Thus, in some embodiments, a sample may be partially processed outside the analyzer system first. For example, the sample may be centrifuged first. The sample may then be partially processed inside the analyzer by a sample preparation system. Processing inside the analyzer includes labeling the sample, mixing the sample with a buffer and other processing steps that will be known to one in the art. In some embodiments, a blood sample is processed outside the analyzer system to provide a serum or plasma sample, which is introduced into the analyzer system and further processed by a sample preparation system to label the particle or particles of interest and, optionally, to remove unbound label. In other embodiments preparation of the sample can include immunodepletion of the sample to remove particles that are not of interest or to remove particles that can interfere with sample analysis. In yet other embodiments, the sample can be depleted of particles that can interfere with the analysis of the sample. For example, sample preparation can include the depletion of heterophilic antibodies, which are known to interfere with immunoassays that use non-human antibodies to directly or indirectly detect a particle of interest. Similarly, other proteins that interfere with measurements of the particles of interest can be removed from the sample using antibodies that recognize the interfering proteins.

In some embodiments, the sample can be subjected to solid phase extraction prior to being assayed and analyzed. For example, a serum sample that is assayed for cAMP can first be subjected to solid phase extraction using a c18 column to which it binds. Other proteins such as proteases, lipases and phosphatases are washed from the column, and the cAMP is eluted essentially free of proteins that can degrade or interfere with measurements of cAMP. Solid phase extraction can be used to remove the basic matrix of a sample, which can diminish the sensitivity of the assay. In yet other embodiments, the particles of interest present in a sample may be concentrated by drying or lyophilizing a sample and solubilizing the particles in a smaller volume than that of the original sample.

In some embodiments the analyzer system provides a sample preparation system that provides complete preparation of the sample to be analyzed on the system, such as complete preparation of a blood sample, a saliva sample, a urine sample, a cerebrospinal fluid sample, a lymph sample, a BAL sample, a biopsy sample, a forensic sample, a bioterrorism sample, and the like. In some embodiments the analyzer system provides a sample preparation system that provides some or all of the sample preparation. In some embodiments, the initial sample is a blood sample that is further processed by the analyzer system. In some embodiments, the sample is a serum or plasma sample that is further processed by the analyzer system. The serum or plasma sample may be further processed by, e.g., contacting with a label that binds to a particle or particles of interest; the sample may then be used with or without removal of unbound label.

In some embodiments, sample preparation is performed, either outside the analysis system or in the sample preparation component of the analysis system, on one or more microtiter plates, such as a 96-well plate. Reservoirs of reagents, buffers, and the like can be in intermittent fluid communication with the wells of the plate by means of tubing or other appropriate structures, as are well-known in the art. Samples may be prepared separately in 96 well plates or tubes. Sample isolation, label binding and, if necessary, label separation steps may be done on one plate. In some embodiments, prepared particles are then released from the plate and samples are moved into tubes for sampling into the sample analysis system. In some embodiments, all steps of the preparation of the sample are done on one plate and the analysis system acquires sample directly from the plate. Although this embodiment is described in terms of a 96-well plate, it will be appreciated that any vessel for containing one or more samples and suitable for preparation of sample may be used. For example, standard microtiter plates of 384 or 1536 wells may be used. More generally, in some embodiments, the sample preparation system is capable of holding and preparing more than about 5, 10, 20, 30, 40, 50, 60, 70, 80, 90, 100, 200, 300, 500, 1000, 5000, or 10,000 samples. In some embodiments, multiple samples may be sampled for analysis in multiple analyzer systems. Thus, in some embodiments, 2 samples, or more than about 2, 3, 4, 5, 7, 10, 15 20, 50, or 100 samples are sampled from the sample preparation system and run in parallel on multiple sample analyzer systems.

Microfluidics systems may also be used for sample preparation and as sample preparation systems that are part of analyzer systems, especially for samples suspected of containing concentrations of particles high enough that detection requires smaller samples. Principles and techniques of microfluidic manipulation are known in the art. See, e.g., U.S. Pat. Nos. 4,979,824; 5,770,029; 5,755,942; 5,746,901; 5,681,751; 5,658,413; 5,653,939; 5,653,859; 5,645,702; 5,605,662; 5,571,410; 5,543,838; 5,480,614; 5,716,825; 5,603,351; 5,858,195; 5,863,801; 5,955,028; 5,989,402; 6,041,515; 6,071,478; 6,355,420; 6,495,104; 6,386,219; 6,606,609; 6,802,342; 6,749,734; 6,623,613; 6,554,744; 6,361,671; 6,143,152; 6,132,580; 5,274,240; 6,689,323; 6,783,992; 6,537,437; 6,599,436; 6,811,668 and published PCT Patent Application No. WO9955461(A1). Samples may be prepared in series or in parallel, for use in a single or multiple analyzer systems.

In some embodiments, the sample comprises a buffer. The buffer may be mixed with the sample outside the analyzer system, or it may be provided by the sample preparation mechanism. While any suitable buffer can be used, the preferable buffer has low fluorescence background, is inert to the detectably labeled particle, can maintain the working pH and, in embodiments wherein the motive force is electrokinetic, has suitable ionic strength for electrophoresis. The buffer concentration can be any suitable concentration, such as in the range from about 1 to about 200 mM. Any buffer system may be used as long as it provides for solubility, function, and delectability of the molecules of interest. In some embodiments, e.g., for application using pumping, the buffer is selected from the group consisting of phosphate, glycine, acetate, citrate, acidulate, carbonate/bicarbonate, imidazole, triethanolamine, glycine amide, borate, MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. The buffer can also be selected from the group consisting of Gly-Gly, bicine, tricine, 2-morpholine ethanesulfonic acid (MES),4-morpholine propanesulfonic acid (MOPS) and 2-amino-2-methyl-1-propanol hydrochloride (AMP). A useful buffer is 2 mM Tris/borate at pH 8.1, but Tris/glycine and Tris/HCl are also acceptable. Other buffers are as described herein.

Buffers useful for electrophoresis are disclosed in a prior application and are incorporated by reference herein from U.S. patent application Ser. No. 11/048,660.

E. Sample Recovery

One highly useful feature of embodiments of the analyzers and analysis systems of the invention is that the sample can be analyzed without consuming it. This can be especially important when sample materials are limited. Recovering the sample also allows one to do other analyses or reanalyze it. The advantages of this feature for applications where sample size is limited and/or where the ability to reanalyze the sample is desirable, e.g., forensic, drug screening, and clinical diagnostic applications, will be apparent to those of skill in the art.

Thus, in some embodiments, the analyzer system of the invention further provides a sample recovery system for sample recovery after analysis. In these embodiments, the system includes mechanisms and methods by which the sample is drawn into the analyzer, analyzed and then returned, e.g., by the same path, to the sample holder, e.g., the sample tube. Because no sample is destroyed and because it does not enter any of the valves or other tubing, it remains uncontaminated. In addition, because all the materials in the sample path are highly inert, e.g., PEEK, fused silica, or sapphire, there is little contamination from the sample path. The use of the stepper motor controlled pumps (particularly the analysis pump) allows precise control of the volumes drawn up and pushed back out. This allows complete or nearly complete recovery of the sample with little if any dilution by the flush buffer. Thus, in some embodiments, more than about 50%, 60%, 70%, 80%, 85%, 90%, 95%, 96%, 97%, 98%, 99%, 99.5%, or 99.9% of the sample is recovered after analysis. In some embodiments, the recovered sample is undiluted. In some embodiments, the recovered sample is diluted less than about 1.5-fold, 1.4-fold, 1.3-fold, 1.2-fold, 1.1-fold, 1.05-fold, 1.01-fold, 1.005-fold, or 1.001-fold.

For sampling and/or sample recovery, any mechanism for transporting a liquid sample from a sample vessel to the analyzer may be used. In some embodiments the inlet end of the analysis capillary has attached a short length of tubing, e.g., PEEK tubing that can be dipped into a sample container, e.g., a test tube or sample well, or can be held above a waste container. When flushing, to clean the previous sample from the apparatus, this tube is positioned above the waste container to catch the flush waste. When drawing a sample in, the tube is put into the sample well or test tube. Typically the sample is drawn in quickly, and then pushed out slowly while observing particles within the sample. Alternatively, in some embodiments, the sample is drawn in slowly during at least part of the draw-in cycle; the sample may be analyzed while being slowly drawn in. This can be followed by a quick return of the sample and a quick flush. In some embodiments, the sample may be analyzed both on the inward (draw-in) and outward (pull out) cycle, which improves counting statistics, e.g., of small and dilute samples, as well as confirming results, and the like. If it is desired to save the sample, it can be pushed back out into the same sample well it came from, or to another. If saving the sample is not desired, the tubing is positioned over the waste container.

VI. Methods Using Highly Sensitive Analysis of Molecules

The systems, system kits, and methods of the present invention make possible measurement of molecules in samples at concentrations far lower than previously measured. The high sensitivity of the instruments, kits, and methods of the invention allows the establishment of markers, e.g., biological markers, that have not previously been possible because of a lack of sensitivity of detection. The invention also includes the use of the compositions and methods described herein for the discovery of new markers.

There are numerous markers currently available which, while potentially of use in determining a biological state, are not currently of practical use because their lower ranges are unknown. In some cases, abnormally high levels of the marker are detectable by current methodologies, but normal ranges have not been established. In some cases, upper normal ranges of the marker are detectable, but not lower normal ranges, or levels below normal. In some cases, for example, markers specific to tumors, or markers of infection, any level of the marker indicates the potential presence of the biological state, and enhancing sensitivity of detection is an advantage for early diagnosis. In some cases, the rate of change, or lack of change, in the concentration of the marker over multiple timepoints provides the most useful information, but present methods of analysis do not permit determination of levels of the marker at timepoint sampling in the early stages of a condition, when it is typically at its most treatable. In many cases, the marker may be detected at clinically useful levels only through the use of cumbersome methods that are not practical or useful in a clinical setting, such as methods that require complex sample treatment and time-consuming analysis.

In addition, there are potential markers of biological states that exist in sufficiently low concentrations that their presence remains extremely difficult or impossible to detect by current methods.

The analytical methods and compositions of the present invention provide levels of sensitivity and precision that allow the detection of markers for biological states at concentrations at which the markers have been previously undetectable, thus allowing the "repurposing" of such markers from confirmatory markers, or markers useful only in limited research settings, to diagnostic, prognostic, treatment-directing, or other types of markers useful in clinical settings and/or in large-scale clinical settings such as clinical trials. Such methods allow, e.g., the determination of normal and abnormal ranges for such markers.

The markers thus repurposed can be used for, e.g., detection of normal state (normal ranges), detection of responder/non-responder (e.g., to a treatment, such as administration of a drug); early disease or pathological occurrence detection (e.g., detection of cancer in its earliest stages, early detection of cardiac ischemia); disease staging (e.g., cancer); disease monitoring (e.g., diabetes monitoring, monitoring for recurrence of cancer after treatment); study of disease mechanism; and study of treatment toxicity, such as toxicity of drug treatments (e.g., cardiotoxicity).

A. Methods

The invention thus provides methods and compositions for the sensitive detection of markers, and further methods of establishing values for normal and abnormal levels of the markers. In further embodiments, the invention provides methods of diagnosis, prognosis, and/or treatment selection based on values established for the markers. The invention also provides compositions for use in such methods, e.g., detection reagents for the ultrasensitive detection of markers.

In some embodiments, the invention provides a method of establishing a marker for a biological state, by establishing a range of concentrations for the marker in biological samples obtained from a first population by measuring the concentrations of the marker the biological samples by detecting single molecules of the marker, e.g., by detecting a label that has been attached to a single molecule of the marker. In some embodiments, the marker is a polypeptide or small molecule. The samples may be any sample type described herein, e.g., blood, plasma, serum, or urine.

The method may utilize samples from a first population where the population is a population that does not exhibit the biological state. In the case where the biological state is a disease state, the first population may be a population that does not exhibit the disease, e.g., a "normal" population. In some embodiments the method may further comprise establishing a range of range of levels for the marker in biological samples obtained from a second population, where the members of the second population exhibit the biological state, by measuring the concentrations of the marker the biological samples by detecting single molecules of the marker. In some embodiments, e.g., cross-sectional studies, the first and second populations are different. In some embodiments, at least one member of the second population is a member of the first population, or at least one member of said the population is a member of the second population. In some embodiments, e.g., longitudinal studies, substantially all the members of the second population are members of the first population who have developed the biological state, e.g., a disease or pathological state.

The detecting of single molecules of the marker is performed using a method as described herein, e.g., a method with a limit of detection for said marker of less than about 1000, 100, 50, 20, 10, 5, 1, 0.5, 0.1, 0.05, 0.01, 0.005, or 0.001 femtomolar of the marker in the samples, by detecting single molecules of the marker. In some embodiments, the limit of detection of said marker is than about 100, 50, 20, 10, 5, 1, 0.5, 0.1, 0.05, 0.01, 0.005, or 0.001 pg/ml of the marker in the samples, by detecting single molecules of the marker.

The biological state may be a phenotypic state; a condition affecting the organism; a state of development; age; health; pathology; disease; disease process; disease staging; infection; toxicity; or response to chemical, environmental, or drug factors (such as drug response phenotyping, drug toxicity phenotyping, or drug effectiveness phenotyping).

In some embodiments, the biological state is a pathological state, including but not limited to inflammation, abnormal cell growth, and abnormal metabolic state. In some embodiments, the state is a disease state. Disease states include, but are not limited to, cancer, cardiovascular disease, inflammatory disease, autoimmune disease, neurological disease, infectious disease and pregnancy related disorders. In some embodiments the state is a disease stage state, e.g., a cancer disease stage state.

The methods may also be used for determination of a treatment response state. In some embodiments, the treatment is a drug treatment. The response may be a therapeutic effect or a side effect, e.g., an adverse effect. Markers for therapeutic effects will be based on the disease or condition treated by the drug. Markers for adverse effects typically will be based on the drug class and specific structure and mechanism of action and metabolism. A common adverse effect is drug toxicity. An example is cardiotoxicity, which can be monitored by the marker cardiac troponin. In some embodiments one or more markers for the disease state and one or more markers for one or more adverse effects of a drug are monitored, typically in a population that is receiving the drug. Samples may be taken at intervals and the respective values of the markers in the samples may be evaluated over time.

The detecting of single molecules of the marker may comprise labeling the marker with a label comprising a fluorescent moiety capable of emitting at least about 200 photons when simulated by a laser emitting light at the excitation wavelength of the moiety, where the laser is focused on a spot not less than about 5 microns in diameter that contains the moiety, and wherein the total energy directed at the spot by the laser is no more than about 3 microJoules. In some embodiments, the fluorescent moiety comprises a molecule that comprises at least one substituted indolium ring system in which the substituent on the 3-carbon of the indolium ring contains a chemically reactive group or a conjugated substance. In some embodiments, the fluorescent moiety may comprise a dye selected from the group consisting of Alexa Fluor 488, Alexa Fluor 532, Alexa Fluor 647, Alexa Fluor 680 or Alexa Fluor 700. In some embodiments, the moiety comprises Alexa Fluor 647. In some embodiments, the label further comprises a binding partner for the marker, e.g., an antibody specific for said marker, such as a polyclonal antibody or a monoclonal antibody. Binding partners for a variety of markers are described herein.

The method may further include establishing a threshold level for the marker based on the first range, or the first and second ranges, where the presence of marker in a biological sample from an individual at a level above or below the threshold level indicates an increased probability of the presence of the biological state in said individual. An example of a threshold determined for a normal population is the suggested threshold for cardiac troponin of greater than the 99th percentile value in a normal population. See Example 3. Other threshold levels may be determined empirically, i.e., based on data from the first and second populations regarding marker levels and the presence, absence, severity, rate of progression, rate of regression, and the like, of the biological state being monitored. It will be appreciated that threshold levels may be established at either end of a range, e.g., a minimum below which the concentration of the marker in a sample indicates an increased probability of a biological state, and/or a maximum above which the concentration of the marker in a sample indicates an increased probability of a biological state. In some embodiments, a risk stratification may be produced in which two or more ranges of marker concentrations correspond to two or more levels of risk. Other methods of analyzing data from two populations and for markers and producing clinically-relevant values for use by, e.g., physicians and other health care professionals, are well-known in the art.

For some biological markers, the presence of any marker at all is an indication of a disease or pathological state, and the threshold is essentially zero. An example is the use of prostate specific antigen (PSA) to monitor cancer recurrence after removal of the prostate gland. As PSA is produced only by the prostate gland, and as the prostate gland and all tumors are presumed to be removed, PSA after removal is zero. Appearance of PSA at any level signals a possible recurrence of the cancer, e.g., at a metastatic site. Thus, the more sensitive the method of detection, the earlier an intervention may be made should such recurrence occur.

Other evaluations of marker concentration may also be made, such as in a series of samples, where change in value, rate of change, spikes, decrease, and the like may all provide useful information for determination of a biological state. In addition, panels of markers may be used if it is found that more than one marker provides information regarding a biological state. If panels of markers are used, the markers may be measured separately in separate samples (e.g., aliquots of a common sample) or simultaneously by multiplexing. Examples of panels of markers and multiplexing are given in, e.g., U.S. patent application Ser. No. 11/048,660.

The establishment of such markers and, e.g., reference ranges for normal and/or abnormal states, allow for sensitive and precise determination of the biological state of an organism. Thus, in some embodiments, the invention provides a method for detecting the presence or absence of a biological state of an organism, comprising i) measuring the concentration of a marker in a biological sample from the organism, wherein said marker is a marker established through establishing a range of concentrations for said marker in biological samples obtained from a first population by measuring the concentrations of the marker the biological samples by detecting single molecules of the marker; and ii) determining the presence of absence of said biological state based on said concentration of said marker in said organism.

In some embodiments, the invention provides a method for detecting the presence or absence of a biological state in an organism, comprising i) measuring the concentrations of a marker in a plurality of biological samples from said organism, wherein said marker is a marker established through establishing a range of concentrations for said marker in biological samples obtained from a first population by measuring the concentrations of the marker the biological samples by detecting single molecules of the marker; and ii) determining the presence of absence of said biological state based on said concentrations of said marker in said plurality of samples. In some embodiments, the samples are of different types, e.g., are samples from different tissue types. In this case, the determining is based on a comparison of the concentrations of said marker in said different types of samples. More commonly, the samples are of the same type, and the samples are taken at intervals. The samples may be any sample type described herein, e.g., blood, plasma, or serum; or urine. Intervals between samples may be minutes, hours, days, weeks, months, or years. In an acute clinical setting, the intervals may be minutes or hours. In settings involving the monitoring of an individual, the intervals may be days, weeks, months, or years.

In many cases, the biological state whose presence or absence is to be detected is a disease phenotype. Thus, in one embodiment, a phenotypic state of interest is a clinically diagnosed disease state. Such disease states include, for example, cancer, cardiovascular disease, inflammatory disease, autoimmune disease, neurological disease, respiratory disease, infectious disease and pregnancy related disorders.

Cancer phenotypes are included in some aspects of the invention. Examples of cancer herein include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Cardiovascular disease may be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial, pulmonary atresia, aortic valve stenosis, Raynaud's disease, cholesterol embolism, Wallenberg syndrome, Hippel-Lindau disease, and telangiectasis.

Inflammatory disease and autoimmune disease may be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemic lupus and erythematosus.

The methods and compositions of the invention can also provide laboratory information about markers of infectious disease including markers of Adenovirus, Bordella pertussis, Chlamydia pneumoiea, Chlamydia trachomais, Cholera Toxin, Cholera Toxin β, *Campylobacter jejuni*, Cytomegalovirus, Diptheria Toxin, Epstein-Barr NA, Epstein-Barr EA, Epstein-Barr VCA, *Helicobacter Pylori*, Hepatitis B virus (HBV)

Core, Hepatitis B virus (HBV) Envelope, Hepatitis B virus (HBV) Survace (Ay), Hepatitis C virus (HCV) Core, Hepatitis C virus (HCV) NS3, Hepatitis C virus (HCV) NS4, Hepatitis C virus (HCV) NS5, Hepititis A, Hepatitis D, Hepatitis E virus (HEV) orf2 3 KD, Hepatitis E virus (HEV) orf2 6 KD, Hepatitis E virus (HEV) orf3 3 KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A $H_3N_2$, Influenza B, Leishmanina donovani, Lyme disease, Mumps, *M. pneumoniae, M. teberculosis*, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15 kd, *T. pallidum* p47, *T. cruzi*, Toxoplasma, and Varicella Zoater.

Detection and monitoring of cancers often depends on the use of crude measurements of tumor growth, such as visualization of the tumor itself, that are either inaccurate or that must reach high levels before they become detectable, e.g., in a practical clinical setting by present methods. At the point of detection, the tumor has often grown to sufficient size that intervention is unlikely to occur before metastasis. For example, detection of lung cancer by X-ray requires a tumor of >1 cm in diameter, or by CT scan of >2-3 mm. Alternatively, a biomarker of tumor growth may be used, but, again, often the tumor is well-advanced by the time the biomarker is detectable at levels accessible to current clinical technology.

Furthermore, after intervention (e.g., surgery, chemotherapy, or radiation to shrink or remove the tumor or tumors), it is often not possible to measure the tumor marker with sufficient sensitivity to determine if there has been a recurrence of the cancer until residual disease has progressed to the point where further intervention is unlikely to be successful. Using the analyzers, systems, and methods of the present invention, it is possible to both detect onset of tumor growth and return of tumor growth at a point where intervention is more likely to be successful, e.g., due to lower probability of metastasis. Markers for cancer that can be detected at levels not previously shown include markers disclosed herein. Examples of assays for the detection of markers that can be repurposed to diagnostic markers include TGFβ, Akt1, Fas ligand and IL-6, as described herein.

B. Exemplary Markers

The instruments, labels, and methods of the invention have been used to establish ranges for markers in, e.g., serum and urine, at levels 10- to 100-fold lower than previous levels, or lower. The markers are indicative of a wide variety of biological states, e.g., cardiac disease and cardiotoxicity (troponin), infection (TREM-1), inflammation and other conditions (LTE4, IL-6 and IL-8), asthma (LTE4), cancer (Akt1, TGF-beta, Fas ligand), and allograft rejection and degenerative disease (Fas ligand).

Markers include protein and non-protein markers. The markers are described briefly here and procedures and results given in the Examples.

1. Cardiac Damage

Cardiac troponin is an example of a marker that is previously detectable only in abnormally high amounts. Cardiac troponin is a marker of cardiac damage, useful in diagnosis, prognosis, and determination of method of treatment in a number of diseases and conditions, e.g., acute myocardial infarct (AMI). In addition, cardiac troponin is a useful marker of cardiotoxicity due to treatment, e.g., drug treatment.

The troponin complex in muscle consists of troponin I, C and T. Troponin C exists as two isoforms, one from cardiac and slow-twitch muscle and one from fast-twitch muscle; because it is found in virtually all striated muscle, its use as a specific marker is limited. In contrast, troponin I and T are expressed as different isoforms in slow-twitch, fast-twitch and cardiac muscle. The unique cardiac isoforms of troponin I and T allow them to be distinguished immunologically from the other troponins of skeletal muscle. Therefore, the release into the blood of cardiac troponin I and T is indicative of damage to cardiac muscle, and provides the basis for their use as diagnostic or prognostic markers, or to aid in determination of treatment.

Currently used markers for cardiac damage suffer disadvantages that limit their clinical usefulness. Cardiac enzyme assays have formed the basis for determining whether or not there is damage to the cardiac muscle. Unfortunately, the standard creatine kinase-MB (CK-MB) assay is not reliable in excluding infarction until 10 to 12 hours after the onset of chest pain. Earlier diagnosis would have very specific advantages with regard to fibrinolytic therapy and triage.

Because the level of troponin found in the circulation of healthy individuals is very low, and cardiac specific troponins do not arise from extra-cardiac sources, the troponins are very sensitive and specific markers of cardiac injury. In addition to cardiac infarct, a number of other conditions can cause damage to the heart muscle, and early detection of such damage would prove useful to clinicians. However, present methods of detection and quantitation of cardiac troponin do not possess sufficient sensitivity to detect the release of cardiac troponin into the blood until levels have reached abnormally high concentrations, e.g., 0.1 ng/ml or greater.

The methods and compositions of the invention thus include methods and compositions for the highly sensitive detection and quantitation of cardiac troponin, and compositions and methods for diagnosis, prognosis, and/or determination of treatment based on such highly sensitive detection and quantitation. A standard curve for cardiac troponin I was established with a limit of detection less than about 1 pg/ml (Example 1). Levels of cardiac troponin I were established in normal individuals and a threshold value at the $99^{th}$ percentile of normal established (Example 3). Serial samples from individuals who suffered acute myocardial infarct were analyzed, and time courses for cardiac troponin I concentrations, including deviations from baseline, were determined (Example 4). Thus, cardiac troponin I serves as an example of a marker that can be detected by the systems and methods of the invention at levels to provide diagnostic and prognostic information of use in clinical and research settings. See also U.S. patent application Ser. No. 11/784,213, filed Mar. 5, 2008 and entitled "Highly Sensitive System and Methods for Analysis of Troponin," which is incorporated by reference herein in its entirety.

Cardiac troponin-I (cTnI) is specific to cardiomyocytes and is released into blood following heart damage. Extensive studies have shown that cTnI is slowly released from damaged cardiomyocytes and often requires 4-8 hours post-trauma to be detectable. Measurement of cTnI concentrations in plasma/serum are the standard of care for diagnosing non-STEMI acute myocardial infarction (AMI). In addition this biomarker has been widely accepted in pre-clinical and clinical drug development settings as an indicator of myocardial damage and hence heart damage. TnI is accepted as a biomarker to assess potential cardiotoxicity of experimental therapies. It is extensively studied in pre-clinical setting and included in clinical drug development programs when pre-clinical data suggests a potential of cardiac-related adverse events.

Even though cTnI is used as the standard of care for diagnosing AMI, as well as in pre-clinical and clinical development, until recently its concentration in the plasma of apparently healthy humans and preclinical animal models had not been reported. Thus it was impossible to benchmark a "normal" level within a given animal or human and measure small increases (velocity) of cTnI which might be associated with subtle cardiac damage. Furthermore, many assays do not equally quantify cTnI across different species and require large plasma sample volumes, limiting their use in pre-clinical settings, especially in rodent model systems. Using the methods of the present invention, normal levels of endogenous cTnI and small changes in plasma cTnI can be quantified in humans, rats, dogs and monkeys providing previously intractable answers around cardiomyocyte pathophysiology. See Examples 1-4.

In some embodiments, the cTnI assay of the present invention is used to: (1) define the concentration of plasma and serum cTnI in healthy humans, rats, dogs and monkeys; (2) identify AMIs earlier; (3) measure heart damage earlier under physical stress or known cardiotoxins; and/or (4) study cTnI concentrations in a single rat using only 10 µL plasma. In other embodiments, the cTnI assay of the present invention is used to: (1) measure the potential cardiac safety and dosing of therapeutics in both pre-clinical and clinical settings; (2) perform studies using individual small animals or precious samples, when sample volume is an issue; (3) design more robust clinical and preclinical studies when velocity of cTnI concentration change from a baseline normal level is used as an endpoint; (4) understand how cTnI levels change from normal levels in a variety of cardiac-related diseases; and/or (5) understand the utility of cTnI as a biomarker to serve as a surrogate endpoint for clinical events.

In some embodiments, the method is capable of detecting cTnI at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting the cTnI at a limit of detection of less than about 100 pg/ml. In some embodiments, the method is capable of detecting the cTnI a limit of detection of less than about 80 pg/ml. In some embodiments, the method is capable of detecting the cTnI a limit of detection of less than about 60 pg/ml. In some embodiments, the method is capable of detecting the cTnI a limit of detection of less than about 50 pg/ml. In some embodiments, the method is capable of detecting the cTnI a limit of detection of less than about 30 pg/ml. In some embodiments, the method is capable of detecting the cTnI a limit of detection of less than about 25 pg/ml. In some embodiments, the method is capable of detecting the cTnI a limit of detection of less than about 10 pg/ml. In some embodiments, the method is capable of detecting the cTnI a limit of detection of less than about 5 pg/ml. In some embodiments, the method is capable of detecting the cTnI a limit of detection of less than about 1 pg/ml. In some embodiments, the method is capable of detecting the cTnI a limit of detection of less than about 0.5 pg/ml. In some embodiments, the method is capable of detecting the cTnI at a limit of detection of less than about 0.1 pg/ml. In some embodiments, the method is capable of detecting the cTnI at a limit of detection of less than about 0.05 pg/ml. In some embodiments, the method is capable of detecting the cTnI at a limit of detection of less than about 0.01 pg/ml. In some embodiments, the method is capable of detecting the cTnI at a limit of detection of less than about 0.005 pg/ml. In some embodiments, the method is capable of detecting the cTnI at a limit of detection of less than about 0.001 pg/ml. In some embodiments, the method is capable of detecting the cTnI at a limit of detection of less than about 0.0005 pg/ml. In some embodiments, the method is capable of detecting the cTnI at a limit of detection of less than about 0.0001 pg/ml.

2. Infection

Recent reports have established TREM-1 as a biomarker of bacterial or fungal infections. See, e.g., Bouchon et al. (2000) J. Immunol. 164:4991-95; Colonna (2003) Nat. Rev. Immunol 3:445-53; Gibot et al. (2004) N. Engl. J. Med. 350:451-58; Gibot et al. (2004) Ann. Intern. Med. 141:9-15. Assays of the invention suggest that TREM-1 may routinely be measured at a concentration of 100 fM or less. See Example 9.

In some embodiments, the method is capable of detecting TREM-1 at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting the TREM-1 at a limit of detection of less than about 100 pg/ml. In some embodiments, the method is capable of detecting the TREM-1 a limit of detection of less than about 80 pg/ml. In some embodiments, the method is capable of detecting the TREM-1 a limit of detection of less than about 60 pg/ml. In some embodiments, the method is capable of detecting the TREM-1 a limit of detection of less than about 50 pg/ml. In some embodiments, the method is capable of detecting the TREM-1 a limit of detection of less than about 30 pg/ml. In some embodiments, the method is capable of detecting the TREM-1 a limit of detection of less than about 25 pg/ml. In some embodiments, the method is capable of detecting the TREM-1a limit of detection of less than about 10 pg/ml. In some embodiments, the method is capable of detecting the TREM-1a limit of detection of less than about 5 pg/ml. In some embodiments, the method is capable of detecting the TREM-1a limit of detection of less than about 1 pg/ml. In some embodiments, the method is capable of detecting the TREM-1a limit of detection of less than about 0.5 pg/ml. In some embodiments, the method is capable of detecting the TREM-1 at a limit of detection of less than about 0.1 pg/ml. In some embodiments, the method is capable of detecting the TREM-1 at a limit of detection of less than about 0.05 pg/ml. In some embodiments, the method is capable of detecting the TREM-1 at a limit of detection of less than about 0.01 pg/ml. In some embodiments, the method is capable of detecting the TREM-1 at a limit of detection of less than about 0.005 pg/ml. In some embodiments, the method is capable of detecting the TREM-1 at a limit of detection of less than about 0.001 pg/ml. In some embodiments, the method is capable of detecting the TREM-1 at a limit of detection of less than about 0.0005 pg/ml. In some embodiments, the method is capable of detecting the TREM-1 at a limit of detection of less than about 0.0001 pg/ml.

3. Cytokines

The normal level of many cytokines, chemokines and growth factors is not known primarily because of the inability of existing technology to detect levels that are below those found in samples from diseased patients. For example, the basal level of other cytokines such as IL-10, TNF-alpha, IL-4, IL-1beta, IL-2, IL-12 and IFN-gamma cannot be detected by routine assays that are performed in a clinical setting, whereas the analyzer systems of the invention can readily determine the level of these and other cytokines. Knowing the level of cytokines and growth factors aids clinicians with the diagnosis, prognosis and treatment of a variety of diseases including cancer, and respiratory, infectious, and cardiovascular diseases. Early cytokine detection to monitor normal and disease states in clinical specimens can be achieved using the analyzer systems of the invention to analyze samples such as plasma, serum, and urine as well as other fluid samples to provide for better translational medicine. For example, determining levels of cytokines for which a normal range of concentration is not known, would aid clinicians with diagnosis and treatment of the following conditions and diseases. Bone Morphogenetic Proteins would be useful to monitor the treatment for fractures, spinal fusions, orthopedic surgery, and oral surgery; Interleukin-10 (IL-10) would be useful for detecting and monitoring for the presence of cancers including non-Hodgkin's lymphoma, multiple myeloma, melanoma, and ovarian cancer, as well as for detecting and monitoring the effect of anti-inflammatory therapy, organ transplantation, immunodeficiencies, and parasitic infections; Interleukin-11 (IL-11) is useful for the detection and monitoring for the presence of cancers such as breast cancer; Interleukin-12 (IL-12) for cancer and HIV infections; TNFα, an inflammatory cytokine, alone or in combination with IL-6, can be used as a good predictor of sepsis, acute pancreatitis, tuberculosis, and autoimmune disease such as rheumatoid arthritis and lupus.

Alternatively, databases may already exist for normal and abnormal values but present methods may not be practical for screening individuals on a routine basis to determine with sufficient sensitivity whether the value of the individual for the marker is within the normal range. For example, most present methods for the determination of IL-6 concentration in a sample are capable of detecting IL-6 only down to a concentration of about 5 pg/ml; the normal range of IL-6 values is about 1 to about 10 pg/ml; hence, present methods are able to detect IL-6 only in the upper part of normal ranges. In contrast, the analyzers and analyzer systems of the invention allow the detection of IL-6 down to a concentration below about 0.01 pg/ml, or less than one-tenth to one-hundredth of normal range values. Thus, the analyzers and analyzer systems of the invention allow a far broader and more nuanced database to be produced for a biomarker, e.g., for IL-6, and also allow screening for that biomarker both within and outside of the normal range, allowing earlier detection. Thus, the analyzers and analyzer systems of the invention allow a far broader and more nuanced database to be produced for a biomarker, e.g., for IL-6, and also allow screening for that biomarker both within and outside of the normal range, allowing earlier detection of conditions in which the biomarker, e.g., IL-6, is implicated.

a. Interleukin 1

IL-1α and -β are pro-inflammatory cytokines involved in immune defense against infection, and are part of the IL-1 superfamily of cytokines. Both IL-1α and IL-1β are produced by macrophages, monocytes and dendritic cells. IL-1 is involved in various immune responses with a primary role in inflammation, making IL-1a target for Rheumatoid Arthritis (RA). IL-1α and IL-1β are produced as precursor peptides, which are proteolytically processed and released in response to cell injury, and thus induce apoptosis. IL-1β production in peripheral tissue has also been associated with hyperalgesia (increased sensitivity to pain) associated with fever.

Amgen currently markets Kineret (anakinra), a synthetic form of the human interleukin-1 receptor antagonist (IL-1Ra). IL-1Ra blocks the biologic activity of IL-1 alpha and beta by competitively inhibiting IL-1 from binding to the interleukin-1 type I receptor (IL1-RI), which is expressed in a wide variety of tissues and organs. IL-1Ra inhibits the biological activities of IL-1 both in vitro and in vivo, and has been shown to be effective in animal models of septic shock, rheumatoid arthritis, graft versus host disease, stroke, and cardiac ischemia. Also in the Amgen pipeline is AMG 108, a fully human monoclonal antibody that targets inhibition of the action of interleukin-1 (IL-1). A Phase 2 clinical study is under way to assess long-term safety of treating rheumatoid arthritis with AMG 108.

i. Interleukin 1, Alpha (IL-1α)

The broad involvement of inflammation in human disease ensures that this protein will remain an attractive diagnostic target. Elevated levels of IL-1α will continue to be a diagnostic target for inflammatory diseases like rheumatoid arthritis. Thus, there is a need to develop assays with sensitivity to quantify low normal levels of IL-1α in order to differentiate between low and high levels of IL-1α which indicate disease. Also, there is a need to evaluate the potential of IL-1α as a therapeutic drug target to decrease elevated levels of IL-1α as a treatment for IL-1α associated disease. This will present a need to detect velocity of decreasing IL-1α levels to evaluate effectiveness and dosing of therapies. This may prevent adverse events like Neutropenia that develop after co-administration of drugs targeted to inflammatory cytokine pathways, like Kineret (IL-1Ra antagonist) and enteracept (TNF-alpha antagonist). To meet these goals, it is essential to have an assay that can detect IL-1α to below normal levels in human plasma.

The present invention provides an IL-1α assay sensitive enough to quantify IL-1α concentration in plasma from healthy, normal human subjects with previously unattainable levels of accuracy and precision. See Example 23. It enables differentiation between IL-1α concentrations in healthy and diseased states, allowing efficient pre-clinical and clinical study design. The IL-1α assay increases the utility of IL-1α by allowing quantification at very low levels and differentiation between small changes in concentration that can provide insights into drug efficacy or disease progression. The IL-1α assay enables the accurate quantification of IL-1α in human plasma with a broad dynamic range. In various embodiments, the assay allows investigators to: (1) measure the efficacy and dosing of therapeutics designed to interfere with the IL-1 mediated inflammatory response, such as Kineret; (2) design more robust clinical and preclinical studies when IL-1α concentration can be used as a therapeutic endpoint, as in the clinical trial of AMG 108; and/or (3) understand how IL-1α levels change in patients as they transition from a healthy to a diseased state.

In some embodiments, the method is capable of detecting IL-1α at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting the IL-1α at a limit of detection of less than about 100 pg/ml. In some embodiments, the method is capable of detecting the IL-1α a limit of detection of less than about 80 pg/ml. In some embodiments, the method is capable of detecting the IL-1α a limit of detection of less than about 60 pg/ml. In some embodiments, the method is capable of detecting the IL-1α a limit of detection of less than about 50 pg/ml. In some embodiments, the method is capable of detecting the IL-1α a limit of detection of less than about 30 pg/ml. In some embodiments, the method is capable of detecting the IL-1α a limit of detection of less than about 25 pg/ml. In some embodiments, the method is capable of detecting the IL-1α a limit of detection of less than about 10 pg/ml. In some embodiments, the method is capable of detecting the IL-1α a limit of detection of less than about 5 pg/ml. In some embodiments, the method is capable of detecting the IL-1α a limit of detection of less than about 1 pg/ml. In some embodiments, the method is capable of detecting the IL-1α a limit of detection of less than about 0.5 pg/ml. In some embodiments, the method is capable of detecting the IL-1α at a limit of detection of less than about 0.1 pg/ml. In some embodiments, the method is capable of detecting the IL-1α at a limit of detection of less than about 0.05 pg/ml. In some embodiments, the method is capable of detecting the IL-1α at a limit of detection of less than about 0.01 pg/ml. In some embodiments, the method is capable of detecting the IL-1α at a limit of detection of less than about 0.005 pg/ml. In some embodiments, the method is capable of detecting the IL-1α at a limit of detection of less than about 0.001 pg/ml. In some embodiments, the method is capable of detecting the IL-1α at a limit of detection of less than about 0.0005 pg/ml. In some embodiments, the method is capable of detecting the IL-1α at a limit of detection of less than about 0.0001 pg/ml.

ii. Interleukin 1, Beta (IL-1β)

Like IL-1α, the broad involvement of inflammation in human disease ensures that IL-1β will remain an attractive diagnostic target. Elevated levels of IL-1β will continue to be a diagnostic target for inflammatory diseases like rheumatoid arthritis. Thus, there is a need to develop assays with sensitivity to quantify low normal levels of IL-1β in order to differentiate between low and high levels of IL-1β which indicate disease. Also, there is a need to evaluate the potential of IL-1β as a therapeutic drug target to decrease elevated levels of IL-1β as a treatment for IL-1β associated disease. This will present a need to detect velocity of decreasing IL-1β levels to evaluate effectiveness and dosing of therapies. This may prevent adverse events like Neutropenia that develop after co-administration of drugs targeted to inflammatory cytokine pathways, like Kineret (IL-1Ra antagonist) and enteracept (TNF-alpha antagonist). To meet these goals, it is essential to have an assay that can detect IL-1β to below normal levels in human plasma.

The present invention provides an IL-1β assay that increases the utility of IL-1β by allowing quantification at very low levels and differentiation between small changes in concentration that can provide insights into drug efficacy or disease progression. See Example 24. The IL-1β assay is sensitive enough to quantify IL-1β concentration in plasma from healthy, normal human subjects with previously unattainable levels of accuracy and precision. The IL-1β assay enables the accurate quantification of IL-1β in human plasma with a broad dynamic range. In various embodiments, this assay will allow investigators to: (1) measure the efficacy and dosing of therapeutics designed interfere with the IL-1 mediated inflammatory response, such as Kineret; (2) design more robust clinical and preclinical studies when IL-1β concentration can be used as a therapeutic endpoint, as in the clinical trial of AMG 108; and (3) understand how IL-1β levels change in patients as they transition from a healthy to diseased state.

In some embodiments, the method is capable of detecting the at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting the IL-1β at a limit of detection of less than about 200 pg/ml. In some embodiments, the method is capable of detecting the IL-1β at a limit of detection of less than about 150 pg/ml. In some embodiments, the method is capable of detecting the IL-1β at a limit of detection of less than about 100 pg/ml. In some embodiments, the method is capable of detecting the IL-1β a limit of detection of less than about 80 pg/ml. In some embodiments, the method is capable of detecting the IL-1β a limit of detection of less than about 60 pg/ml. In some embodiments, the method is capable of detecting the IL-1β a limit of detection of less than about 50 pg/ml. In some embodiments, the method is capable of detecting the IL-1β a limit of detection of less than about 30 pg/ml. In some embodiments, the method is capable of detecting the IL-1β a limit of detection of less than about 25 pg/ml. In some embodiments, the method is capable of detecting the IL-1β a limit of detection of less than about 10 pg/ml. In some embodiments, the method is capable of detecting the IL-1β a limit of detection of less than about 5 pg/ml. In some embodiments, the method is capable of detecting the IL-1β a limit of detection of less than about 1 pg/ml. In some embodiments, the method is capable of detecting the IL-1β a limit of detection of less than about 0.5 pg/ml. In some embodiments, the method is capable of detecting the IL-1β at a limit of detection of less than about 0.1 pg/ml. In some embodiments, the method is capable of detecting the IL-1β at a limit of detection of less than about 0.05 pg/ml. In some embodiments, the method is capable of detecting the IL-1β at a limit of detection of less than about 0.01 pg/ml. In some embodiments, the method is capable of detecting the IL-1β at a limit of detection of less than about 0.005 pg/ml. In some embodiments, the method is capable of detecting the IL-1β at a limit of detection of less than about 0.001 pg/ml. In some embodiments, the method is capable of detecting the IL-1β at a limit of detection of less than about 0.0005 pg/ml. In some embodiments, the method is capable of detecting the IL-1β at a limit of detection of less than about 0.0001 pg/ml.

b. Interleukin 4 (IL-4)

Interleukin-4 (IL-4) is a cytokine that is a key regulator in humoral and adaptive immunity IL-4 induces differentiation of naive helper T cells (Th0 cells) to Th2 cells. It has many biological roles, including the stimulation of activated B-cell and T-cell proliferation, and the differentiation of CD4+ T-cells into Th2 cells IL-4 plays an important role in the development of allergic inflammatory responses. IL-4 controls the production of IgE, expands IL-4 producing T cell subsets and stabilizes effector cell functions.

IL-4 has therapeutic potential due to its role in the development of allergic inflammatory responses. IL-4 also has shown to have promise in drug targeting for cancer. For example, PRX321 (Protox) is a targeted therapeutic toxin in which IL-4 is linked to a *Pseudomonas* exo-toxin, a potent substance that can destroy cancer cells. Besides brain, kidney and lung cancer, PRX321 has shown promising pre-clinical results in a number of cancers over-expressing IL-4 receptors including pancreatic, ovarian, breast, head and neck, melanoma, prostate and blood cancers such as chronic lymphocytic leukemia (CLL) and Hodgkin's lymphoma.

The concentration of plasma IL-4 in healthy human subjects has yet to be defined. Thus it is difficult to understand the role that differences in IL-4 concentrations play between disease and healthy states. In addition, measuring the efficacy of experimental therapeutics that target lowering IL-4 by measuring the velocity of IL-4 decreases is hindered by lack of assay sensitivity. Furthermore the reading range of the most sensitive ELISAs is limited to less than two logs, which forces sample retesting and wastage. Thus there is need for a highly sensitive assay that can detect the velocity of subtle changes in concentration, and that can measure baseline concentration of IL-4 in normal subjects.

The IL-4 Assay provided by the present invention is sensitive enough to quantify IL-4 concentrations in plasma from healthy, normal human subjects with a level of accuracy and precision currently unobtainable using other high sensitivity assays. See Example 25. This assay enables the quantification of very low levels of plasma IL-4. In some embodiments, the assay allows the measurement of small changes in IL-4 level that can provide insights into therapeutic efficacy. In various embodiments, this assay allows investigators to: (1) measure the efficacy and dosing of therapeutics designed interfere with general inflammatory and allergic responses; (2) design more robust clinical and preclinical studies when IL-4 concentration is used as a therapeutic endpoint; and (3) understand how IL-4 levels change in patients as they transition from a healthy to diseased state.

In some embodiments, the method of the present invention is capable of detecting IL-4 at a limit of detection of less than about 100, 80, 60, 50, 30, 20, 10, 5, 1, 0.5, 0.01, 0.005, 0.001, 0.0005 or 0.0001 pg/ml, e.g., less than about 100 pg/ml. In some embodiments, the method is capable of detecting the IL-4 at a limit of detection of less than about 100 pg/ml. In some embodiments, the method is capable of detecting the IL-4 a limit of detection of less than about 80 pg/ml. In some embodiments, the method is capable of detecting the IL-4 a limit of detection of less than about 60 pg/ml. In some embodiments, the method is capable of detecting the IL-4 a limit of detection of less than about 50 pg/ml. In some embodiments, the method is capable of detecting the IL-4 a limit of detection of less than about 30 pg/ml. In some embodiments, the method is capable of detecting the IL-4 a limit of detection of less than about 25 pg/ml. In some embodiments, the method is capable of detecting the IL-4 a limit of detection of less than about 10 pg/ml. In some embodiments, the method is capable of detecting the IL-4 a limit of detection of less than about 5 pg/ml. In some embodiments, the method is capable of detecting the IL-4 a limit of detection of less than about 1 pg/ml. In some embodiments, the method is capable of detecting the IL-4 a limit of detection of less than about 0.5 pg/ml. In some embodiments, the method is capable of detecting the IL-4 at a limit of detection of less than about 0.1 pg/ml. In some embodiments, the method is capable of detecting the IL-4 at a limit of detection of less than about 0.05 pg/ml. In some embodiments, the method is capable of detecting the IL-4 at a limit of detection of less than about 0.01 pg/ml. In some embodiments, the method is capable of detecting the IL-4 at a limit of detection of less than about 0.005 pg/ml. In some embodiments, the method is capable of detecting the IL-4 at a limit of detection of less than about 0.001 pg/ml. In some embodiments, the method is capable of detecting the IL-4 at a limit of detection of less than about 0.0005 pg/ml. In some embodiments, the method is capable of detecting the IL4 at a limit of detection of less than about 0.0001 pg/ml.

c. Interleukin 6 (IL-6)

Interleukin-6 (IL-6) is a pro-inflammatory cytokine secreted by T cells and macrophages to stimulate immune response to trauma, especially burns or other tissue damage leading to inflammation. IL-6 is also secreted by macrophages in response to specific microbial molecules, referred to as pathogen associated molecular patterns (PAMPs), which trigger the innate immune response and initiate inflammatory cytokine production. IL-6 is one of the most important mediators of fever and of the acute phase response. IL-6 is also called a "myokine," a cytokine produced from muscle, and is elevated in response to muscle contraction. Additionally, osteoblasts secrete IL-6 to stimulate osteoclast formation.

IL-6-related disorders include but are not limited to sepsis, peripheral arterial disease, and chronic obstructive pulmonary disease. Interleukin-6 mediated inflammation is also the common causative factor and therapeutic target for atherosclerotic vascular disease and age-related disorders including osteoporosis and type 2 diabetes. In addition, IL-6 can be measured in combination with other cytokines, for example TNFα to diagnose additional diseases such as septic shock. IL-6 has therapeutic potential as a drug target which would result in an anti-inflammatory and inhibition of the acute phase response. In terms of host response to a foreign pathogen, IL-6 has been shown, in mice, to be required for resistance against the bacterium, *Streptococcus pneumoniae* Inhibitors of IL-6 (including estrogen) are used to treat post-menopausal osteoporosis. There is also therapeutic potential for cancer, as IL-6 is essential for hybridoma growth and is found in many supplemental cloning media such as briclone.

Circulating levels of IL-6 in the plasma of healthy subjects is difficult to determine with many currently available assays, thus it is difficult to differentiate disease from healthy states. Furthermore, when used as a therapeutic target, it is desirous to measure therapeutic efficacy by measuring IL-6 levels as they decrease below normal state levels. This can not be achieved with assays currently available. An IL-6 assay is currently available outside the U.S. for diagnostic use, and for research use only (RUO) in the U.S. and Japan.

The present invention provides an IL-6 assay that enables the quantification of very low levels of plasma IL-6 and allows for accurate measurement of small changes in its level due to disease processes or therapeutic intervention. See Example 26. This high level of sensitivity can provide insights into therapeutic efficacy. In various embodiments, this assay will allow investigators to: (1) measure the efficacy and dosing of therapeutics designed interfere with the inflammatory response; (2) design more robust clinical and preclinical studies when IL-6 concentration is used as a therapeutic endpoint; and (3) understand how IL-6 levels change in patients as they transition from a healthy to diseased state.

In some embodiments, the present invention provides a method capable of detecting IL-6 at a limit of detection of less than about 100, 80, 60, 50, 30, 20, 10, 5, 1, 0.5, 0.01, 0.005, 0.001, 0.0005 or 0.0001 pg/ml, e.g., less than about 100 pg/ml. In some embodiments, the method is capable of detecting the IL-6 at a limit of detection of less than about 100 pg/ml. In some embodiments, the method is capable of detecting the IL-6 a limit of detection of less than about 80 pg/ml. In some embodiments, the method is capable of detecting the IL-6 a limit of detection of less than about 60 pg/ml. In some embodiments, the method is capable of detecting the IL-6 a limit of detection of less than about 50 pg/ml. In some embodiments, the method is capable of detecting the IL-6 a limit of detection of less than about 30 pg/ml. In some embodiments, the method is capable of detecting the IL-6 a limit of detection of less than about 25 pg/ml. In some embodiments, the method is capable of detecting the IL-6 a limit of detection of less than about 10 pg/ml. In some embodiments, the method is capable of detecting the IL-6 a limit of detection of less than about 5 pg/ml. In some embodiments, the method is capable of detecting the IL-6 a limit of detection of less than about 1 pg/ml. In some embodiments, the method is capable of detecting the IL-6 a limit of detection of less than about 0.5 pg/ml. In some embodiments, the method is capable of detecting the IL-6 at a limit of detection of less than about 0.1 pg/ml. In some embodiments, the method is capable of detecting the IL-6 at a limit of detection of less than about 0.05 pg/ml. In some embodiments, the method is capable of detecting the IL-6 at a limit of detection of less than about 0.01 pg/ml. In some embodiments, the method is capable of detecting the IL-6 at a limit of detection of less than about 0.005 pg/ml. In some embodiments, the method is capable of detecting the IL-6 at a limit of detection of less than about 0.001 pg/ml. In some embodiments, the method is capable of detecting the IL-6 at a limit of detection of less than about 0.0005 pg/ml. In some embodiments, the method is capable of detecting the IL-6 at a limit of detection of less than about 0.0001 pg/ml.

d. Interleukin 8 (IL-8)

Figure 17E:
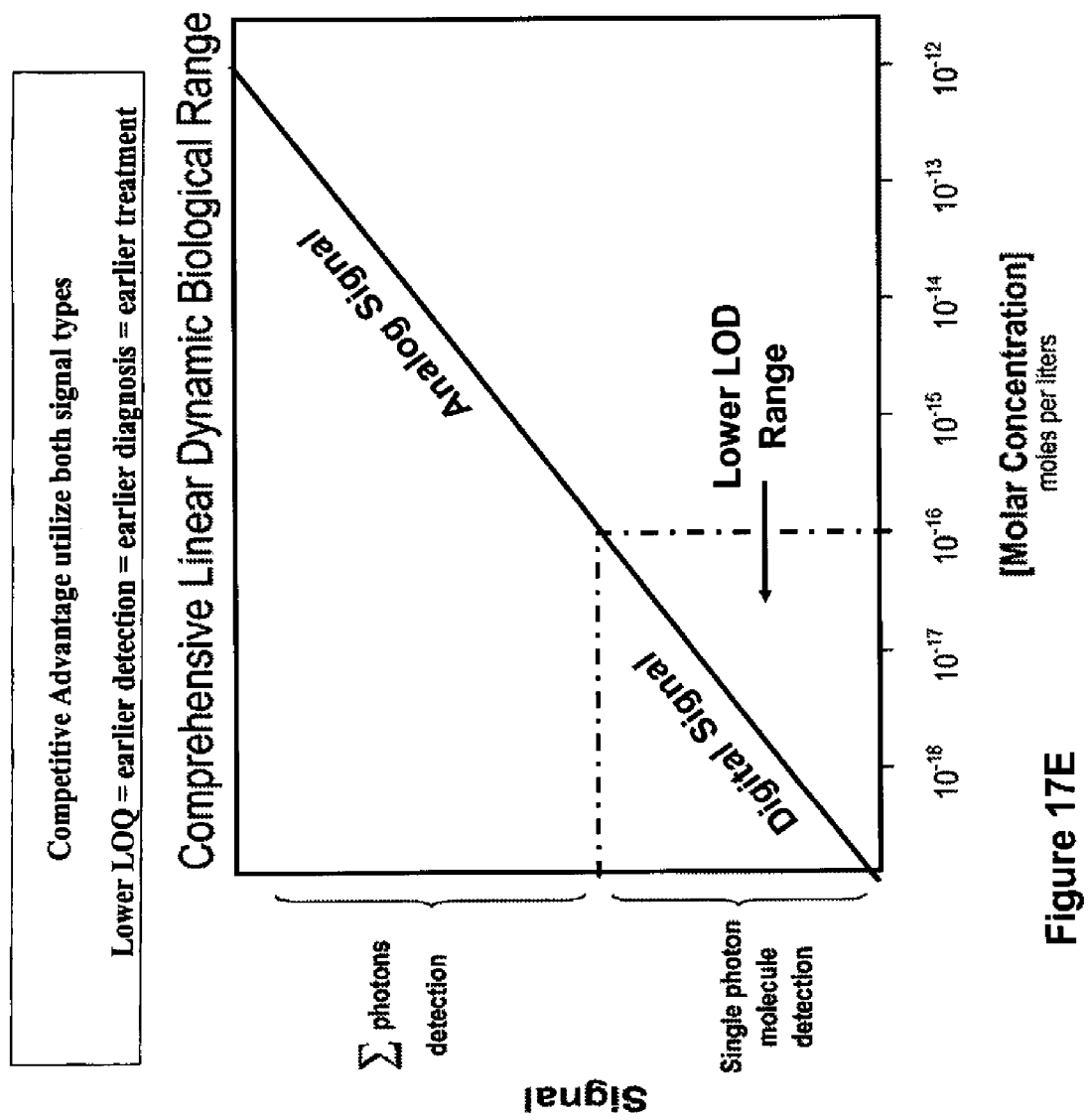

Like IL-6, the present invention provides an Interleukin 8 (IL-8) assay that enables the quantification of very low levels of plasma IL-8 and allows for accurate measurement of small changes in its level due to disease processes or therapeutic intervention. See FIG. 17. In some embodiments, the present invention provides a method capable of detecting IL-8 at a limit of detection of less than about 100, 80, 60, 50, 30, 20, 10, 5, 1, 0.5, 0.01, 0.005, 0.001, 0.0005 or 0.0001 pg/ml, e.g., less than about 100 pg/ml. In some embodiments, the method is capable of detecting the IL-8 at a limit of detection of less than about 100 pg/ml. In some embodiments, the method is capable of detecting the IL-8 a limit of detection of less than about 80 pg/ml. In some embodiments, the method is capable of detecting the IL-8 a limit of detection of less than about 60 pg/ml. In some embodiments, the method is capable of detecting the IL-8 a limit of detection of less than about 50 pg/ml. In some embodiments, the method is capable of detecting the IL-8 a limit of detection of less than about 30 pg/ml. In some embodiments, the method is capable of detecting the IL-8 a limit of detection of less than about 25 pg/ml. In some embodiments, the method is capable of detecting the IL-8 a limit of detection of less than about 10 pg/ml. In some embodiments, the method is capable of detecting the IL-8 a limit of detection of less than about 5 pg/ml. In some embodiments, the method is capable of detecting the IL-8 a limit of detection of less than about 1 pg/ml. In some embodiments, the method is capable of detecting the IL-8 a limit of detection of less than about 0.5 pg/ml. In some embodiments, the method is capable of detecting the IL-8 at a limit of detection of less than about 0.1 pg/ml. In some embodiments, the method is capable of detecting the IL-8 at a limit of detection of less than about 0.05 pg/ml. In some embodiments, the method is capable of detecting the IL-8 at a limit of detection of less than about 0.01 pg/ml. In some embodiments, the method is capable of detecting the IL-8 at a limit of detection of less than about 0.005 pg/ml. In some embodiments, the method is capable of detecting the IL-8 at a limit of detection of less than about 0.001 pg/ml. In some embodiments, the method is capable of detecting the IL-8 at a limit of detection of less than about 0.0005 pg/ml. In some embodiments, the method is capable of detecting the IL-8 at a limit of detection of less than about 0.0001 pg/ml.

4. Inflammatory Markers

Other cytokines that can be useful in detecting early onset of inflammatory disease include markers and panels of markers of inflammation as described herein. Examples of cytokines that can be used to detect inflammatory disorders are Leukotriene 4 (LTE4), which can be an early marker of asthma, and TGFβ, which can be used to detect and monitor the status of inflammatory disorders including fibrosis, sclerosis. Some markers can be used to detect more than one disorder, e.g., TGFβ, can also be used to detect the presence of cancer.

a. Leukotriene E4

Cysteinyl leukotrienes (LTC4, LTD4, LTE4) play an important role in the pathogenesis of asthma. Leukotrienes are produced by mast cells, eosinophils, and other airway inflammatory cells and increase vascular permeability, constrict bronchial smooth muscle, and mediate bronchial hyperresponsiveness. Levels of urinary LTE4, the stable metabolite of LTC4 and LTD4, are increased in children and adults with asthma compared with healthy controls and in asthmatics after bronchial challenge with antigen, after oral challenge with aspirin in aspirin sensitive asthmatic subjects, and during exercise induced bronchospasm. The importance of leukotrienes in the pathology of asthma has been further demonstrated in large clinical trials with agents that block the actions of leukotrienes. For example, montelukast, a potent leukotriene receptor antagonist taken orally once daily, significantly improves asthma control in both children (aged 2-14 years) and adults and attenuates exercise induced bronchoconstriction.

Activation of the leukotriene pathways is accompanied by rises in urinary levels of LTE4, and acute exacerbations of asthma are accompanied by increased levels of LTE4 in urine followed by a significant decrease during resolution. The degree of airflow limitation correlates with levels of urinary LTE4 during the exacerbation and follow up periods, thus indicating that the leukotriene pathway is activated during acute asthma. In addition, inhalation of bronchoconstricting doses of LTC4 or LTE4 alter urinary LTE4 excretion in a dose-dependent manner thus indicating that urinary LTE4 can be used as a marker of sulphidopeptide leukotriene synthesis in the lungs of patients with asthma.

The methods of the invention can be used to detect changes in LTE4 in biological samples such as urinary samples. See Example 5. Measurements of subnanogram levels of LTE4 can be useful as a reference for detecting and monitoring sulphidopeptide leukotriene synthesis in the lungs of patients with chronic or acute asthma.

In some embodiments, the methods of the present invention are capable of detecting LTE4 at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting LTE4 at a limit of detection of less than about 100 pg/ml. In some embodiments, the method is capable of detecting the LTE4 a limit of detection of less than about 80 pg/ml. In some embodiments, the method is capable of detecting the LTE4 a limit of detection of less than about 60 pg/ml. In some embodiments, the method is capable of detecting the LTE4 a limit of detection of less than about 50 pg/ml. In some embodiments, the method is capable of detecting the LTE4 a limit of detection of less than about 30 pg/ml. In some embodiments, the method is capable of detecting the LTE4 a limit of detection of less than about 25 pg/ml. In some embodiments, the method is capable of detecting the LTE4 a limit of detection of less than about 10 pg/ml. In some embodiments, the method is capable of detecting the LTE4 a limit of detection of less than about 5 pg/ml. In some embodiments, the method is capable of detecting the LTE4 a limit of detection of less than about 1 pg/ml. In some embodiments, the method is capable of detecting the LTE4 a limit of detection of less than about 0.5 pg/ml. In some embodiments, the method is capable of detecting the LTE4 at a limit of detection of less than about 0.1 pg/ml. In some embodiments, the method is capable of detecting the LTE4 at a limit of detection of less than about 0.05 pg/ml. In some embodiments, the method is capable of detecting the LTE4 at a limit of detection of less than about 0.01 pg/ml. In some embodiments, the method is capable of detecting the LTE4 at a limit of detection of less than about 0.005 pg/ml. In some embodiments, the method is capable of detecting the LTE4 at a limit of detection of less than about 0.001 pg/ml. In some embodiments, the method is capable of detecting the LTE4 at a limit of detection of less than about 0.0005 pg/ml. In some embodiments, the method is capable of detecting the LTE4 at a limit of detection of less than about 0.0001 pg/ml.

b. TGFβ

The methods of the invention can also be performed to detect the early onset of diseases for which TGFβ is a marker. Examples of TGFβ-related diseases include fibrotic diseases. Fibrosis refers to the excessive and persistent formation of scar tissue, which is responsible for morbidity and mortality associated with organ failure in a variety of chronic diseases affecting the lungs, kidneys, eyes, heart, liver, and skin. TGFβ is well known for its role as a mediator of chronic fibrotic effects. For example, TGFβ is implicated in promoting fibroblastic proliferation and matrix accumulation in fibrotic lung disease. Inhibition of TGFβ has been proposed as a potential therapeutic avenue for the management of lung fibrosis. TGFβ not only stimulates the synthesis of many extracellular matrix molecules, including fibronectin and type I collagen and their receptors, but also decreases matrix degradation via differential effects on the expression of proteases and their inhibitors, strongly promoting generation of extracellular matrix. Thus the analyzer systems of the invention can detect abnormal levels of TGFβ, e.g., associated with fibrotic diseases, including but not limited to idiopathic pulmonary fibrosis, diabetic nephropathy, progressive nephropathies including glomerulosclerosis and IgA nephropathy (causes of kidney failure and the need for dialysis and retransplant); diabetic retinopathy and advanced macular degeneration (fibrotic diseases of the eye and leading causes of blindness); cirrhosis and biliary atresia (leading causes of liver fibrosis and failure); congestive heart failure; myocardiopathy associated with progressive fibrosis in Chagas disease; lung fibrosis; and scleroderma.

TGFβ is also a marker for cancers including prostate cancer, cervical cancer, lung carcinoma, and Hodgkin's disease. Plasma levels of TGFβ in patients with lung cancer are often elevated. It has been shown that in patients with an elevated plasma TGF beta 1 level at diagnosis, monitoring this level may be useful in detecting both disease persistence and recurrence after radiotherapy.

Transforming growth factor-beta (TGFβ) is also a multipotent growth factor affecting development, homeostasis, and tissue repair. Increased expression of TGFβ has been reported in different malignancies, suggesting a role for this growth factor in tumorigenesis. In particular, it has been demonstrated that the presence of TGFβ in the endothelial and perivascular layers of small vessels in the tumor stroma of osteosarcomas suggests an angiogenic activity of this growth factor, and that increased expression of TGF-beta isoforms have been suggested to play a role in the progression of osteosarcoma (Kloen et al., Cancer, 80:2230-39 (1997)). TGFβ is one of the few known proteins that can inhibit cell growth. However, although the notion is controversial, some researchers believe that some human malignancies such as breast cancer subvert TGFβ for their own purposes. In a paradox that is not understood, these cancers make TGFβ and steadily increase its expression until it becomes a marker of advancing metastasis and decreased survival. For example, levels of plasma TGFβ are markedly elevated in men with prostate cancer metastatic to regional lymph nodes and bone. In men without clinical or pathologic evidence of metastases, the preoperative plasma TGF-β level is a strong predictor of biochemical progression after surgery, presumably because of an association with occult metastatic disease present at the time of radical prostatectomy.

In some embodiments, the method is capable of detecting TGF-β at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting the TGF-β at a limit of detection of less than about 100 pg/ml. In some embodiments, the method is capable of detecting the TGF-β a limit of detection of less than about 80 pg/ml. In some embodiments, the method is capable of detecting the TGF-β a limit of detection of less than about 60 pg/ml. In some embodiments, the method is capable of detecting the TGF-β a limit of detection of less than about 50 pg/ml. In some embodiments, the method is capable of detecting the TGF-β a limit of detection of less than about 30 pg/ml. In some embodiments, the method is capable of detecting the TGF-β a limit of detection of less than about 25 pg/ml. In some embodiments, the method is capable of detecting the TGF-β a limit of detection of less than about 10 pg/ml. In some embodiments, the method is capable of detecting the TGF-β a limit of detection of less than about 5 pg/ml. In some embodiments, the method is capable of detecting the TGF-β a limit of detection of less than about 1 pg/ml. In some embodiments, the method is capable of detecting the TGF-β a limit of detection of less than about 0.5 pg/ml. In some embodiments, the method is capable of detecting the TGF-β at a limit of detection of less than about 0.1 pg/ml. In some embodiments, the method is capable of detecting the TGF-β at a limit of detection of less than about 0.05 pg/ml. In some embodiments, the method is capable of detecting the TGF-β at a limit of detection of less than about 0.01 pg/ml. In some embodiments, the method is capable of detecting the TGF-β at a limit of detection of less than about 0.005 pg/ml. In some embodiments, the method is capable of detecting the TGF-β at a limit of detection of less than about 0.001 pg/ml. In some embodiments, the method is capable of detecting the TGF-β at a limit of detection of less than about 0.0005 pg/ml. In some embodiments, the method is capable of detecting the TGF-β at a limit of detection of less than about 0.0001 pg/ml.

Other markers of abnormal cell growth that are detected by the methods of the invention include Akt1, Fas ligand, VEGF, Aβ-40, Aβ-42, cTnI, IL-1α, IL-1β, IL-4, and IL-6 as described herein.

5. Akt1

Akt1 is v-akt murine thymoma viral oncogene homolog 1 and is a serine-threonine protein kinase encoded by the AKT1 gene. Akt kinases have been implicated in disparate cell responses, including inhibition of apoptosis and promotion of cell proliferation, angiogenesis, and tumor cell invasiveness.

Best known for its ability to inhibit apoptotic and non-apoptotic cell death, Akt can be monitored to predict tumor response to anticancer treatment. Predicting tumor response by assessing the influence of apoptosis and nonapoptotic cell death, would allow for developing a more efficient strategy for enhancing the therapeutic effect of anticancer treatment. Anticancer treatment-induced apoptosis is regulated by the balance of proapoptotic and antiapoptotic proteins through mitochondria, and resistance to apoptosis is mediated by Akt-dependent and Bcl-2-dependent pathways. Bcl-2 partially inhibits nonapoptotic cell death as well as apoptosis, whereas Akt inhibits both apoptotic and nonapoptotic cell death through several target proteins. Since drug sensitivity is likely correlated with the accumulation of apoptotic and non-apoptotic cell deaths, which may influence overall tumor response in anticancer treatment. The ability to predict overall tumor response from the modulation of several important cell death-related proteins may result in a more efficient strategy for improving the therapeutic effect.

Akt1 is also involved in Epithelial-mesenchymal transition (EMT), which is an important process during development and oncogenesis by which epithelial cells acquire fibroblast-like properties and show reduced intercellular adhesion and increased motility. AKT is activated in many human carcinomas, and the AKT-driven EMT may confer the motility required for tissue invasion and metastasis. Thus future therapies based on AKT inhibition may complement conventional treatments by controlling tumor cell invasion and metastasis. Akt is constitutively activated in most melanoma cell lines and tumor samples of different progression stages, and activation of AKT has been linked to the expression of invasion/metastasis-related melanoma cell adhesion molecule (Mel-CAM), which in turn is strongly associated with the acquisition of malignancy by human melanoma. Akt1 is also activated in pancreatic cancer, and AKT activation has been shown to correlate with higher histologic tumor grade. Thus, AKT activation is associated with tumor grade, an important prognostic factor. Akt1 is also upregulated in prostate cancer and that expression is correlated with tumor progression. Thus, Akt1 could be targeted for therapeutic intervention of cancer while at its earliest stages. In some embodiments, the analyzer systems of the invention provide a method for providing an early diagnosis of a cancer by determining the presence or concentration of Akt1 in a sample from a patient when the level of Akt1 is less than about 100, 50, or 25 pg/ml. See Example 6.

In some embodiments, the methods of the present invention are capable of detecting Akt1 at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting Akt1 at a limit of detection of less than about 100 pg/ml. In some embodiments, the method is capable of detecting the Akt1 a limit of detection of less than about 80 pg/ml. In some embodiments, the method is capable of detecting the Akt1 a limit of detection of less than about 60 pg/ml. In some embodiments, the method is capable of detecting the Akt1 a limit of detection of less than about 50 pg/ml. In some embodiments, the method is capable of detecting the Akt1 a limit of detection of less than about 30 pg/ml. In some embodiments, the method is capable of detecting the Akt1 a limit of detection of less than about 25 pg/ml. In some embodiments, the method is capable of detecting the Akt1 a limit of detection of less than about 10 pg/ml. In some embodiments, the method is capable of detecting the Akt1 a limit of detection of less than about 5 pg/ml. In some embodiments, the method is capable of detecting the Akt1 a limit of detection of less than about 1 pg/ml. In some embodiments, the method is capable of detecting the Akt1 a limit of detection of less than about 0.5 pg/ml. In some embodiments, the method is capable of detecting the Akt1 at a limit of detection of less than about 0.1 pg/ml. In some embodiments, the method is capable of detecting the Akt1 at a limit of detection of less than about 0.05 pg/ml. In some embodiments, the method is capable of detecting the Akt1 at a limit of detection of less than about 0.01 pg/ml. In some embodiments, the method is capable of detecting the Akt1 at a limit of detection of less than about 0.005 pg/ml. In some embodiments, the method is capable of detecting the Akt1 at a limit of detection of less than about 0.001 pg/ml. In some embodiments, the method is capable of detecting the Akt1 at a limit of detection of less than about 0.0005 pg/ml. In some embodiments, the method is capable of detecting the Akt1 at a limit of detection of less than about 0.0001 pg/ml.

6. Fas Ligand

Fas Ligand (FasL), also known as CD95L, is a member of the TNF family and induces apoptosis via binding to Fas (CD95). The protein exists in two forms; either membrane FasL or soluble FasL, which migrate at molecular weight of 45 kDa and 26 kDa, respectively. FasL is expressed on a variety of cells including activated lymphocytes, natural killer cells and monocytes. Interaction of FasL and Fas plays an important role in physiological apoptotic processes. Malfunction of the Fas-FasL system causes hyperplasia in peripheral lymphoid organs and accelerates autoimmune disease progression and tumorigenesis. There are limited data about the levels of soluble apoptotic factors in general, and more specifically about their modulation with therapeutic regimens.

The systems and methods of the invention can detect concentrations of Fas ligand that are as low as 2.4 pg/ml. Thus, in some embodiments, the analyzer systems and methods of the invention provide for the detection of Fas ligand to identify pathological conditions such as abnormal levels of apoptosis. Measurements of Fas in patient samples can be used to diagnose conditions such as polycystic ovarian syndrome, tumors such as testicular germ cell tumors, bladder cancer, lung cancer, and rare tumors such as follicular dendritic cell tumors. In addition, Fas measurements of Fas ligand can be used to diagnose allograft rejection and degenerative disease such as osteoarthritis. Thus, in some embodiments, the analyzer systems and methods of the invention can be used to determine the concentration of Fas ligand in a sample from a patient suspected of suffering from Fas ligand related disorder to diagnose the disorder, or the concentration of Fas ligand can be used to monitor the progress or status of a Fas ligand related disorder in a patient undergoing therapy for the disorder. In some embodiments, the assay is capable of determining the level of Fas ligand in the sample at a concentration less than about 100, 50, 25, 10, or 5 pg/ml. See Example 8.

In some embodiments, the methods of the present invention are capable of detecting FasL at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting FasL at a limit of detection of less than about 100 pg/ml. In some embodiments, the method is capable of detecting the FasL a limit of detection of less than about 80 pg/ml. In some embodiments, the method is capable of detecting the FasL a limit of detection of less than about 60 pg/ml. In some embodiments, the method is capable of detecting the FasL a limit of detection of less than about 50 pg/ml. In some embodiments, the method is capable of detecting the FasL a limit of detection of less than about 30 pg/ml. In some embodiments, the method is capable of detecting the FasL a limit of detection of less than about 25 pg/ml. In some embodiments, the method is capable of detecting the FasL a limit of detection of less than about 10 pg/ml. In some embodiments, the method is capable of detecting the FasL a limit of detection of less than about 5 pg/ml. In some embodiments, the method is capable of detecting the FasL a limit of detection of less than about 1 pg/ml. In some embodiments, the method is capable of detecting the FasL a limit of detection of less than about 0.5 pg/ml. In some embodiments, the method is capable of detecting the FasL at a limit of detection of less than about 0.1 pg/ml. In some embodiments, the method is capable of detecting the FasL at a limit of detection of less than about 0.05 pg/ml. In some embodiments, the method is capable of detecting the FasL at a limit of detection of less than about 0.01 pg/ml. In some embodiments, the method is capable of detecting the FasL at a limit of detection of less than about 0.005 pg/ml. In some embodiments, the method is capable of detecting the FasL at a limit of detection of less than about 0.001 pg/ml. In some embodiments, the method is capable of detecting the FasL at a limit of detection of less than about 0.0005 pg/ml. In some embodiments, the method is capable of detecting the FasL at a limit of detection of less than about 0.0001 pg/ml.

7. VEGF

Vascular endothelial growth factor-A (VEGF-A), commonly known as VEGF, is a member of a family of secreted glycoproteins that promote endothelial cell growth, survival, migration, and vascular permeability, all of which contribute to angiogenesis. The binding of VEGF to its receptor triggers the activation of a cell signaling pathway that is critical for the growth of blood vessels from pre-existing vasculature. VEGF is implicated in a variety of diseases including cancer, age-related macular degeneration, diabetic retinopathy and rheumatoid arthritis. As such, it is an attractive candidate for the development of therapies to these diseases, particularly cancer.

The first anti-VEGF drug, the monoclonal antibody Avastin, was approved by the FDA in 2004 and is approved to treat metastatic colon and non small-cell lung cancer. The drug is also under study for the treatment of many other cancers. Other compounds that target VEGF-mediated cell signaling include the monoclonal antibody fragment Lucentis, approved to treat age related macular degeneration, and two small molecules, Sutent and Nexavar, which target receptor tyrosine kinases, including the VEGF receptor. Other drug candidates targeting this path are in development.

With the efficacy seen with drugs that target VEGF and its pathway, VEGF is an attractive development target. In addition, as researchers study various cancers and other diseases where VEGF signaling is implicated, measuring small changes in VEGF levels will help them understand biological changes that occur as disease progresses. However, current commercially available immunoassays can only measure elevated concentrations of VEGF. They are not sensitive enough to measure VEGF in plasma obtained from healthy human subjects or detect the small changes in VEGF levels that may be indicative of an early disease state. However, the plasma VEGF assay according to the present invention provides the power needed to use VEGF as a biomarker for disease and the sensitivity to quantify VEGF in healthy human subjects as well as those undergoing anti-VEGF therapy. In some embodiments, the human VEGF assay has an LOD of about 0.1 pg/ml and a lower limit of quantitation (LLOQ) of 0.3 pg/ml, making it 90× more sensitive than the commonly used ELISA assay. See Examples 11-21.

The present invention increases the clinical utility of VEGF by allowing scientists to detect very low levels of VEGF and measure small changes in its level that can provide insights into drug efficacy or disease progression. Among other improvements, the assay allows investigators to: (1) measure the efficacy and dosing of therapeutics designed to lower the levels of VEGF, particularly when VEGF levels should go much lower than that seen in normal states; (2) design more robust clinical and preclinical studies when VEGF concentration is used as a therapeutic endpoint; and (3) understand how VEGF levels change in patients as they transition from a healthy to diseased state with cancer and other diseases involving angiogenesis.

In some embodiments, the present invention provides methods to quantify normal levels of VEGF, and identify abnormally elevated levels of VEGF indicative of the presence of an early stage cancer/tumor. Typical healthy levels of VEGF in humans are less than 50 pg/mL, and are significantly elevated (>100 pg/mL, often 200-500 pg/mL) in subjects with cancer. In other embodiments, the methods described herein can be used to indicate the presence of other cancers, such as prostate and lymphoma. The method can be used to indicate the presence of solid tumors that are undergoing vascularization, which will have increased levels of VEGF.

In some embodiments, the present invention provides methods to quantify normal levels of VEGF, and identify abnormally elevated levels of VEGF indicative of the presence of vascular inflammation. This measurement can be augmented by co-measurement of other inflammatory cytokines in healthy individuals, where elevated levels are indicative of inflammation. In some embodiments, because of the role of VEGF in angiogenesis and artherosclerosis, the invention can also be used to quantify abnormally elevated levels of VEGF as indicative of cardiac disease in conjunction with elevated levels of cTnI which is the gold standard for detecting myocardial infarction. This measurement can be augmented by co-measurement of other cardiac markers (i.e., pro-BNP) or inflammatory markers (i.e., hsCRP, cytokines) in healthy individuals, where elevated levels are indicative of cardiac disease. In some embodiments, the method described can be used to quantify normal levels of VEGF, and identify abnormally elevated levels of VEGF indicative of the presence of artherosclerosis in subjects with diabetes. This measurement can be augmented by co-measurement of other markers for diabetes (i.e., insulin) and for metabolic disease (i.e., glucagon like peptide-1 (GLP-1)).

The present invention provides methods to measure VEGF in very small sample volumes that are less than the standard sample volume of 100 µl. The methods are enabled by the sensitivity of the assay and enable a greater number of samples to provide quantifiable results in small volume samples compared to other methods. In one embodiment, the methods measure VEGF in human or mouse plasma samples of less than or equal to 10 µl. In another embodiment, the methods measure VEGF in tissue lysates from human or mouse plasma samples of less than or equal to 10 µl. These methods have been tested in lysates from human breast cancer tissue biopsies, as well as in mouse tissue lysates from several strains of mice. In another embodiment, the methods measure VEGF in lysates prepared from tissue biopsies in healthy and diseased individuals. Based on a typical 1 mm needle biopsy, and resulting lysates volume of less than or equal to 10 µl this method enables quantification of VEGF from a needle biopsy. Small volume sample sizes are also provided with other markers of the present invention.

In one aspect, the present invention provides a method for determining the presence or absence of a single molecule of VEGF or a fragment or complex thereof in a sample, by i) labeling the molecule, fragment, or complex, if present, with a label; and ii) detecting the presence or absence of the label, where the detection of the presence of the label indicates the presence of the single molecule, fragment, or complex of VEGF in the sample. In some embodiments, the methods of the present invention are capable of detecting VEGF at a limit of detection of less than about 115, 100, 80, 60, 50, 30, 20, 10, 5, 1, 0.5, 0.1, 0.05, 0.01, 0.005, 0.001, 0.0005 or 0.0001 pg/ml, e.g., less than about 115 pg/ml. In some embodiments, the method is capable of detecting VEGF at a limit of detection of less than about 115 pg/ml. In some embodiments, the method is capable of detecting VEGF at a limit of detection of less than about 100 pg/ml. In some embodiments, the method is capable of detecting the VEGF a limit of detection of less than about 80 pg/ml. In some embodiments, the method is capable of detecting the VEGF a limit of detection of less than about 60 pg/ml. In some embodiments, the method is capable of detecting the VEGF a limit of detection of less than about 50 pg/ml. In some embodiments, the method is capable of detecting the VEGF a limit of detection of less than about 30 pg/ml. In some embodiments, the method is capable of detecting the VEGF a limit of detection of less than about 25 pg/ml. In some embodiments, the method is capable of detecting the VEGF a limit of detection of less than about 10 pg/ml. In some embodiments, the method is capable of detecting the VEGF a limit of detection of less than about 5 pg/ml. In some embodiments, the method is capable of detecting the VEGF a limit of detection of less than about 1 pg/ml. In some embodiments, the method is capable of detecting the VEGF a limit of detection of less than about 0.5 pg/ml. In some embodiments, the method is capable of detecting the VEGF at a limit of detection of less than about 0.1 pg/ml. In some embodiments, the method is capable of detecting the VEGF at a limit of detection of less than about 0.05 pg/ml. In some embodiments, the method is capable of detecting the VEGF at a limit of detection of less than about 0.01 pg/ml. In some embodiments, the method is capable of detecting the VEGF at a limit of detection of less than about 0.005 pg/ml. In some embodiments, the method is capable of detecting the VEGF at a limit of detection of less than about 0.001 pg/ml. In some embodiments, the method is capable of detecting the VEGF at a limit of detection of less than about 0.0005 pg/ml. In some embodiments, the method is capable of detecting the VEGF at a limit of detection of less than about 0.0001 pg/ml.

8. Aβ-40 and Aβ-42

Amyloid beta proteins (40 and 42 amino acids) are the main constituent of amyloid plaques in the brains of Alzheimer's disease (AD) patients. In healthy and diseased states Aβ-40 is the more common form (10-20× higher than Aβ-42) of the two in both cerebrospinal fluid (CSF) and plasma. In patients with AD, Aβ-42 primarily aggregates and deposits in the brain forming plaques. Thus the concentration of Aβ-42 is decreased in the CSF of many AD patients. Recent studies suggest that a decrease in Aβ-42 concentrations (with a paralleled change in the ratio of Aβ-40/Aβ-42) in CSF and plasma are predictive of the onset of AD.

There is no cure for Alzheimer's disease and currently available therapeutics minimize some of the symptoms associated with AD but do not slow disease progression. Numerous experimental approaches focus on minimizing Aβ-42 levels by preventing production of or lowering Aβ-42 concentrations, stimulating the immune system to attack Aβ proteins as well as preventing Aβ proteins from aggregating and forming plaques. An important component in designing therapeutic trials is to identify patients that are at risk for developing AD such that studies can be performed in a cost effective timely manner. Hence biomarkers would be invaluable for both understanding Aβ levels as surrogate endpoints as well as in efficient study design.

Preventive therapy is a major focus as the best way to manage AD. Guidelines describe the need for non-invasive biomarkers that can be used to predict and diagnose the formation of AD. Such information will be invaluable for clinical study design, as well as the evaluation of therapeutic effectiveness. Measuring Aβ-40 and Aβ-42 concentrations in plasma provide promise for such information. In healthy normal humans, plasma concentrations range from 200-400 pg/ml (Aβ-40) and 15-30 pg/ml (Aβ-42). However with AD, Aβ-42 levels decrease, and are often undetectable by currently available EIA technology. Furthermore, interventional strategies based on depleting Aβ-42 formation require methods that measure decreases in Aβ-42. Thus there is a need to accurately and precisely quantify low concentrations of amyloid proteins in plasma.

The Aβ-40 and Aβ-42 assays according to the present invention allow the quantification of amyloid beta proteins from human plasma with exceptional sensitivity, enabling the use of Aβ-40/Aβ-42 as a velocity biomarker in Alzheimer's disease studies and to evaluate therapeutic interventions. See Example 22. Among other advantages, this assay allows investigators to: (1) identify subjects with potential high risk for developing AD and hence design interventional studies that include high risk for disease development; (2) design more robust clinical and preclinical studies when Aβ protein concentrations are used as a therapeutic endpoint; and (3) understand how Aβ protein levels change in humans as they transition from a healthy to a diseased state.

In some embodiments, the methods of the present invention are capable of detecting the Aβ-40 at a limit of detection of less than about 100, 80, 60, 50, 30, 20, 10, 5, 1, 0.5, 0.1, 0.05, 0.01, 0.005, 0.001, 0.0005 or 0.0001 pg/ml, e.g., less than about 100 pg/ml. In some embodiments, the method is capable of detecting Aβ-40 at a limit of detection of less than about 100 pg/ml. In some embodiments, the method is capable of detecting the Aβ-40 a limit of detection of less than about 80 pg/ml. In some embodiments, the method is capable of detecting the Aβ-40 a limit of detection of less than about 60 pg/ml. In some embodiments, the method is capable of detecting the Aβ-40 a limit of detection of less than about 50 pg/ml. In some embodiments, the method is capable of detecting the Aβ-40 a limit of detection of less than about 30 pg/ml. In some embodiments, the method is capable of detecting the Aβ-40 a limit of detection of less than about 25 pg/ml. In some embodiments, the method is capable of detecting the Aβ-40 a limit of detection of less than about 10 pg/ml. In some embodiments, the method is capable of detecting the Aβ-40 a limit of detection of less than about 5 pg/ml. In some embodiments, the method is capable of detecting the Aβ-40 a limit of detection of less than about 1 pg/ml. In some embodiments, the method is capable of detecting the Aβ-40 a limit of detection of less than about 0.5 pg/ml. In some embodiments, the method is capable of detecting the Aβ-40 at a limit of detection of less than about 0.1 pg/ml. In some embodiments, the method is capable of detecting the Aβ-40 at a limit of detection of less than about 0.05 pg/ml. In some embodiments, the method is capable of detecting the Aβ-40 at a limit of detection of less than about 0.01 pg/ml. In some embodiments, the method is capable of detecting the Aβ-40 at a limit of detection of less than about 0.005 pg/ml. In some embodiments, the method is capable of detecting the Aβ-40 at a limit of detection of less than about 0.001 pg/ml. In some embodiments, the method is capable of detecting the Aβ-40 at a limit of detection of less than about 0.0005 pg/ml. In some embodiments, the method is capable of detecting the Aβ-40 at a limit of detection of less than about 0.0001 pg/ml.

In some embodiments, the method is capable of detecting the Aβ-42 at a limit of detection of less than about 250, 200, 150, 100, 80, 60, 50, 30, 20, 10, 5, 1, 0.5, 0.1, 0.05, 0.01, 0.005, 0.001, 0.0005 or 0.0001 pg/ml, e.g., less than about 200 pg/ml. In some embodiments, the method is capable of detecting Aβ-42 at a limit of detection of less than about 200 pg/ml. In some embodiments, the method is capable of detecting Aβ-42 at a limit of detection of less than about 150 pg/ml. In some embodiments, the method is capable of detecting Aβ-42 at a limit of detection of less than about 100 pg/ml. In some embodiments, the method is capable of detecting the Aβ-42 a limit of detection of less than about 80 pg/ml. In some embodiments, the method is capable of detecting the Aβ-42 a limit of detection of less than about 60 pg/ml. In some embodiments, the method is capable of detecting the Aβ-42 a limit of detection of less than about 50 pg/ml. In some embodiments, the method is capable of detecting the Aβ-42 a limit of detection of less than about 30 pg/ml. In some embodiments, the method is capable of detecting the Aβ-42 a limit of detection of less than about 25 pg/ml. In some embodiments, the method is capable of detecting the Aβ-42 a limit of detection of less than about 10 pg/ml. In some embodiments, the method is capable of detecting the Aβ-42 a limit of detection of less than about 5 pg/ml. In some embodiments, the method is capable of detecting the Aβ-42 a limit of detection of less than about 1 pg/ml. In some embodiments, the method is capable of detecting the Aβ-42 a limit of detection of less than about 0.5 pg/ml. In some embodiments, the method is capable of detecting the Aβ-42 at a limit of detection of less than about 0.1 pg/ml. In some embodiments, the method is capable of detecting the Aβ-42 at a limit of detection of less than about 0.05 pg/ml. In some embodiments, the method is capable of detecting the Aβ-42 at a limit of detection of less than about 0.01 pg/ml. In some embodiments, the method is capable of detecting the Aβ-42 at a limit of detection of less than about 0.005 pg/ml. In some embodiments, the method is capable of detecting the Aβ-42 at a limit of detection of less than about 0.001 pg/ml. In some embodiments, the method is capable of detecting the Aβ-42 at a limit of detection of less than about 0.0005 pg/ml. In some embodiments, the method is capable of detecting the Aβ-42 at a limit of detection of less than about 0.0001 pg/ml.

C. Multiple Marker Panels

Medical diagnostics have traditionally relied upon the detection of single molecular markers (e.g., gene mutations, elevated PSA levels). Unfortunately, single markers approaches are suboptimal to detect or differentiate many biological states or diseases, e.g., cancer. Thus, in some cases, assays that recognize only a single marker have limited predictive value. According to the methods of the present invention, the screening, diagnosis, and therapeutic monitoring of such biological states, e.g., diseases, using a plurality of markers can provide significant improvements over methods that use single marker analyses. This multiplexed approach is particularly well suited for cancer diagnostics because cancer is a highly complex disease, this multi-factorial "panel" approach is consistent with the heterogeneous nature of cancer, both cytologically and clinically.

Key to the successful implementation of a panel approach to medical tests is the design and development of optimized panels of markers that can characterize and distinguish biological states. Two key evaluative measures of any medical screening or diagnostic test are its sensitivity and specificity, which measure how well the test performs to accurately detect all affected individuals without exception, and without falsely including individuals who do not have the target disease (predicitive value). Historically, many diagnostic tests have been criticized due to poor sensitivity and specificity.

A true positive (TP) result is where the test is positive and the condition is present. A false positive (FP) result is where the test is positive but the condition is not present. A true negative (TN) result is where the test is negative and the condition is not present. A false negative (FN) result is where the test is negative but the condition is present. In this context: Sensitivity=TP/(TP+FN); Specificity=TN/(FP+TN); and Predictive value=TP/(TP+FP).

Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state. An example of a test that has high specificity is a gene-based test that can detect a p53 mutation. Specificity is important when the cost or risk associated with further diagnostic procedures or further medical intervention is very high.

Those of skill in the art will appreciate that statistical approaches have been developed to combine the data from multiple marker and provide a statistical likelihood of the presence of a biological state, e.g., the presence of a disease such as cancer. Examples of such methods are disclosed in U.S. patent application Ser. Nos. 11/934,008; 11/939,484; and 11/640,511. In one embodiment, the concentration of the panel members in a patient sample can be combined using a logistical regression and the disease status of the subject can be determined using a Receiver-Operating Characteristic (ROC) analysis. See, e.g., U.S. patent application Ser. Nos. 11/934,008; 11/939,484; and 11/640,511. In other approaches, statistical methods can be used to classify the sample based on the detection of the marker panels. E.g., the results of the marker assays can be used to classify a sample as diseased or healthy. Such classification (pattern recognition) methods include, e.g., Bayesian classifiers, profile similarity, artificial neural networks, support vector machines (SVM), logistic or logic regression, linear or quadratic discriminant analysis, decision trees, clustering, principal component analysis, Fischer's discriminate analysis or nearest neighbor classifer analysis. Machine learning approaches to classification include, e.g., weighted voting, k-nearest neighbors, decision tree induction, support vector machines (SVM), and feed-forward neural networks. Such methods are known to those of skill in the art.

In other embodiments, simpler schemes can be used. For example, in one embodiment, the elevated concentration of two markers may indicate the presence of a biological state, e.g., a disease. In another embodiment, the decreasing concentration of two markers may indicate the presence of a biological state, e.g., a disease. In another embodiment, an increased concentration of one marker and a decreased concentration of another marker may indicate the presence of a biological state, e.g., a disease. Using such methodology, the results of a second marker provide a medical practitioner with increased confidence in a diagnosis, prognosis, or course of treatment. The multiple markers can provide a confirmatory detection, diagnosis, prognosis, or the like. It will be appreciated that any of the above methods can be used for three markers, four markers, etc.

1. Multiple Biomarker Panels

Figure 4:
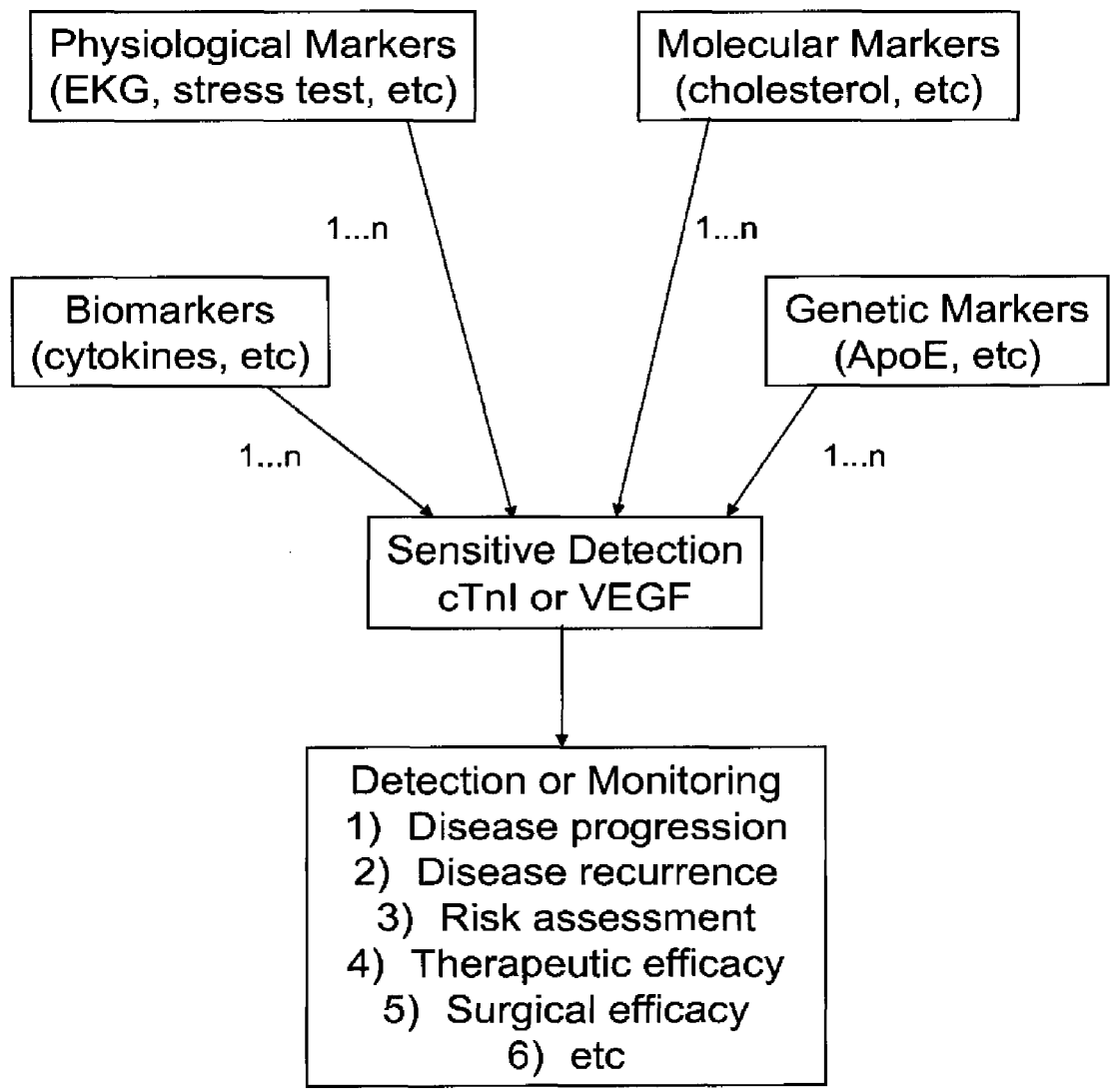
FIG. 4 illustrates a flow chart for multiple marker detection or monitoring of a condition.

The methods of the present invention described for quantitative measurement of biomarkers, e.g., cTnI, cytokines, or VEGF, can be combined with measurement of other biomarkers quantified utilizing the same technology. See FIG. 4. These multiple marker assays can improve the sensitivity and specificity of the detection and monitoring of a condition in a subject. Such assays remain highly sensitive and have the capability to accurately quantify each analyte across a normal, healthy reference range. As disclosed herein, markers of the present invention include, for example, any composition and/or molecule or a complex of compositions and/or molecules that is associated with a biological state of an organism (e.g., a condition such as a disease or a non-disease state).

In one embodiment, the present invention provides a method to detect or monitor a condition in a subject, comprising detecting a first marker in a first sample from the subject and detecting a second marker, wherein the first marker comprises Cardiac Troponin-I (cTnI) or Vascular Endothelial Growth Factor (VEGF), and wherein the limit of detection of the first marker is less than about 10 pg/ml. In some embodiments, the limit of detection of the first marker is less than about 100 pg/ml. In some embodiments, the limit of detection of the first marker is less than about 50 pg/ml. In some embodiments, the limit of detection of the first marker is less than about 5 pg/ml. In some embodiments, the limit of detection of the first marker is less than about 1 pg/ml. In some embodiments, the limit of detection of the first marker is less than about 0.5 pg/ml. In some embodiments, the limit of detection of the first marker is less than about 0.1 pg/ml. In some embodiments, the limit of detection of the first marker is less than about 0.05 pg/ml. In some embodiments, the limit of detection of the first marker is less than about 0.01 pg/ml. In some embodiments, the limit of detection of the first marker is less than about 0.005 pg/ml. In some embodiments, the limit of detection of the first marker is less than about 0.001 pg/ml. In some embodiments, the limit of detection of the first marker is less than about 0.0005 pg/ml. In some embodiments, the limit of detection of the first marker is less than about 0.0001 pg/ml. In some embodiments, the limit of detection of the first marker ranges from about 10 pg/ml to about 0.01 pg/ml. In some embodiments, the limit of detection of the first marker ranges from about 5 pg/ml to about 0.01 pg/ml. In some embodiments, the limit of detection of the first marker ranges from about 1 pg/ml to about 0.01 pg/ml. In some embodiments, the limit of detection of the first marker ranges from about 10 pg/ml to about 0.001 pg/ml. In some embodiments, the limit of detection of the first marker ranges from about 5 pg/ml to about 0.001 pg/ml. In some embodiments, the limit of detection of the first marker ranges from about 1 pg/ml to about 0.001 pg/ml. In some embodiments, the limit of detection of the first marker ranges from about 10 pg/ml to about 0.0001 pg/ml. In some embodiments, the limit of detection of the first marker ranges from about 5 pg/ml to about 0.0001 pg/ml. In some embodiments, the limit of detection of the first marker ranges from about 1 pg/ml to about 0.0001 pg/ml.

In some embodiments, the sample comprises plasma, serum, cell lysates or other samples as disclosed herein. For example, the present invention can be used to measure VEGF in the plasma of humans and mice, as disclosed herein.

An advantage of the present invention is its robustness. The level of reproducibility allows for more sensitive detection across a broad range of detection. The present invention provides advantages even when the limit of detection is below the typical or expected level of a given marker because the variation at higher levels can be reduced. In some embodiments, the coefficient of variation (CV) of the limit of detection ranges from about 100% to about 1%. In some embodiments, the coefficient of variation (CV) of the limit of detection ranges from about 90% to about 1%. In some embodiments, the coefficient of variation (CV) of the limit of detection ranges from about 80% to about 1%. In some embodiments, the coefficient of variation (CV) of the limit of detection ranges from about 70% to about 1%. In some embodiments, the coefficient of variation (CV) of the limit of detection ranges from about 60% to about 1%. In some embodiments, the coefficient of variation (CV) of the limit of detection ranges from about 50% to about 1%. In some embodiments, the coefficient of variation (CV) of the limit of detection ranges from about 40% to about 1%. In some embodiments, the coefficient of variation (CV) of the limit of detection ranges from about 30% to about 1%. In some embodiments, the coefficient of variation (CV) of the limit of detection ranges from about 20% to about 1%. In some embodiments, the coefficient of variation (CV) of the limit of detection ranges from about 15% to about 1%. In some embodiments, the coefficient of variation (CV) of the limit of detection ranges from about 10% to about 1%. In some embodiments, the coefficient of variation (CV) of the limit of detection ranges from about 5% to about 1%.

Because of the sensitivity of the methods of the present invention, very small sample volumes can be used. For example, the methods here can be used to measure VEGF in small sample volumes, e.g., 10 ml or less, compared to the standard sample volume of 100 µl. The present invention enables a greater number of samples to provide quantifiable results in small volume samples compared to other methods. For example, a lysate prepared from a typical 1 mm needle biopsy may have a volume less than or equal to 10 µl. Using the present invention, such sample can be assayed. In some embodiments, the present invention allows the use of sample volume under 100 µl. In some embodiments, the present invention allows the use of sample volume under 90 µl. In some embodiments, the present invention allows the use of sample volume under 80 µl. In some embodiments, the present invention allows the use of sample volume under 70 µl. In some embodiments, the present invention allows the use of sample volume under 60 µl. In some embodiments, the present invention allows the use of sample volume under 50 µl. In some embodiments, the present invention allows the use of sample volume under 40 µl. In some embodiments, the present invention allows the use of sample volume under 30 µl. In some embodiments, the present invention allows the use of sample volume under 25 µl. In some embodiments, the present invention allows the use of sample volume under 20 µl. In some embodiments, the present invention allows the use of sample volume under 15 µl. In some embodiments, the present invention allows the use of sample volume under 10 µl. In some embodiments, the present invention allows the use of sample volume under 5 µl. In some embodiments, the present invention allows the use of sample volume under 1 µl. In some embodiments, the present invention allows the use of sample volume under 0.05 µl. In some embodiments, the present invention allows the use of sample volume under 0.01 µl. In some embodiments, the present invention allows the use of sample volume under 0.005 µl. In some embodiments, the present invention allows the use of sample volume under 0.001 µl. In some embodiments, the present invention allows the use of sample volume under 0.0005 µl. In some embodiments, the present invention allows the use of sample volume under 0.0001 µl. In some embodiments, the range of the sample size is about 10 µl to about 0.1 µl. In some embodiments, the range of the sample size is about 10 µl to about 1 µl. In some embodiments, the range of the sample size is about 5 ml to about 1 µl. In some embodiments, the range of the sample size is about 5 µl to about 0.1 µl.

In some embodiments, the second marker comprises a biomarker, e.g., a protein or a nucleic acid. As disclosed herein, when the first marker or the second marker is a protein, this is understood to encompass a fragment or complex of the protein, or a polypeptide. In embodiments wherein the second marker is such a protein, the limit of detection of the second marker can range from about 10 pg/ml to about 0.1 pg/ml. In some embodiments, the limit of detection of the second marker is less than about 100 pg/ml. In some embodiments, the limit of detection of the second marker is less than about 10 pg/ml. In some embodiments, the limit of detection of the second marker is less than about 5 pg/ml. In some embodiments, the limit of detection of the second marker is less than about 1 pg/ml. In some embodiments, the limit of detection of the second marker is less than about 0.5 pg/ml. In some embodiments, the limit of detection of the second marker is less than about 0.1 pg/ml. In some embodiments, the limit of detection of the second marker is less than about 0.05 pg/ml. In some embodiments, the limit of detection of the second marker is less than about 0.01 pg/ml. In some embodiments, the limit of detection of the second marker is less than about 0.005 pg/ml. In some embodiments, the limit of detection of the second marker is less than about 0.001 pg/ml. In some embodiments, the limit of detection of the second marker is less than about 0.0005 pg/ml. In some embodiments, the limit of detection of the second marker is less than about 0.0001 pg/ml. In some embodiments, the limit of detection of the second marker ranges from about 10 pg/ml to about 0.01 pg/ml. In some embodiments, the limit of detection of the second marker ranges from about 5 pg/ml to about 0.01 pg/ml. In some embodiments, the limit of detection of the second marker ranges from about 1 pg/ml to about 0.01 pg/ml. In some embodiments, the limit of detection of the second marker ranges from about 10 pg/ml to about 0.001 pg/ml. In some embodiments, the limit of detection of the second marker ranges from about 5 pg/ml to about 0.001 pg/ml. In some embodiments, the limit of detection of the second marker ranges from about 1 pg/ml to about 0.001 pg/ml. In some embodiments, the limit of detection of the second marker ranges from about 10 pg/ml to about 0.0001 pg/ml. In some embodiments, the limit of detection of the second marker ranges from about 5 pg/ml to about 0.0001 pg/ml. In some embodiments, the limit of detection of the second marker ranges from about 1 pg/ml to about 0.0001 pg/ml.

The second marker can be any biomarker indicative of a biological state. Numerous such biomarkers are disclosed herein. The second marker may be measured by the methods of the present invention or may be measured using alternate, e.g., preexisting methods. In some embodiments, the second marker is detected using the methods of the present invention. In some embodiments, the second marker is detected using commercially available kits from a variety of suppliers. These include commercially available kits which can be used to detect the second marker include affinity purified antibodies and conjugates, western blotting kits and reagents, recombinant protein detection and analysis, elisa kits and reagents, immunohistology kits and reagents, sample preparation and protein purification, and protein labeling kits and reagents. Companies providing such kits include Invitrogen, Millipore, R&D Systems, Cogent Diagnostics, Bühlmann Laboratories AG, Quidel, and Scimedx Corporation. Indeed, the methods of the present invention can be combined with any method to detect another biomarker.

In some embodiments, the second marker is a biomarker that comprises proBNP, IL-1α, IL-1β, IL-6, IL-8, IL-10, TNF-α, IFN-γ, cTnI, VEGF, insulin, GLP-1, TREM1, Leukotriene E4, Akt1, Aβ-40, Aβ-42, or Fas ligand. In some embodiments, the second marker is a cytokine. As disclosed herein, currently over 100 cytokines/chemokines whose coordinate or discordant regulation is of clinical interest, any of which can be detected with the methods of the invention. In some embodiments, the cytokine is G-CSF, MIP-1α, IL-10, IL-22, IL-8, IL-5, IL-21, INF-γ, IL-15, IL-6, TNF-α, IL-7, GM-CSF, IL-2, IL-4, IL-1α, IL-12, IL-17α, IL-1β, MCP, IL-32 or RANTES. In some embodiments, the cytokine is IL-10, IL-8, INF-γ, IL-6, TNF-α, IL-7, IL-1α, or IL-1β. In other embodiments, the second marker is a high abundance protein. In such embodiments, the second marker can be an apolipoprotein, ischemia-modified albumin (IMA), fibronectin, C-reactive protein (CRP), B-type Natriuretic Peptide (which includes BNP, proBNP and NT-proBNP), or Myeloperoxidase (MPO).

In some embodiments, the methods provided comprise determining a concentration for the first marker, i.e., cTnI or VEGF, and determining a concentration for the second marker if the second marker is a biomarker, e.g., a protein. In some embodiments, the methods provided comprise determining a ratio of a concentration of the first marker compared to a concentration for the second marker. Methods to determine a concentration using the devices and methods of the present invention are disclosed herein. Commercial kits, e.g., commercial ELISA kits, can also be used to determine a protein concentration, e.g., by comparing the level of the biomarker being detected against a standard curve.

2. Mixed Marker Panels

The methods of the present invention can also be combined with other types of markers which serve as a metric for a desired biological state, e.g., a disease state. See FIG. 4. Examples include physiological markers (stress testing, insulin tolerance, BMI, blood pressure, sleep apnea), molecular markers (cholesterol, LDL/HDL, vitamin-D), high abundance proteins (apolipoproteins, IMA, fibronectin), and genetic markers for disease. In some embodiments, the second marker is a physiological marker. In some embodiments, the second marker is a molecular marker. In some embodiments, the second marker is a genetic marker.

In one embodiment, the present invention provides a method to detect or monitor a condition in a subject, comprising detecting a first marker in a first sample from the subject and detecting a second marker, wherein the first marker comprises Cardiac Troponin-I (cTnI) or Vascular Endothelial Growth Factor (VEGF) and the second marker comprises a physiological marker. Examples of physiological markers include an electrocardiogram (EKG), stress testing, nuclear imaging, ultrasound, insulin tolerance, body mass index, bone mass, blood pressure, age, sex, sleep apnea, medical history, or other physiological conditions. In one embodiment, the second marker comprises a medical procedure for determining whether a subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MRI), and magnetic resonance angiography (MRA). The present methods are also useful for monitoring subjects at risk of having a cardiovascular disease, wherein the second marker is a risk factor. Risk factors for cardiac diseases include elevated levels of circulating MPO, hypertension, family history of premature CVD, smoking, high total cholesterol, low HDL cholesterol, obesity, diabetes, etc. Because cardiovascular disease, typically, is not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. Subjects who are at risk of having cardiovascular disease are at risk of having an abnormal stress test or abnormal cardiac catherization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atheroscleorotic plaque burden, a characteristic that can be examined using intravascular ultrasound.

Screening tests are of particular importance for patients with risk factors for ischemic heart disease (IHD). A common initial screening test for IHD is to measure the electrical activity over a period of time which is reproduced as a repeating wave pattern, commonly referred to as an electrocardiograph (ECG or EKG), showing the rhythmic depolarization and repolarization of the heart muscles. Analysis of the various waves and normal vectors of depolarization and repolarization yields important diagnostic information. However, ECG measurements are not particularly sensitive nor are the data very useful for detecting cardiovascular abnormalities or malfunctions. Therefore, stressing the heart under controlled conditions and measuring changes in the ECG data is usually, but not always, the next step. A stress test, sometimes called a treadmill test or exercise test, can show if there's a lack of blood supply through the arteries that go to the heart. In a stress test, the patient exercises under controlled conditions while various parameters are monitored, including pulse, EKG, blood pressure and tiredness. The stresses may be applied by the performance of physical exercise or alternatively, by administration of pharmaceutical compounds such as dobutamine, which mimic the physiological effects of exercise. Another type of stress test used in screening tests for IED include the radionucleotide (nuclear) stress test which involves injecting a radioactive isotope (typically thallium or cardiolyte) into a patient's bloodstream, then visualizing the spreading of the radionucleotide throughout the vascular system and its absorption into the heart musculature. The patient then undergoes a period of physical exercise after which, the imaging is repeated to visualize changes in distribution of the radionucleotide throughout the vascular system and the heart. Stress echocardiography involves ultrasound visualization of the heart before, during and after physical exercise. The radionucleotide stress test and stress echocardiography are often used in combination with ECG measurements in order to gain a clearer understanding of the state of individual's cardiovascular health.

In one embodiment, elevated levels of a marker, e.g., cTnI or VEGF, detected by the devices of the present invention and the presence of a physiological marker are indicative of a biological state, e.g., a disease. For example, a condition in a subject may be detected by elevated levels of the first marker and an irregular EKG or stress test result.

In one embodiment, the present invention provides a method to detect or monitor a condition in a subject, comprising detecting a first marker in a first sample from the subject and detecting a second marker, wherein the first marker comprises Cardiac Troponin-I (cTnI) or Vascular Endothelial Growth Factor (VEGF) and the second marker comprises a molecular marker. A molecular marker comprises any substance whose presence is indicative of a biological state. Examples of molecular markers native to an organism include total cholesterol, high-density lipoproteins (HDL), low-density lipoproteins (LDL) LDL/HDL ratio, triglycerides, uric acid, or creatinine. In some embodiments, the molecular marker include total cholesterol, high-density lipoproteins (HDL), low-density lipoproteins (LDL) LDL/HDL ratio, triglycerides, uric acid, or creatinine. In some embodiments, the molecular marker comprises subfractions of LDL/HDL/Q-LDL, triglycerides. The American Heart Association offers the following recommendations for lipid profile measures:

HDL: "normal" readings vary between 40-50 mg/dL for men and 50-60 mg/dL for women; measurements above 60 mg/dL are considered "protective."

LDL: less than 130 mg/dL considered good; less than 100 considered "optimal"

Triglycerides: less than 150 mg/dL considered "normal"

Total Cholesterol (add 1/5 triglyceride measure to LDL and HDL numbers): under 200 mg/dL considered "desirable"

An HDL/LDL ratio between 0.3 and 0.4 or higher is generally seen as desirable.

A molecular marker can also be introduced into a subject, e.g., rubidium chloride is used as a radioactive isotope to evaluate perfusion of heart muscle. Other molecular markers include blood sugar, e.g., blood glucose, and vitamin-D.

In one embodiment, elevated levels of a marker, e.g., cTnI or VEGF, detected by the devices of the present invention and the presence of a molecular marker are indicative of a biological state, e.g., a disease. For example, a condition in a subject may be detected by elevated levels of the first marker and a low HDL/LDL reading.

In one embodiment, the present invention provides a method to detect or monitor a condition in a subject, comprising detecting a first marker in a first sample from the subject and detecting a second marker, wherein the first marker comprises Cardiac Troponin-I (cTnI) or Vascular Endothelial Growth Factor (VEGF) and the second marker comprises a genetic marker. A genetic marker comprises a segment of DNA with an identifiable physical location on a chromosome whose inheritance can be followed. Genetic markers include restriction fragment length polymorphism (RFLP), amplified fragment length polymorphism (AFLP), random amplification of polymorphic DNA (RAPD), variable number tandem repeat (VNTR), microsatellite polymorphism, minisatellites, single nucleotide polymorphisms (SNPs), short tandem repeat (STR), and single feature polymorphism (SFP). Many genetic markers, e.g., SNPs, have been linked as risk factors for a variety of diseases. For example, one of the genes associated with Alzheimer's disease, apolipoprotein E (ApoE) contains two SNPs that result in three possible alleles for this gene: E2, E3, and E4. Each allele differs by one DNA base, and the protein product of each gene differs by one amino acid. A person who inherits at least one E4 allele has a greater chance of developing Alzheimer's disease, whereas inheriting the E2 allele seems to indicate a reduced likelihood of developing Alzheimer's. A database of SNPs is maintained by the HapMap project, available at http://www.hapmap.org/. Examples of SNPs associated with cardiovascular conditions are disclosed in U.S. patent application Ser. Nos. 12/109,137; 12/139,139; 12/151,275; 12/077,935; and 12/019,651. Genetic markers further comprise mutations including insertions, deletions or fusions. Genetic markers further comprise epigenetic markers, such as DNA methylation, e.g., the methylation of a cytosine in the context of a CpG sequence. DNA methylation patterns can be altered in cells in response to certain conditions. For example, aberrant DNA methylation is a hallmark of cancer. Imprinting, which comprises the allele specific expression of a gene, e.g., by DNA methylation silencing of one allele, can also be indicative of a condition, e.g., increased risk of a condition such as cancer. Such markers are well understood by those of skill in the art. See, e.g., Laird, Cancer epigenetics, Hum Mol Genet. 2005 Apr. 15; 14 Spec No 1:R65-76; Tang and Ho, Epigenetic reprogramming and imprinting in origins of disease. Rev Endocr Metab Disord. 2007 June; 8(2):173-82.

In one embodiment, elevated levels of a marker, e.g., cTnI or VEGF, detected by the devices of the present invention and the presence of a genetic marker are indicative of a biological state, e.g., a disease. For example, a condition in a subject may be detected by elevated levels of a first marker and a SNP correlative of the condition. For example, a condition in a subject may be detected by elevated levels of a first marker and a DNA methylation pattern found to correlate with the condition.

D. Detection and Monitoring

The methods of the present invention can quantify minute changes in level of a biomarker, e.g., VEGF, over time when longitudinal samples are collected from an individual over a defined period of time. The ability to quantify discreet changes is enabled by the combined sensitivity and precision of measurements made when using the described method.

The methods described herein can be used to monitor levels of biomarkers, e.g., VEGF, cytokines, cTnI, in healthy individuals, with the ability to detect minute elevations in level of analyte indicative of disease risk or early disease. Such elevations above normal can be quantified over time when regular longitudinal samples are collected from an individual. The ability to monitor discreet changes is enabled by the combined sensitivity and precision of measurements made when using the described method.

The method described can be used to monitor levels of biomarkers, e.g., VEGF, cytokines, cTnI, in individuals for who elevated levels have been observed, with the ability to detect minute decreases in the level of analyte indicative of a return towards a healthy state. Such decreases can be quantified over time when regular longitudinal samples are collected from an individual, and compared to the healthy range. This information can be used to determine success of a therapeutic intervention or a return to a normal, healthy state. The ability to monitor discreet changes is enabled by the combined sensitivity and precision of measurements according to the present invention.

The method described can be used to monitor minute changes in level of analyte, e.g., VEGF, cytokines, cTnI, over time when longitudinal samples are collected from an individual over a defined period of time. The ability to monitor discreet changes is enabled by the combined sensitivity and precision of measurements according to the present invention.

In one embodiment, the present invention provides a method to detect or monitor a condition in a subject, comprising detecting a first marker in a first sample from the subject and detecting a second marker, wherein the concentration of the first marker is determined and the concentration of the second marker is determined, further comprising measuring a change in concentration of the markers between the first sample and a second sample from the subject. In some embodiments, the first marker comprises Cardiac Troponin-I (cTnI) or Vascular Endothelial Growth Factor (VEGF). According to the method, the change is used to detect or monitor the condition.

In one embodiment, the present invention provides a method to detect or monitor a condition in a subject, comprising detecting a first marker in a first sample from the subject and detecting a second marker, wherein the concentration of the first marker is determined and the concentration of the second marker is determined, further comprising determining a change in the ratio of the concentrations of the first marker and the second marker between the first sample and a second sample from the subject, whereby the change is used to detect or monitor the condition. In some embodiments, the first marker comprises Cardiac Troponin-I (cTnI) or Vascular Endothelial Growth Factor (VEGF).

In some embodiments, a medical procedure is performed between acquiring the first sample and the second sample from the subject. In some embodiments, the medical procedure comprises a surgical procedure, stress testing, radionucleotide stress testing or a therapeutic intervention. In some embodiments, the present invention provides a method to detect or monitor a condition in a subject, comprising detecting a first marker in a first sample from the subject and detecting a second marker, performing a surgical procedure, and detecting the first and second markers after the procedure, wherein the change in the markers before and after the procedure is used to detect or monitor the condition. In some embodiments, the first marker comprises Cardiac Troponin-I (cTnI) or Vascular Endothelial Growth Factor (VEGF). In some embodiments, the present invention provides a method to detect or monitor a condition in a subject, comprising detecting a first marker in a first sample from the subject and detecting a second marker, performing a stress test on the subject, and detecting the first and second markers after the stress test, wherein the change in the markers before and after the procedure is used to detect or monitor the condition. In some embodiments, the first marker comprises Cardiac Troponin-I (cTnI) or Vascular Endothelial Growth Factor (VEGF). In some embodiments, the present invention provides a method to detect or monitor a condition in a subject, comprising detecting a first marker in a first sample from the subject and detecting a second marker, wherein the first marker comprises Cardiac Troponin-I (cTnI), performing a stress test on the subject, and detecting the first and second markers after the stress test, wherein the change in the markers before and after the procedure is used to detect or monitor the condition. In some embodiments, the present invention provides a method to detect or monitor a condition in a subject, comprising detecting a first marker in a first sample from the subject and detecting a second marker, wherein the first marker comprises Vascular Endothelial Growth Factor (VEGF), performing a stress test on the subject, and detecting the first and second markers after the stress test, wherein the change in the markers before and after the procedure is used to detect or monitor the condition. In some embodiments, the present invention provides a method to detect or monitor a condition in a subject, comprising detecting a first marker in a first sample from the subject and detecting a second marker, performing a therapeutic intervention on the subject, and detecting the first and second markers after the stress test, wherein the change in the markers before and after the procedure is used to detect or monitor the condition. In some embodiments, the first marker comprises Cardiac Troponin-I (cTnI) or Vascular Endothelial Growth Factor (VEGF).

In one embodiment, the present invention provides a method to monitor a condition in a subject, comprising detecting a first marker in a first sample from the subject and detecting a second marker, wherein the monitoring comprises monitoring of a disease progression, disease recurrence, risk assessment, therapeutic efficacy or surgical efficacy. In some embodiments, the first marker comprises Cardiac Troponin-I (cTnI) or Vascular Endothelial Growth Factor (VEGF). In some embodiments, monitoring comprises detecting the markers in a series of samples, e.g., two or more samples, from a subject. In some embodiments, the series of samples are collected over time at various time intervals as disclosed herein. In some embodiments, the present invention comprises comparing the level of a marker from each sample from the series of samples to the level of the marker in the sample taken from the first sample. In some embodiments, the series of samples are collected from different bodily fluids, tissues, or other biological origins. Such samples can be collected at identical or similar time points, and/or over time as above. A change in the markers or lack thereof in the series of samples can be used to monitor a biological state, e.g., a disease progression, therapeutic efficacy, disease recurrence, risk assessment or surgical efficacy. In some embodiments, the methods comprise an analysis selected from the group consisting of comparing the concentration or series of concentrations of a marker or markers to a normal value for the concentration of the marker or markers, comparing the concentration or series of concentrations to a baseline value, and determining a rate of change of concentration for the series of concentrations. In some embodiments, the methods comprise comparing the concentration of a marker in a sample with a predetermined threshold concentration, and determining a diagnosis, prognosis, or method of treatment if the sample concentration is greater than the threshold level.

In one embodiment, the present invention provides a method to monitor a condition in a subject, comprising detecting a first marker in a first sample from the subject and detecting a second marker, wherein the monitoring comprises monitoring of a disease progression. In some embodiments, the first marker comprises Cardiac Troponin-I (cTnI) or Vascular Endothelial Growth Factor (VEGF). In one embodiment, an increase in a marker indicates a disease progression. In one embodiment, a decrease in a marker indicates a disease progression. In one embodiment, lack of change in a marker indicates a disease progression. For example, an increase in a marker may indicate the growth of cells that express the marker, e.g., increase in a marker could indicate a growth of tumor cells. In some embodiments, medical testing or treatment is altered in response to the monitoring of the marker or markers. In some embodiments, additional testing may be prescribed for the subject. For example, the results of an assay according to the present invention may indicate progression of cardiovascular disease and a stress test or similar may be ordered in response. In another example, the results of an assay according to the present invention may indicate progression of a cancer and an imaging technique or similar may be ordered in response. In some embodiments, a therapeutic agent or surgerical procedure may be administered to the subject if the assay indicates disease progression. One of skill in the art will appreciate that such medical testing or treatment will depend on the marker, condition, subject history, etc.

In one embodiment, the present invention provides a method to monitor a condition in a subject, comprising detecting a first marker in a first sample from the subject and detecting a second marker, wherein the monitoring comprises monitoring of a disease recurrence. In some embodiments, the first marker comprises Cardiac Troponin-I (cTnI) or Vascular Endothelial Growth Factor (VEGF). In one embodiment, an increase in a marker indicates a disease recurrence. In one embodiment, a decrease in a marker indicates a disease recurrence. In one embodiment, lack of change in a marker indicates a disease recurrence. For example, an increase in a marker may indicate the presence of cells that express the marker, e.g., tumor cells, thereby indicating recurrence of a condition, e.g., cancer. In some embodiments, medical testing or treatment is proscribed in response to the monitoring of the marker or markers. For example, a therapeutic agent or surgical procedure can be administered or performed if the assay indicates disease recurrence. One of skill in the art will appreciate that such medical testing or treatment will depend on the marker, condition, subject history, etc.

In one embodiment, the present invention provides a method to monitor a condition in a subject, comprising detecting a first marker in a first sample from the subject and detecting a second marker, wherein the monitoring comprises monitoring of risk assessment. In some embodiments, the first marker comprises Cardiac Troponin-I (cTnI) or Vascular Endothelial Growth Factor (VEGF). In one embodiment, an increase in a marker indicates a disease recurrence. In one embodiment, a decrease in a marker indicates a disease recurrence. In one embodiment, lack of change in a marker indicates a disease recurrence. For example, an increase in a marker may indicate risk of, increased risk of, or decreased risk of a cardiovascular complication, e.g., a heart attack. In some embodiments, medical testing or treatment is prescribed in response to the monitoring of the marker or markers. For example, a therapeutic agent or surgical procedure can be administered to the subject if the assay indicates risk or increased risk. Likewise, therapeutic treatment may be decreased if risk has declined, e.g., in response to patient lifestyle changes or therapeutic efficacy. One of skill in the art will appreciate that such medical testing or treatment will depend on the marker, condition, subject history, etc.

In one embodiment, the present invention provides a method to monitor a condition in a subject, comprising detecting a first marker in a first sample from the subject and detecting a second marker, wherein the monitoring comprises monitoring of a therapeutic efficacy. In some embodiments, the first marker comprises Cardiac Troponin-I (cTnI) or Vascular Endothelial Growth Factor (VEGF). In one embodiment, an increase in a marker indicates suboptimal therapeutic efficacy. In one embodiment, a decrease in a marker indicates suboptimal therapeutic efficacy. In one embodiment, lack of change in a marker indicates suboptimal therapeutic efficacy. For example, an increase or lack of change in a marker can indicate that the therapy has failed to slow a disease progression, e.g., by being ineffective in halting tumor growth. In some embodiments, the invention provides a method of monitoring the effectiveness of a therapeutic treatment in an individual comprising measuring the concentration of a marker in a first sample from the individual wherein the first sample is taken prior to administration of the therapeutic treatment and further comprising measuring the concentration of the marker in a series of samples taken from the individual at different time points subsequent to beginning the therapeutic treatment and further comparing the concentration of the marker prior to the therapeutic treatment to the level of the marker subsequent to the therapeutic treatment to determine the effectiveness of the therapeutic treatment. As disclosed herein, additional markers can be assessed to provide confirmatory or complementary results. In some embodiments, therapeutic treatment is altered in response to the monitoring of the marker or markers. In some embodiments, the dosage of a therapeutic agent, e.g., a drug or biological agent, may be altered in response to the results. In some embodiments, treatment with a therapeutic agent, e.g., a drug or biological agent, may be halted in response to the results. In some embodiments, additional therapeutic agents, e.g., a drug or biological agent, may be administered in addition to or in place of the first agent in response to the results.

In one embodiment, the present invention provides a method to monitor a condition in a subject, comprising detecting a first marker in a first sample from the subject and detecting a second marker, wherein the first marker comprises Cardiac Troponin-I (cTnI) or Vascular Endothelial Growth Factor (VEGF), wherein the monitoring comprises monitoring of a surgical efficacy. In one embodiment, an increase in a marker indicates suboptimal surgical efficacy. In one embodiment, a decrease in a marker indicates suboptimal surgical efficacy. In one embodiment, lack of change in a marker indicates suboptimal surgical efficacy. For example, an increase or lack of change in a marker can indicate that the surgery failed to remove all diseased tissue, e.g., tissue derived from a tumor. In some embodiments, the treatment of the subject is affected by the results of the test. For example, if the results of the assay indicate that surgical resection was unsuccessful in removing all cancer from a subject, the subject may be treated with chemotherapy. Likewise, if the results of the assay indicate that surgical resection was successful, additional treatment may be avoided. One of skill in the art will appreciate that such medical testing or treatment will depend on the marker, condition, subject history, etc.

E. Cardiovascular Biomarker Panels

Numerous risk factors for cardiovascular disease have been identified. These risk factors can be grouped into two broad categories: unmodifiable factors (such as male gender, and family history of premature heart diseases) and modifiable factors. Modifiable factors can be further subdivided into life style factors and underlying disorder/disease factors. In many instances lifestyle and underlying disease are intertwined, such as in obesity and diabetes. Combined, all of these factors can be used to identify those in the general population who are at especially high risk of developing cardiovascular disease.

Attempts to prevent cardiovascular disease are more effective when they remove and prevent causes, and they often take the form of modifying risk factors. A non-exhaustive list of risk factors that can be modified, either through life style changes or medicine, include the following:

Life style risk factors. Cigarette smoking, obesity, and physical inactivity.

Disease risk factors. High blood pressure, high cholesterol levels, metabolic syndrome, diabetes, rheumatoid arthritis, systemic lupus erythematosus (SLE), and obstructive sleep apnea.

High Blood Pressure. High blood pressure is a powerful risk factor for cerebrovascular disease as well as for coronary heart disease. An estimated 50 million people have high blood pressure.

Blood Cholesterol Levels. A clear and positive relationship between blood cholesterol levels and subsequent coronary heart disease has repeatedly been demonstrated. The cholesterol level associated with the low-density lipoprotein (LDL) fraction is positively correlated with coronary heart disease, whereas the cholesterol associated with the high-density lipoprotein (HDL) is negatively correlated (the higher the level, the lower the risk).

Metabolic Syndrome. The main features of metabolic syndrome include insulin resistance, hypertension (high blood pressure), cholesterol abnormalities, and an increased risk for clotting. Patients are most often overweight or obese. This clustering, or development of several risk factors at once, leads to a greatly increased risk for CVD.

Diabetes. Diabetes is a powerful and independent risk factor for cardiovascular disease, the major cause of death in diabetic persons. Factors in addition to blood-glucose level elevate the risk.

Rheumatoid Arthritis (RA). Rheumatoid arthritis patients have a higher risk of early death, most likely due to cardiovascular disease.

Systemic lupus erythematosus (SLE). Women with the autoimmune disease systemic lupus erythematosus (SLE) have a more than two-fold increased risk of cardiovascular disease over women without the disease.

Obstructive Sleep Apnea (OSA). OSA is characterized by repetitive interruption of ventilation during sleep caused by collapse of the pharyngeal airway. Population-based epidemiology studies and observations of OSA patients have consistently shown the prevalence of hypertension, type II diabetes, cardiovascular disease, and stroke to be higher in people with OSA.

Cardiovascular disorders, e.g., congestive heart failure (CHF), are often first diagnosed after the onset of clinical symptoms, eliminating potential for early intervention. In one embodiment, the present invention provides a multi-marker immunoassay for more sensitive assay for early detection of CHF in blood samples, e.g., plasma. Use of a panel of multiple markers, where the markers are quantified using ultra-sensitive single molecule counting methods, demonstrates improved diagnostic sensitivity and specificity and can be used to improve treatments and modification of risk factors.

In one embodiment, the present invention provides a method to assess the integrity of heart muscle function using biomarkers. For example, the concentration of natriuretic peptides (BNP and NTproBNP) can be used to test for and diagnose congestive heart failure in both asymptomatic and symptomatic patients, with left ventricular dysfunction. Higher concentrations of the peptides are associated with worse CVD outcomes; thus providing strong prognostic information. The cardiac Troponins are another class of biomarkers that can assess cardiac muscle pathology. Troponins are produced by cardiac myocytes. Injury to these cells in either a reversible or non-reversible manner results in the release of troponins into circulating blood. Elevated blood troponin concentrations in asymptomatic populations are prognostic of subsequent cardiac events, with a higher troponin concentration providing a higher risk classification. These inflammatory cytokine blood biomarkers and heart muscle specific blood biomarkers a means to assess CVD risk in patients prior to CVD events as well as risk in recurring CVD. Furthermore, these markers are dynamic with higher concentrations being assisted with worse outcomes. In some embodiments, a panel of cardiac pathology and vascular inflammation biomarkers is used.

The biomarkers proBNP, cTnI, IL-6, TNF-alpha, IL-17a, and hsCRP present at various stages of elevation in patients with various stages of cardiovascular disease. In some embodiments, these blood biomarkers are combined in a multi-marker panel to provide a more sensitive and specific assessment of cardiovascular disease risk and status. In some embodiments, additional biomarkers are added to the panel. In some embodiments, two or more of the markers are used to assess CVD. Furthermore, these markers are dynamic with higher concentrations being correlated with worse outcomes. These highly sensitive multi-marker panels, wherein in the markers are quantified using single molecule detection devices and methods as provided herein, can be combined with traditional tests based upon physiological biomarkers for heart disease to assess the degree of cardiovascular risk as well as monitor at-risk patients for improvements in disease status. Traditional diagnostic modality testing includes, but is not limited to, treadmill/EKG stress testing, obstructive sleep disorder (OSD) assessment, and carotid artery intima-media thickness (CIMT) evaluation. These traditional tests are enhanced through the addition of highly sensitive blood biomarkers to create ancillary diagnostic modalities (ADMs), as described below.

Enhanced Stress Test. In some embodiments, the performance of a standard treadmill stress test with EKG is enhanced with the addition of plasma cardiac troponin-I (cTnI) biomarker measurements. cTnI measured according to the present invention provides insight into heart muscle physiology during cardiac stress. Plasma cTnI concentrations increase in individuals with stress test induced ischemia, which can be measured using nuclear perfusion imaging and other techniques. Even mild levels of ischemia can induce increases in cTnI concentrations. The magnitude of increase in cTnI correlates positively with the degree of ischemia. High grade ischemia induces the highest release of cTnI from heart muscle myocytes into blood. Using multivariable analysis comparing cTnI increase with all other stress EKG output variables, only cTnI increases correlated with ischemia. Other methods to detect cTnI, e.g., Siemens ultrasensitive cTnI and Roche cTnT, do not provide the sensitivity and accuracy to correlate troponin changes with ischemia.

In some embodiments, plasma cTnI measurements are used to monitor cardio-pathology. Plasma cTnI can be measured specifically and accurately in healthy humans, with a range of 1-8 pg/ml. Within a single individual, cTnI is a stable biomarker and displays minimal variation on an hourly or weekly basis. A greater than 2-fold increase in cTnI concentration over time is significant. Moreover, a single elevated cardiac troponin measurement is correlated with adverse cardiac events, 3 months to 8 years after the measurement. Thus, the monitoring of blood cTnI as provided herein provides a method to monitor cardiomyocyte integrity and hence cardiopathology, shedding insight into the likelihood of future cardiovascular events.

Enhanced Sleep Test. Obstructive sleep disorder (OSD) is highly prevalent yet underappreciated as a strong CVD risk factor. The American Heart Association recently issued an Expert Consensus Document, highlighting the relevance of OSD to individuals who are either at risk for or already have established CVD. See Somers V K, et al. (2008) Sleep apnea and cardiovascular disease: an American Heart Association/American College of Cardiology Foundation Scientific Statement from the American Heart Association Council for High Blood Pressure Research Professional Education Committee, Council on Clinical Cardiology, Stroke Council, and Council on Cardiovascular Nursing. J Am Coll Cardiol. 52:686-717. The hallmarks of OSD include hypoxia, vasoconstriction significantly elevated blood pressure. Such perturbations can result in vascular inflammation with increases in plasma biomarker cytokines such as TNF-$\alpha$, IL-6 and IL-17a and hsCRP. These biomarker elevations can diminish with successful intervention.

OSD can be diagnosed through a simple home testing procedure. The present invention provides a method to enhance the home sleep test with the addition of one or more biomarkers, e.g., plasma cytokines such as TNF-a or IL-17a. These measurements provide a broader and deeper picture of the magnitude of sleep disorder and its impact on systemic inflammation. Because these inflammatory biomarkers are dynamic, they can be monitored in OSD patients as a marker for successful therapeutic intervention towards both sleep apnea and vascular inflammation.

Enhanced CIMT test. Carotid intima-media thickness (CIMT) is a measure of atherosclerosis in all arteries, including the coronary artery. CIMT provides a picture of the arterial wall, allowing assessment of the degree of stenosis even in the case of sub-clinical atherosclerosis. The present invention provides an improved CIMT test based upon ultrasonography. Atherosclerosis is an end product of vascular inflammation. In some embodiments, measurement of biomarkers in blood, e.g., pro-inflammatory cytokines in plasma, can enhance CIMT by providing physical and biochemical assessments of arterial disease risk and status, including subclinical disease. Plasma biomarkers, e.g., hsCRP, IL-6, TNF-$\alpha$ and IL-1, can be elevated with vascular inflammation and correlate with stenosis measured with CIMT testing. These biomarkers provide insight into the magnitude of inflammatory risk. Furthermore, since they are dynamic, changes in their plasma concentrations can be used to assess therapeutic effectiveness during patient monitoring.

F. Clinical Methods

The present invention relates to systems and methods (including clinical methods) for establishing markers that can be used for diagnosing a biological state or a condition in an organism, preparing diagnostics based on such markers, and commercializing/marketing diagnostics and services utilizing such diagnostics.

In one embodiment, the clinical methods herein comprise: establishing one or more markers using a method comprising: establishing a range of concentrations for said marker or markers in biological samples obtained from a first population by measuring the concentrations of the marker or markers in the biological samples by detecting single molecules of the marker or markers; and commercializing the one or more markers identified in the above step, e.g., in a diagnostic product. The biomarkers identified are preferably polypeptides or small molecules. Such polypeptides can be previously known or unknown. The diagnostic product herein can include one or more antibodies that specifically binds to the marker (e.g., polypeptide).

In one embodiment, the clinical methods herein comprise: establishing one or more markers using a system comprising: establishing a range of concentrations for said marker in biological samples obtained from a first population by measuring the concentrations of the marker the biological samples by detecting single molecules of the marker; and providing a diagnostic service to determine if an organism has or does not have a biological state or condition of interest. A diagnostic service herein may be provided by a CLIA approved laboratory that is licensed under the business or the business itself. The diagnostic services herein can be provided directly to a health care provider, a health care insurer, or a patient. Thus the clinical methods herein can make revenue from selling, e.g., diagnostic services or diagnostic products.

The clinical methods herein also contemplate providing diagnostic services to, for example, health care providers, insurers, patients, etc. The business herein can provide diagnostic services by either contracting out with a service lab or setting up a service lab (under Clinical Laboratory Improvement Amendment (CLIA) or other regulatory approval). Such service lab can then carry out the methods disclosed herein to identify if a particular marker or pattern of markers is within a sample.

The one or more markers are polypeptides or small molecules, or new chemical entities.

In other embodiments, data collected using the methods of the present invention is acquired and submitted to a medical practitioner to direct a medical treatment. In an exemplary embodiment, a sample from a subject is sent to a laboratory, wherein the sample is assayed using the methods of the present invention. The results of the assays are then communicated to a medical professional, e.g., a doctor. The medical professional might then direct a course of treatment for the subject based on the assay results. In one embodiment, the assay provides for elevated levels of cTnI or VEGF in a sample from the subject. The assay results are submitted to the medical professional, e.g., by electronic communications or by standard paper mail. The medical professional can suggest a course of therapy for the patient, e.g., a drug preventitive of heart disease. The medical professional may also combine the assay results with other medical markers, e.g., medical history, smoking, age, weight, race, stress testing, blood pressure, etc., when deciding a course of action.

In some embodiments, computer systems are used to perform a variety of logic operations of the present invention. The computer systems can include one or more computers, databases, memory systems, and system outputs (e.g., a computer screen or printer). In some embodiments, computer executable logic or program code is stored in a storage medium, loaded into and/or executed by a computer, or transmitted over some transmission medium, such as over electrical wiring or cabling, through fiber optics, or via electromagnetic radiation, e.g., wirelessly. When implemented on a general-purpose microprocessor, the computer executable logic can configure the microprocessor to create specific logic circuits. In some embodiments, multiple computer systems are used. In one embodiment, a patient or organization can provide assay data either by uploading such data on a secure server (meeting industry requirements for security) or by sending the information in a high-density portable form (such as CDROM, DVD). The data can then be analyzed at a remote location.

In some embodiments, the computer system comprises a computer readable medium, e.g., floppy diskettes, CD-ROMs, hard drives, flash memory, tape, or other digital storage medium, with a program code comprising one or more sets of instructions for performing a variety of logic operations. In some embodiments, a computer system is used to direct the operations of the analyzer device. In some embodiments, a computer system is used to analyze the assay data. In some embodiments, a computer system is used to combine the data from multiple markers thereby assisting in the detection or monitoring of a biological state, e.g., a disease.

Figure 5:
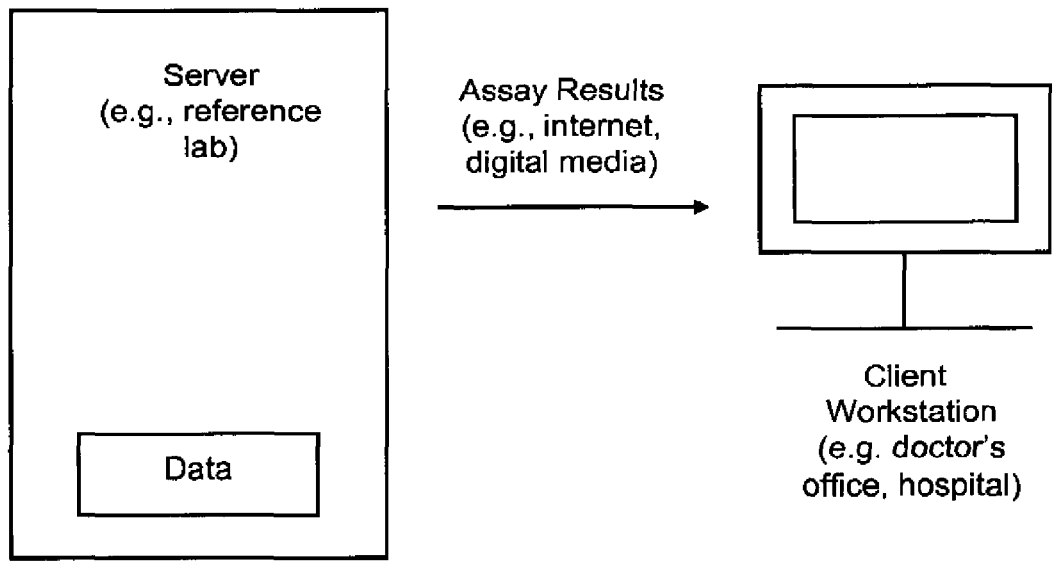
FIG. 5 illustrates a computer system wherein a client workstation receives assay results from a remote computer.

In some embodiments, a database of relevant information, e.g., experimental protocols, marker properties or algorithms to combine multiple markers, can be stored on a digital storage medium, e.g., floppy diskettes, CD-ROMs, hard drives, flash memory, tape, or other digital storage medium. Such databases can be stored locally or remotely with respect to other computer systems, e.g., those used to perform logic operations or present data to a medical practitioner. See FIG. 5.

VII. Kits

The invention further provides kits. In some embodiments, kits include an analyzer system and a label, as previously described. Kits of the invention include one or more compositions useful for the sensitive detection of a molecule, such as a marker, as described herein, in suitable packaging. In some embodiments, kits of the invention provide a label, as described herein, together with other components such as instructions, reagents, or other components. In some embodiments, the kit provides the label as separate components, in separate containers, such as an antibody and a fluorescent moiety, for attachment before use by the consumer. In some embodiments kits of the invention provide binding partner pairs, e.g., antibody pairs, that are specific for a molecule, e.g., a marker, where at least one of the binding partners is a label for the marker, as described herein. In some embodiments, the binding partners, e.g., antibodies, are provided in separate containers. In some embodiments, the binding partners, e.g., antibodies, are provided in the same container. In some embodiments, one of the binding partners, e.g., antibody, is immobilized on a solid support, e.g., a microtiter plate or a paramagnetic bead. In some of these embodiments, the other binding partner, e.g., antibody, is labeled with a fluorescent moiety as described herein.

Binding partners, e.g., antibodies, solid supports, and fluorescent labels for components of the kits may be any suitable such components as described herein.

The kits may additionally include reagents useful in the methods of the invention, e.g., buffers and other reagents used in binding reactions, washes, buffers or other reagents for preconditioning the instrument on which assays will be run, filters for filtering reagents, and elution buffers or other reagents for running samples through the instrument.

Kits may include one or more standards, e.g., standards for use in the assays of the invention, such as standards of highly purified, e.g., recombinant, protein markers, or various fragments, complexes, and the like, thereof. Kits may further include instructions.

VIII. Examples

The following examples are offered by way of illustration and not by way of limiting the remaining disclosure.

Unless otherwise specified, processing samples in the Examples were analyzed in a single molecule detector (SMD)

as described herein, with the following parameters: Laser: continuous wave gallium arsenite diode laser of wavelength 639 nm (Blue Sky Research, Milpitas, Calif.), focused to a spot size of approximately 2 microns (interrogation space of 0.004 pL as defined herein); flow rate=5 microliter/min through a fused silica capillary of 100 micron square ID and 300 micron square OD; non-confocal arrangement of lenses (see, e.g., FIG. 1A); focusing lens of 0.8 numerical aperture (Olympus); silicon avalanche photodiode detector (Perkin Elmer, Waltham, Mass.).

Example 1

Sandwich Assays for Biomarkers: Cardiac Troponin I (cTnI)

The assay: The purpose of this assay was to detect the presence of cardiac Troponin I (cTNI) in human serum. The assay format was a two-step sandwich immunoassay based on a mouse monoclonal capture antibody and a goat polytonal detection antibody. Ten microliters of sample were required. The working range of the assay is 0-900 pg/ml with a typical analytical limit of detection of 1-3 pg/ml. The assay required about four hours of bench time to complete.

Materials: the following materials were used in the procedure described below: Assay plate: Nunc Maxisorp, product 464718, 384 well, clear, passively coated with monoclonal antibody, BiosPacific A34440228P Lot # A0316 (5 µg/ml in 0.05 M sodium carbonate pH 9.6, overnight at room temperature); blocked with 5% sucrose, 1% BSA in PBS, and stored at 4° C. For the standard curve, Human cardiac Troponin I (BiosPacific Cat # J34000352) was used. The diluent for the standard concentrations was human serum that was immonodepleted of endogenous cTNI, aliquoted and stored at −20° C. Dilution of the standards was done in a 96 well, conical, polypropylene, (Nunc product # 249944). The following buffers and solutions were used: (a) assay buffer: BBS with 1% BSA and 0.1% TritonX-100; (b) passive blocking solution in assay buffer containing 2 mg/ml mouse IgG, (Equitech Bio); 2 mg/ml goat IgG, (Equitech Bio); and 2 mg/ml MAK33 poly, Roche# 11939661; (c) detection Antibody (Ab): Goat Polyclonal antibody affinity purified to Peptide 3, (BiosPacific G129C), which was label with a fluorescent dye Alexa Fluor 647, and stored at 4° C.; detection antibody diluent: 50% assay buffer, 50% passive blocking solution; wash buffer: borate buffer saline Triton Buffer (BBST) (1.0 M borate, 15.0 M sodium chloride, 10% Triton X-100, pH 8.3); elution buffer: BBS with 4M urea, 0.02% Triton X-100 and 0.001% BSA.

Preparation of Alexa Fluor 647 labeled antibodies: the detection antibody G-129-C was conjugated to Alexa Fluor 647 by first dissolving 100 µg of G-129-C in 400 ml of the coupling buffer (0.1 M NaHCO$_3$). The antibody solution was then concentrated to 50 µl by transferring the solution into YM-30 filter and subjecting the solution and filter to centrifugation. The YM-30 filter and antibody was then washed three times by adding 400 µl of the coupling buffer. The antibody was recovered by adding 50 µl to the filter, inverting the filter, and centrifuging for 1 minute at 5,000×g. The resulting antibody solution was 1-2 µg/µl. Alexa Fluor 647 NHS ester was reconstituted by adding 20 µl DMSO to one vial of Alexa Fluor 647, this solution was stored at −20° C. for up to one month. 3 µl of Alexa Fluor 647 stock solution was added to the antibody solution, which was then mixed and incubated in the dark for one hour. After the one hour, 7.5 µl 1M tris was added to the antibody Alexa Fluor 647 solution and mixed. The solution was ultrafiltered with YM-30 to remove low molecular weight components. The volume of the retentate, which contained the antibody conjugated to Alexa Fluor 647, was adjusted to 200-400 µl by adding PBS. 3 µl 10% NaN$_3$ was added to the solution, the resulting solution was transferred to an Ultrafree 0.22 centrifugal unit and spun for 2 minutes at 12,000×g. The filtrate containing the conjugated antibody was collected and used in the assays.

Procedure: cTnI standard and sample preparation and analysis:

The standard curve was prepared as follows: working standards were prepared (0-900 pg/ml) by serial dilutions of the stock of cTnI into standard diluent or to achieve a range of cTnI concentrations of between 1.2 pg/ml-4.3 µg/ml.

10 µl passive blocking solution and 10 µl of standard or of sample were added to each well. Standards were run in quadruplicate. The plate was sealed with Axyseal sealing film, centrifuged for 1 min at 3000 RPM, and incubated for 2 hours at 25° C. with shaking. The plate was washed five times, and centrifuged until rotor reached 3000 RPM in an inverted position over a paper towel. A 1 nM working dilution of detection antibody was prepared, and 20 µl detection antibody were added to each well. The plate was sealed and centrifuged, and the assay incubated for 1 hour at 25° C. with shaking. Thirty µl of elution buffer was added per well, the plate was sealed and the assay incubated for ½ hour at 25° C. The plate was either stored for up to 48 hours at 4° C. prior to analysis, or the sample was analyzed immediately.

For analysis, 20 µl per well were acquired at 40 µl/minute, and 5 µl were analyzed at 5 µl/minute. The data were analyzed based on a threshold of 4 sigma. Raw signal versus concentration of the standards was plotted. A linear fit was performed for the low concentration range, and a non-linear fit was performed for the full standard curve. The limit of detection (LoD) was calculated as LOD=(3× standard deviation of zeros)/slope of linear fit. The concentrations of the samples were determined from the equation (linear or non-linear) appropriate for the sample signal.

An aliquot was pumped into the analyzer. Individually-labeled antibodies were measured during capillary flow by setting the interrogation volume such that the emission of only 1 fluorescent label was detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention was determined by the mean+3 SD method.

Results: Data for a typical cTnI standard curve measured in quadruplicate using the assay protocol is shown in Table 3.

TABLE 3

Standard Curve for cTnI

| cTnI (pg/ml) | Signal | Standard Deviation | % CV |
|---|---|---|---|
| 0 | 233 | 25 | 10.8 |
| 1.5625 | 346 | 31 | 8.9 |
| 3.125 | 463 | 35 | 7.5 |
| 6.25 | 695 | 39 | 5.6 |
| 12.5 | 1137 | 61 | 5.3 |
| 25 | 1988 | 139 | 7.0 |
| 50 | 3654 | 174 | 4.8 |
| 100 | 5493 | 350 | 6.4 |
| 200 | 8264 | 267 | 3.2 |
| 400 | 9702 | 149 | 1.5 |
| 800 | 9976 | 50 | 0.5 |

The sensitivity of the analyzer system was tested in 15 runs and was found routinely to detect sub femtomolar (fM) levels of calibrator, as shown by the data in Table 4. The precision was 10% at 4 and 12 pg/ml cTnI.

TABLE 4

Instrument Sensitivity

| Calibrator (fM) | Signal counts | CV |
|---|---|---|
| 0 | 11 | |
| 12 | 302 | 9 |
| 60 | 1341 | 8 |
| 300 | 4784 | 7 |

Figure 6:
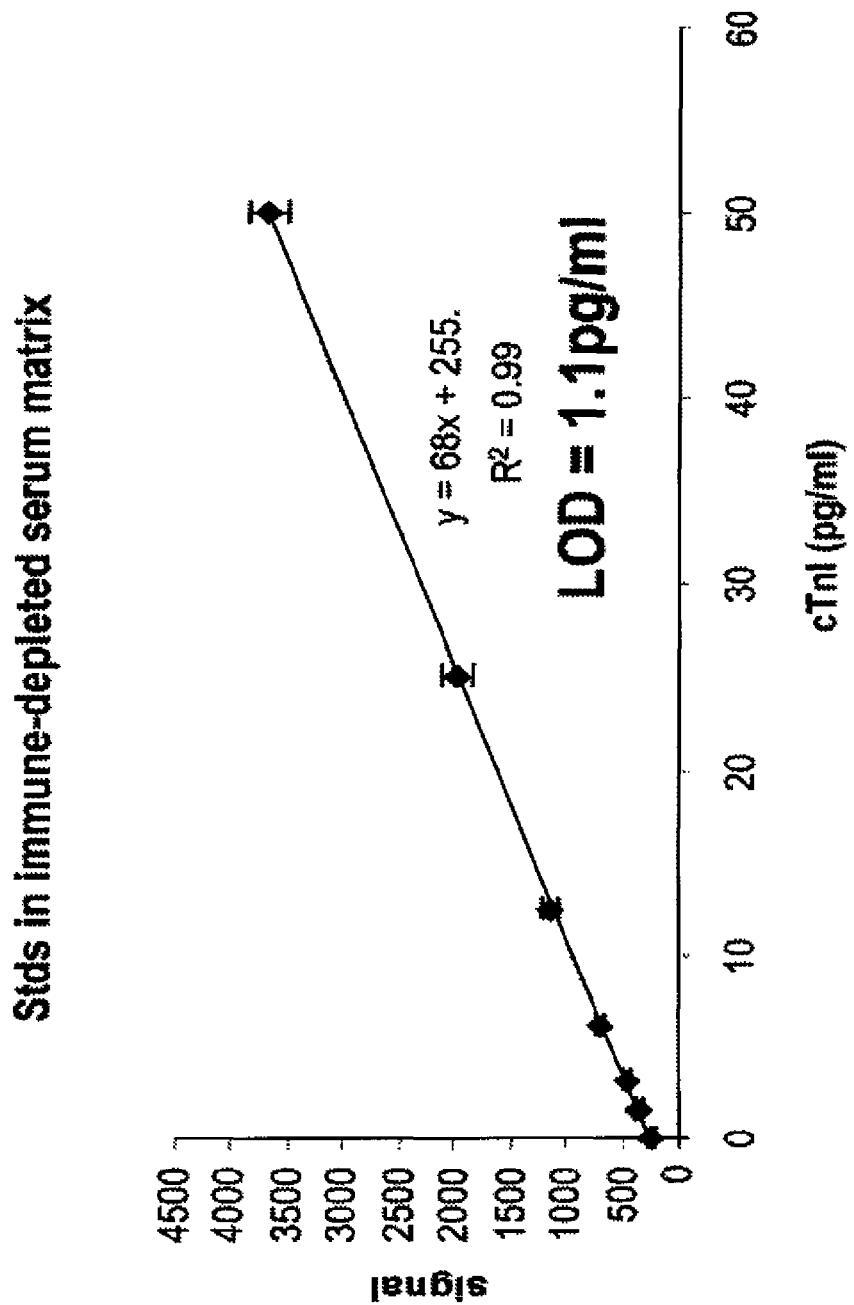
FIG. 6 illustrates a linearized standard curve for the range concentrations of cTnI.

Linearized standard curve for the range concentrations of cTnI are shown in FIG. 6.

The analytical limit of detection (LoD) was determined across 15 sequential assays. The LoD was the mean of the 0 std+3 SD (n=4) intra-assay determinations. The average LoD was 1.7 pg/ml (range 0.4-2.8 pg/ml).

The recovery of the sample was determined by analyzing samples of serum that had been immunodepleted of cTnI and spiked with known amounts of cTnI. Table 5 shows the data for sample recovery by the system analyzed over 3 days.

TABLE 5

Sample Recovery

| Spike (pg/ml) | Recovery (mean) | Standard Deviation | % CV |
|---|---|---|---|
| 5 | 5.7 | 0.9 | 16 |
| 15 | 13.7 | 0.2 | 2 |
| 45 | 43 | 0.6 | 2 |
| 135 | 151 | 6.2 | 4 |

The linearity of the assay was determined in pooled human serum that was spiked with cTnI and diluted with standard diluent. The results in Table 6 show the dilutions and % of the signal expected for the corresponding dilution.

TABLE 6

Assay Linearity

| Serum Dilution | % of expected |
|---|---|
| 1:2 | 79 |
| 1:4 | 87 |
| 1:8 | 96 |

Figure 7A:
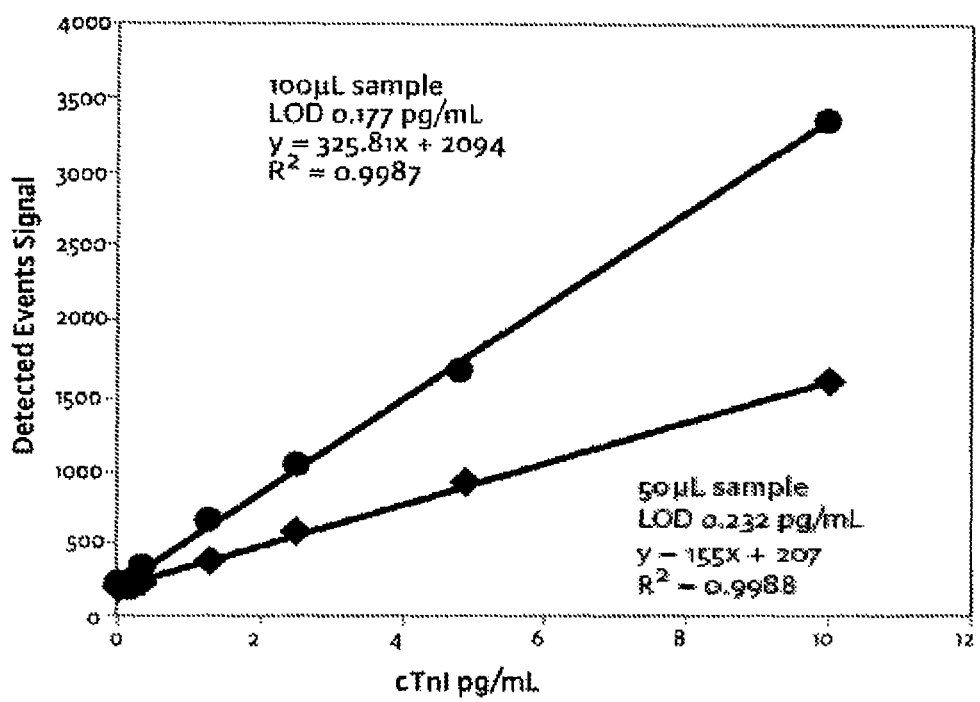
FIG. 7A is a graph illustrating the analytical sensitivity of cTnI of a 100 µl sample and a 50 µl sample at an LoD of 0.1-0.2 pg/ml.
Figure 7B:
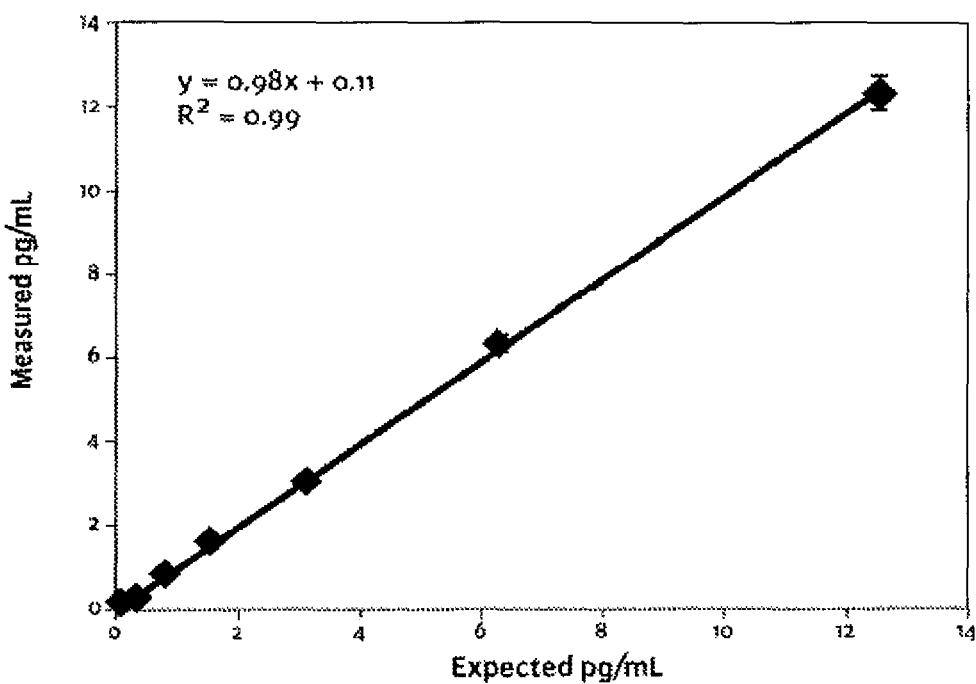
FIG. 7B is a graph illustrating the low end of a standard curve signal.

In further experiments, the present invention provides cTnI quantification to normal levels, e.g., 0.8 pg/ml at a CV of 10% and less. The analytical sensitivity of the assay system for cTnI is presented graphically in FIG. 7A. The LoD was between 0.1-0.2 pg/ml. For 100 µl samples, the LoD was 0.117 pg/ml. For a 50 ml sample the LoD was 0.232 pg/ml. The low end standard curve signal is shown in FIG. 7B.

These data show that the analyzer system of the invention allows for performing highly sensitive laser-induced immunoassay for sub-femtomolar concentrations of cTnI. The assay can be used to equilaterally quantify cTnI across humans, rats, dogs and monkeys.

Example 2

Sandwich Bead-based Assays for TnI

The assays described above use the same microtiter plate format where the plastic surface is used to immobilize target molecules. The single particle analyzer system also is compatible with assays done in solution using microparticles or beads to achieve separation of bound from unbound entities.

Materials: MyOne Streptavidin C1 microparticles (MPs) are obtained from Dynal (650.01-03, 10 mg/ml stock). Buffers use in the assay include: 10× borate buffer saline Triton Buffer (BBST) (1.0 M borate, 15.0 M sodium chloride, 10% Triton X-100, pH 8.3); assay buffer (2 mg/ml normal goat IgG, 2 mg/ml normal mouse IgG, and 0.2 mg/ml MAB-33-IgG-Polymer in 0.1 M Tris (pH 8.1), 0.025 M EDTA, 0.15 M NaCl, 0.1% BSA, 0.1% Triton X-100, and 0.1% $NaN_3$, stored at 4° C.); and elution buffer (BBS with 4 M urea, 0.02% Triton X-100, and 0.001% BSA, stored at 2-8C). Antibodies used in the sandwich bead-based assay include: Bio-Ab (A34650228P (BiosPacific) with 1-2 biotins per IgG) and Det-Ab (G-129-C (BiosPacific) conjugated to A647, 2-4 fluors per IgG). The standard is recombinant human cardiac troponin I (BiosPacific, cat #J34120352). The calibrator diluent is 30 mg/ml BSA in TBS wEDTA.

Microparticles Coating: 100 µl of the MPs stock is placed in an eppendorf tube. The MPs are washed three times with 100 µl of BBST wash buffer by applying a magnet, removing the supernatant, removing the magnet, and resuspending in wash buffer. After the washes the MPs are resuspended in 100 ml of assay buffer and 15 µg of Bio-Ab are added. The mixture is then incubated for an hour at room temperature with constant mixing. The MPs are washed five times with 1 ml wash buffer as described above. After the washes the MPs are resuspended in 15 ml of assay buffer (or 100 µl to store at 4° C.).

Preparation of Standard and Samples: the Standard is Diluted with Calibrator Diluent to Prepare proper standard curve (usually 200 pg/ml down to 0.1 pg/ml). Frozen serum and plasma samples need to be centrifuged 10 minutes at room temperature at 13 K rpm. Clarified serum/plasma is removed carefully to avoid taking any possible pellets or floaters and put into fresh tubes. 50 µl of each standard or sample is pippetted into appropriate wells.

Capture Target: 150 µl of MPs (after resuspension to 15 ml in assay buffer+400 mM NaCl) are added to each well. The mixture is incubated on JitterBug, 5 at room temperature for 1 hr.

Washes and Detection: The plate is placed on a magnet and the supernatant is removed after ensuring that all MPs are captured by the magnet. 250 µl of wash buffer are added after removing the plate from the magnet. The plate is then placed on the magnet and the supernatant is removed after ensuring that all MPs are captured by the magnet. 20 µl Det-Ab are added per well (Det-Ab to 500 ng/ml is diluted in assay buffer+400 mM NaCl)). The mixture is incubated on Jitter-Bug, 5 at room temperature for 30 min.

Washes and Elution: The plate is placed on a magnet and washed three times with wash buffer. The supernatant is removed after ensuring that all MPs are captured by the magnet and 250 µl of wash buffer are added. After the washes the samples are transferred into a new 96-well plate. The new plate is then placed on the magnet and the supernatant is removed after ensuring that all MPs are captured by the magnet. 250 µl of wash buffer are then added after removing the plate from the magnet. The plate is then placed on the magnet and the supernatant is removed after ensuring that all MPs are captured by the magnet. 20 µl of elution buffer are then added and the mixture is incubated on JitterBug, 5 at room temperature for 30 min.

Filter out MPs and transfer to 384-well plate: The standard and samples are transferred into a 384-well filter plate placed on top of a 384-well assay plate. The plate is then centrifuged at room temperature at 3000 rpm with a plate rotor. The filter plate is removed and the appropriate calibrators are added. The plate is covered and is ready to be run on SMD.

SMD: An aliquot is pumped into the analyzer. Individually-labeled antibodies are measured during capillary flow by setting the interrogation volume such that the emission of only 1 fluorescent molecule is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention is determined by the mean+3 SD method.

Example 3

Concentration Range for cTnI in a Population of Normal Non-diseased Subjects

A reference range or normal range for cTnI concentrations in human serum was established using serum samples from 88 apparently healthy subjects (non-diseased). A sandwich immunoassay as described in Example 1 was performed and the number of signals or events as described above were counted using the single particle analyzer system of the invention. The concentration of serum troponin I was determined by correlating the signals detected by the analyzer with the standard curve as described above. All assays were perfumed in quadruplicate.

Figure 8:
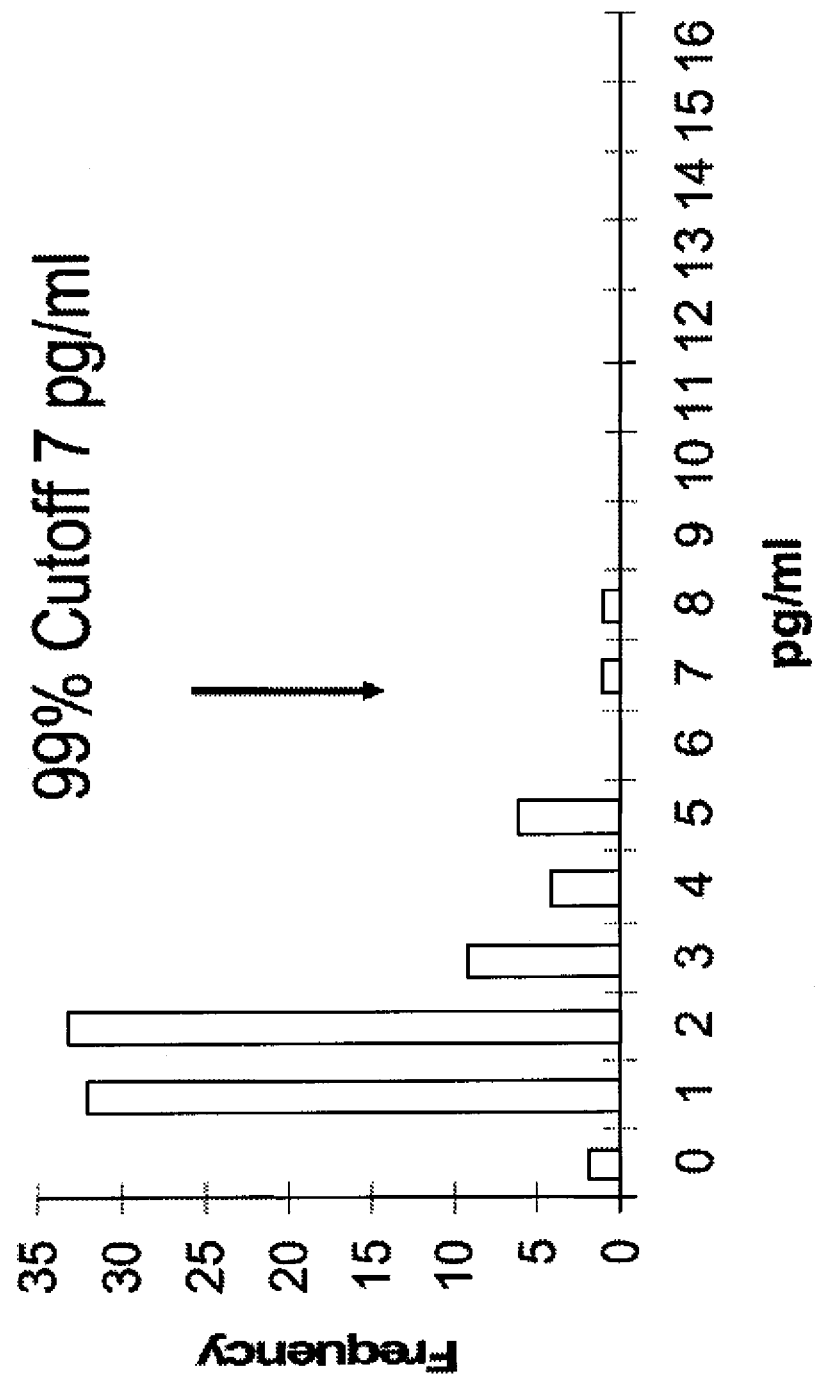
FIG. 8 illustrates a biological threshold (cutoff concentration) for cTnI at a cTnI concentration of 7 pg/ml, as established at the 99th percentile with a corresponding coefficient of variation (CV) of 10%.

In accordance with recommendations by the current European and American Cardiology Societies (ESC/ACC) troponin assays should quantify accurately the 99th percentile of the normal range with an assay imprecision (CV) of less than 10% in order to distinguish reliably between patients with ACS and patients without ischemic heart disease, and risk stratification for adverse cardiac events. The assay showed that the biological threshold (cutoff concentration) for TnI is at a TnI concentration of 7 pg/ml, which is established at the 99th percentile with a corresponding CV of 10% (FIG. 8). At the 10% CV level the precision profile points at a TnI concentration of 4 and 12 pg/ml.

Figure 9:
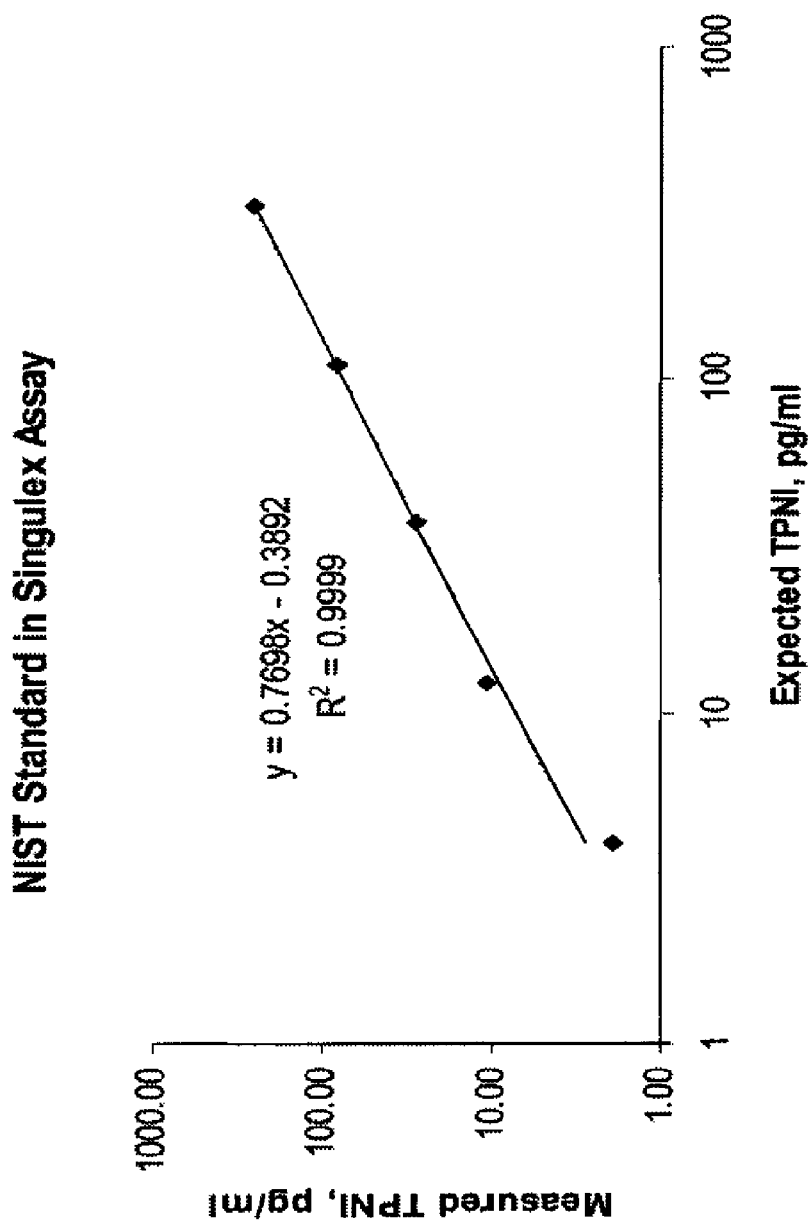
FIG. 9 illustrates a correlation of assay results of cTnI determined using the analyzer system of the invention with standard measurements provided by the National Institute of Standards and Technology (NIST) ($R^2$=0.9999).

In addition, the assay correlates well with the Troponin-I standard measurements provided by the National Institute of Standards and Technology (FIG. 9).

The assay of the invention is sufficiently sensitive and precise to fulfill the requirements of the ESC/ACC, and it is the most sensitive assay for cardiac troponin I when compared to assays such as those described by Koerbin et al., Ann Clin Biochem, 42:19-23 (2005). The assay of the invention has a 10-20 fold greater sensitivity than currently available assays, which has determined the biological threshold range to be 111-333 pg/ml cTnI.

Example 4

Detection of Early Release of TnI into the Circulation of Patients with Acute Myocardial Infarction (AMI)

Study 1: 47 samples were obtained serially from 18 patients that presented with chest pain in the emergency department (ED). These patients all had non-ST elevated ECG were, and were diagnosed with AMI. The concentration of cTnI in the initial samples from all 18 patients was determined according to a commercial assay at the time of admission to the emergency room to be <350 pg/ml (10% cutpoint), and 12 were <100 pg/ml (99th %) percentile. These samples were tested at later times using the same commercial assay, and were determined to test positive for cTnI. The same serum samples were also assayed for TnI according to the assay of the invention as described in Examples 1 and 3, and the results compared to the results obtained using the commercial assay.

Figure 10:
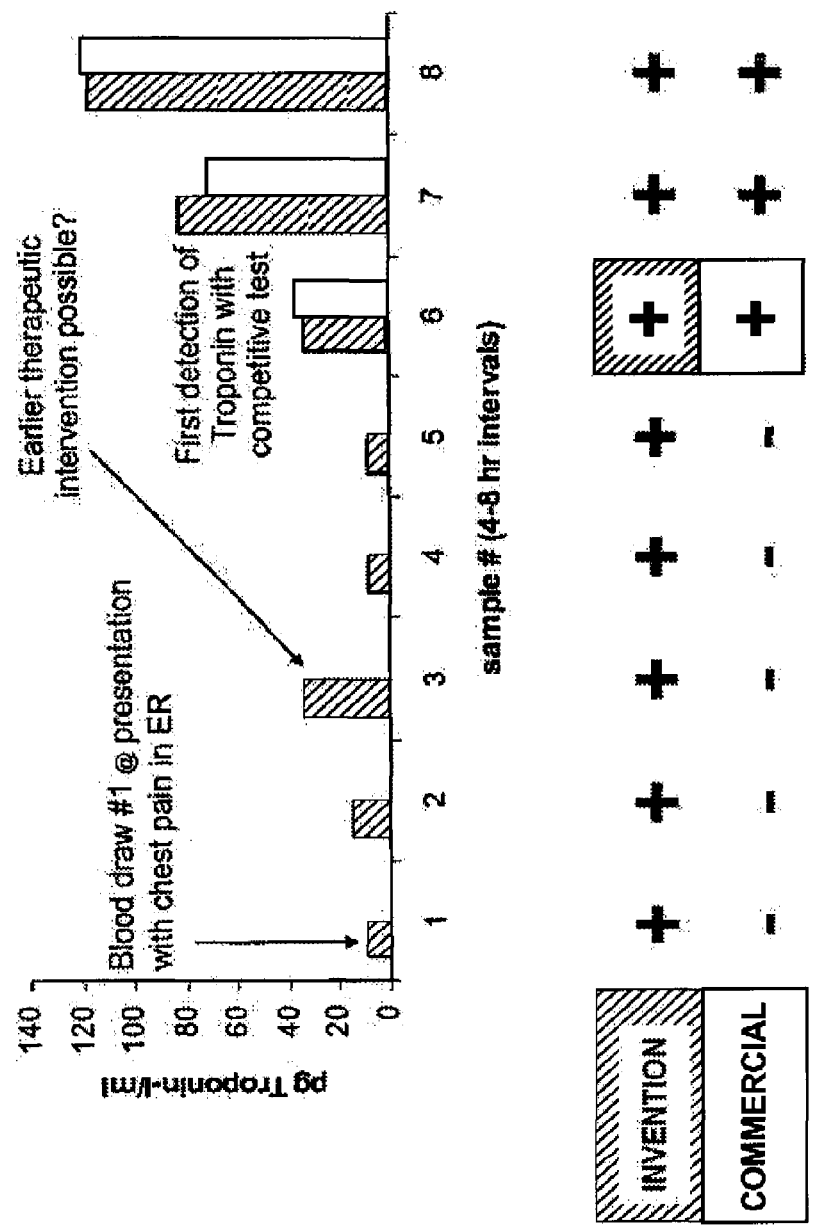
FIG. 10 illustrates detection of cTnI in serial serum samples from patients who presented at the emergency room with chest pain. The measurements made with the analyzer system of the invention were compared to measurements made with a commercially available assay.

Blood was drawn for the first time at the time the patient presented with chest pain (sample 1), and subsequently at intervals between 4-8 hours (samples 2 at 12 hours; sample 3 at 16 hours; sample 4 at 24 hours; sample 5 at 30 hours; sample 6 at 36 hours; sample 7 at 42 hours; and sample 8 at 48 hours). The serum was analyzed by the methods of the invention and by a current commercial method, and the results obtained are shown in FIG. 10. The analyzer of the invention detected TnI at the time the patient presented with chest pain (sample 1), while the commercial assay first detected cTnI at a much later time (sample 6 at 36 hours). The concentration of TnI in sample 3 exceeded the biological threshold level that was established using the analyzer of the invention (7 pg/ml, see FIG. 8), and indicated that sample 3 is positive for TnI to suggest the incidence of a cardiac event. The biological threshold for the commercial assay lies between 111 and 333 pg/ml of TnI. Accordingly, sample 3 would not have been considered to indicate a possible cardiac event.

In addition, the methods and compositions of the present invention allow for much earlier diagnosis and possible intervention based on cardiac troponin levels, as evidenced by results for the first sample taken from the patients. In the 3 cases that had initial commercial assay cTnI values of between 100 and 350 ng/ml, all were positive for cTnI by the analytical methods of the invention (i.e., cTnI over 7 pg/ml). In the 12 cases that had initial commercial cTnI values of less than 100 pg/ml, 5 were determined to be positive for a cardiovascular event according to the assay of the invention (i.e., cTnI over 7 pg/ml). The prospective use of the assay of the invention would have detected 53% more AMI cases than the current commercial assay when the admission sample was tested.

Figure 11:
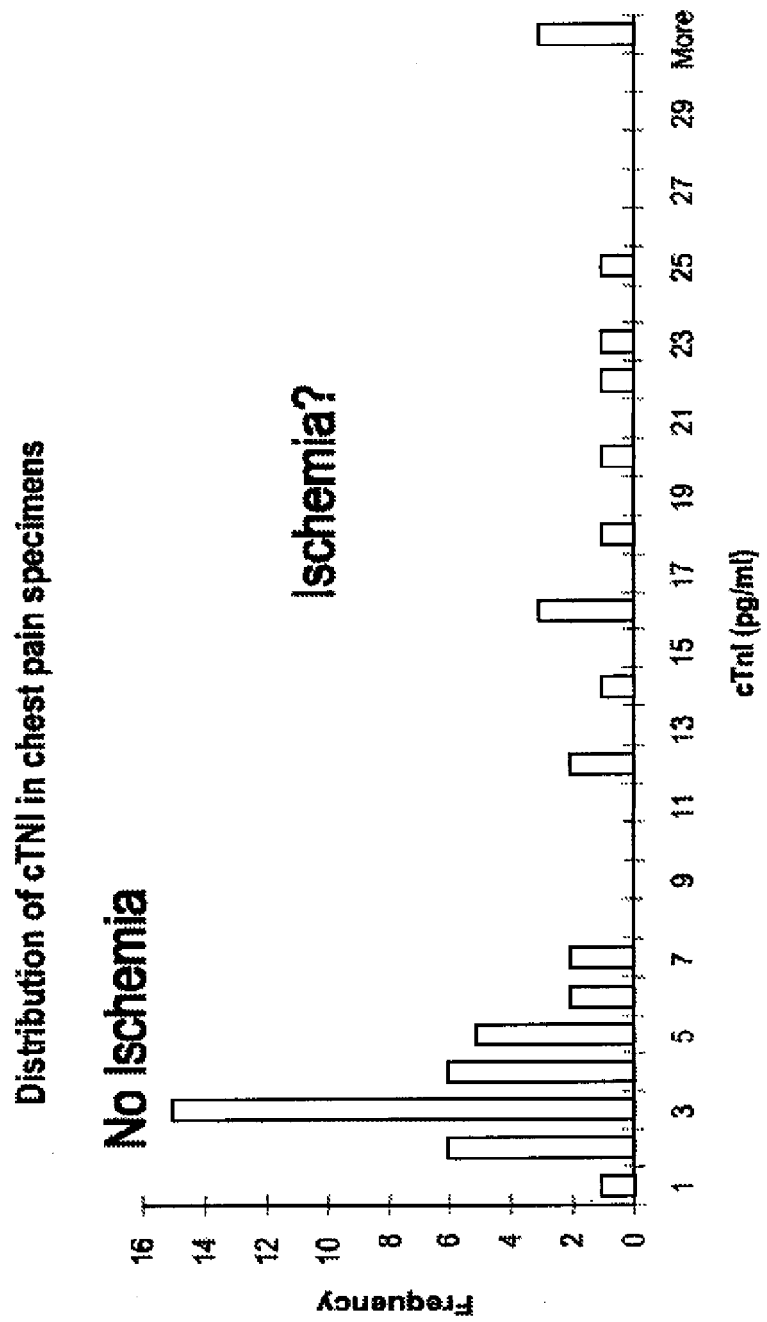
FIG. 11 illustrates distribution of normal biological concentrations of cTnI and concentrations of cTnI in serum samples from patients presenting with chest pain.

Study 2: 50 additional serum samples, which tested negative according to the commercial assay, were tested using the analyzer and assay of the invention. The results are shown in FIG. 11. Of the 50 samples, 36 were within the 99th % and determined to be within the normal range established by the assay of the invention. However, the remaining 14 samples that were determined to be within the commercial "normal" or non-diseased range, tested above the biological threshold established by the invention.

Therefore, the high sensitivity cTnI assay of the invention allows for the detection of myocardial damage in patients when cTnI serum levels are below threshold values by commercially available technology. The use of the highly sensitive and precise cTnI assay of the invention enables detection of AMI earlier than with existing cTnI assays, and thereby provides the opportunity for appropriate diagnosis and early medical intervention to improve the outcome.

Example 5

Detection of Leukotriene T4 (LTE4)

The assay was developed to quantify Leukotriene $E_4$ ($LTE_4$) in buffer as a preliminary assay for assays using, e.g., urine specimens. The assay format was a one-step single antibody competitive immunoassay. Fifty microliters of sample were required. The typical working range of this assay was 0-300 pg/ml with a typical limit of detection of 2-3 pg/ml (0.1-0.15 pg/sample). The assay required about four hours of bench time to complete.

The following materials were prepared and used in the procedure described below: Mouse anti-rabbit IgG coated plate provided in Cayman Chemical Leukotriene $E_4$ (EIA Kit, Catalog #520411); stock $LTE_4$ Standard (purified LTE4 at 100 ng/ml in ethanol (Cayman Chemical Leukotriene $E_4$ EIA Kit, Catalog #520411)); assay buffer (10×EIA buffer concentrate (Cayman Chemical Leukotriene $E_4$ EIA Kit, Catalog #520411)) diluted 1:10 with 90 ml Nanopure water; buffer for dilution of standards (3% ethanol); anti-$LTE_4$ antibody (Leukotriene $E_4$ EIA antiserum (Cayman Chemical Leukotriene $E_4$ EIA Kit, Catalog #520411) diluted with 30 ml EIA buffer; streptavidin-Alexa detection reagent stock solution of 31 µM (streptavidin labeled with Alexa Fluor™ 647); tracer ($LTE_4$-biotin conjugate) was made compatible for detection by the analyzer; wash buffer (400× concentrate (Cayman Chemical Leukotriene $E_4$ EIA Kit, Catalog #520411)) diluted 1:40; elution buffer (borate buffered saline, pH 8.3 with 4M urea, 0.02% Triton X-100 and 0.001% BSA). The matrix of the tracer and the antiserum concentrations were tested to identify the most sensitive assay conditions.

A standard curve was prepared as follows: working standards were prepared by making serial dilutions of the 100 ng/ml stock into assay buffer to achieve a range of concentrations between 0.005 pg/ml and 3000 pg/ml. 50 ml standard (or sample) were added per well of the assay plate. All standards were run in duplicate. Working tracer was prepared by diluting the tracer stock to 1 pg/ml with assay buffer. 50 µl tracer (or buffer) were added per well of the assay plate. A 10% working antiserum solution was prepared by diluting 100% stock (made according to the kit instructions) into assay buffer. 50 µl antiserum (or buffer) were added per well of the assay plate; the plate was sealed and incubated overnight at 25° C. with shaking. A working streptavidin-Alexa detection reagent was prepared by diluting stock to 140 µM with assay buffer. 15 µl of detection reagent were added to each well, and the plate was incubated for 30 min at 25° C. with shaking. The plate was washed 5 times. 50 µl of elution buffer were added to each well, and the plate was incubated for ½ hour at 25° C. with shaking. The plate was use immediately or stored for up to 48 hours at 4° C. prior to analysis.

20 µl were pumped into the analyzer at a rate of 40 µl/minute, and 5 µl of sample were analyzed at 5 µl/minute. The data files were analyzed using a threshold=4 sigma, and a cross correlation of between 0-8 msec. Raw signal versus concentration was plotted for the standards, and a linear fit was used for low range standards, while a non-linear fit was used for full standard curve. The limit of detection was calculated as LOD=80% of the maximum signal (no target control) (the concentration at which $B/B_0$=80%). The concentrations of samples were calculated from the equation (linear or non-linear) appropriate for the sample signal.

Figure 12:
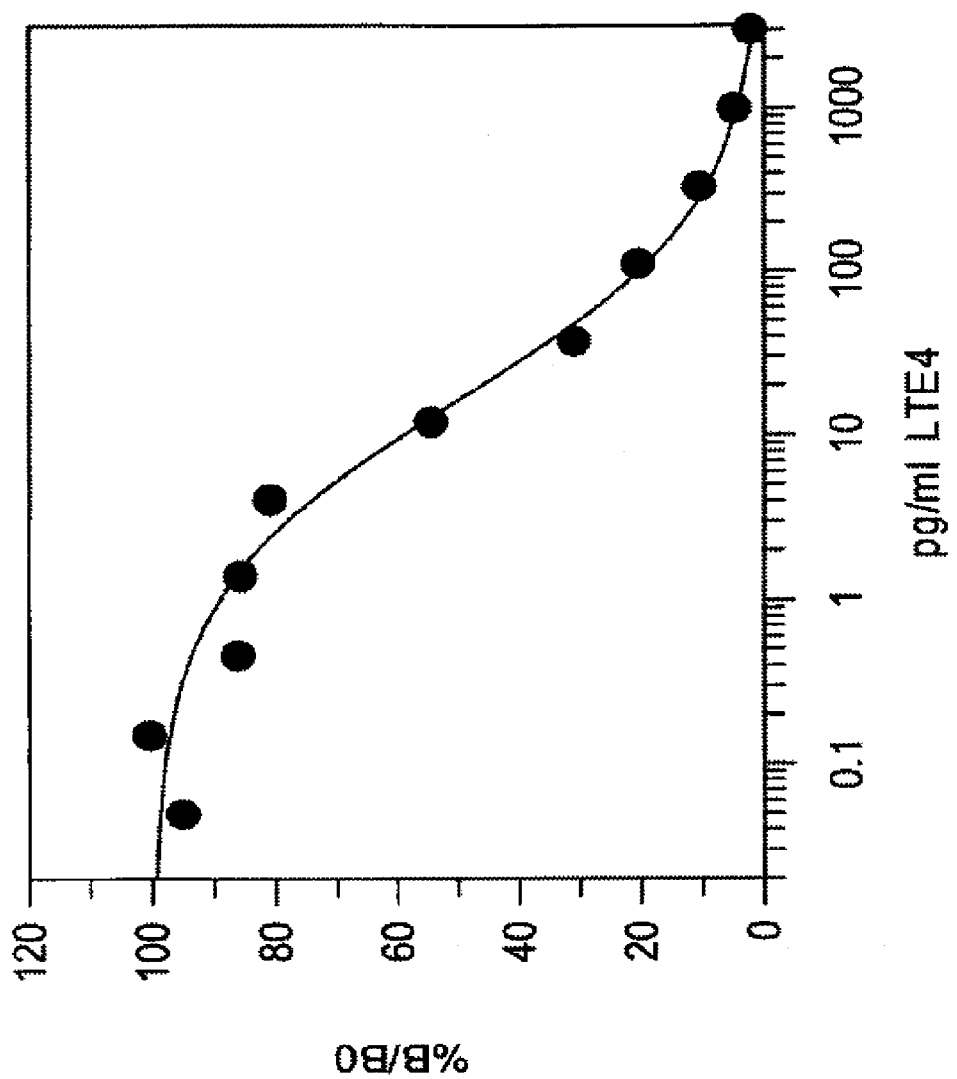
FIG. 12 illustrates a competition curve for LTE4. The LOD was determined to be 1.5 pg/ml LTE4.

The competition curve of LTE4 is shown in FIG. 12. The LOD was calculated to be 80% $B/B_O$=1.5 pg/ml (approximately 5 pM). The LTE4 assay performed using a commercially available kit can detect LTE4 only if present at a concentration of at least 30 pg/ml.

Therefore, the analyzer system can be used to detect levels of LTE4 to indicate the presence of an LTE4-related disorder, e.g., asthma at the onset of disease, and alert clinicians to the need for therapeutic intervention at an early stage of the disease to improve the clinical outcome.

Example 6

Detection of Human Akt1

A sandwich immunoassay was developed for the quantification of low levels of Akt1 in serum samples. A standard curve was generated by dilution of a concentrated standard into a buffered protein solution. Ten microliters (µl) of assay buffer and 10 µl of sample or standard were added to each well of a 384-well plate that had been coated with an antibody specific for Akt1 and incubated for two hours. More specifically antibody 841660 (R&D Systems) was coated onto Nunc Maxisorp plates at 2.5 micrograms/ml. The plate was washed, and 20 µl of labeled detection antibody specific for Akt1, AF1775 (R&D Systems), labeled with Alexa Fluor 647, 2-4 fluors/IgG, was added to each well. After one hour of incubation the plate was washed to remove unbound detection antibody. Bound detection antibody was eluted and measured in the analyzer instrument.

The following materials were used in the assay procedure described below. Coated 384 well plate; assay buffer; resuspension buffer; dilution buffer; standard diluent; Akt1 standard; detection antibody reagent for Akt1; wash buffer (10 mM Borate, 150 mM NaCl, 0.1% TritonX-100, pH 8.3); elution buffer (4 M urea with 0.02% Triton X-100 and 0.001% BSA), Microplate shaker set at "7", Microplate washer, Plate centrifuge, Axyseal sealing film, Axygen product 321-31-051, Nunc pierceable sealing tape, Nunc product 235306.

Materials:
Provided Reagents
Capture antibody: 841660 (R&D Systems), coated onto Nunc Maxisorp plates @ 2.5 micrograms/ml (384 well plate)
Assay buffer
Resuspension Buffer
Dilution Buffer
Standard diluent
Akt 1 standard
Detection antibody reagent for Akt1, AF1775 (R&D Systems), labeled with Alexa Fluor 647, 2-4 fluors/IgG
Other Required Reagents
   TritonX-100 Wash buffer (10 mM Borate, 150 mM NaCl, 0.1% TritonX-100, pH 8.3)
   Elution buffer (4 M urea with 0.02% Triton X-100 and 0.001% BSA)
   Microplate shaker, set at "7"
   Microplate washer
   Plate centrifuge
   Axyseal sealing film, Axygen product 321-31-051
   Nunc pierceable sealing tape, Nunc product 235306
Procedure:
Akt1 standard preparation
   Resuspend standard in 0.5 ml Resuspension Buffer, final concentration=170 ng/ml
   Dilute standard 1:3 in Dilution Buffer=57 ng/ml
   Dilute standard 1: 19 in Standard Diluent=3 ng/ml
Do serial 3 fold dilutions down to 4.1 pg/ml in Standard Diluent
Add 10 µl Assay Buffer per well
Add 10 µl standard or sample per well
Seal plate with Axyseal sealing film
Spin 1 min at 3000 RPM
Incubate 2 hours at 25° C. with shaking
Wash plate five times
Spin plate inverted on a paper towel 1 min at 3000 RPM
Add 20 µl detection antibody reagent per well
Seal plate with Axyseal sealing film Spin plate inverted on a paper towel 1 min at 3000 RPM
Incubate 1 hour at 25° C. with shaking
Wash plate five times
Spin plate inverted on a paper towel 1 min at 3000 RPM
Add 30 µl elution buffer per well
Spin 1 min at 3000 RPM
Seal with Nunc pierceable sealing tape, secure tight seal with roller
Incubate ½ hour at 25° C. with shaking
The plate may be stored for up to 48 hours at 4° C. prior to analysis
Analyze on ZeptX instrument The Akt1 standard curve was generated as follows. Akt1 standards were prepared to achieve a range of between 4.1 pg/ml to 170 ng/ml Akt1. 10 µl of each standard dilution (or sample) were added to the assay plate wells. The plate was sealed and incubated for 2 hours at 25° C. with shaking. The plate was washed and centrifuged dry. 20 µl detection antibody reagent was added per well and incubated for 1 hour at 25° C. with shaking. The antibody-Akt1 complex was disrupted by adding 30 µl elution buffer per well and incubating for ½ hour at 25° C. with shaking. The plate was either used immediately or stored for up to 48 hours at 4° C. prior to analysis. Eluate was pumped into the analyzer.

Figure 13:
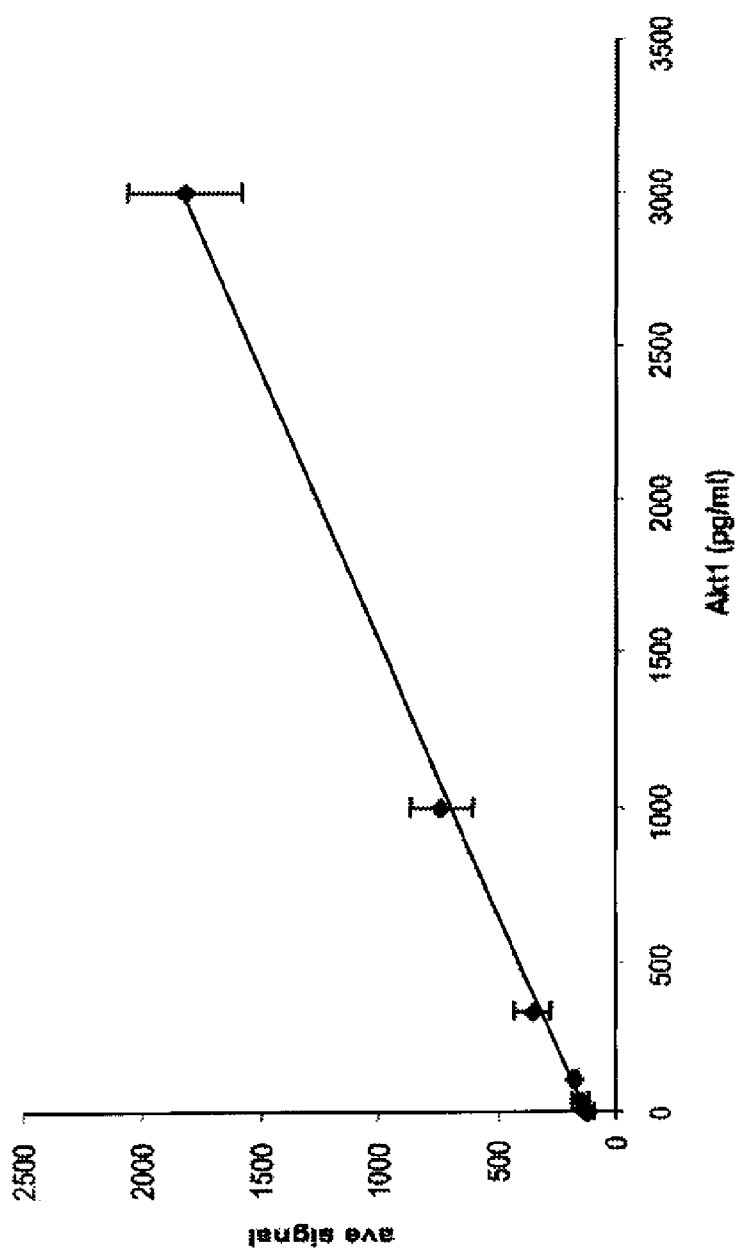
FIG. 13 illustrates a graph showing the standard curve for concentrations of Akt1. The LOD was calculated to be 25 pg/ml Akt1.

Data for a typical Akt1 standard curve measured in quadruplicate using the assay protocol is given in Table 7, and the graphed data is shown in FIG. 13.

TABLE 7

Standard curve for Akt1

| Concentration Akt1 standard (pg/ml) | Average Signal | Standard deviation | % CV |
|---|---|---|---|
| 0 | 113 | 16 | 14 |
| 4.1 | 126 | 10 | 8 |
| 12.4 | 133 | 1 | 0 |
| 37 | 151 | 34 | 22 |
| 111 | 173 | 15 | 8 |
| 333 | 350 | 74 | 21 |
| 1000 | 733 | 136 | 19 |
| 3000 | 1822 | 243 | 13 |

Intra-Assay Precision was tested using 36 replicate samples of the 1000 pg/ml standard by assaying the samples on a single plate. The average signal was 1822±243 with a % CV=13. The limit of detection of the assay (LoD) was determined by adding two standard deviations to the mean signal of thirty six zero standard replicates and calculating the corresponding Akt1 concentration from the standard curve. The LoD was calculated to be 25 pg/ml.

Therefore, the analyzer system can be used to detect levels of Akt1 to determine the presence or absence of an Akt1-related disorder, e.g., cancer.

Example 7

Detection of TGF-β

A sandwich immunoassay was developed for the quantification of low levels of TGFβ in serum. A standard curve was generated by dilution of a concentrated standard into a buffered protein solution. Ten microliters (µl) of assay buffer and 10 µl of sample or standard were added to each well of a 384-well plate coated with an antibody specific for TGFβ and incubated for two hours. The plate was washed and 20 ml of labeled detection antibody specific for TGFβ was added to each well. After 1 h of incubation the plate was washed to remove unbound detection antibody. Bound detection antibody was eluted and measured in the analyzer instrument.

The following materials were used in the assay procedure described below. Coated 384 well plate; assay buffer; standard diluent; 10 µg/ml stock solution of TGFβ standard; detection antibody reagent for TGFβ; TritonX-100 Wash buffer (100 mM Borate, 150 mM NaCl, 0.1% TritonX-100, pH 8.3); elution buffer (4 M urea with 0.02% Triton X-100 and 0.001% BSA).

The TGF-β standard curve was generated as follows. TGF-β standards were prepared to achieve a range of between 100 ng/ml to 4.1 pg/ml TGFβ. 10 µl assay buffer and 10 ml standard or sample were added to each well. The plate was sealed and incubated for 2 hours at 25° C. with shaking. The plate was sealed and incubated for 2 hours at 25° C. with shaking. The plate was washed and centrifuged dry. 20 µl detection antibody reagent was added per well and incubated for 1 hour at 25° C. with shaking. The antibody—TGF-β complex was disrupted by adding 30 µl elution buffer per well and incubating for ½ hour at 25° C. with shaking. The plate was either used immediately or stored for up to 48 hours at 4° C. prior to analysis. Eluate was pumped into the analyzer.

Figure 14:
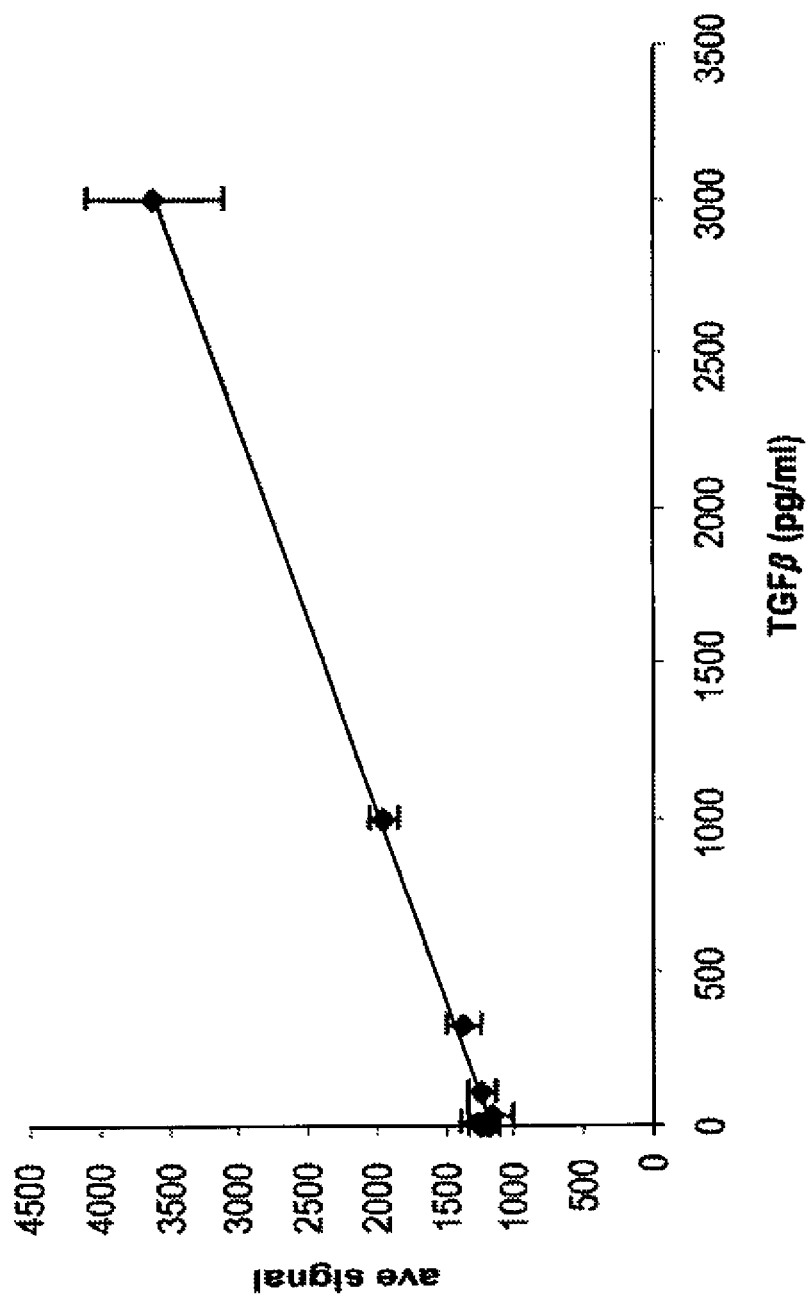
FIG. 14 illustrates a graph showing the standard curve for concentrations of TGFβ. The LOD was calculated to be 350 pg/ml TGFβ.

Data for a typical TGF-β standard curve measured in quadruplicate using the assay protocol is given in Table 8, and the graphed data is shown in FIG. 14.

TABLE 8

Standard curve for TGF-β

| Concentration (pg/ml) | Average Signal | Standard deviation | % CV |
|---|---|---|---|
| 0 | 1230 | 114 | 9 |
| 4 | 1190 | 68 | 6 |
| 12 | 1261 | 132 | 10 |
| 37 | 1170 | 158 | 14 |
| 111 | 1242 | 103 | 8 |
| 333 | 1364 | 135 | 10 |
| 1000 | 1939 | 100 | 5 |
| 3000 | 3604 | 497 | 14 |

The limit of detection of the assay (LoD) was determined by adding two standard deviations to the mean signal of twenty zero standard replicates and calculating the corresponding TGFβ concentration from the standard curve. The LoD=350 pg/ml.

Therefore, the analyzer system can be used to detect levels of TGFβ to determine the presence or absence of a TGFβ-related disorder, e.g., cancer.

Example 8

Detection of Fas Ligand

A sandwich immunoassay for the quantification of low levels of Fas ligand in serum. A standard curve was generated by dilution of a concentrated standard into a buffered protein solution. Ten microliters (µl) of assay buffer and 10 µl of sample or standard were added to each well of a 384-well plate coated with an antibody specific for Fas ligand and incubated for 2 hours. The plate was washed and 20 µl of labeled detection antibody specific for Fas ligand was added to each well. After 1 hour incubation the plate was washed to remove unbound detection antibody. Bound detection antibody was eluted and measured in the ZeptX™ instrument.

The Fas ligand standard curve was generated as follows. Fas ligand standards were prepared to achieve a range of between 100 ng/ml to 4.1 pg/ml Fas ligand. 10 µl assay buffer and 10 µl standard or sample were added to each well. The plate was sealed and incubated for 2 hours at 25° C. with shaking. The plate was sealed and incubated for 2 hours at 25° C. with shaking. The plate was washed and centrifuged dry. 20 µl detection antibody reagent was added per well and incubated for 1 hour at 25° C. with shaking. The antibody-Fas ligand complex was disrupted by adding 30 µl elution buffer per well and incubating for ½ hour at 25° C. with shaking. The plate was either used immediately or stored for up to 48 hours at 4° C. prior to analysis.

Data for a typical Fas ligand standard curve measured in quadruplicate using the assay protocol is given in Table 9.

TABLE 9

Standard curve for Fas ligand

| Concentration Fas ligand standard (pg/ml) | Average Signal | Standard deviation | % CV |
|---|---|---|---|
| 0 | 935 | 82 | 9 |
| 1.2 | 1007 | 44 | 4 |
| 3.4 | 1222 | 56 | 5 |
| 11 | 1587 | 70 | 4 |
| 33 | 2869 | 52 | 2 |
| 100 | 5939 | 141 | 2 |
| 300 | 9276 | 165 | 2 |
| 900 | 11086 | 75 | 1 |

Intra-Assay Precision was tested using 12 replicate samples of 3 standard concentrations by assaying the samples on a single plate. The mean, standard deviation and CV for the 12 values for each of the three points are shown in Table 10.

TABLE 10

Intra-assay precision for Fas ligand

| Concentration (pg/ml) | Average Signal | Standard deviation | % CV |
|---|---|---|---|
| 11 | 1717 | 128 | 7 |
| 33 | 3031 | 262 | 9 |
| 100 | 6025 | 257 | 4 |

The limit of detection of the assay (LoD) was determined by adding two standard deviations to the mean signal of twenty zero standard replicates and calculating the corresponding Fas ligand concentration from the standard curve. The LoD was calculated to be 2.4 pg/ml.

Therefore, the analyzer system of the invention can detect levels of Fas ligand to indicate the presence of a Fas ligand-related disorder, e.g., cancer, allograft rejection and degenerative diseases such as osteoarthritis.

Example 9

Sandwich Assays for Biomarker TREM-1

Assays for TREM-1 have been developed using a sandwich assay format (Sandwich Assay for Detection of Individual Molecules, U.S. Provisional Patent Application No. 60/624,785). Assay reagents for TREM-1 detection are available commercially (R&D Systems, Minneapolis, Minn.). The assay was done in a 96 well plate. A monoclonal antibody was used as the capture reagent, and either another monoclonal or a polyclonal antibody was used for detection. The detection antibody was labeled with Alexa Fluor 647®.

The assay protocol was as follows:
1. Coat plates with the capture antibody, washed 5×,
2. Block in 1% BSA, 5% sucrose in PBS,
3. Add the target diluted in serum, incubate, wash 5×,
4. Add the detection antibody, incubate, wash 5×
5. Add 0.1 M glycine pH 2.8 to release the bound assay components from the plate.
6. Transfer samples from the processing plate to the detection plate, bring the pH of the sample to neutral and run on the single particle analyzer system.

Figure 16:
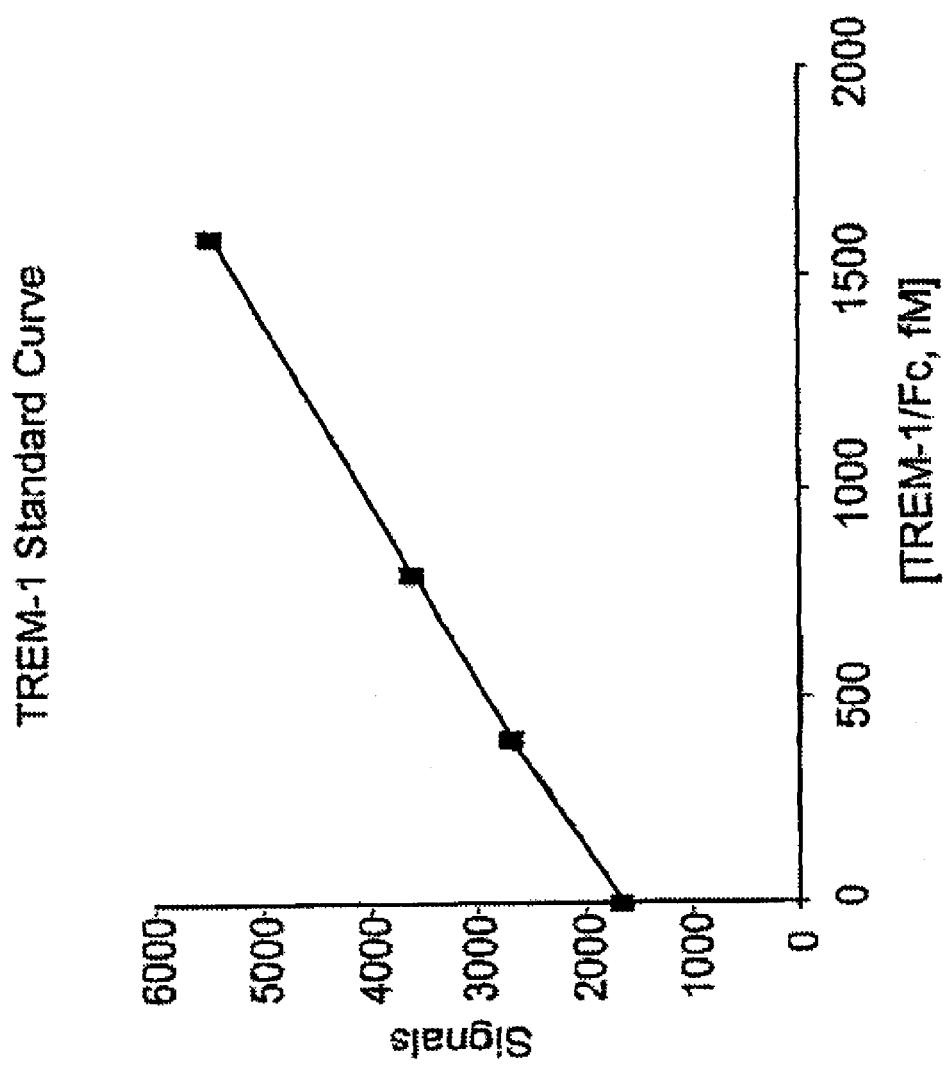
FIG. 16 illustrates a standard curve of TREM-1 measured in a sandwich molecule immunoassay developed for the single particle analyzer system. The linear range of the assay is 100-1500 fM.
Figure 18:
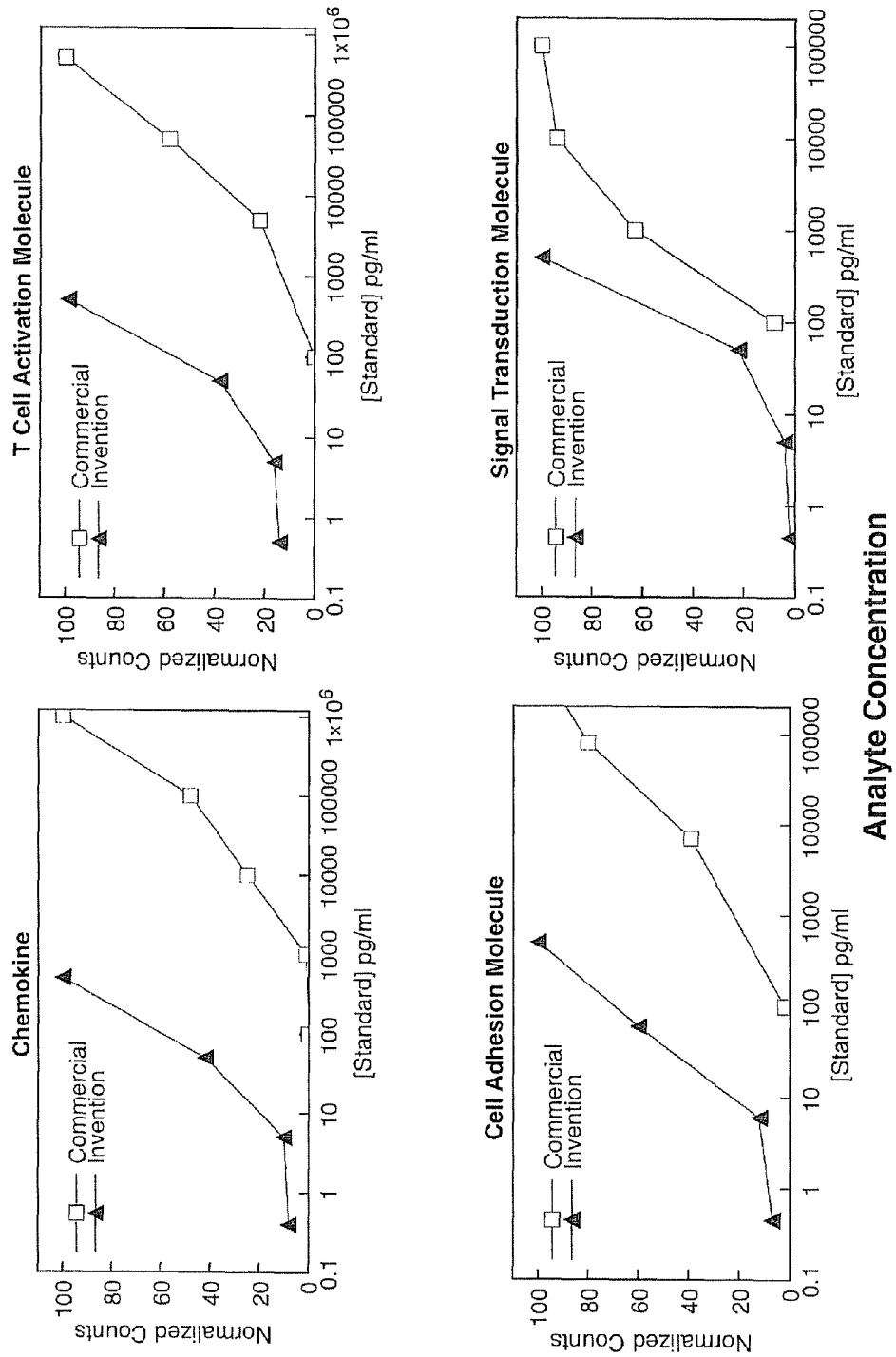
FIG. 18 illustrates a comparison of assays of the invention with conventional assays.

FIG. 16 shows a standard curve of TREM-1 generated using the assay. The assay was linear in the measured range of 100-1500 femtomolar. An ELISA assay from R&D Systems has recently been introduced. The standard curve reported for their ELISA assay is between 60-4000 pg/ml. This Example suggests we can routinely measure 100 fM (4.7 pg/ml) in a standard curve, allowing for about 10× more sensitive measurements. In addition, standard curves for chemokines, T cell activation molecules, cell adhesion molecules and signal transduction molecules have been generated. See FIG. 18. The results show that the detection by the detection of analyte using the single particle analyzer is consistently between 10- and 100-fold more sensitive than detection using ELISA assays.

Example 10

Sandwich Assays for Biomarkers: IL-6 and IL-8 Levels in Serum

The assay: This protocol describes a sandwich immunoassay for the quantification of low levels of IL-6 in serum using the single particle analyzer system of the invention. A standard curve was generated by dilution of a concentrated standard into a buffered protein solution. Ten microliters (µl) of assay buffer and 10 ml of sample or standard were added to each well of a 384-well plate coated with an antibody specific for IL-6 and incubated for two hours. The plate was washed, and 20 µl of labeled detection antibody specific for IL-6 was added to each well. After one hour of incubation the plate was washed to remove unbound detection antibody. Bound detection antibody was eluted and measured in the single particle analyzer instrument.

Materials: The following materials were used in the procedure described below: coated 384 well plate; assay buffer; standard diluent; 100 ng/ml stock solution of IL-6 standard; detection antibody for IL-6 (R&D Systems) labeled with Alexa Fluor 647 dye; TritonX-100 Wash buffer (10 mM Borate, 150 mM NaCl, 0.1% TritonX-100, pH 8.3); Elution buffer (4 M urea with 0.02% Triton X-100 and 0.001% BSA); Microplate shaker set at "7"; Microplate washer; Plate centrifuge; Axyseal sealing film, Axygen product 321-31-051; and Nunc pierceable sealing tape, Nunc product 235306.

Procedure: A standard curve for IL-6 was prepared as follows: 100 ng/ml stock solution was thawed and diluted 1:1000 to 100 pg/ml in standard diluent by doing six serial, 3 fold dilutions to obtain a range of concentration having the lowest standard concentration of 0.14 pg/ml. 10 µl assay buffer and 10 µl standard or sample were added to each well per well of the coated 384 well plate. The plate was sealed with Axyseal sealing film, and centrifuged for one minute at 3000 RPM. The assay plate was incubated for 2 hours at 25° C. with shaking; washed five times; and centrifuged while inverted on a paper towel for one minute at 3000 RPM. 20 µl detection antibody reagent was added to each well; the plate was sealed with Axyseal sealing film, and centrifuged for one minute at 3000 RPM. The assay plate was incubated for one hour at 25° C. with shaking, washed five times, and centrifuged while inverted on a paper towel for one minute at 3000 RPM. 30 µl elution buffer was added to each well; the plate was sealed with Nunc pierceable sealing tape, and a tight seal was secured using with roller. The assay plate was centrifuged for one minute at 3000 RPM, and incubated for ½ hour at 25° C. with shaking. Analysis of the assay was performed immediately. Alternatively, the plate was stored for up to 48 hours at 4° C. prior to analysis.

Samples of serum from EDTA treated whole blood of 32 blood bank donors were analyzed for IL-6.

Results: Data for a typical IL-6 standard curve measured in quadruplicate using the assay protocol is shown in Table 11.

TABLE 11

Standard Curve for IL-6

| Concentration (pg/ml) | Average Signal | Standard deviation | CV |
|---|---|---|---|
| 370 | 11035 | 206 | 2% |
| 125 | 9983 | 207 | 2% |
| 41 | 8522 | 95 | 1% |
| 14 | 5023 | 108 | 2% |
| 4.5 | 2577 | 124 | 5% |
| 1.7 | 1178 | 114 | 10% |
| 0.5 | 577 | 36 | 6% |
| 0 | 106 | 15 | 14% |

Linearized standard curves for higher and low range concentrations of IL-6 are shown in FIGS. 17A-B, respectively. The assay allowed for detection of IL-6 at less than 0.5 pg/ml (FIGS. 17A-B). The limit of detection (LoD) was calculated to be 0.06 pg/ml. The limit of detection of the assay (LoD) was determined by adding two standard deviations to the mean signal of the zero standard replicates and calculating the corresponding IL-6 concentration from the standard curve. This level of sensitivity is excellent for detection of even normal levels of IL-6 which ranges between 0.5 and 10 pg/ml.

Assays to detect IL-6 and IL-8 in serum of blood samples from blood bank donors were performed, and the results of the analysis are shown in FIGS. 17C-D. IL-6 was quantified in 100% of the samples (32/32). The average concentration of IL-6 was 2.3 pg/ml, and the range of concentration was 0.2 to >26 pg/ml (FIG. 17C). The same samples were also assayed for IL-8 essentially using the procedure described for IL-6. IL-8 standards and IL-8 specific antibodies were used. A standard curve for IL-8 was established (not shown) and used to determine the concentration of IL-8 in the samples (FIG. 17D). IL-8 was quantified in 100% (32/32) samples. The average concentration for IL-8 was 7.3 pg/ml, and the range of concentration was 1.2 to >26 pg/ml.

Figure 17F:
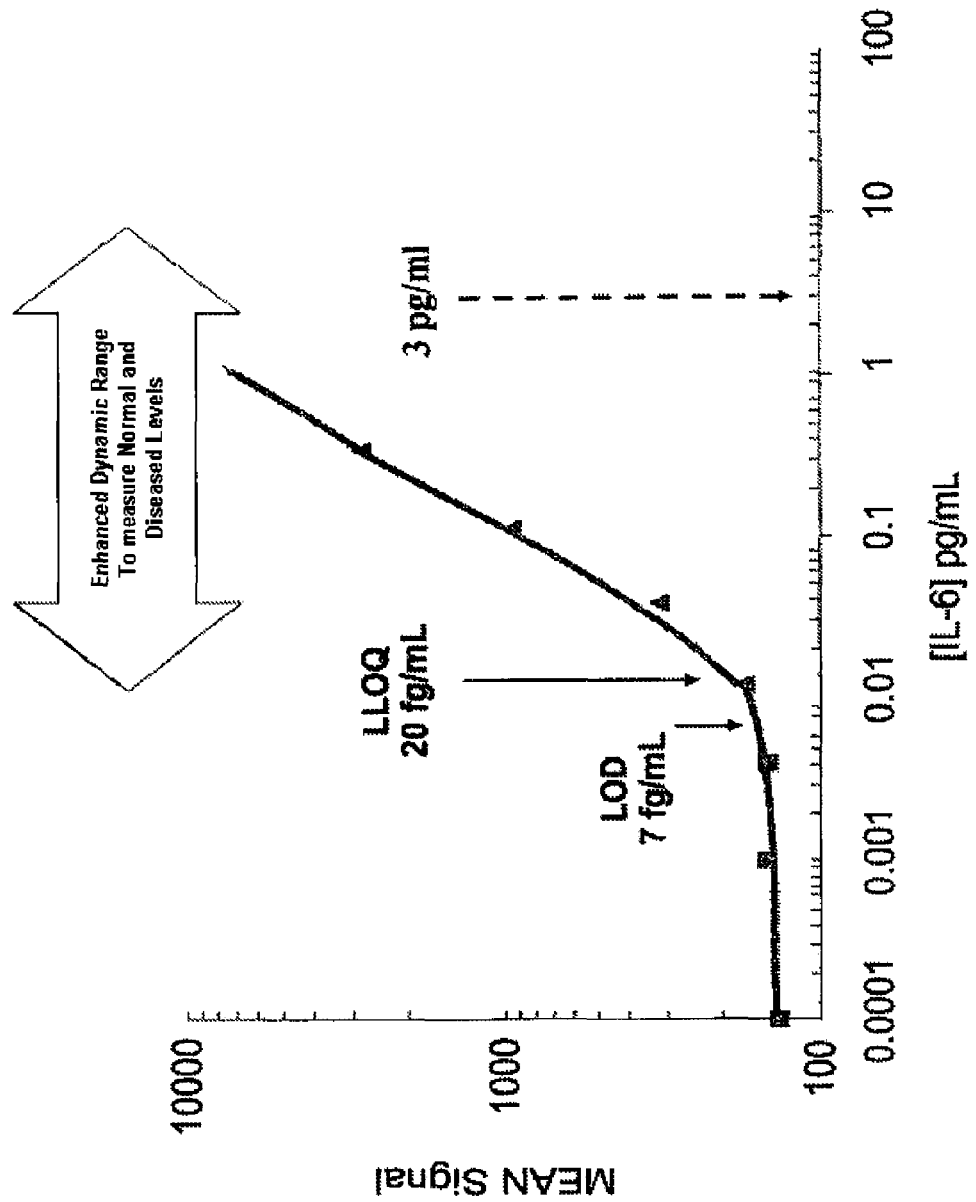

Measurements of IL-6 or any particle of interest can be measured at low and higher concentrations (FIGS. 17A and B) by switching the detection of the analyzer from counting molecules (digital signal) to detecting the sum of photons (analog signal) that are generated at the higher concentrations of analyte. This is shown in a general way in FIG. 17E. The single particle analyzer has an expanded linear dynamic range of 6 logs. The ability to increase the dynamic range for detecting the concentration of a particle in a sample allows for the determination of the concentration of a particle for normal (lower concentration range) and disease levels (higher concentration range). The range of detection for normal and disease levels of IL-6 is shown in FIG. 17F.

Example 11

Vascular Endothelial Growth Factor-A (VEGF-A) Assay

Assays to detect VEGF were developed for both human VEGF and mouse VEGF. In some embodiments, the human VEGF assay has an LOD of about 0.1 pg/ml and an LLOQ of 0.3 pg/ml, making it 90× more sensitive than the commonly used ELISA assay. Cross-reactivity with mouse VEGF was minimal for all sample types tested. The assay was capable of measuring VEGF concentrations in 100% of the plasma, cell lysate, and spent media samples tested. In contrast, an ELISA was typically able to accurately detect human VEGF in only 6% of healthy plasma samples, and 10% of healthy cell lysate samples. Where both assays measured the VEGF concentration in a sample, the levels determined were comparable for the two assays, with the exception of spent media where the ELISA detected considerably more VEGF. This discrepancy is likely due to the fact that the ELISA measures total VEGF while the assay of the present invention measures free VEGF. Soluble VEGF receptors released into the spent media would significantly decrease the free VEGF concentration. The intra-assay variability was <10% for most plasma samples, and <15% for plasma samples with high VEGF concentrations. Inter-assay CVs for analysis of plasma samples was <10%.

Example 12

Sandwich Immunoassay for the Detection of Mouse and Human VEGF

Preparation of Antibody and Antigen Reagents:

Generation the necessary antibody and antigen reagents required for developing the mouse VEGF bioassays. To identify optimal reagents for the mouse VEGF assay, recombinant mouse VEGF protein (from R&D Systems and Sigma) and anti-mouse VEGF antibodies (from R&D Systems, Abcam, and Sigma) were tested for suitability. For the human VEGF assay recombinant VEGF protein (from R&D Systems and Abcam) and anti-human VEGF antibodies (from R&D Systems and Abcam) were obtained and tested. Magnetic particles were coated with anti-VEGF antibodies for use in the capture step of the sandwich-immunoassay format. Potential detection antibodies were conjugated with Alexa Fluor® dye.

Antibody pairs for both assays were screened as part of the assay optimization process using a basic set of initial assay conditions.

Preparation of Sandwich VEGF Immunoassay:

Using optimal antibody pairs as prepared in the preparation of antibody and antigen reagents, assays were run to optimize the concentrations for capture antibody, detection antibody, and magnetic particles. In addition, various assay components were tested to design the optimal assay buffers for each assay. This included identifying the best blocking agents and detergents, then optimizing the concentrations of each component.

Methods for Performing Human VEGF Assay:

A solution of recombinant human VEGF protein standard at a concentration of 1 ng/ml was serially-diluted. Triplicate samples were prepared. The VEGF assay was used to measure the concentrations of these samples. The concentrations determined using the assay were plotted against the expected VEGF concentration.

Results:

The performance of the assays were demonstrated and found to provide highly linear correlation with the concentration of input recombinant VEGF used as standards. The human VEGF assay has an LOD of 0.1 pg/ml and an LLOQ of 0.3 pg/ml (Table 12 and FIGS. 19A-B). Table 12 shows human VEGF assay performance data wherein the assay demonstrates a CVs<10%, and recoveries of 84-107%.

TABLE 12

| hVEGF (pg/ml) | Detected Events (Mean) | std dev | CV | Recovery |
|---|---|---|---|---|
| 0.24 | 197 | 8 | 4% | 95% |
| 0.48 | 311 | 11 | 3% | 100% |
| 0.98 | 484 | 27 | 6% | 89% |
| 1.95 | 885 | 40 | 5% | 93% |
| 3.9 | 1537 | 57 | 4% | 90% |
| 7.8 | 2975 | 225 | 8% | 116% |
| 15.6 | 4972 | 110 | 2% | 114% |
| 31.3 | 7349 | 70 | 1% | 111% |
| 62.5 | 9401 | 95 | 1% | 114% |
| 125 | 10023 | 96 | 1% | 100% |
| 250 | 10091 | 160 | 2% | 84% |
| 500 | 10236 | 99 | 1% | 95% |
| 1000 | 10029 | 34 | <1% | 107% |

Table 13 shows human VEGF assay performance data wherein the assay demonstrates an LOD of 0.07 pg/ml.

TABLE 13

| BACKGROUND (DETECTED EVENTS) | SLOPE [(DETECTED EVENT)/(PG/ML)] | LOD [PG/ML] |
|---|---|---|
| 81 | 202 | 0.07 |

Figure 19A:
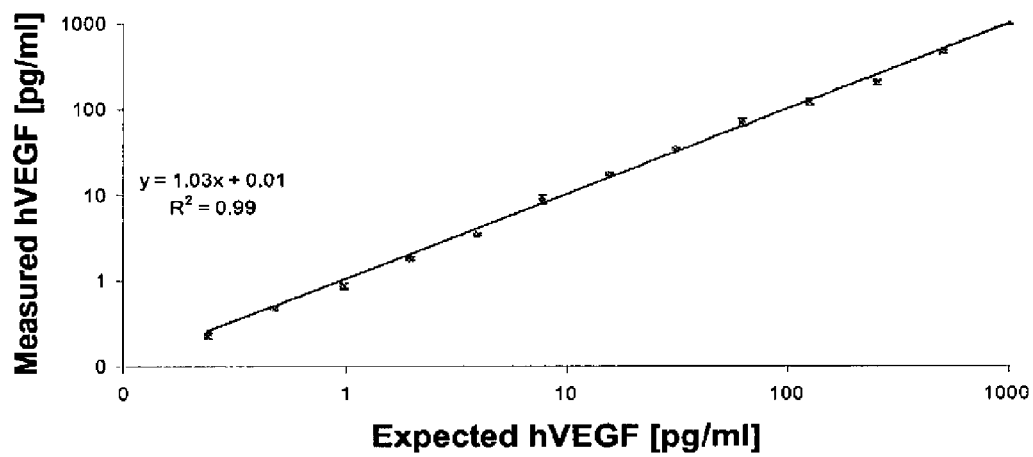
FIG. 19A is a graph illustrating the performance of a human VEGF assay.
Figure 19B:
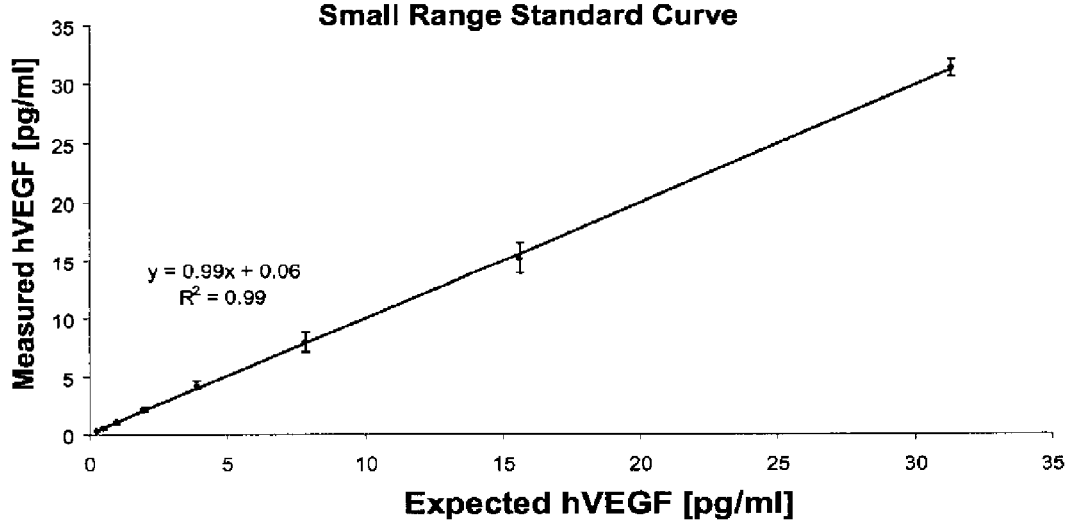
FIG. 19B is a graph of the assay performance at the lowest concentrations.

The data presented in Tables 12 and 13 are shown graphically in FIGS. 19A-B.

Similarly, the mouse VEGF assay has an LOD of 2 pg/ml and an LLOQ of 3 pg/ml (Tables 14 and 15).

TABLE 14

| mVEGF [pg/ml] | Observed mVEGF | stdev | % CV | % recovery |
|---|---|---|---|---|
| 1000 | 982 | 106 | 11 | 98 |
| 250 | 256 | 12 | 5 | 102 |
| 63 | 62 | 4 | 7 | 99 |
| 16 | 15 | 3 | 19 | 94 |
| 3.9 | 7.7 | 3 | 36 | 197 |

TABLE 15

| Slope | Bkg | StDev bkg | LoD 10% [pg/ml] | LoD [pg/ml] |
|---|---|---|---|---|
| 12 | 217 | 30 | 3.6 | 4.9 |

Figure 20A:
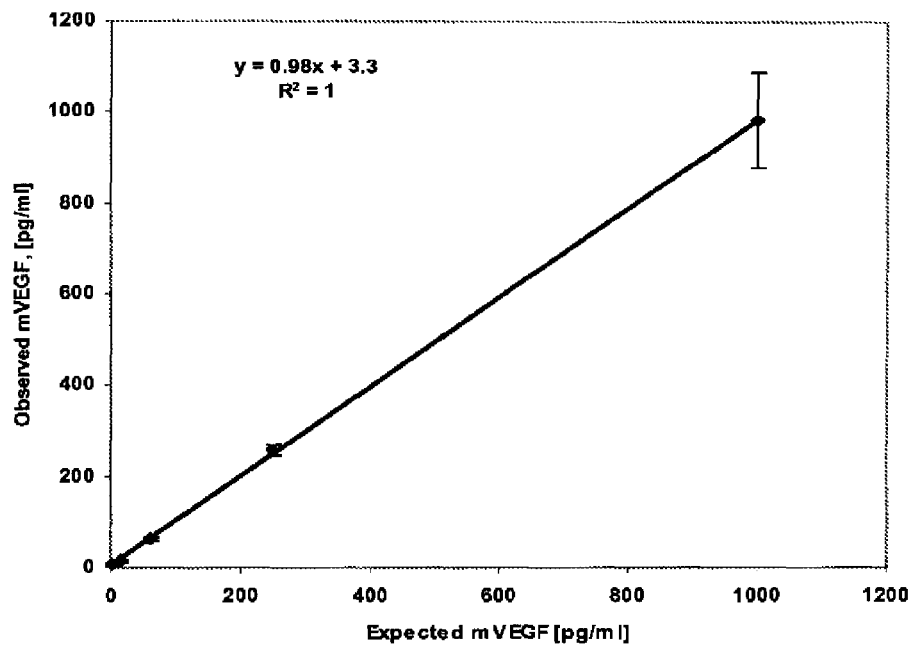
FIG. 20A is a graph illustrating the performance of a mouse VEGF assay.
Figure 20B:
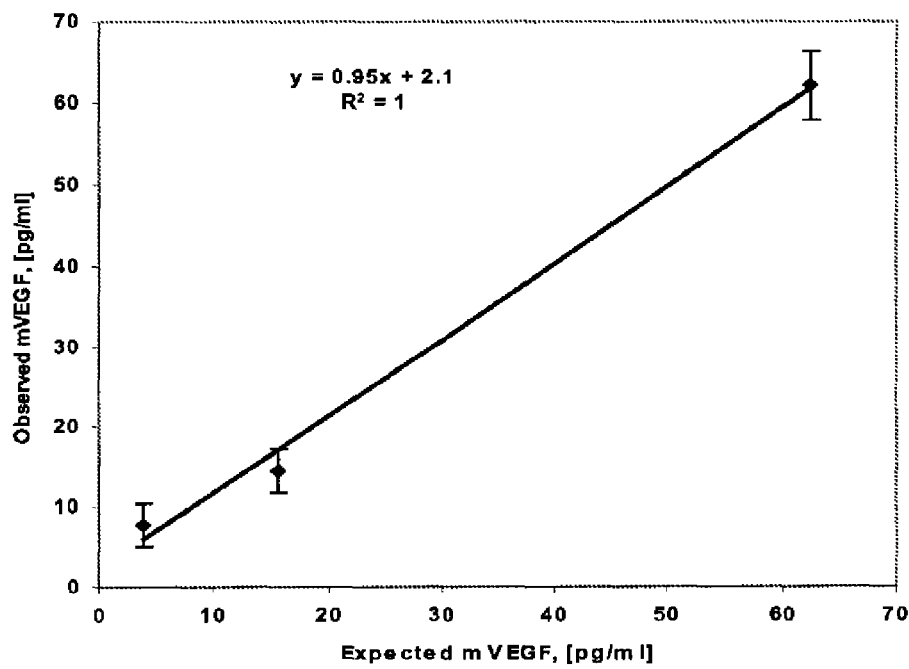
FIG. 20B is a graph of the assay performance at the lowest concentrations.

The data presented in Tables 14 and 15 are shown graphically in FIGS. 20A-B.

The data demonstrate that the mouse VEGF assay is 3× more sensitive and the human VEGF assay is 90× more sensitive when compared to the stated sensitivities of the respective benchmark R&D Systems VEGF ELISA assay kits (mVEGF assay sensitivity of 9 pg/ml; human VEGF assay sensitivity of 32 pg/ml). [Note that the R&D Systems stated LOD of 6.8 pg/ml for human VEGF assay must be multiplied by 5 to accurately define the LOD of the assay. This adjustment is needed to account for the 1:5 dilution of the samples required in the R&D Systems assay (the standards in this assay are not diluted, and the 1:5 dilution of the sample is not included as part of their sensitivity calculation)]. For the human VEGF assay of the Example, magnetic particles coated with a monoclonal antibody are used for the capture step and an Alexa-labeled polyclonal antibody is used for the detection step. For the mouse VEGF assay polyclonal antibodies are used for both the capture and detection steps, similar to the R&D Systems ELISA kit.

In order to ensure equal comparison between the present invention and the ELISA assay, a comparison was made between standard analyte concentrations used for value assignment. As a result of this information, the standard according to the present invention was revalued in accordance with results from the assay of the ELISA Standards. When the present data were adjusted for this standard-revaluation, the VEGF concentrations determined using both assays were similar. The original and re-valued data are presented in Table 16 below.

Example 13

Determination of Reproducibility, Variability, and Accuracy of Human and Mouse VEGF Biomarker Assays in Plasma Comparison of Analysis of Human Plasma:

Plasma samples from 24 individual mice were analyzed using an assay according to the present invention; 12 of these samples also were tested using the R&D Systems ELISA (claimed sensitivity of LoD=31.2 pg/mL in serum/plasma). The assay of the invention determined the VEGF concentration of all 12 samples, whereas the ELISA assay quantified only 1/12 (8.3%) of the tested samples (Table 16 and FIG. 21). Table 16 shows the comparison between the assay and ELISA human VEGF assays for plasma analysis.

TABLE 16

| Lot # | Present Assay | | | | | | R & D ELISA | | | |
|---|---|---|---|---|---|---|---|---|---|---|
| | Original hVEGF [pg/ml] mean | std dev | % CV | N | Re-Valued hVEGF [pg/ml] mean | std dev | Measured hVEGF [pg/ml] mean | st dev | % CV | N |
| 10947388 | 60 | 2.1 | 3 | 3 | 19 | 0.64 | 8 | 1.0 | 13 | 3 |
| 10947393 | 43 | 4.0 | 9 | 3 | 13 | 1.23 | 5 | 0.4 | 8 | 3 |
| 10947392 | 38 | 4.1 | 11 | 3 | 12 | 1.27 | 11 | 0.7 | 6 | 3 |
| 6110053 | 81 | 1.0 | 1 | 3 | 25 | 0.31 | 44 | 1.8 | 4 | 3 |
| 6110054 | 30 | 4.2 | 14 | 3 | 9 | 1.31 | ND | | | 3 |
| 6110050 | 45 | 7.4 | 16 | 3 | 14 | 2.30 | 5 | 0.8 | 17 | 3 |
| 6110051 | 26 | 2.1 | 8 | 3 | 8 | 0.65 | ND | | | 3 |
| 6110055 | 49 | 3.5 | 7 | 3 | 15 | 1.09 | 8 | 0.4 | 5 | 3 |
| 10852081 | 45 | 1.8 | 4 | 3 | 14 | 0.57 | NT | | | |
| 10852068 | 27 | 1.7 | 6 | 3 | 8 | 0.54 | NT | | | |
| 10852072 | 27 | 0.4 | 2 | 3 | 8 | 0.13 | NT | | | |
| 10852059 | 21 | 2.4 | 11 | 3 | 7 | 0.73 | NT | | | |
| 10590341 | 16 | 1.9 | 12 | 3 | 5 | 0.60 | ND | | | 3 |
| 10590346 | 35 | 1.2 | 3 | 3 | 11 | 0.37 | 16 | 0.7 | 4 | 3 |
| 10590343 | 14 | 1.8 | 13 | 3 | 4 | 0.57 | 7 | 0.4 | 5 | 3 |
| 10590348 | 18 | 1.6 | 9 | 3 | 6 | 0.50 | 6 | 0.7 | 11 | 3 |
| 1012990 | 142 | 2.8 | 2 | 3 | 44 | 0.86 | NT | | | |
| 1012996 | 122 | 4.7 | 4 | 3 | 38 | 1.46 | NT | | | |
| 101292 | 106 | 3.6 | 3 | 3 | 33 | 1.12 | NT | | | |
| 1012998 | 81 | 3.7 | 5 | 3 | 25 | 1.16 | NT | | | |
| 1013057 | 56 | 4.6 | 8 | 3 | 17 | 1.44 | NT | | | |
| 1013186 | 44 | 3.4 | 8 | 3 | 14 | 1.05 | NT | | | |
| 1012930 | 114 | 2.7 | 2 | 3 | 35 | 0.83 | NT | | | |
| 1012938 | 78 | 3.4 | 4 | 3 | 24 | 1.06 | NT | | | |

ND = none detected
Shaded = tested in both assays
NT = not tested

Figure 21:
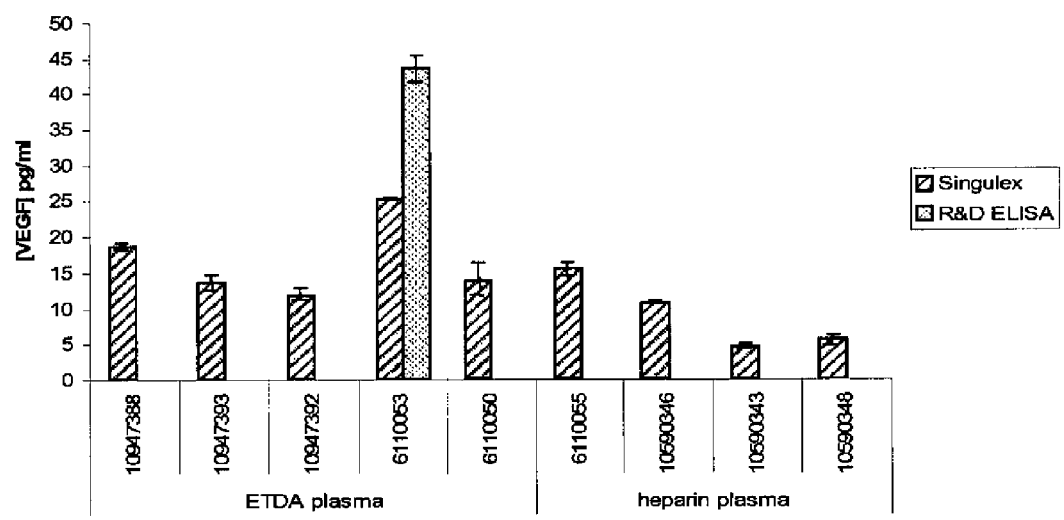
FIG. 21 is a graph comparing the VEGF assays of the present invention and ELISA assays of human plasma.

Select date shown in Table 16 is illustrated graphically in FIG. 21 as a comparison between Singulex and ELISA assays of human plasma. The ELISA assay detected VEGF in one sample (1 of 16 tested); VEGF values for the other plasma samples were below the lowest point on the ELISA standard curve and therefore could not be reliably determined. CVs for Singulex assay averaged <20%.

Determination of hVEGF Levels in Cell Lysates and Culture Media in Different Cell Lines:

Two different human cell lines were grown and harvested. Cells were lysed according to the NCI SOP #340506 with the exception that a lower concentration of SDS was used and the samples were not boiled. The cell lines used were human cell lines MDA-MB-231 breast adenocarcinoma and HT-29 colon adenocarcinoma.

Figure 22A:
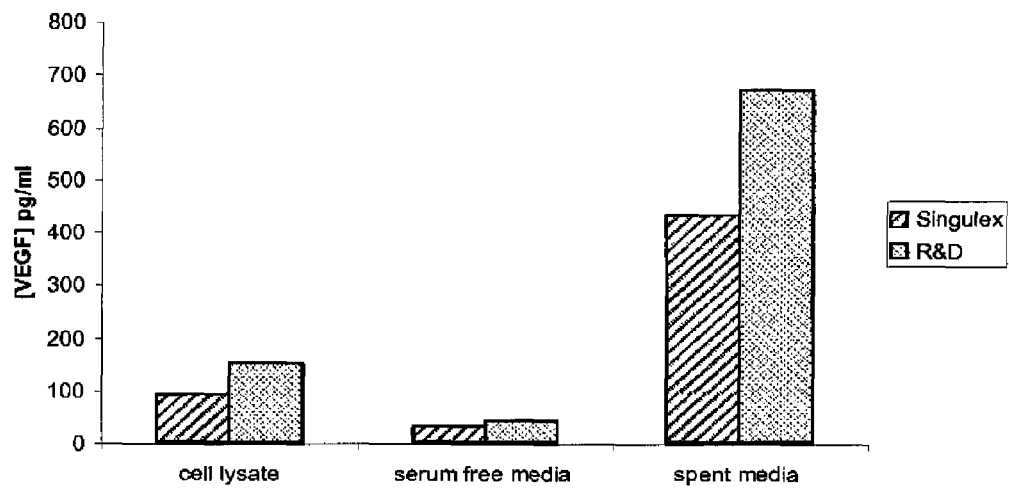
FIG. 22A is a graph comparing the level of VEGF detected in cell lysates and culture media using MDA-MB-231 breast adenocarcinoma cells.
Figure 22B:
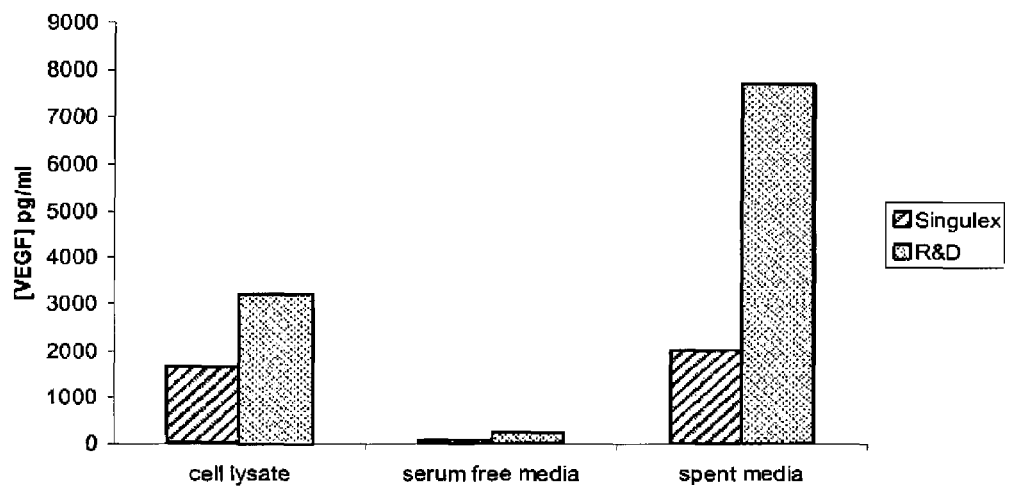
FIG. 22B is a graph comparing the level of VEGF detected in cell lysates and culture media using HT-29 colon adenocarcinoma cells.

Samples were run in duplicate in both the present and the R&D ELISA assays. Lysates were initially diluted 1:8, then (3) serial 1:2 dilutions were made. Media were analyzed neat and diluted 1:4, 1:16, and 1:64. Duplicates of each sample were tested. A comparison of the values from the two assays is shown in FIG. 21. Both assays detected VEGF in the cell extracts and in the spent media (FIGS. 22A-B). Assay results were in general agreement, with less VEGF detected in the cell extracts than in the spent media. Overall VEGF levels were significantly lower in the MDA-MD231 samples, and this was confirmed by both assays.

Figure 23:
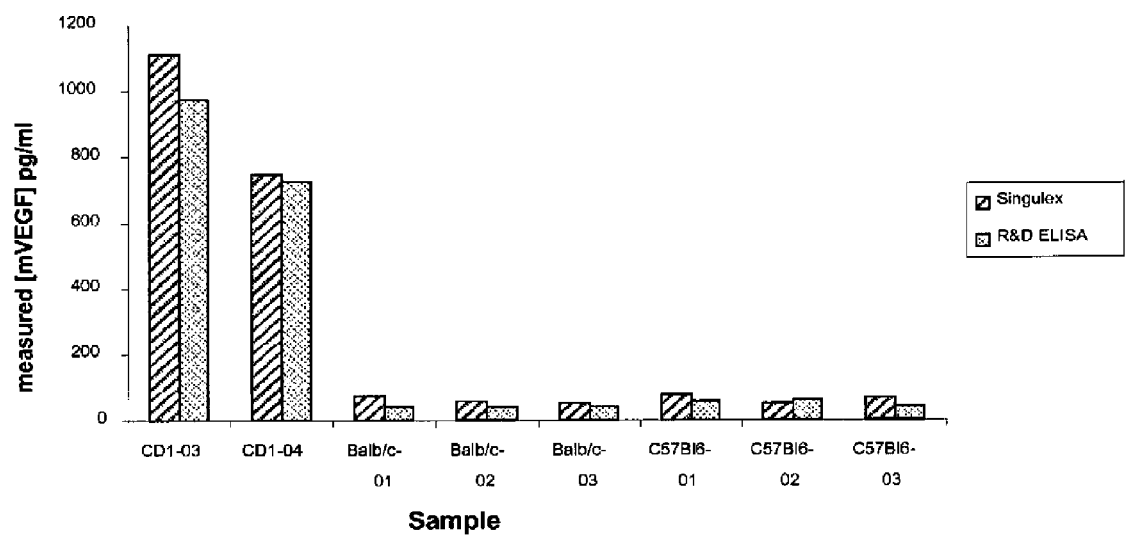
FIG. 23 is a comparison of VEGF assays of the present invention and ELISA assays for mouse plasma samples.

Comparison of Analysis of Mouse Plasma Samples:

Eight mouse plasma samples from individual mice were analyzed using an assay of the present invention and the R&D Systems ELISA. Comparable values were observed in both of the assays (FIG. 23).

Determining mVEGF Levels in Cell Lysates and Culture Media:

Three different mouse cell lines were grown and harvested. Cells were lysed as above. The cell lines used were mouse cell lines: B16 melanoma, 4T1 mammary carcinoma, and CT26 colon carcinoma.

Figure 24A:
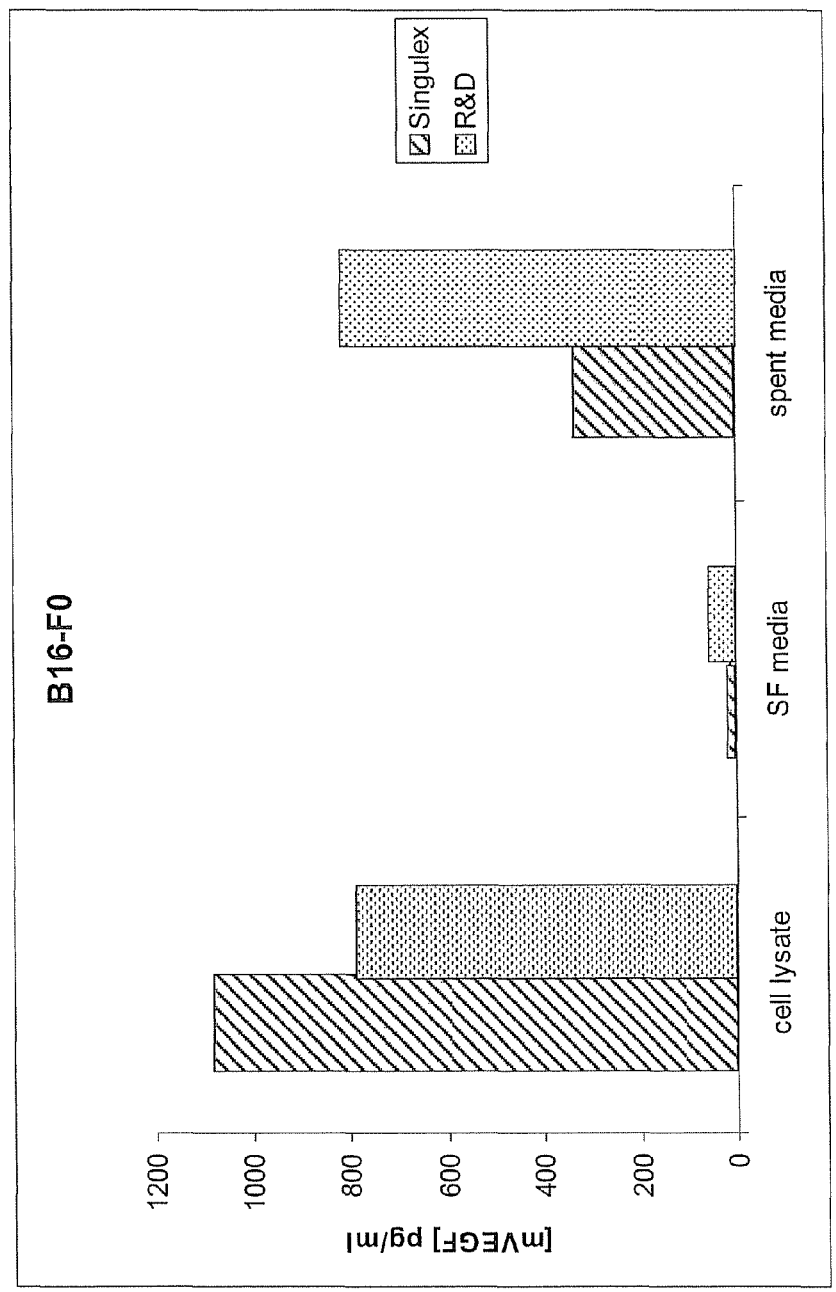
FIG. 24A is a graph illustrating the concentration of mouse VEGF detected in cell lysates and culture media using B16 melanoma mouse cell lines.
Figure 24B:
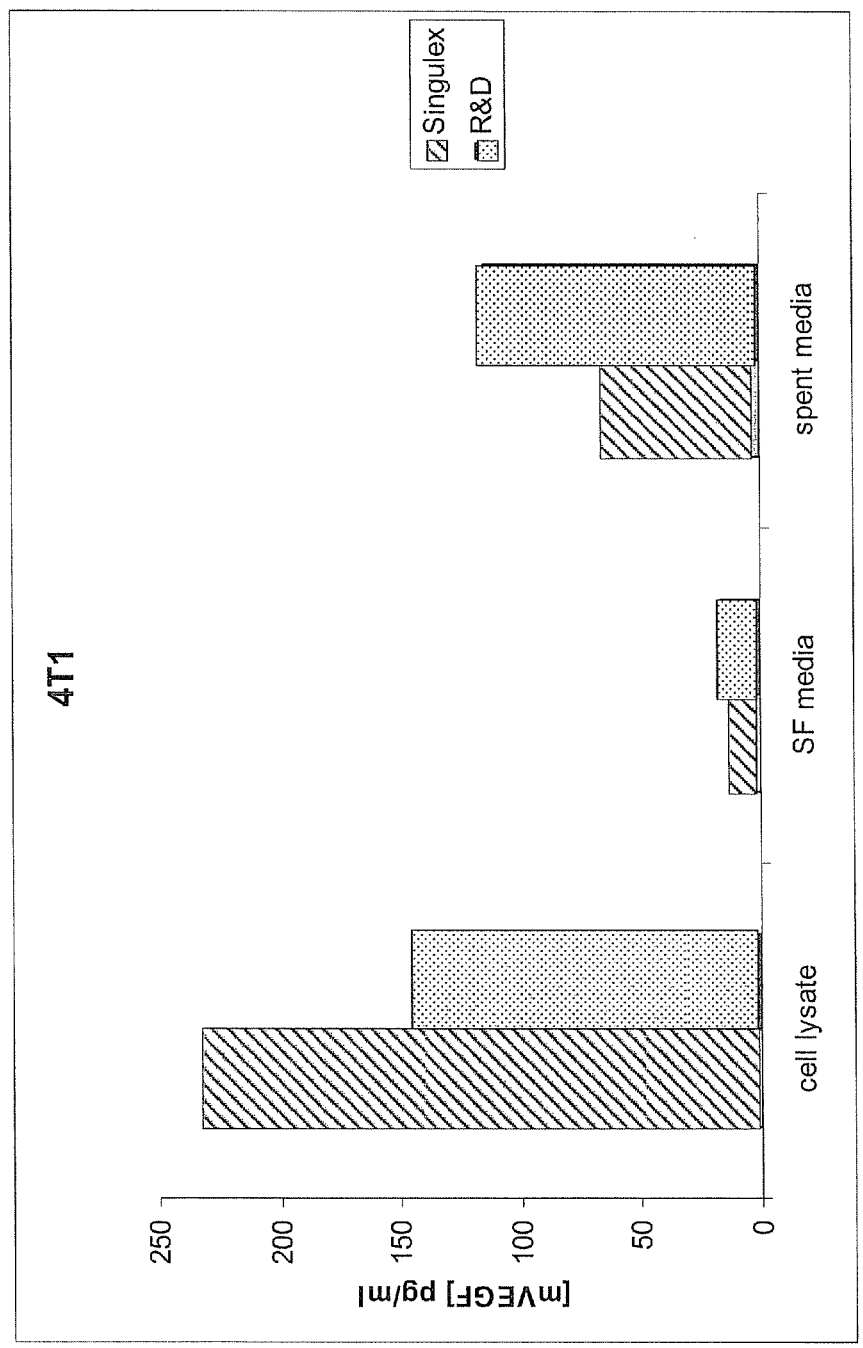
FIG. 24B is a graph illustrating the concentration of mouse VEGF detected in cell lysates and culture media using 4T1 mammary carcinoma.
Figure 24C:
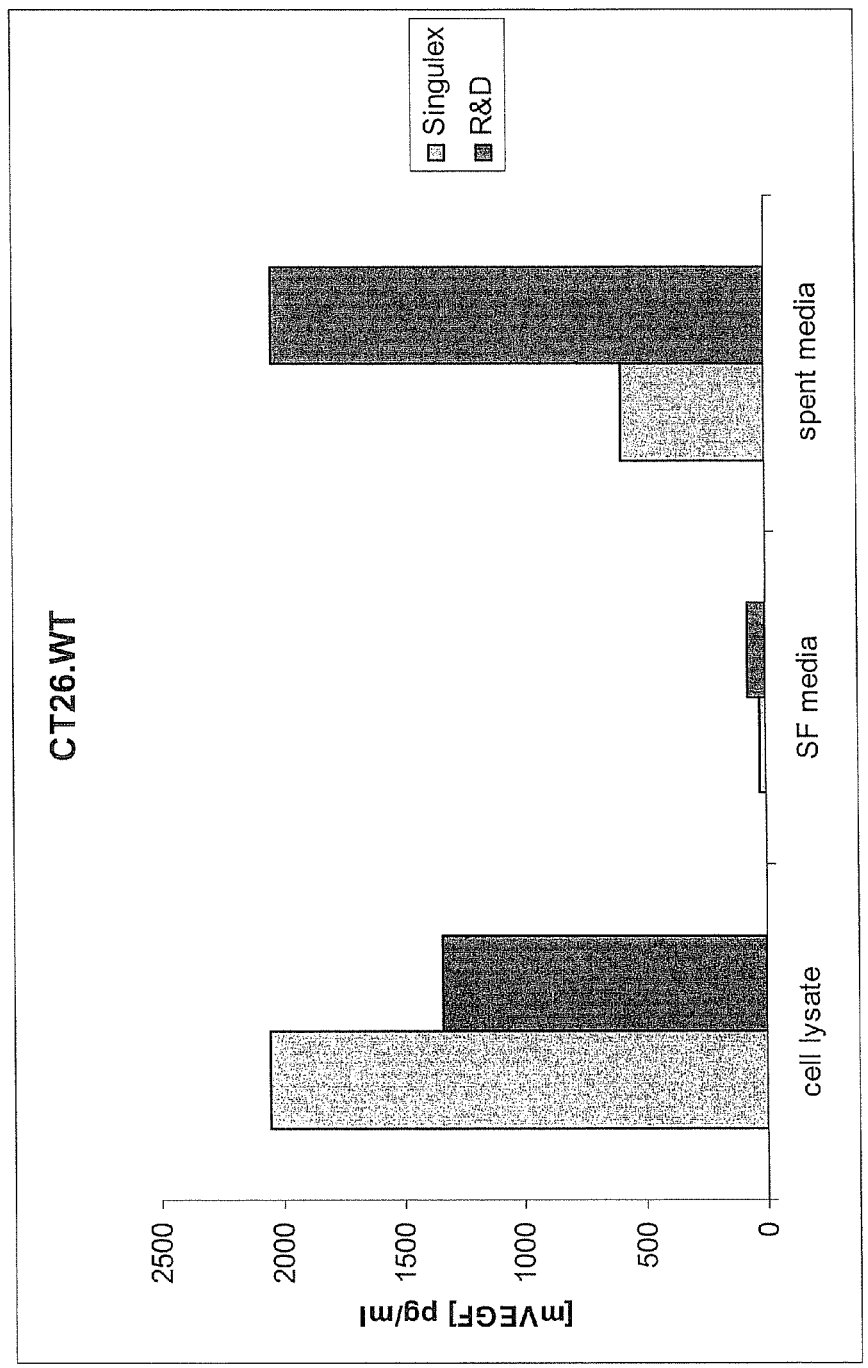
FIG. 24C is a graph illustrating the concentration of mouse VEGF detected in cell lysates and culture media using CT26 colon carcinoma cell lines.

Samples were run in duplicate in both the present and the R&D ELISA assays. Lysates were initially diluted 1:8, then (3) serial 1:2 dilutions were made. Media were analyzed neat and diluted 1:4, 1:16, and 1:64. Duplicates of each sample were tested. A comparison of the values from the two assays is shown in FIG. 24. Both assays detected VEGF in the cell extracts and in the spent media. Assay results were in similar ranges for each of the cell lines and are shown in FIGS. 24A-C. As seen between the figures, 4T1 mammary cell line had the lowest levels; B16 melanoma samples had about 4× the levels of 4T1, and CT26 colon samples were about twice as high as for B16. There was a consistent difference between the two assays. The present assay detected more VEGF in the cell lysates and less in the spent media. In addition, the ratio of cellular VEGF to released VEGF was consistently about 5:1 for the Singulex assay, but the ratio of intracellular VEGF to extracellular VEGF varied considerably for the ELISA assay results.

Example 14

VEGF Intra-assay and Inter-assay Performance

Human VEGF (hVEGF) Intra-assay Reproducibility:
Sample Preparation:

Two different normal human plasma samples were assayed multiple times using a single microassay plate. The P1 plasma sample was assayed neat and as a 1:8 dilution. The diluted plasma provided a source of samples to determine intra-assay at low hVEGF concentrations. Samples were tested in replicates of 18, 21, and 18.
Results:

A summary of intra-assay reproducibility for human plasma samples is shown in Table 17. The data summary in Table 17 indicates CVs for the sample replicates as 7, 12, and 9%. The last column in Table 17 shows the corrected, measured VEGF concentrations based upon benchmarking the concentration of the assay standards relative to the standards used in the ELISA assay. VEGF concentrations under 2 pg/ml were measured with a CV<10%.

Mouse VEGF Intra-assay Reproducibility:
Sample Preparation:

Replicate samples from three different EDTA mouse plasma were assayed on a single microtiter plate according to the present invention.
Results:

The intra-assay reproducibility for mouse plasma samples is shown in Table 19. Data for the 18-21 individual replicates from each plasma sample are shown in Table 19. CVs for the replicates of the three plasma samples ranged from 14% to 16% (Table 19).

TABLE 19

| MOUSE PLASMA | DETECTED EVENTS MEAN | STD DEV | CV | MEASURED MVEGF [PG/ML] MEAN | STD DEV | CV |
|---|---|---|---|---|---|---|
| M1 | 3979 | 525 | 13% | 485 | 78 | 16% |
| M2 | 2682 | 349 | 13% | 300 | 43 | 14% |
| M3 | 4838 | 516 | 11% | 635 | 91 | 14% |

TABLE 17

| Plasma Sample | Detected Events (mean) | std dev | CV | N | Measured hVEGF [pg/ml] mean | std dev | CV | Corrected hVEGF [pg/ml] |
|---|---|---|---|---|---|---|---|---|
| P1 diluted | 933 | 53 | 6% | 21 | 6 | 0.4 | 7% | 1.9 |
| P1 | 4692 | 395 | 8% | 21 | 41 | 5.0 | 12% | 12.6 |
| P2 | 4502 | 626 | 14% | 21 | 40 | 3.4 | 9% | 12.3 |

Human VEGF Inter-assay Reproducibility:
Sample Preparation:

To test the inter-assay reproducibility of the standard curves and values for human plasma samples assays were independently run 7 times by different personnel over 3 days with 3 replicates per sample.
Results:

The inter-assay variability between human plasma samples is shown in Table 18. Coefficients of Variation (CVs) for the plasma assays were under 10% (Table 18). CVs for the plasma analyses likewise were under 10% with the exception of the plasma P2 results for assay Run #6 (Table 18). In this assay two of the three values were in close agreement and one of the values was substantially lower. If this one replicate were removed from the series, the overall CV's for the VEGF plasma sample analyses would be <10%.

Singulex Inter-assay Reporducibility—Mouse Plasma Samples

Sample Preparation:

Four different mouse EDTA plasma samples were clarified by centrifugation for 10 minutes at 13,000×g. The samples were then tested in triplicate on 6 different days.

Results:

A summary of the inter-assay reproducibility of the mouse plasma VEGF assay is shown in Tables 20 & 21. The CVs for the mouse plasma samples were <25% over the six assays (Tables 20 & 21).

TABLE 18

| Plasma Sample | MEASURED HVEGF [PG/ML] | | | | | | Barb's Run | INTERASSAY CALCULATIONS | | | | INTERASSAY CALCULATIONS (N = 7) | | | |
|---|---|---|---|---|---|---|---|---|---|---|---|---|---|---|---|
| | Run 1 | Run 2 | Run 3 | Run 4 | Run 5 | Run 6 | | Measured hVEGF mean [pg/ml] | Std Dev | Interassay Sample CV | N | Measured hVEGF mean [pg/ml] | Std Dev | Interassay Sample CV | N |
| P1 | 26 | 23 | 23 | 20 | 23 | 22 | 20 | 23 | 2 | 9% | 6 | 22 | 2 | 9% | 7 |
| P2 | 16 | 16 | 17 | 18 | 16 | 10 | 16 | 16 | 3 | 19% | 6 | 16 | 3 | 17% | 7 |
| P3 | 26 | 29 | 28 | 24 | 29 | 27 | 26 | 27 | 2 | 7% | 6 | 27 | 2 | 6% | 7 |
| P4 | 8 | 9 | 10 | 9 | 9 | 10 | 9 | 9 | 1 | 7% | 6 | 9 | 1 | 6% | 7 |

TABLE 20

| MOUSE PLASMA | MEASURED MVEGF [PG/ML] MEAN | STD DEV | CV |
|---|---|---|---|
| M1 | 825.5 | 159.2 | 19% |
| M2 | 2107.0 | 422.8 | 20% |
| M3 | 1342.4 | 341.2 | 25% |
| M4 | 2582.8 | 398.7 | 15% |

TABLE 21

| Mouse Plasma | BACK INTERPOLATED VALUES - MVEGF [PG/ML] | | | | | |
|---|---|---|---|---|---|---|
| | Run 1 | Run 2 | Run 3 | Run 4 | Run 5 | Run 6 |
| M1 | 1134 | 756 | 704 | 758 | 745 | 857 |
| M2 | 2044 | 2591 | 1785 | 1730 | 1814 | 2677 |
| M3 | 1282 | 908 | 1027 | 1738 | 1705 | 1394 |
| M4 | 2760 | 2361 | 3044 | 2550 | 2853 | 1929 |

Example 15

VEGF in Xenograft Mice

Samples from mouse breast cancer xenografts were obtained from the laboratory of Dr. Matthew Ellis at Washington University. Plasma and breast cancer tissue was obtained from five different xenograft lines. As controls, plasma and mouse breast tissue from SCID mice were used. All samples were tested for the presence of mouse VEGF and human VEGF. Mouse VEGF ranged from 86-109 pg/ml in normal mouse plasma. Three of the xenograft mice had VEGF levels twice as high as the normals, and the other two xenograft samples had VEGF levels on the low side of the apparent normal range (80-86 pg/ml). Data are presented in Table 22.

Example 16

Immunoassay Kit for the Quantitative Determination of Human VEGF in Plasma and Cellular Lysates The Erenna™ Human VEGF Immunoassay uses a quantitative fluorescent sandwich immunoassay technique to measure Vascular Endothelial Growth Factor (VEGF) in human plasma and cellular lysates. A capture antibody specific for human VEGF has been pre-coated onto paramagnetic micro particles (MP). The user pipettes MP, standards and samples into uncoated microplate wells. During incubation, the free VEGF present in the sample binds to the capture antibody on the coated MP. Unbound VEGF molecules are washed away during the subsequent buffer exchange and wash steps. Fluorescent-labeled dye detection antibody specific for VEGF is added to each well and incubated. This detection antibody will recognize and bind to VEGF that has been captured onto the MP. During the following wash step the MP's are transferred to a clean plate. Elution buffer is then added and incubated. The elution buffer dissociates the bound protein sandwiches from the MP surface. The fluorescent antibodies are now free-floating in the wells. These antibodies are separated from the microparticles during transfer to a final microplate and the plate is loaded into the Erenna System where the fluorescent molecules are counted. The number of fluorescently-labeled detection antibodies counted is directly proportional to the amount of free VEGF present in the sample when captured. The amount of free VEGF in unknown samples is interpolated off of a standard curve.

TABLE 22

| mVEGF assay | Detected Events (DE) | | | | Back Interpolation | | | |
|---|---|---|---|---|---|---|---|---|
| Mouse Plasma | Detected Events mean | std dev | CV | N | Measured mVEGF [pg/ml] mean | std dev | CV | |
| N1 | 1029 | 91 | 9% | 3 | 100 | 14 | 14% | |
| N2 | 882 | 152 | 17% | 3 | 92 | 21 | 22% | |
| N3 | 1046 | 146 | 14% | 3 | 107 | 17 | 16% | |
| N4 | 867 | 150 | 17% | 3 | 86 | 18 | 21% | |
| N5 | 1066 | 116 | 11% | 3 | 109 | 14 | 13% | |
| T1 | 1733 | 64 | 4% | 3 | 191 | 8 | 4% | |
| T2 | 1875 | 168 | 9% | 3 | 210 | 22 | 10% | |
| T3 | 2022 | 194 | 10% | 3 | 228 | 25 | 11% | |
| T4 | 822 | 61 | 7% | 3 | 80 | 7 | 9% | |
| T5 | 886 | 114 | 13% | 3 | 88 | 13 | 15% | |

N = Normal mouse heparin plasma

T = Mouse (xenograft) heparin plasma

Reagents Provided

TABLE 23

Reagent Data

| ITEM # | DESCRIPTION | SHIPPING CONDITIONS | STORAGE CONDITIONS | COMPONENT PART NUMBERS |
|---|---|---|---|---|
| 1. | Human VEGF Standard Diluent | With cold pack | 2-8° C. | 02-0182-00 |
| 2. | Human VEGF Capture Reagent | With cold pack | 2-8° C. | 02-0187-00 |
| 3. | Human VEGF Detection Reagent | With cold pack | 2-8° C. | 02-0188-00 |
| 4. | Erenna ™ VEGF Human Immunoassay Kit Instructions | N/A | Ambient | |
| 5. | Human VEGF Standard (frozen, shipped in separate box) | On Dry Ice | ≦−70° C. | 02-0180-00 |
| 6. | 10X Wash Buffer | With cold pack | 2-8° C. | 02-0180-00 |
| 7. | Elution Buffer | With cold pack | 2-8° C. | 02-0002-02 |

1. Storage Instructions & Stability

The Erenna VEGF Reagent Kit is to be stored at 2-8° C. The standard is shipped on dry ice in a separate container and should be stored at <−70° C. It is important that the standard remain frozen upon kit arrival. The expiration date of the kit components can only be guaranteed if the components are stored properly, and if each component is used once. Components are labeled with appropriate expiration dates.

2. Additional/Other Supplies

TABLE 24

Consumables and Supplies

| ITEM ## | DESCRIPTION | MFR SUPPLIER | COMPONENT PART NUMBERS | PRODUCT USES | PACKAGING DETAIL |
|---|---|---|---|---|---|
| 1. | Erenna ™ 10X Systems Buffer | Singulex | 02-0111-00, 02-0111-01 | Systems (Analysis) Buffer, fluid used to run Erenna System | 1 L (10 L mixed) 2 L (20 L mixed) |
| 2. | Reservoirs for 12-Channel Pipetters | VWR | 80092-466 | Transfer of reagents | 10/pkg |
| 3. | 96-Well V-Bottom PP Plate, 500 µL | Axygen | P-96-450V-C or P-96-450V-C-S | Additional assay plate, dilutions | 10 plates/unit 5 units/case |
| 4. | 96-Well Deep Well PP Plate (2.2 mL, 1.64 mL or 1.09 mL) | Axygen | P-2ML-SQ-C, P-DW-20-C or P-DW-11-C | Prepare standard curves (choose size) | Variable |
| 5. | 384-Well Round Bottom PP, 120 µL | Nunc | 264573 | Receiver/analysis plate | 20/pk or 120/cs |
| 6. | AcroPrep ™ 384-Filter Plates, 100 µL, for sample preparation and detection | Pall | 5070 | Remove MPs from assay | 10/pkg |
| 7. | Advanced Pierceable Sealer, Polyethylene | Nunc | 235306 | Permanent seal for analysis plate, used prior to Erenna run | 100 units/pk 100 pks/cs |
| 8. | AxySeal-PCRSP Plate sealing film series | Axygen | PCR-SP | Sealing plates during incubation/mix/store | 100 films/case |

3. Microparticle Parts and Supplies

TABLE 25

Microparticle Hardware

| ITEM # | DESCRIPTION | MFR SUPPLIER | COMPONENT PART ## | PRODUCT USES | PKG DETAIL |
|---|---|---|---|---|---|
| 1. | Dynal MPC ®-96S | Dynal ™ | 120.27 | Rare Earth Magnet, capture MP during wash | 1 plate |
| 2. | Microplate Wash Station | — | — | Wash MP following capture on magnet | — |
| 3. | Centrifuge w/ Plate Rotor | — | — | Remove MP via filter plate ≧3000 RPM | 1 |
| 4. | Centrifuge Adapter Collar | Pall | 5225 | Creates fit b/n 384-well filter plate 384-well assay plate | 2/pkg |
| 5. | Vacuum Pump | Welch | 2511B-01 | Degassing systems buffer | 1 |
| 6. | Microplate Incubator/Shaker | Boekel Scientific | #130000 The Jitterbug ™ | Incubating plate | 1 |
| 7. | Plate Seal Roller, VWR Plate Roller, Film + Foil CS1# | VWR | 60941-118 | Secures plate seal permanent plate seal | 1 |

4. Other Useful Supplies (Unspecified)
De-ionized or distilled water
Multichannel pipette capable of transferring or adding 20 µL, 100 µL and 250 µL
Micro-centrifuge tubes
Mini-centrifuge
250 mL container
250 mL graduated cylinder
Precautions
Always use caution when handling any biological samples by wearing protective clothing and gloves.
Components of this reagent kit contain approximately 0.1% of sodium azide as a preservative. Sodium azide is a toxic and dangerous compound when combined with acids or metals. Solutions containing sodium azide should be disposed of properly.
Technical Hints Due to High Sensitivity of Assay
Wipe down bench and pipettes with 70% Isopropanol before use.
Quick spin concentrated standard and initial standard dilution before opening vials.
Use sterile pipette tips and reagent trays to help avoid cross-contamination.
Use filter tips while transferring concentrated standard.
It is recommended to use a 96-well 1 mL polypropylene dilution plate for preparing standards and samples.
It is recommended to transfer 3 replicates of each standard point from the dilution plate then into the 96-well VEGF Assay Plate.
Pre-wet tips (aspirate and dispense within well) twice before each transfer.
Reagent Preparation
1. Warm all reagents to room temperature prior to use.
2. Prepare 1× Wash Buffer (from 10× Wash Buffer) as follows:
 a. Pour 25 mL bottle of 10× Wash Buffer into 250 mL container.
 b. Add 225 mL of de-ionized water.
 c. Mix thoroughly by gentle inversion.
3. Re-suspend MP by inverting the vial via a rotator for 30 minutes immediately prior to use to help ensure that the MP are evenly distributed in the vial.
Assay Preparation
Standard—Initial Standard Dilution Directions
 1. Vortex and quick spin standard vial in a mini-centrifuge prior to opening vial. Use care when opening this concentrated standard vial to prevent loss of materials or aerosol contamination of specimens or plates.
 2. Refer to Certificate of Analysis for Standard for concentration of the VEGF standard. Dilute the stock to 10 ng/mL with Standard Diluent.
5. Plasma Sample Standard Curve
Prepare standard curve into a column on a 96-well 1 ml deep dilution plate. Perform 1:2 serial dilutions to achieve a curve from 200 pg/ml to 0.05 pg/ml. Run the standards in triplicate.
C. Cell Lysates and Media Standard Curve
Prepare standard curve into a column on a 96-well 1 ml deep dilution plate. Perform 1:2 serial dilutions to achieve a curve from 4000 pg/ml to 0.24 pg/ml. Run the standards in triplicate.
D. Sample Preparation
It is critical that plasma samples are centrifuged at >15,800×g for 10 minutes immediately prior to use. Carefully pipette, avoiding particulates; slowly aspirate below the lipid layer. Avoid repeated freeze-thaw cycles. Add samples to the 96-well plate for ease in transferring.
Lysates should be centrifuged at 4,600×g for 5 minutes at 4° C. immediately prior to use. Carefully pipette the supernatant. Avoid freeze-thaw cycles.

Lysates should be diluted at least 10 fold into standards diluent prior to loading onto the assay.

Human VEGF Assay Procedure

Assay Setup

Perform the Reagent Preparation per instructions included in the kit and bulk reagent package inserts. Prepare the standard curve and samples as described above.

Target Capture

After micro particles (MP) have been re-suspended, add 100 µL of VEGF Capture Reagent to 96-well polypropylene plate (PPP). Pipette 100 µL per well of Standards/Samples to 96-well PPP. Seal plate with a temporary plate seal (AxySeal, PCRSP Plate Sealing Film) or equivalent. Incubate/shake at medium setting for 2 hours at room temperature (RT). Carefully remove temporary plate seal to avoid splashing. Set plate onto magnet (Dynal MPC®-96S), wait 2 minutes for MP to settle (ensure all MP are amassed as a pellet by magnet), then aspirate the supernatant (MP remain visible). With the MP secured, add 250 µL of Wash Buffer to each well. Wait 2 minutes (MP remain amassed) and aspirate buffer.

Detection

Remove plate from the magnet and add 20 µL of VEGF Detection Reagent to each well. Seal plate with temporary seal. Pulse in centrifuge up to 100×g. Remove the plate from the centrifuge and incubate/shake for 1 hour at (RT). Remove plate seal and set plate onto magnet. Wait 2 minutes and aspirate the supernatant. Add and then remove 250 µL of Wash Buffer 3 times (3×) while MP are magnetized/amassed. Pause for 2 minutes after each buffer addition. Do not suspend or remove MP from the magnet. Remove plate from the magnet and add 250 µL of Wash Buffer to each well. Shake plate for 10 seconds to re-suspend MP. Transfer contents of each well to a new 96-well PPP. Set a new 96-well plate onto magnet and wait 2 minutes for MP to amass/settle. Remove Wash Buffer. Remove plate from magnet, add 250 µL of Wash Buffer and shake for 10 sec. Load plate on magnet, wait 2 minutes, then aspirate buffer. Repeat cycle, magnetized MP should be visible.

Elution

Remove plate from the magnet and add 20 µL of per well Elution Buffer. Seal plate with temporary seal and pulse in centrifuge up to 100×g. Incubate/shake for 30 minutes at RT. Separately, set a 384-well filter-plate over a 384-well polypropylene plate making a filter-bottom plate using a centrifuge adapter column. Remove seal from 96-well plate, allow the MP to mass for 2 minutes while on the magnet before transferring the specimens to the 384-well filter-bottom plate. Cover the top of the filter-bottom plate with temporary plate seal and set plates into centrifuge. Spin plates at 850×g for 1 minute at RT. Remove filter plate and discard, cover assay plate using the piercable (permanent) plate seal (Nunc, 235306). To ensure a good seal, use Plate Seal Roller (VWR # 60941-118). Load completed assay plate onto Erenna Immunoassay System.

Human VEGF Quick Assay Guide

1. Prepare all reagents, standard curve, and samples as instructed.
2. Add 100 µL of Capture Reagent, followed by 100 µL of Standards/Samples to each well of 96-well polypropylene plate.
3. Cover and incubate/shake for two hours at RT.
4. Remove cover, set plate onto magnet, allow 2 minutes for MP to settle/amass and remove supernatant.
5. With plate on magnet, add 250 µL of Wash Buffer. Wait 2 minutes and remove buffer.
6. Remove from magnet and add 20 µL of VEGF Detection Reagent per well. Pulse centrifuge at 100×g.
7. Cover and incubate/shake for 1 hour at RT.
8. Set plate onto magnet and wait 2 minutes for MP to amass. Remove supernatant.
9. Add and then remove 250 µL of Wash Buffer 3× with MP magnetically amassed near the magnet. Wait 2 minutes before aspirating the buffer between each cycle.
10. Remove from magnet, add 250 µL of Wash Buffer and shake plate for 10 seconds to re-suspend MP. Transfer entire contents to new 96-well plate.
11. Set plate onto magnet, wait 2 minutes. Remove supernatant.
12. Remove from magnet, add 250 µL of Wash Buffer and shake plate for 10 seconds.
13. Repeat steps 11 and 12 respectively.
14. Remove from magnet and add 20 µL of Elution Buffer to each well. Pulse centrifuge at 100×g.
15. Cover and incubate/shake at RT for 30 minutes.
16. Set a filter plate over 384-well plate (assay plate).
17. Transfer contents of 96-well plate to 384-well filter plate/assay plate combo.
18. Cover filter plate combo, centrifuge for 1 minute at 850×g.
19. Remove top filter plate and discard. Cover 384-well plate with pierceable plate seal cover.
20. Load the plate onto the Erenna System.

Additional Sample Information

This assay may be used to test various types of plasma and serum.

Performance Characteristics

Typical Standard Curve

The Standard Curve shown in Table 26 is provided for informational purposes. A standard curve should be generated for each set of samples assayed.

TABLE 26

| Standard Curve | | | | | | | | | |
|---|---|---|---|---|---|---|---|---|---|
| Expected hVEGF [pg/ml] | DE mean | std dev | cv | EP mean | std dev | cv | TP mean | std dev | cv |
| 0.0 | 153 | 18 | 12% | 17199 | 2170 | 13% | 6615461 | 28222 | 0% |
| 0.6 | 418 | 12 | 3% | 41438 | 3697 | 9% | 6663194 | 13673 | 0% |
| 1.2 | 636 | 8 | 1% | 59525 | 2384 | 4% | 6692487 | 124775 | 2% |
| 2.4 | 1153 | 76 | 7% | 112940 | 13057 | 12% | 6842728 | 106599 | 2% |

TABLE 26-continued

Standard Curve

| Expected hVEGF [pg/ml] | DE mean | std dev | cv | EP mean | std dev | cv | TP mean | std dev | cv |
|---:|---:|---:|---:|---:|---:|---:|---:|---:|---:|
| 4.8 | 1885 | 192 | 10% | 183411 | 16850 | 9% | 6974526 | 119540 | 2% |
| 9.7 | 3263 | 212 | 6% | 366427 | 18106 | 5% | 7541609 | 60299 | 1% |
| 19.5 | 5552 | 112 | 2% | 778196 | 35582 | 5% | 8686751 | 29150 | 0% |
| 39.0 | 7342 | 213 | 3% | 1323456 | 45408 | 3% | 10765907 | 264979 | 2% |
| 78.3 | 8803 | 258 | 3% | 2168907 | 90905 | 4% | 14280963 | 82371 | 1% |
| 156.3 | 9371 | 170 | 2% | 3233333 | 71024 | 2% | 22666397 | 1186338 | 5% |
| 312.5 | 9683 | 179 | 2% | 4813765 | 103021 | 2% | 37355527 | 1599907 | 4% |
| 625.0 | 9691 | 268 | 3% | 6064170 | 88983 | 1% | 63385314 | 816036 | 1% |
| 1,250.0 | 9607 | 11 | 0% | 7597939 | 35178 | 0% | 107624478 | 4993201 | 5% |
| 2,500.0 | 9203 | 149 | 2% | 8444198 | 467406 | 6% | 168143795 | 7431591 | 4% |

KEY:
Detected Events (DE),
Event Photons (EP),
Total Photons (TP)

Example 17

Immunoassay Kit for the Quantitative Determination of Mouse VEGF in Plasma and Cellular Lysates The Erenna™ Mouse VEGF Immunoassay uses a quantitative fluorescent sandwich immunoassay technique to measure Vascular Endothelial Growth Factor (VEGF) in mouse plasma and cellular lysates. A capture antibody specific for mouse VEGF has been pre-coated onto paramagnetic micro particles (MP). The user pipettes MP, standards and samples into uncoated microplate wells. During incubation, the VEGF present in the sample binds to the capture antibody on the coated MP. Unbound VEGF molecules are washed away during the subsequent buffer exchange and wash steps. Fluorescent-labeled dye detection antibody is added to each well and incubated. This detection antibody will recognize and bind to VEGF that has been captured onto the MP. During the following wash step the MP's are transferred to a clean plate. Elution buffer is then added and incubated. The elution buffer dissociates the bound protein sandwiches from the MP surface. The fluorescent antibodies are now free-floating in the wells. These antibodies are separated during transfer to a final microplate and the plate is loaded into the Erenna System where the fluorescent molecules are counted. The number of fluorescently-labeled detection antibodies counted is directly proportional to the amount of VEGF present in the sample when captured. The amount of VEGF in unknown samples is interpolated off of a standard curve.

Reagents Provided

TABLE 27

Reagent Data

| ITEM # | DESCRIPTION | SHIPPING CONDITIONS | STORAGE CONDITIONS | COMPONENT PART NUMBERS |
|---|---|---|---|---|
| 8. | Mouse VEGF Standard Diluent | With cold pack | 2-8° C. | 02-0207-00 |
| 9. | Mouse VEGF Capture Reagent | With cold pack | 2-8° C. | 02-0201-00 |
| 10. | Mouse VEGF Detection Reagent | With cold pack | 2-8° C. | 02-0205-00 |
| 11. | Erenna ™VEGF Mouse Immunoassay Kit Instructions | N/A | Ambient | |
| 12. | Mouse VEGF Standard (frozen, shipped in separate box) | On Dry Ice | ≦−70° C. | 02-0200-00 |
| 13. | 10X Wash Buffer | With cold pack | 2-8° C. | 02-0179-00 |
| 14. | Elution Buffer | With cold pack | 2-8° C. | 02-0002-02 |

Storage Instructions & Stability

The Erenna VEGF Reagent Kit is to be stored at 2-8° C. The standard is shipped on dry ice in a separate container and should be stored at <−70° C. It is important that the standard remain frozen upon kit arrival. The expiration date of the kit components can only be guaranteed if the components are stored properly, and if each component is used once. Components are labeled with appropriate expiration dates. Additional/Other Supplies

TABLE 28

Consumables and Supplies

| ITEM # | DESCRIPTION | MFR SUPPLIER | COMPONENT PART NUMBERS | PRODUCT USES | PACKAGING DETAIL |
|---|---|---|---|---|---|
| 1. | Erenna ™ 10X Systems Buffer | Singulex | 02-0111-00, 02-0111-01 | Systems (Analysis) Buffer, fluid used to run Erenna System | 1 L (10 L mixed) 2 L (20 L mixed) |
| 2. | Reservoirs for 12-Channel Pipetters | VWR | 80092-466 | Transfer of reagents | 10/pkg |
| 3. | 96-Well V-Bottom PP Plate, 500 µL | Axygen | P-96-450V-C or P-96-450V-C-S | Additional assay plate, dilutions | 10 plates/unit 5 units/case |
| 4. | 96-Well Deep Well PP Plate (2.2 mL, 1.64 mL or 1.09 mL) | Axygen | P-2ML-SQ-C, P-DW-20-C or P-DW-11-C | Prepare standard curves (choose size) | Variable |
| 5. | 384-Well Round Bottom PP, 120 µL | Nunc | 264573 | Receiver/analysis plate | 20/pk or 120/cs |
| 6. | AcroPrep ™ 384-Filter Plates, 100 µL, for sample preparation and detection | Pall | 5070 | Remove MPs from assay | 10/pkg |
| 7. | Advanced Pierceable Sealer, Polyethylene | Nunc | 235306 | Permanent seal for analysis plate, used prior to Erenna run | 100 units/pk 100 pks/cs |
| 8. | AxySeal-PCRSP Plate sealing film series | Axygen | PCR-SP | Sealing plates during incubation/mix/store | 100 films/case |

Microparticle Parts and Supplies

TABLE 29

Microparticle Hardware

| ITEM ## | DESCRIPTION | MFR SUPPLIER | COMPONENT PART # | PRODUCT USES | PKG DETAIL |
|---|---|---|---|---|---|
| 1. | Dynal MPC ®-96S | Dynal ™ | 120.27 | Rare Earth Magnet, capture MP during wash | 1 plate |
| 2. | Microplate Wash Station | — | — | Wash MP following capture on magnet | — |
| 3. | Centrifuge w/ Plate Rotor | — | — | Remove MP via filter plate ≧3000 RPM | 1 |
| 4. | Centrifuge Adapter Collar | Pall | 5225 | Creates fit b/n 384-well filter plate 384-well assay plate | 2/pkg |
| 5. | Vacuum Pump | Welch | 2511B-01 | Degassing systems buffer | 1 |
| 6. | Microplate Incubator/Shaker | Boekel Scientific | # 130000 The Jitterbug ™ | Incubating plate | 1 |
| 7. | Plate Seal Roller, VWR Plate Roller, Film + Foil CS1# | VWR | 60941-118 | Secures plate seal permanent plate seal | 1 |

Other Useful Supplies (Unspecified)
De-ionized or distilled water
Multichannel pipette capable of transferring or adding 20 μL, 100 μL and 250 μL
Micro-centrifuge tubes
Mini-centrifuge
250 mL container
250 mL graduated cylinder Precautions:
Always use caution when handling any biological samples by wearing protective clothing and gloves. Components of this reagent kit contain approximately 0.1% of sodium azide as a preservative. Sodium azide is a toxic and dangerous compound when combined with acids or metals. Solutions containing sodium azide should be disposed of properly.

Technical Hints Due To High Sensitivity of Assay:
Wipe down bench and pipettes with 70% Isopropanol before use.
Quick spin concentrated standard and initial standard dilution before opening vials.
Use sterile pipette tips and reagent trays to help avoid cross-contamination.
Use filter tips while transferring concentrated standard.
It is recommended to use a 96-well 1 mL polypropylene dilution plate for preparing standards and samples.
It is recommended to transfer 3 replicates of each standard point from the dilution plate then into the 96-well VEGF Assay Plate.
Pre-wet tips (aspirate and dispense within well) twice before each transfer.

Reagent Preparation
Warm all reagents to room temperature prior to use. Prepare 1× Wash Buffer (from 10× Wash Buffer) as follows: Pour 25 mL bottle of 10× Wash Buffer into 250 mL container; Add 225 mL of de-ionized water; Mix thoroughly by gentle inversion. Re-suspend MP by inverting the vial via a rotator for 30 minutes prior to use to ensure that the MP are evenly distributed in the vial.

Assay Preparation
Standard—Initial Standard Dilution Directions
Vortex and quick spin standard vial in a mini-centrifuge prior to opening vial. Use care when opening this concentrated standard vial to prevent loss of materials or aerosol contamination of specimens or plates. Refer to Certificate of Analysis for Standard for concentration of the VEGF standard. Dilute the stock to 10 ng/mL with Standard Diluent.

Standard Curve
Prepare standard curve into a column on a 96-well 1 ml deep dilution plate. Perform 1:2 serial dilutions to achieve a curve from 4000 pg/ml to 3.9 pg/ml. Run the standards in triplicate.

Sample Preparation
Plasma samples are centrifuged at >15,800×g for 10 minutes immediately prior to use. Carefully pipette, avoiding particulates; slowly aspirate below the lipid layer. Avoid repeated freeze-thaw cycles. Add samples to the 96-well plate for ease in transferring. Lysates should be centrifuged at 4,600×g for 5 minutes at 4° C. immediately prior to use. Carefully pipette the supernatant. Avoid freeze-thaw cycles. Lysates should be diluted at least 10-fold prior to loading onto the assay.

Mouse VEGF Assay Procedure
Assay Setup
Perform the Reagent Preparation per instructions included in the kit and bulk reagent package inserts. Prepare the standard curve and the samples as described above.

Target Capture
After micro particles (MP) have been re-suspended, add 50 μL per well of VEGF Capture Reagent to 96-well polypropylene plate (PPP). Pipette 10 μL per well of Standards/Samples to 96-well PPP. Pulse spin the plate up to 100×g to ensure all of sample is in the MP mixture. Seal plate with a temporary plate seal (AxySeal, PCRSP Plate Sealing Film) or equivalent. Incubate/shake at medium setting for 2 hours at room temperature (RT). Carefully remove temporary plate seal to avoid splashing. Set plate onto magnet (Dynal MPC®-96S), wait 2 minutes for MP to settle (ensure all MP are amassed as a pellet by magnet), then aspirate the supernatant (MP remain visible). With the MP secured, add 250 μL of Wash Buffer. Wait 2 minutes (MP remain amassed) and aspirate buffer.

Detection
Remove plate from the magnet and add 20 μL of VEGF Detection Reagent to each well. Seal plate with temporary seal. Pulse in centrifuge up to 100×g. Remove the plate from the centrifuge and Incubate/shake for 2 hours at (RT). Remove plate seal and set plate onto magnet. Wait 2 minutes and aspirate the supernatant. Add and then remove 250 μL of Wash Buffer 3 times (3×) while MP are magnetized/amassed. Pause for 2 minutes after each buffer addition. Do not suspend or remove MP from the magnet. Remove plate from the magnet and add 250 μL of Wash Buffer to each well. Shake plate for 10 seconds to re-suspend MP. Transfer contents of each well to a new 96-well PPP. Set new 96-well plate onto magnet and wait 2 minutes for MP to amass/settle. Remove Wash Buffer. Remove plate from magnet, add 250 μL of Wash Buffer and shake for 10 sec. Load plate on magnet, wait 2 minutes, then aspirate buffer. Repeat cycle, magnetized MP should be visible.

Elution
Remove plate from the magnet and add 20 μL of per well Elution Buffer. Seal plate with temporary seal and pulse in centrifuge up to 100×g. Incubate/shake for 30 minutes at RT. Separately, place a 384-well filter-plate over a 384-well PPP assay plate, making a filter-bottom plate. Remove seal from 96-well plate, transfer specimens to the 384-well filter-bottom plate. Cover the top of the filter-bottom plate with temporary plate seal and set plates into centrifuge. Spin plates at 850×g for 1 minute at RT. Remove filter plate and discard, cover assay plate using the pierceable (permanent) plate seal (Nunc, 235306). To ensure a good seal, use Plate Seal Roller (VWR # 60941-118). Load completed assay plate onto Erenna Immunoassay System.

Mouse VEGF Quick Assay Guide
1. Prepare all reagents, standard curve, and samples as instructed.
2. Add 50 μL of Capture Reagent, followed by 10 μL of Standards/Samples to each well of 96-well polypropylene plate.
3. Pulse spin plate up to 100×g to ensure samples are in the MP solution.
4. Cover and incubate/shake for two hours at RT.
5. Remove cover, set plate onto magnet, allow 2 minutes for MP to settle/amass and remove supernatant.
6. With plate on magnet, add 250 μL of Wash Buffer. Wait 2 minutes and remove buffer.
7. Remove from magnet and add 20 μL of VEGF Detection Reagent per well. Pulse centrifuge at 1000 RPM.
8. Cover and incubate/shake for 2 hours at RT.
9. Set plate onto magnet and wait 2 minutes for MP to amass. Remove supernatant.
10. Add and then remove 250 μL of Wash Buffer 3× with MP magnetically amassed near the magnet. Wait 2 minutes before aspirating the buffer between each cycle.

11. Remove from magnet, add 250 μL of Wash Buffer and shake plate for 10 seconds to re-suspend MP. Transfer entire contents to new 96-well plate.
12. Set plate onto magnet, wait 2 minutes. Remove supernatant.
13. Remove from magnet, add 250 μL of Wash Buffer and shake plate for 10 seconds.
14. Repeat steps 11, 12, and 13 respectively.
15. Remove from magnet and add 20 μL of Elution Buffer to each well. Pulse centrifuge at 100×g.
16. Cover and incubate/shake at RT for 30 minutes.
17. Set a filter plate over 384-well plate (assay plate).
18. Transfer contents of 96-well plate to 384-well filter plate/assay plate combo.
19. Cover filter plate combo, centrifuge for 1 minute at 850×g.
20. Remove top filter plate and discard. Cover 384-well plate with pierceable plate seal cover.
21. Load the plate onto the Erenna System.

This assay may be used to test various types of plasma and cellular lysates.

Performance Characteristics
Typical Standard Curve

The Standard Curve shown in Table 30 is provided for informational purposes. A standard curve should be generated for each set of samples assayed.

TABLE 30

Standard Curve

| Expected mVEGF [pg/ml] | DE mean | std dev | cv | EP mean | std dev | cv | TP mean | std dev | cv |
|---|---|---|---|---|---|---|---|---|---|
| 0.0 | 168 | 28 | 17% | 15207 | 2114 | 14% | 6163670 | 87902 | 1% |
| 3.9 | 177 | 27 | 15% | 15807 | 1406 | 9% | 6239587 | 98719 | 2% |
| 7.8 | 242 | 26 | 11% | 21854 | 2342 | 11% | 6360689 | 80386 | 1% |
| 15.6 | 302 | 11 | 4% | 28145 | 1949 | 7% | 6429962 | 44791 | 1% |
| 31.3 | 418 | 42 | 10% | 38805 | 3818 | 10% | 6370440 | 101262 | 2% |
| 62.5 | 652 | 6 | 1% | 62375 | 2971 | 5% | 6533290 | 50260 | 1% |
| 125.0 | 1112 | 127 | 11% | 118599 | 15256 | 13% | 7141792 | 531505 | 7% |
| 250.0 | 2104 | 123 | 6% | 225687 | 13232 | 6% | 7071139 | 80642 | 1% |
| 500.0 | 3871 | 865 | 22% | 491548 | 94923 | 19% | 8753982 | 1946419 | 22% |
| 1000.0 | 6693 | 399 | 6% | 1078600 | 94079 | 9% | 9319958 | 293189 | 3% |
| 2000.0 | 9292 | 298 | 3% | 2142047 | 11297 | 1% | 12032097 | 166349 | 1% |
| 4000.0 | 10193 | 58 | 1% | 3719950 | 81130 | 2% | 18770298 | 660699 | 4% |

KEY:
Detected Events (DE),
Event Photons (EP),
Total Photons (TP)

Example 18

Highly Sensitive Detection of VEGF

Figure 25A:
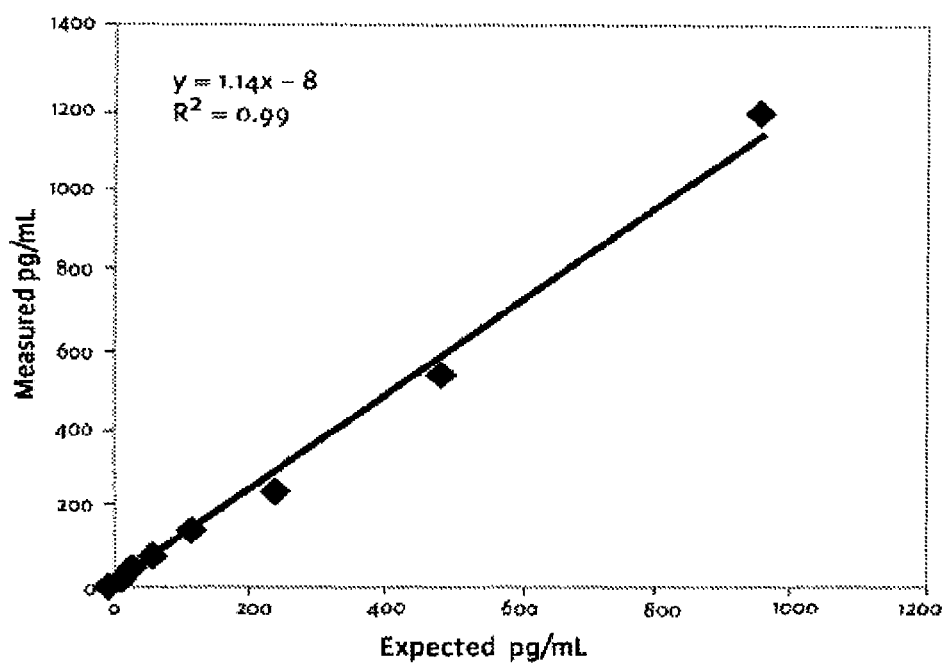
FIG. 25A illustrates a graph showing highly sensitive detection of VEGF.

The sensitivity of the system for different concentrations of VEGF in plasma is presented in Table 31. The data is presented graphically in FIG. 25A.

TABLE 31

VEGF-A Curve Fit Data

| Expected hVEGF [pg/ml] | Measured hVEGF [pg/ml] | Standard deviation | CV | Recovery |
|---|---|---|---|---|
| 0.00 | ND | — | — | — |
| 0.06 | 0.08 | 0.03 | 41% | 127% |
| 0.12 | 0.12 | 0.02 | 14% | 104% |

TABLE 31-continued

VEGF-A Curve Fit Data

| Expected hVEGF [pg/ml] | Measured hVEGF [pg/ml] | Standard deviation | CV | Recovery |
|---|---|---|---|---|
| 0.24 | 0.26 | 0.03 | 10% | 107% |
| 0.48 | 0.52 | 0.04 | 8% | 108% |
| 0.98 | 0.96 | 0.19 | 20% | 97% |
| 1.95 | 1.86 | 0.09 | 5% | 96% |
| 3.90 | 3.96 | 0.15% | 4% | 101% |
| 8 | 9 | 1.27 | 15% | 111% |
| 16 | 17 | 2.09 | 12% | 109% |
| 31 | 31 | 2.96 | 10% | 99% |
| 63 | 62 | 1.50 | 2% | 99% |
| 125 | 123 | 3.79 | 3% | 98% |
| 250 | 227 | 11.61 | 5% | 91% |
| 500 | 500 | 18.06 | 4% | 100% |
| 1000 | 1175 | 191.67 | 16% | 118% |

At the low end of the VEGF-A standard curve the concentration of VEGF-A detected is shown in Table 32.

TABLE 32

Low-end VEGF-A Standard Curve Data

| Expected hVEGF [pg/ml] | Mean DE | Standard deviation | CV | N |
|---|---|---|---|---|
| 0.00 | 99 | 11.4 | 11% | 3 |
| 0.06 | 161 | 29.3 | 18% | 3 |
| 0.12 | 207 | 17.3 | 8% | 3 |
| 0.24 | 335 | 26.6 | 8% | 3 |
| 0.48 | 595 | 43.5 | 7% | 3 |
| 0.98 | 1006 | 152.6 | 15% | 3 |
| 1.95 | 1771 | 52.9 | 3% | 3 |
| 3.90 | 3167 | 101.7 | 3% | 3 |
| 7.80 | 5311 | 476.3 | 9% | 3 |
| 15.60 | 7591 | 362.1 | 5% | 3 |

Figure 25B:
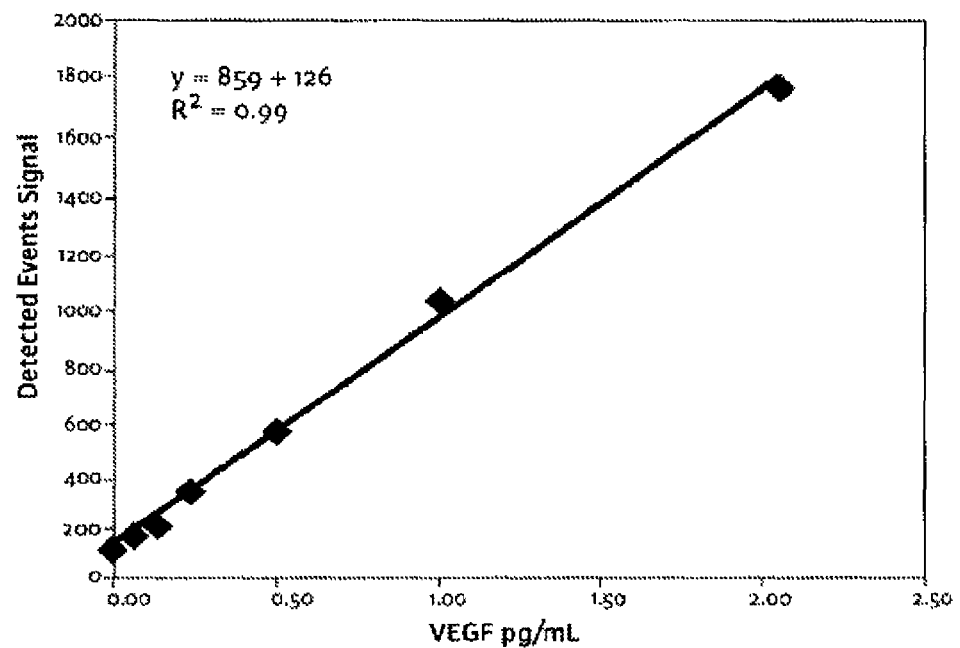
FIG. 25B illustrates the low end standard curve signal.

This data corresponds to the graph shown in FIG. 25B.

Example 19

Measured versus Expected Values for VEGF

Figure 26:
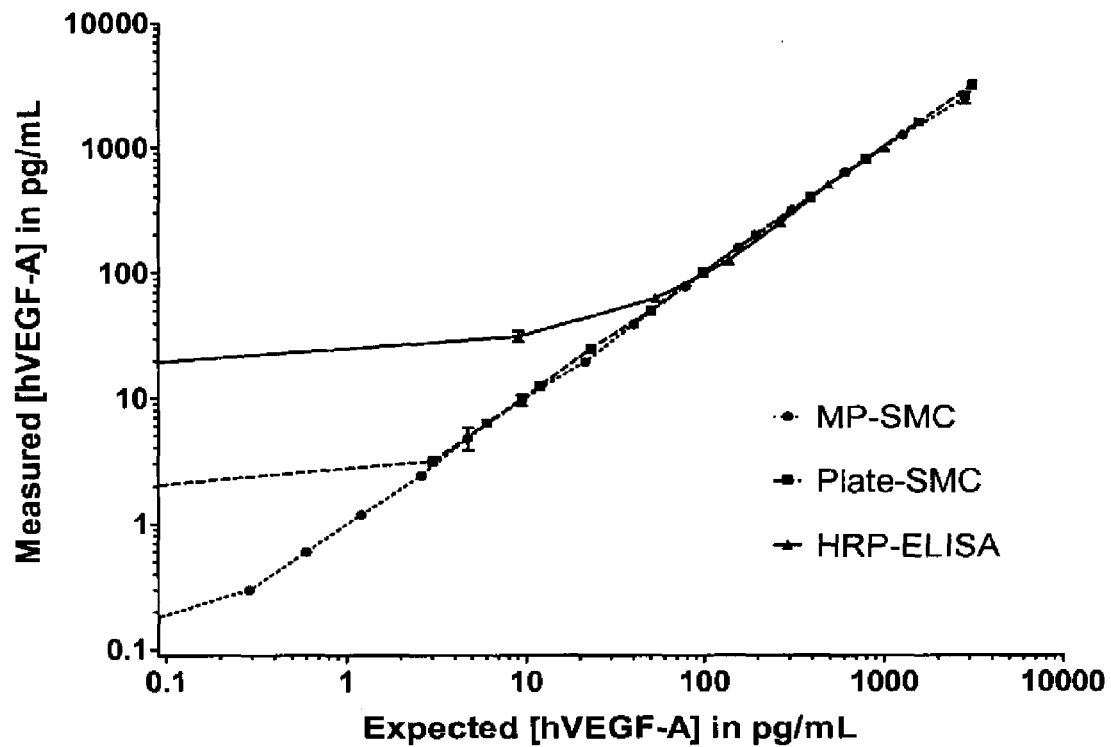
FIG. 26 illustrates the measured versus expected levels of detection of human VEGF using three different immunoassay formats: 1) Magnetic Microparticle based Single Molecule Counting (MP-SMC); 2) 384-well Plate based Single Molecule Counting (Plate-SMC); and 3) Horseradish peroxidase based Enzyme Linked Immunosorbent Assay (HRP-ELISA).

FIG. 26 shows measured versus expected values for VEGF in three different assay formats. Standard calibration curves for the three human VEGF assays using different solid phase immunoassay formats were run on a common set of serially diluted calibrators. The hVEGF MP-based assay uses paramagnetic microparticles coated with detection antibody as the solid phase capture format, and a fluorescently labeled detection antibody. The hVEGF Plate-based assay uses a uses 384-well plate, where wells have been coated with detection antibody as the solid phase capture format, and a fluorescently labeled detection antibody. The hVEGF HRP-ELISA assay is a commercially available ELISA assay from R&D Systems (LoD=31.2 pg/mL) consisting of a 96-well solid phase capture format, and uses an enzymatically conjugated detection antibody.

Example 20

Detection of VEGF in Plasma and Cell Lysate Small Volume Samples

Figure 27:
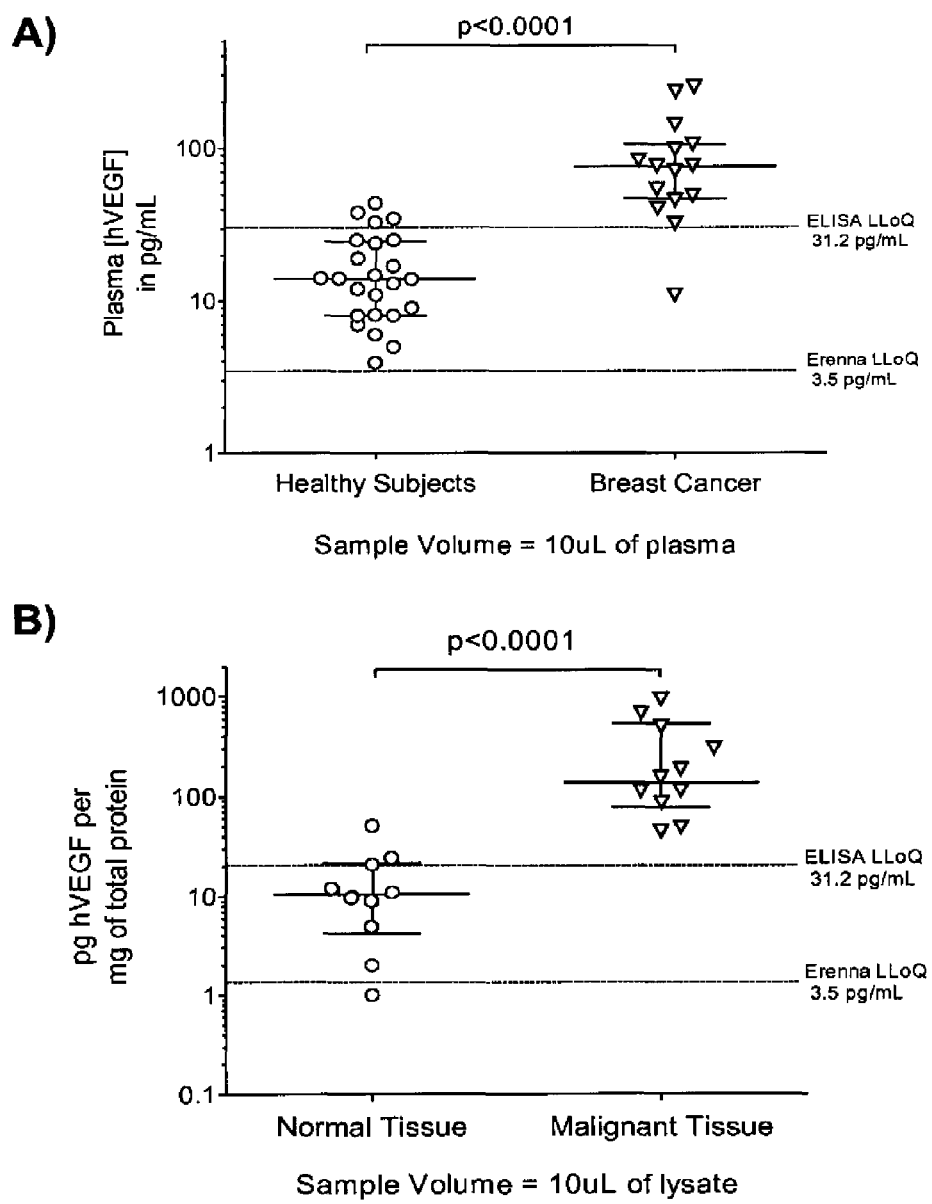
FIG. 27A illustrates the levels of human VEGF detected in 10 µl plasma samples from healthy and breast cancer patients. The limit of detection (LOD) using the method of the present invention (Errena; LOD=3.5 pg/ml) versus a standard ELISA format (LOD=31.2 pg/ml) is shown.
FIG. 27B illustrates similar data in 10 µl lysate samples.

The levels of human VEGF detected in 10 µl samples from healthy and breast cancer patients were compared. The limit of detection (LOD) using the method of the present invention (Errena; LOD=3.5 pg/ml) versus a standard ELISA format (LOD=31.2 pg/ml) is shown. Human plasma (FIG. 27A) and tissue (FIG. 27B) samples were tested with the Erenna hVEGF-A immunoassay. (FIG. 27A) Circulating concentration of hVEGF-A was determined in plasma samples from healthy blood donors (n=24) and subjects with breast cancer (n=15). The median and interquartile range of plasma VEGF levels were calculated, and compared between healthy blood donors and subjects with breast cancer. (FIG. 27B) Comparison of median and interquartile range of matched malignant and non-malignant tissue biopsy samples from subjects with breast cancer (n=10). Tissue samples were designated post-surgically as either normal or malignant, and results are shown in pg of VEGF protein per mg of total protein per sample. Quantification of the plasma samples with the present invention included all samples tested from healthy and cancerous subjects, while quantification using the standard ELISA assay showed poor quantification of healthy samples. Similar to the case in plasma, quantification of tissue samples with the present invention included all samples tested from healthy and cancerous subjects, while quantification using the standard ELISA assay showed poor quantification of healthy samples.

Example 21

Combined Analog and Digital Measurements of VEGF

Figure 28:
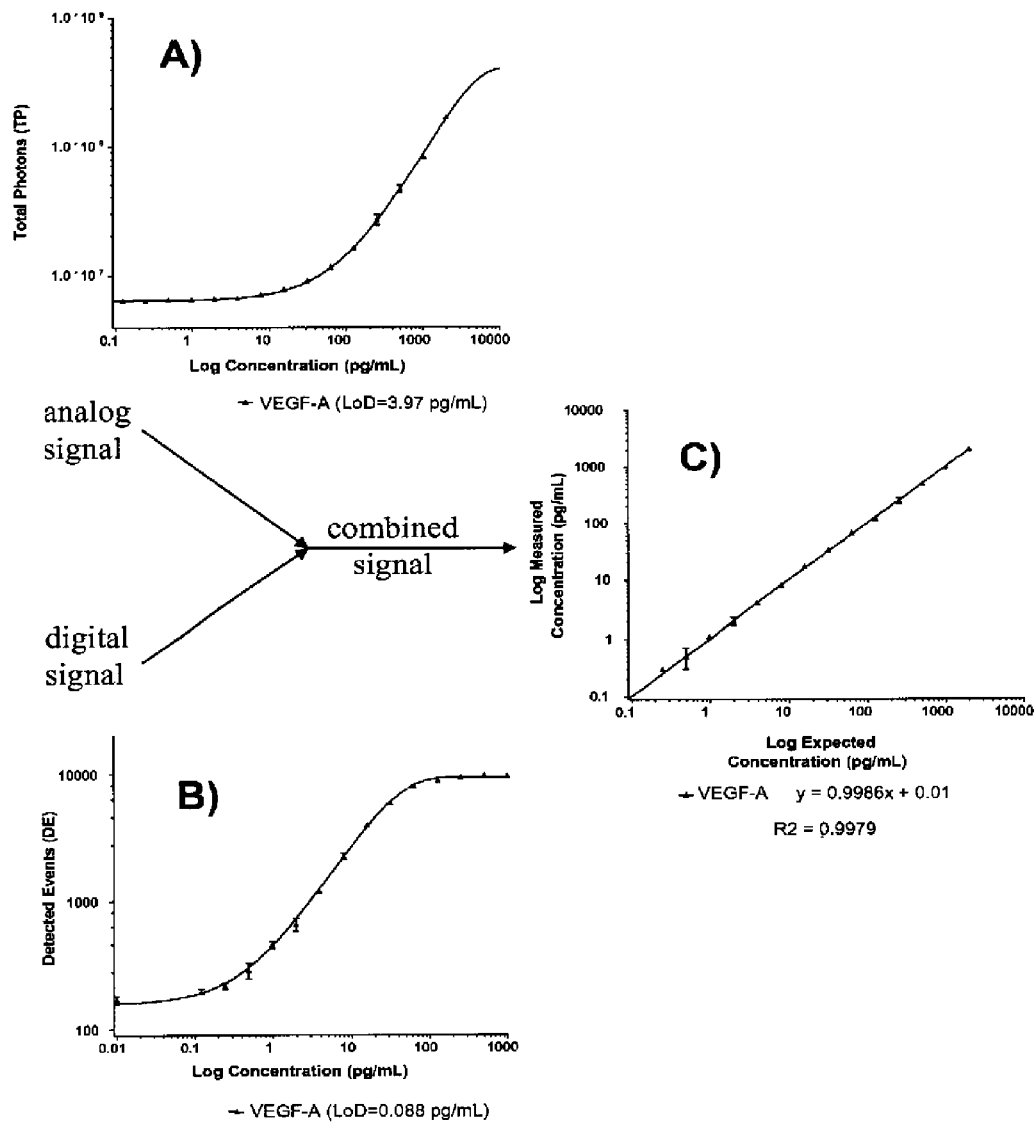
FIG. 28A-C illustrates combined analog and digital measurements of VEGF.

FIG. 28 shows the correlation of readout methods for the present invention. A standard curve was generated for the hVEGF analyte and measured with the Erenna system. Results are shown for each of three different read-out methods: (a) total photons (TP), which is analogous to standard ELISA plate reader technology; (b) detected events (DE), which counts single molecules passing through the interrogation zone as discreet events; and (c) using a processing algorithm which combines total photons and detected events. (FIG. 28A) and (FIG. 28B) LoD was calculated using the results of each method (DE and TP) using two standard deviations of the mean divided by slope. Data in FIG. 28A and FIG. 28B were analyzed using four-parameter curves. Data in FIG. 28C was analyzed using linear regression, resulting equations and correlation statistics are shown.

Example 22

Aβ-40 and Aβ-42 (Amyloid Beta Proteins 40 and 42) Assay

The present invention provides an assay for Aβ-40 and Aβ-42. The specification of the system for Aβ-40 and Aβ-42 in a sample is presented in Table 33.

TABLE 33

| Specifications of Singulex Aβ-40 and Aβ-42 assays | | |
|---|---|---|
| Attribute | Aβ-40 | Aβ-42 |
| LoD | 0.2 pg/ml | 0.1 pg/ml |
| LLoQ | 0.8 pg/ml | 0.5 pg/ml |
| Range | 0.2-100 pg/ | 0.1-250 pg/ml |
| Levels in human plasma: average (range) | 8.1 pg/ml (4.9-11.6 pg/ml) | 30.7 pg/ml (18.5-351 pg/ml) |

Figure 29A:
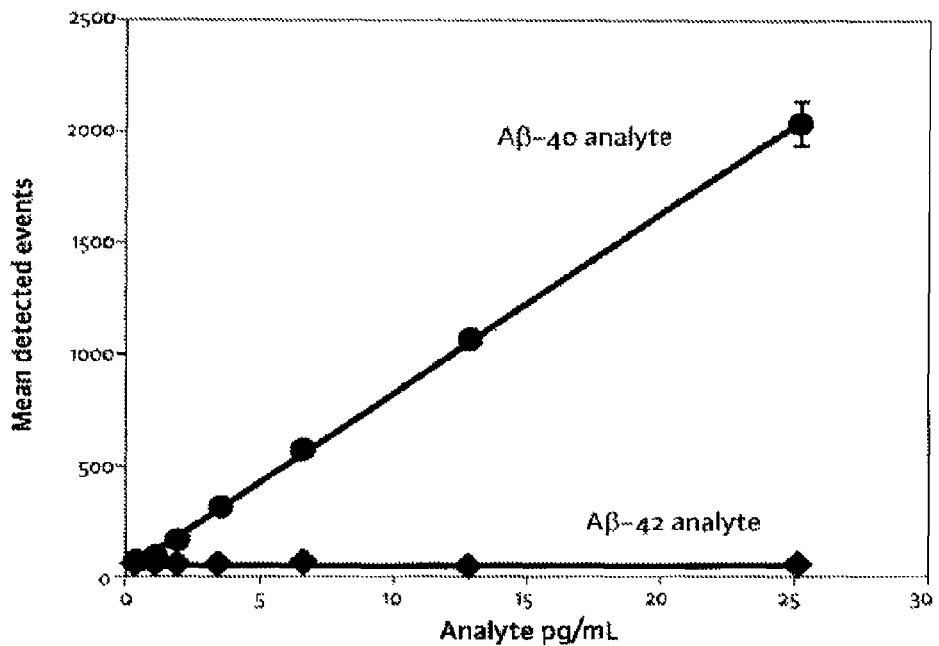
FIG. 29A illustrates a graph showing the specificity and linearity of Aβ-40 assay.
Figure 29B:
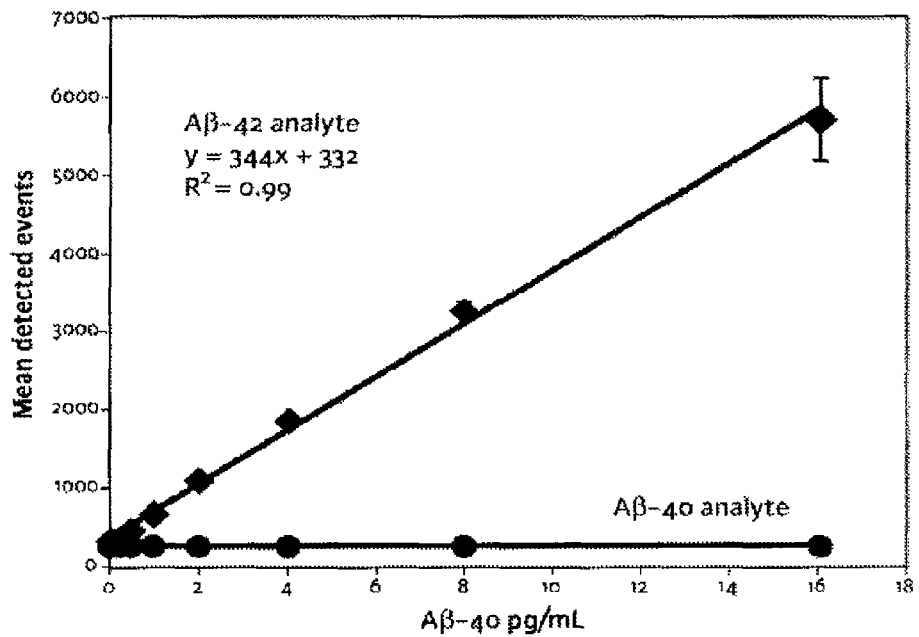
FIG. 29B is a graph showing the specificity and linearity of an Aβ-42 assay.

The events detected by the system in relation to the analyte concentrations of Aβ-40 and Aβ-42 are shown in FIG. 129A. FIG. 29B shows the specificity and linearity of the Aβ-42 assay.

Example 23

Interleukin 1, Alpha (IL-1α) Assay

Figure 30A:
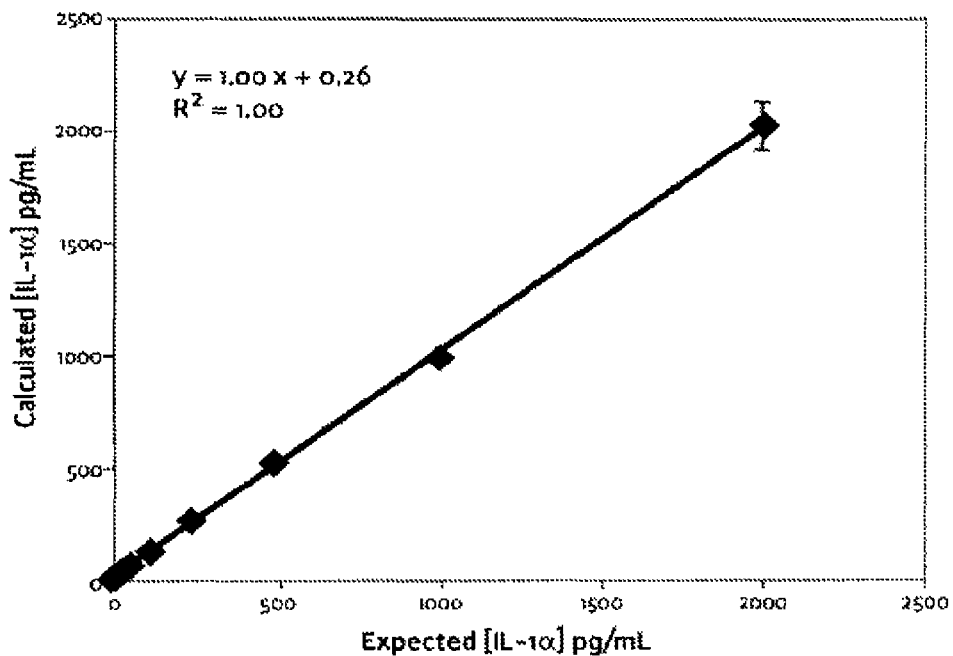
FIG. 30A is a graph illustrating an assay curve fit for IL-1α.

Sensitivity of an assay provided by the present invention in detecting IL-1α is shown in Table 34. The LoD is typically around 0.1 pg/ml or less. FIG. 30A illustrates a graph corresponding to the data presented in Table 34.

TABLE 34

| IL-1α Curve Fit Data | | | | |
|---|---|---|---|---|
| Expected IL-1α [pg/ml] | Measured IL-1α [pg/ml] | Standard deviation | CV | Recovery |
| 2000 | 2019 | 104 | 5% | 101% |
| 1000 | 976 | 54 | 6% | 98% |
| 500 | 516 | 18 | 4% | 103% |
| 250 | 256 | 17 | 7% | 102% |
| 125 | 120 | 2 | 2% | 96% |
| 63 | 63 | 5 | 7% | 100% |
| 31 | 31 | 0.5 | 1% | 100% |
| 16 | 17 | 3.42 | 21% | 106% |
| 7.8 | 8.4 | 0.40 | 5% | 107% |
| 3.9 | 3.9 | 0.19 | 5% | 100% |
| 1.95 | 1.94 | 0.06 | 3% | 99% |
| 0.98 | 0.98 | 0.03 | 3% | 98% |
| 0.49 | 0.5 | 0.08 | 16% | 100% |
| 0.24 | 0.27 | 0.02 | 9% | 103% |

Figure 30B:
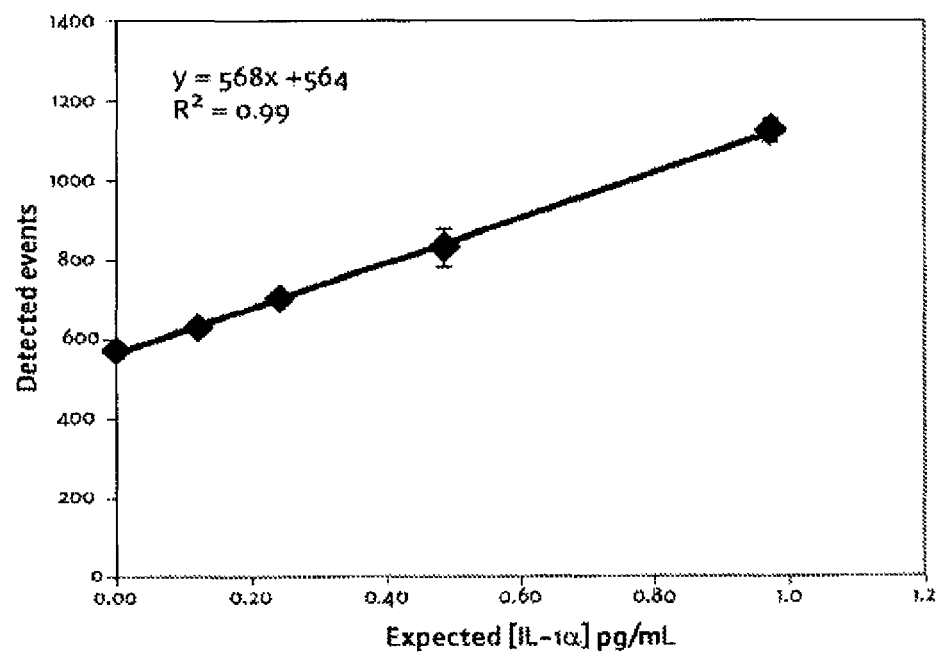
FIG. 30B is a graph illustrating the low end of an IL-1α assay standard curve signal.

The low end of the IL-1α curve is described in Table 35 and is graphically represented in FIG. 30B.

TABLE 35

Low-end IL-1α Standard Curve Data

| IL-1α [pg/ml] | Detected Events | Standard deviation | CV |
|---|---|---|---|
| 0.98 | 1123 | 22 | 2% |
| 0.49 | 832 | 46 | 6% |
| 0.24 | 703 | 12 | 2% |
| 0.12 | 628 | 9 | 1% |
| 0.00 | 572 | 28 | 5% |

Example 24

Interleukin 1, Beta (IL-1β) Assay

Figure 31A:
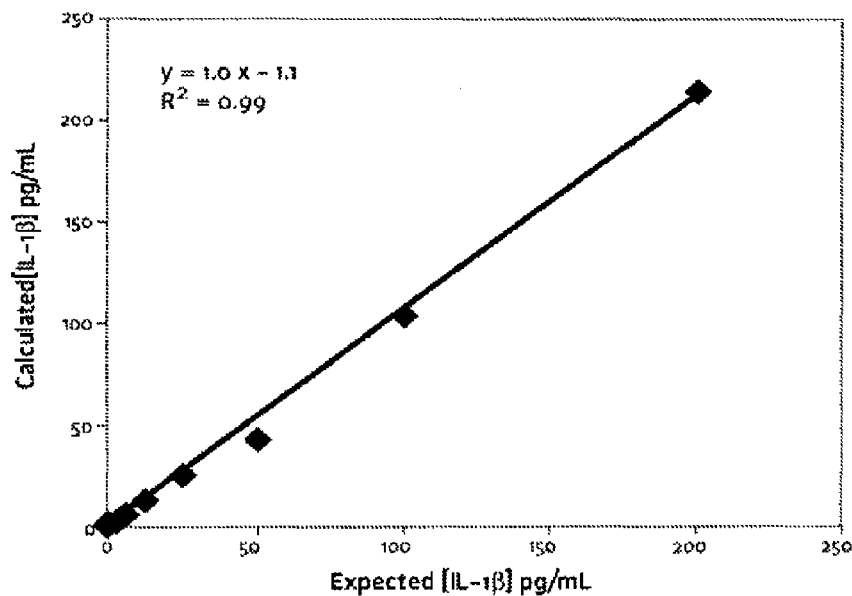
FIG. 31A is a graph illustrating an IL-1β assay curve fit.

Sensitivity of one embodiment for different concentrations of IL-1β are shown in Table 36 below. The LoD is typically 0.02 pg/ml or less. The expected concentration versus the measured or calculated concentration of IL-1β is shown graphically in FIG. 31A.

TABLE 36

IL-1β Curve Fit Data

| Expected IL-1β [pg/ml] | Measured IL-1β [pg/ml] | Standard deviation | CV | Recovery |
|---|---|---|---|---|
| 2000 | 2019 | 104 | 5% | 101% |
| 1000 | 976 | 54 | 6% | 98% |
| 500 | 516 | 18 | 4% | 103% |
| 250 | 256 | 17 | 7% | 102% |
| 125 | 120 | 2 | 2% | 96% |
| 63 | 63 | 5 | 7% | 100% |
| 31 | 31 | 0.5 | 1% | 100% |
| 16 | 17 | 3.42 | 21% | 106% |
| 7.8 | 8.4 | 0.40 | 5% | 107% |
| 3.9 | 3.9 | 0.19 | 5% | 100% |
| 1.95 | 1.94 | 0.06 | 3% | 99% |
| 0.98 | 0.98 | 0.03 | 3% | 98% |
| 0.49 | 0.5 | 0.08 | 16% | 100% |
| 0.24 | 0.27 | 0.02 | 9% | 103% |

Figure 31B:
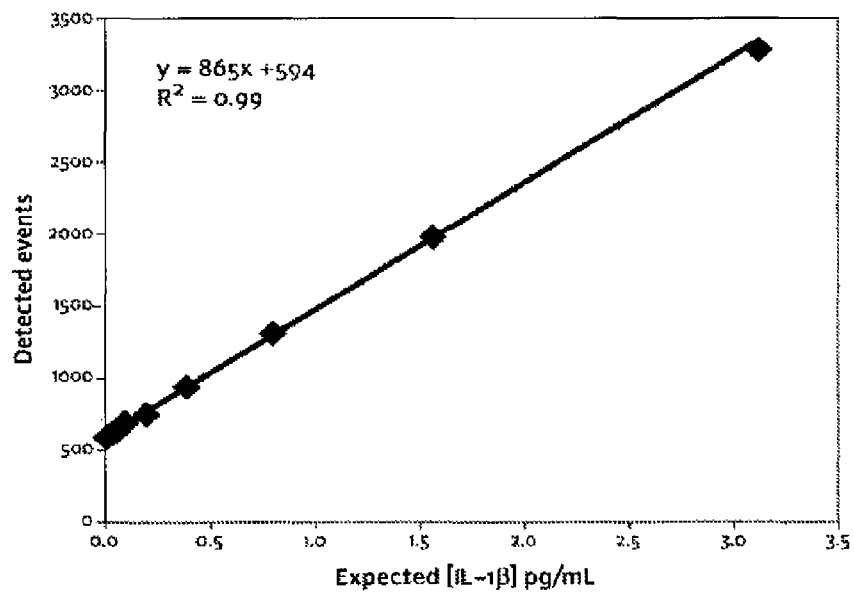
FIG. 31B illustrates the low end standard curve of IL-1β curve signal.

The low-end IL-1β standard curve data is presented in Table 37 below. These values are presented graphically in FIG. 31B.

TABLE 37

Low-end IL-1β standard curve data

| IL-1β [pg/ml] | Detected Events | Standard deviation | CV |
|---|---|---|---|
| 3.13 | 3282 | 19 | 0% |
| 1.56 | 1968 | 93 | 1% |
| 0.78 | 1300 | 56 | 5% |
| 0.39 | 936 | 45 | 4% |
| 0.20 | 745 | 36 | 5% |
| 0.10 | 691 | 18 | 5% |
| 0.05 | 631 | 48 | 3% |
| 0.02 | 616 | 19 | 8% |
| 0.01 | 583 | 14 | 3% |
| 0.00 | 590 | 45 | 2% |

Example 25

Interleukin 4 (IL-4) Assay

Figure 32A:
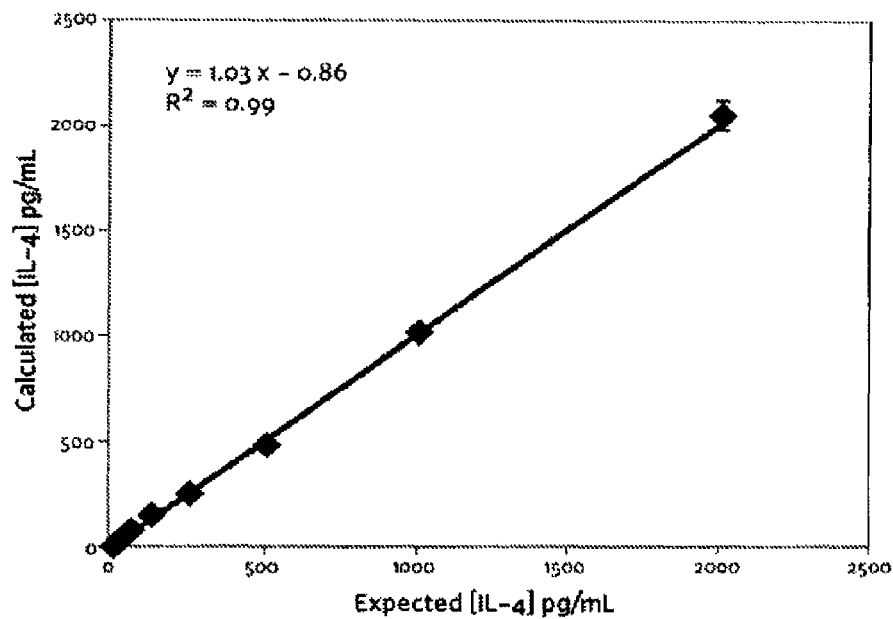
FIG. 32A is a graph illustrating an IL-4 assay curve fit.

The sensitivity of an IL-4 assay provided by the present invention is presented in Table 38. The expected IL-4 concentration levels versus the calculated or measured IL-4 levels are shown in FIG. 32A.

TABLE 38

IL-4 Curve Fit Data

| Expected IL-4 [pg/ml] | Measured IL-4 [pg/ml] | Standard deviation | CV | Recovery |
|---|---|---|---|---|
| 2000 | 2063 | 71 | 3% | 103% |
| 1000 | 1023 | 50 | 5% | 102% |
| 500 | 482 | 18 | 4% | 96% |
| 250 | 252 | 45 | 18% | 101% |
| 125 | 147 | 5 | 3% | 117% |
| 63 | 73 | 0 | 1% | 117% |
| 31 | 29 | 3 | 11% | 94% |
| 16 | 13 | 2 | 14% | 84% |
| 7.8 | 6.8 | 1.3 | 19% | 87% |
| 3.9 | 3.6 | 0.1 | 3% | 92% |
| 1.95 | 1.83 | 0.10 | 6% | 94% |
| 0.98 | 1.01 | 0.11 | 11% | 103% |
| 0.49 | 0.58 | 0.20 | 3% | 118% |
| 0.24 | 0.36 | 0.10 | 28% | 146% |

Figure 32B:
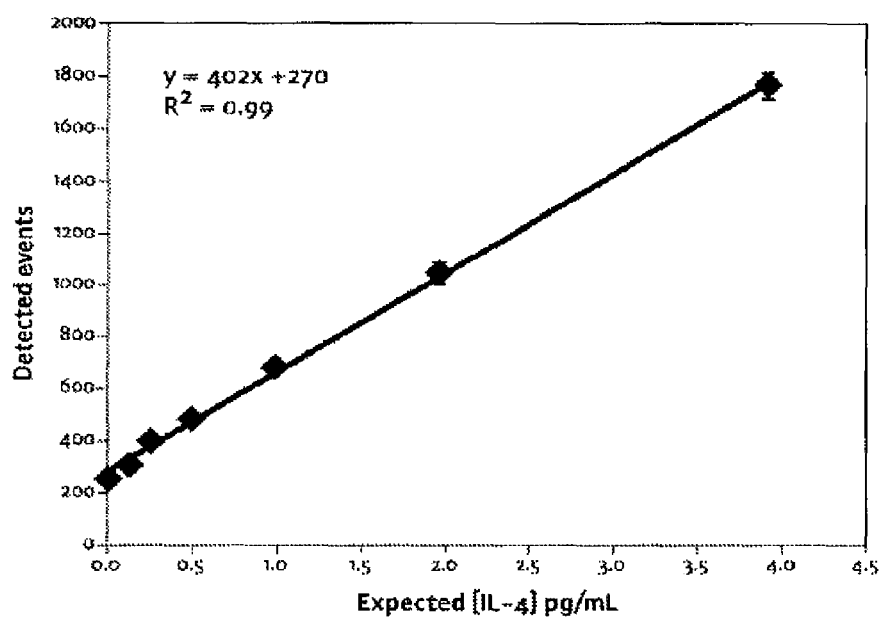
FIG. 32B is an IL-4 assay standard curve signal at the low end.

The IL-4 assay quantified as little as 0.04 pg/ml of plasma IL-4 with a CV<20%. In some embodiments, the LoD is 0.04 pg/ml. Table 39 lists the concentrations of IL-4 detected on the low end IL-4 standard curve data. FIG. 32B corresponds to the data presented in Table 39.

TABLE 39

Low-end IL-4 Standard Curve Data

| IL-4 [pg/ml] | Detected Events | Standard deviation | CV |
|---|---|---|---|
| 3.91 | 1761 | 44 | 3% |
| 1.95 | 1042 | 50 | 5% |
| 0.98 | 674 | 46 | 7% |
| 0.49 | 488 | 7 | 1% |
| 0.24 | 392 | 41 | 11% |
| 0.12 | 300 | 35 | 12% |
| 0.00 | 245 | 8 | 3% |

Example 26

Interleukin 6 (IL-6) Assay

Figure 33A:
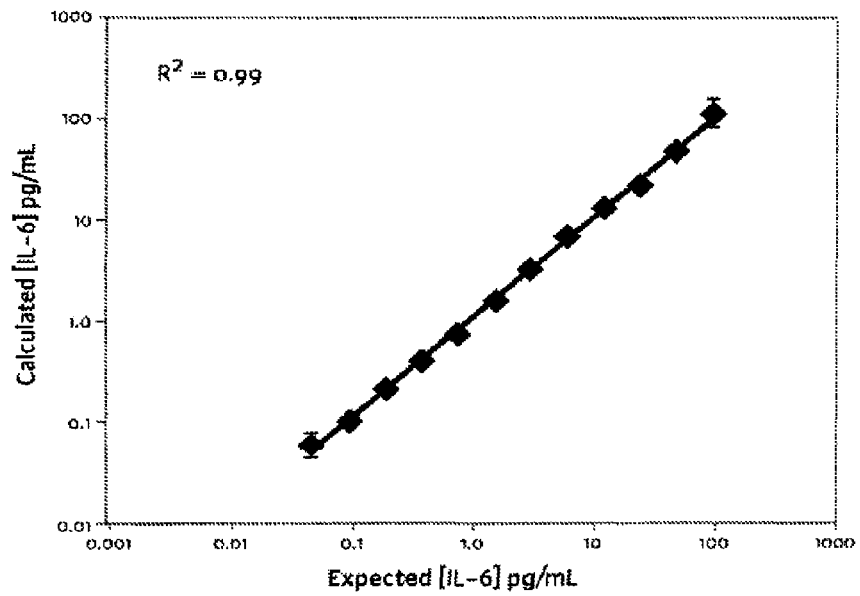
FIG. 33A is a graph illustrating an IL-6 assay curve fit.

The sensitivity and accuracy of one embodiment of an IL-6 assay provided by the present invention is illustrated in Table 40. The expected IL-6 concentration versus the concentration calculated or measured by the assay is depicted graphically in FIG. 33A.

TABLE 40

IL-6 Curve Fit Data

| Expected IL-6 [pg/ml] | Measured IL-6 [pg/ml] | Standard deviation | CV | Recovery |
|---|---|---|---|---|
| 100 | 119 | 32.76 | 28% | 119% |
| 50 | 49 | 6.99 | 14% | 98% |

TABLE 40-continued

IL-6 Curve Fit Data

| Expected IL-6 [pg/ml] | Measured IL-6 [pg/ml] | Standard deviation | CV | Recovery |
|---|---|---|---|---|
| 25 | 22 | 2.39 | 11% | 90% |
| 12.5 | 12.8 | 0.57 | 4% | 102% |
| 6.3 | 6.9 | 1.17 | 17% | 111% |
| 3.1 | 3.2 | 0.21 | 7% | 102% |
| 1.56 | 1.47 | 0.03 | 2% | 94% |
| 0.78 | 0.73 | 0.04 | 6% | 94% |
| 0.39 | 0.39 | 0.02 | 5% | 100% |
| 0.20 | 0.21 | 0.02 | 12% | 107% |
| 0.10 | 0.10 | 0.02 | 18% | 100% |
| 0.05 | 0.06 | 0.01 | 24% | 114% |

Figure 33B:
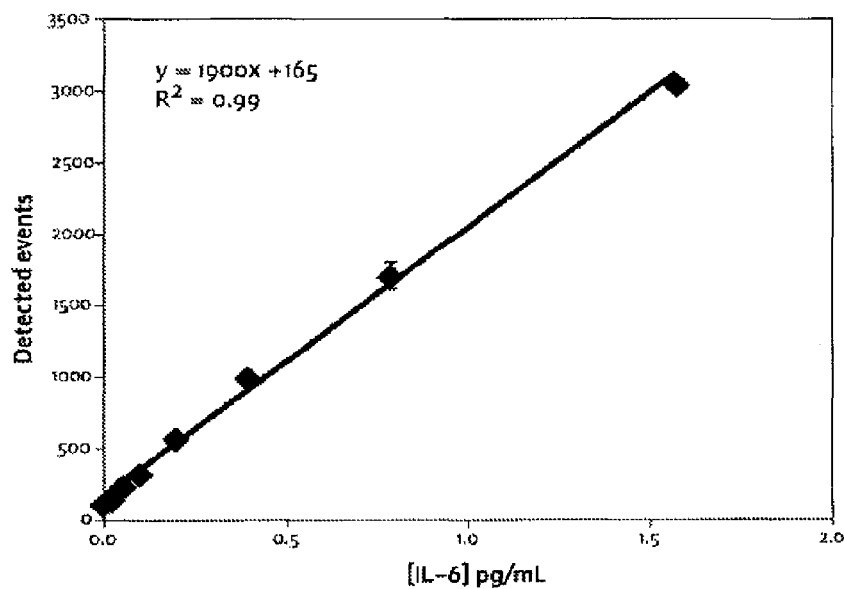
FIG. 33B is an IL-6 assay standard curve signal at the low end.

The low-end IL-6 standard curve data is depicted in Table 41 and is presented graphically in FIG. 33B.

TABLE 41

Low-end IL-6 Standard Curve Data

| IL-6 [pg/ml] | Detected Events | Standard deviation | CV |
|---|---|---|---|
| 1.56 | 3067 | 47 | 2% |
| 0.78 | 1728 | 97 | 6% |
| 0.39 | 1002 | 38 | 4% |
| 0.20 | 589 | 58 | 10% |
| 0.10 | 338 | 41 | 12% |
| 0.05 | 247 | 30 | 12% |
| 0.02 | 168 | 18 | 10% |
| 0.01 | 137 | 6 | 4% |
| 0 | 127 | 8 | 6% |

The IL-6 assay quantifies as little as 0.01 pg/ml of plasma IL-6 at a CV of <20%. The LoD is 0.01 pg/ml or less. This enables the accurate quantification of IL-6 in human plasma, obtained from healthy subjects, with ranges from 0.36-1.17 pg/ml or less.

Example 27

Biomarker Assays

The limits of detection (LODs) of various markers disclosed herein were assayed according to the present invention. The results of the assays are presented in Tables 42 and 43. Applications for various markers are indicated in Tables 42, 43 and 44.

TABLE 42

Limits of Detection for Various Biomarkers

| Biomarker | Class | Indications | LoD |
|---|---|---|---|
| cTnI | Cardiac | Necrosis | 0.01 |
| proBNP | Cardiac | Myocardial Disfunction | 0.03 |
| IL-1-alpha | Inflammation | | 0.07 |
| IL-1-beta | Inflammation | Unstable angina (UAP) | 0.01 |
| IL-6 | Inflammation | Plaques, Heart failure (HF), Coronary artery disease (CAD), Myocardial infarction (MI) | 0.01 |
| IL-8 | Inflammation | UAP | 0.36 |
| IL-10 | Inflammation | Anti-inflammatory | 0.46 |
| TNF-alpha | Inflammation | UAP, CAD, HF, Congestive heart failure (CHF), MI | 0.01 |
| IFN-gamma | Inflammation | Rheumatic heart disease (RHD), auto-immune | 0.14 |
| VEGF | Cancer | Angiogenesis | 0.10 |
| Insulin | Metabolic | Metabolic Syndrome | 12 |
| GLP-1 (T&A) | Inflammation | Metabolic Syndrome | 0.01 |

TABLE 43

Limits of Detection for Various Cytokines

| Biomarker | Indications | LoD |
|---|---|---|
| IL-1-alpha | Inflammation | 0.07 |
| IL-1-beta | UAP | 0.01 |
| IL-6 | Plaques, HF, CAD, MI | 0.01 |
| IL-8 | UAP | 0.36 |
| IL-10 | Anti-inflammatory | 0.46 |
| IL-17 | | |
| IL-21 | | |
| IFN-gamma | RA, Systemic lupus erythematosus (SLE), RHD, auto-immunity | 0.14 |
| Mip 1-alpha | | |
| RANTES | | |
| TNF-alpha | Cancer, Alzheimer's disease (AD), UAP, CAD, HF, CHF, MI | 0.01 |
| VEGF | Cancer, Angiogenesis, Artherosclreosis, Diabetes | 0.10 |

TABLE 44

Exemplary Marker Indications

| Assay | Neurologic | Metabolic | Oncology | Inflammatory |
|---|---|---|---|---|
| IL-1a | | | | X |
| IL-1b | | | | X |
| IL-4 | | | X | X |
| IL-6 | | X | X | X |
| IL-8 | | | X | X |
| IL-17 | X | X | | X |
| IFN-g | | | | X |
| Oxytocin | | X | | |
| cAMP | X | X | X | X |
| VEGF | | | X | |
| TNF-a | | | X | X |
| PSA total | | | X | |
| PSA free | | | X | |
| Ab-40 | X | | | |
| Ab-42 | X | | | |
| Insulin | | X | | |
| GLP-1 | | X | | |
| Troponin-1 | X | X | X | X |
| TGFb-1 | X | X | X | X |

Example 28

Biomarker Panels for Cardiovascular Disease Detection

Materials & Methods: EDTA-plasma were collected from subjects with CHF (N=32, 40% female, 76±11 yrs, 56% NYHA I/II, 44% NYHA III) and from an age and sex matched control cohort of apparently healthy subjects (N=32, 40% female, mean age 75±10 yrs). Collected panels of EDTA plasma were purchased from ProMedDx.

Samples were tested for a broad panel of protein biomarkers immunoassays developed for the Erenna® immunoassay system, which is based upon single molecule counting. Assays in the initial multi-panel included: the cardiac pathology markers cTnI and pro-BNP; the vascular inflammation marker VEGFa; and the inflammatory cytokines IL-1-alpha, IL-6, IL-8, IL-10, IL-17a, IL-17f, TNF-alpha and IFN-gamma. The SOP for a standard Erenna immunoassays is described below.

Samples were read in the Erenna instrument, detected events, event photons and total photons values were determined, and analyte concentrations were calculated in pg/mL using SMD Curve Fit, v 2.0 for all samples tested. Hierarchical clustering methods were used to develop a training set for inclusion/exclusion, and the resulting panel was evaluated for diagnostic specificity. Data were arranged into a data matrix and hierarchical clustering was performed using Cluster v 3.0. Data were log-transformed, centered against the mean, and normalized. Hierarchical clustering of both the protein set and the EDTA plasma samples was performed using average distance. The initial data set was used as a training set, and clustering was repeated on successive data sets until diagnostic specificity was optimized.

The resulting panel was further tested for individual significance in a cohort comparison between CHF and control subjects using a student's T-test. Markers with significant differences between the cohorts were identified for the final panel. Cut-points determined for each individual marker using the mean+3 standard deviations (99% CI) of the control subject values. The number of individuals in the CHF panel above and below the cut-points were determined for each individual marker and used to calculate the diagnostic sensitivity of that marker, as well as the cumulative diagnostic sensitivity of the panel.

Figure 34:
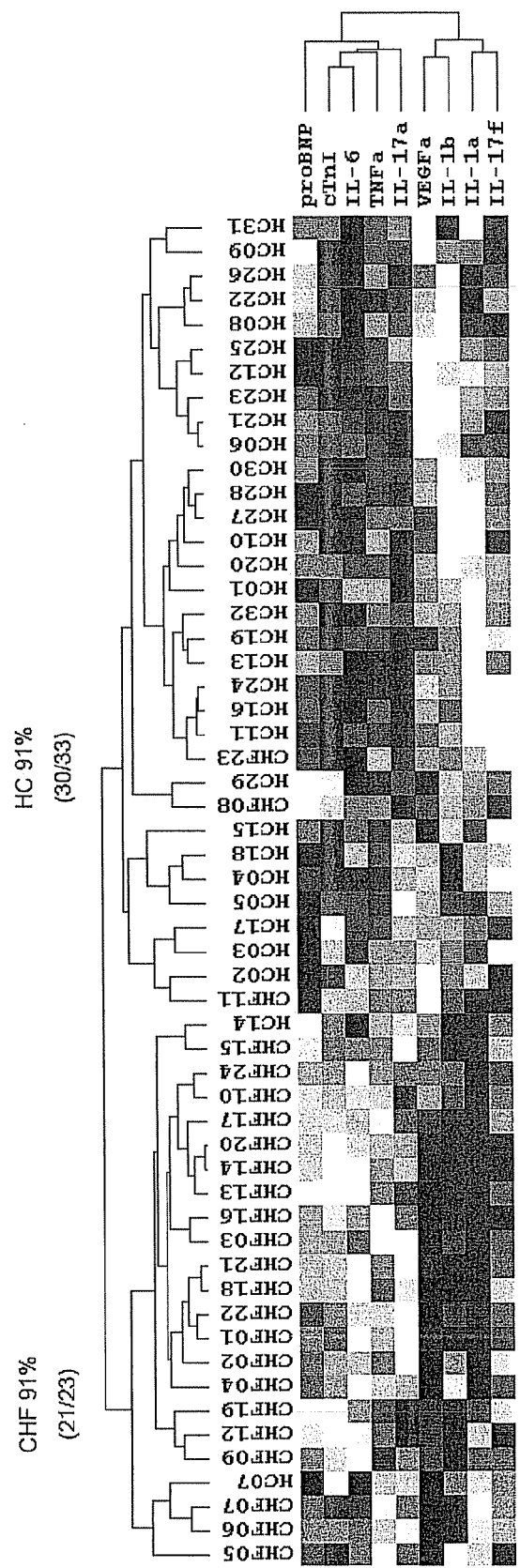
FIG. 34 illustrates diagnostic specificity of the cardiovascular disease (CVD) panel for conjestive heart failure (CHF) subjects compared to age and sex matched healthy control subjects.
Figure 35:
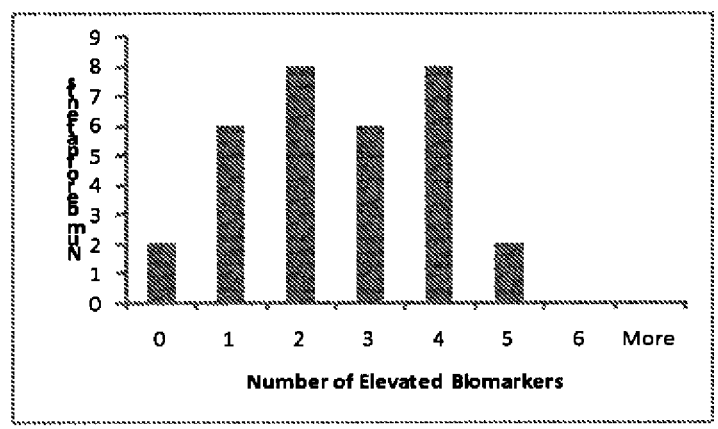
FIG. 35 illustrates the number of elevated biomarkers for the cardiovascular disease (CVD) panel in conjestive heart failure (CHF) subjects.

The standard operating procedure for the Erenna Immunoassay System is as follows:

Construct standard curve dilution series using urea assay buffer and the appropriate range for the experimental purpose, using standard analyte
Dilute microparticles (MP) in urea assay buffer to optimized final concentration
Combine 100 ul of diluted MP plus 100 ul of standard or sample in a 96 well polypropylene plate
Incubate 2 hrs with shaking
Wash to remove unbound proteins
Add 20 ul of filtered detection Ab diluted in TBS/BSA based assay buffer with goat/mouse/rabbit IgG+NaF
Incubate 1 hr with shaking
Wash to remove unbound detection Ab
Add 20 ul elution reagent/well and incubate with shaking for 10 min
Transfer to 384 well filter plate
Spin filter into 384 well polypropylene plate containing 4 ul of 1 M Tris
Read in Erenna System Results: Hierarchical clustering of the training set yielded a preliminary multi-marker panel with 91% diagnostic specificity for CHF compared to age and sex matched control subjects (FIG. 34). A subset of markers were further identified that showed significant differences between the two cohorts: cTnI (p=0.0025), BNP (p<0.0001), IL-6 (p<0.0001), TNFα (p<0.0001) and IL-17a (p=0.0166). These markers were used for the final panel, cut-points and diagnostic specificities were determined (TABLE 35). Based on established cut-points, diagnostic sensitivity of the individual markers was low compared to the cumulative sensitivity of the panel. Inclusion of all 5 protein biomarkers in the panel yielded a combined diagnostic sensitivity of 94%. In addition, multiple biomarkers were elevated for 75% (24/32) subjects in the CHF panel (FIG. 35) suggesting that synergistic biomarker elevation is a contributing factor.

TABLE 35

Individual and cumulative diagnostic sensitivity of the CVD biomarker panel

| Marker | cTnI | BNP | IL-6 | TNFα | IL-17a |
|---|---|---|---|---|---|
| Cutpoint (pg/ml) | 8.0 | 241 | 4.6 | 6.68 | 2.65 |
| # below | 17 | 13 | 23 | 15 | 28 |
| # above | 15 | 19 | 9 | 17 | 4 |
| Sensitivity (alone) | 47% | 59% | 28% | 53% | 13% |
| (cumulative) | — | 66% | 78% | 91% | 94% |

What is claimed is:

1. A method for detecting cardiomyocyte damage in a subject, comprising detecting Troponin-I (cTnI), Interleukin 6 (IL-6), Interleukin 17a (IL-17a) and at least one additional biomarker in a sample from the subject, wherein the at least one additional biomarker is selected from the group consisting of B-type Natriuretic Peptide (BNP), proBNP and NT-proBNP, and Tumor Necrosis Factor alpha (TNF-α), and wherein the limit of detection of at least one of the cTnI, IL-6, IL-17A, and the at least one additional biomarker is less than about 20 pg/ml.

2. The method of claim 1, wherein the detection of the at least one of the cTnI, IL-6, IL-17A and the at least one additional biomarker having the limit of detection less than about 20 pg/ml comprises contacting the sample with a label for the marker and detecting the presence or absence of the label wherein detection of the presence of the label indicates the presence of the corresponding marker.

3. The method of claim 2, wherein the label comprises a fluorescent moiety, and the at least one biomarker having the limit of detection less that about 20 pg/mL is detected in an interrogation space comprising a label corresponding to a single molecule of the biomarker.

4. The method of claim 2, wherein the label comprises a fluorescent moiety, and the detection comprises passing the label through a single molecule detector, wherein the single molecule detector comprises:
    (a) an electromagnetic radiation source for stimulating the fluorescent moiety;
    (b) an interrogation space for receiving electromagnetic radiation emitted from the electromagnetic source; and
    (c) an electromagnetic radiation detector operably connected to the interrogation space for determining an electromagnetic characteristic of the stimulated fluorescent moiety.

5. The method of claim 1, wherein the limit of detection of the at least one of cTnI, IL-6 and IL-17A and the at least one additional biomarker ranges from about 10 pg/ml to about 0.01 pg/ml.

6. A method to detect cardiomyocyte damage in a subject, comprising measuring a physiological biomarker and detecting Troponin-I (cTnI), Interleukin 6 (IL-6), Interleukin 17a (IL-17a) and at least one additional biomarker in a blood sample from the subject, wherein the at least one additional biomarker is selected from the group consisting B-type Natriuretic Peptide (BNP), proBNP, NT-proBNP, and Tumor Necrosis Factor alpha (TNF), and wherein the limit of detection of at least one of the cTnI, IL-6, IL-17a, and the at least one additional biomarker is less than about 20 pg/ml.

7. The method of claim 6, wherein the physiological biomarker is a stress test.

8. The method of claim 6, wherein the physiological biomarker is a sleep test.

9. The method of claim 6, wherein the physiological biomarker is Carotid intima-media thickness (CIMT).

10. The method of claim 6, wherein the physiological biomarker is Carotid intima-media thickness (CIMT).

11. A method for detecting congestive heart failure in a subject, comprising detecting whether one or more members of a panel of biomarkers comprising Troponin-I (cTnI), Interleukin 6 (IL-6) and at least one additional biomarker are elevated compared to the level of the Troponin-I (cTnI), Interleukin 6 (IL-6), Interleukin 17a (IL-17a), and at least one additional biomarker in a normal population, wherein the at least one additional biomarker is selected from the group consisting of B-type Natriuretic Peptide (BNP), proBNP, NT-proBNP, and Tumor Necrosis Factor alpha (TNF-α), and wherein the limit of detection of at least one member of the panel is less than about 20 pg/ml.

12. The method of claim 11, wherein the at least one member of the panel having a detection limit less than about 20 pg/ml is cTnI.

13. The method of claim 11, wherein the detection of the at least one member of the panel having the limit of detection less than about 20 pg/ml comprises contacting the sample with a label for the marker and detecting the presence or absence of the label, wherein detection of the presence of the label indicates the presence of the corresponding marker.

14. The method of claim 11, wherein the label comprises a fluorescent moiety, and the at lease one biomarker having the limit of detection less that about 20 pg/nl is detected in an interrogation space comprising a label corresponding to a single molecule of the biomarker.

15. The method of claim 11, wherein the label comprises a fluorescent moiety, and the detection comprises passing the label through a single molecule detector, wherein the single molecule detector comprises:
  (a) an electromagnetic radiation source for stimulating the fluorescent moiety;
  (b) an interrogation space for receiving electromagnetic radiation emitted from the electromagnetic source; and
  (c) an electromagnetic radiation detector operably connected to the interrogation space for determining an electromagnetic characteristic of the stimulated fluorescent moiety.

16. The method of claim 15, wherein the limit of detection of at least one member the panel ranges from about 10 pg/ml to about 0.01 pg/ml.

17. The method of claim 1, wherein the limit of detection of cTnI, IL-6 and IL-17A, and the at least one additional biomarker is less than about 20 pg/ml.

18. The method of claim 6, wherein the limit of detection of cTnI, IL-6 and IL-17A is less than about 20 pg/ml.

19. The method of claim 11, wherein the limit of detection of cTnI, IL-6 and IL-17A is less than about 20 pg/ml.

* * * * *